US012630565B2

(12) United States Patent
Qi et al.

(10) Patent No.: US 12,630,565 B2
(45) Date of Patent: May 19, 2026

(54) DNA-DEPENDENT PROTEIN KINASE INHIBITOR

(71) Applicant: DIZAL (JIANGSU) PHARMACEUTICAL CO., LTD., Shanghai (CN)

(72) Inventors: Changhe Qi, Shanghai (CN); Honchung Tsui, Shanghai (CN); Qingbei Zeng, Shanghai (CN); Zhenfan Yang, Shanghai (CN); Xiaolin Zhang, Shanghai (CN)

(73) Assignee: DIZAL (JIANGSU) PHARMACEUTICAL CO., LTD., Shanghai (CN)

( * ) Notice: Subject to any disclaimer, the term of this patent is extended or adjusted under 35 U.S.C. 154(b) by 975 days.

(21) Appl. No.: 17/614,384

(22) PCT Filed: May 26, 2020

(86) PCT No.: PCT/CN2020/092351

§ 371 (c)(1),
(2) Date: Nov. 26, 2021

(87) PCT Pub. No.: WO2020/238900

PCT Pub. Date: Dec. 3, 2020

(65) Prior Publication Data

US 2022/0242884 A1 Aug. 4, 2022

(30) Foreign Application Priority Data

May 27, 2019 (WO) ................ PCT/CN2019/088573

(51) Int. Cl.

| | |
|---|---|
| ***C07D 473/32*** | (2006.01) |
| ***A61K 31/519*** | (2006.01) |
| ***A61K 31/52*** | (2006.01) |
| ***A61P 35/00*** | (2006.01) |
| ***C07D 487/04*** | (2006.01) |
| ***C07D 519/00*** | (2006.01) |

(52) U.S. Cl.
CPC ......... *C07D 519/00* (2013.01); *C07D 487/04* (2013.01)

(58) Field of Classification Search
CPC .. C07D 473/32; C07D 487/04; C07D 519/00; A61K 31/519; A61K 31/52; A61P 35/00
See application file for complete search history.

(56) References Cited

FOREIGN PATENT DOCUMENTS

| | | | |
|---|---|---|---|
| CN | 101594871 | A | 12/2009 |
| CN | 102666545 | A | 9/2012 |
| CN | 103180322 | A | 6/2013 |
| CN | 103874699 | A | 6/2014 |
| CN | 110885331 | A | 3/2020 |
| CN | 111433208 | A | 7/2020 |
| JP | 2006241089 | A | 9/2006 |
| JP | 2008530191 | A | 8/2008 |
| JP | 2016510045 | A | 4/2016 |
| KR | 20090014219 | A | 2/2009 |
| KR | 20120102601 | A | 9/2012 |
| KR | 20130098151 | A | 9/2013 |
| WO | 2005/107760 | A1 | 11/2005 |
| WO | 2006074984 | A1 | 7/2006 |
| WO | 2006074985 | A1 | 7/2006 |
| WO | 2007/140222 | A2 | 12/2007 |
| WO | 2011156698 | A2 | 12/2011 |
| WO | 2012022681 | A2 | 2/2012 |
| WO | 2013163190 | A1 | 10/2013 |
| WO | 2014159690 | A1 | 10/2014 |
| WO | 2018114999 | A1 | 6/2018 |
| WO | 2019238929 | A1 | 12/2019 |

OTHER PUBLICATIONS

Wu et al., The Multifaceted Functions of DNA-PKcs: Implications for the Therapy of Human Diseases, MedComm, vol. 5, No. 7, e613 (Year: 2024).*
International Search Report of PCT/CN2020/092351, mailed on Aug. 27, 2020.
First Office Action for the counterpart Chinese application 202080039438.4, issued on Jul. 25, 2023.
Extended European search report for the counterpart EP applicaiton 20815132.4, issued on May 17, 2023.
Office Action for the counterpart KR application 10-2021-7039462, mailed on Apr. 8, 2025.

* cited by examiner

*Primary Examiner* — Brenda L Coleman
(74) *Attorney, Agent, or Firm* — Junhe Law Office P.C.; Zhaohui Wang

(57) ABSTRACT

Disclosed herein are compounds of Formula (I), and pharmaceutically acceptable salts thereof, that are useful as DNA-PK inhibitors. Also disclosed are pharmaceutical compositions comprising one or more compounds of Formula (I), and methods of using such compounds or compositions to treat DNA-PK related disorder (e.g., cancer).

25 Claims, No Drawings

DNA-DEPENDENT PROTEIN KINASE INHIBITOR

CROSS-REFERENCE TO RELATED APPLICATIONS

This application is a national phase application, filed pursuant to 35 U.S.C § 371 of PCT Application No. PCT/CN2020/092351 filed on May 26, 2020, which claims foreign priority of PCT Application No. PCT/CN2019/088573 filed on May 27, 2019, now abandoned. Each of these applications is hereby incorporated by reference herein in its entirety.

FIELD OF THE DISCLOSURE

The specification generally relates to novel compounds selectively modulating DNA-dependent protein kinase ("DNA-PK"), and pharmaceutically acceptable salts thereof. The present disclosure also relates to pharmaceutical compositions comprising one or more of the compounds as an active ingredient, and use of the compounds in the treatment of DNA-PK related disease, including cancer.

BACKGROUND

DNA-PK is a nuclear serine/threonine protein kinase complex composed of the catalytic subunit DNA-PKcs and a heterodimer of Ku proteins (Ku70/Ku80). Functionally, DNA-PK is a crucial component in the repair of DNA double strand breaks (DSBs), serving to maintain genomic integrity, and in the process of V(D)J recombination, resulting in the highly diverse repertoire of antibodies/immunoglobulins and T cell receptors found on B- and T-cells respectively. In addition, DNA-PK and its components are involved in a variety of other physiological processes, including modulation of chromatin structure, telomere maintenance, transcriptional regulation, and the response to replication stress (Smith and Jackson, 1999; Goodwin and Knudsen, 2014).

The human genome in the form of DNA is constantly exposed to the onslaught of reactive oxygen species (ROS), which are predominantly by-products of oxidative metabolism. ROS are able to cause DNA damage in the form of single-strand breaks. DSBs can occur if previous single-strand breaks occur in close proximity. In addition, single and single-double strand breaks are caused when the DNA replication fork encounters damaged base patterns. Furthermore, foreign influences, such as ionizing radiation (eg. Gamma or particle radiation), and certain anti-cancer drugs (e.g. B. Bleomycin) are able to elicit DSBs. DSBs may also occur as intermediates of somatic recombination, a process important to the formation of a functional immune system of all vertebrates.

If DSBs are not corrected or corrected incorrectly, mutations and/or chromosomal aberrations occur, which can lead to cell death. To address the serious threats posed by DSBs, eukaryotic cells have evolved several mechanisms (for example, DNA non-homologous end-joining (NHEJ) and homologous recombination (HR)) to mediate their repair, in which the DNA-PK plays the key role. Biochemical studies have shown that DNA-PK is most efficiently activated by the appearance of DNA DSBs. Cell lines whose DNA-PK components are mutated and nonfunctional turn out to be sensitive to radiation (Smith and Jackson, 1999). DNA-PK inhibitors may also be effective as single agents in tumors with high endogenous levels of DNA damage. DNA-PK inhibitors were demonstrated to be useful in oncology could include targeting tumors with high levels of replication stress (Lin et al., 2014; Ashley et al., 2014; Buisson et al., 2015), either as a monotherapy or in combination with other agents in prostate (Goodwin et al., 2013) and breast (Medunjanin et al., 2010) cancers.

Therefore, compounds that inhibiting DNA-PK are needed as pharmacological tools and are of considerable interest as drugs for treating DNA-PK related disorders such as cancer.

SUMMARY

In one aspect, the present disclosure provides a compound represented by Formula (I):

Formula I

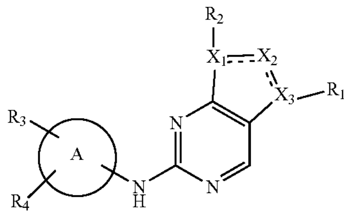

or a pharmaceutically acceptable salt thereof, wherein $X_1$, $X_2$, $X_3$, $R^1$, $R^2$, $R^3$, $R^4$ and Ring A are as herein defined.

In another aspect, the present disclosure provides a compound represented by Formula (Ia):

Formula Ia

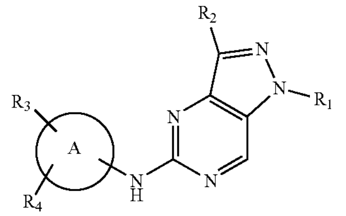

or a pharmaceutically acceptable salt thereof, wherein or a pharmaceutically acceptable salt thereof, wherein $R^1$, $R^2$, $R^3$, $R^4$, n and Ring A are as herein defined.

In another aspect, the present disclosure provides a compound represented by Formula (Ib):

Formula Ib

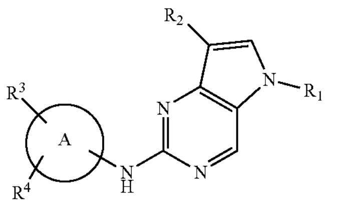

or a pharmaceutically acceptable salt thereof, wherein or a pharmaceutically acceptable salt thereof, wherein $R^1$, $R^2$, $R^3$, $R^4$ and Ring A are as herein defined.

In another aspect, the present disclosure provides a compound represented by Formula (Ic):

Formula Ic

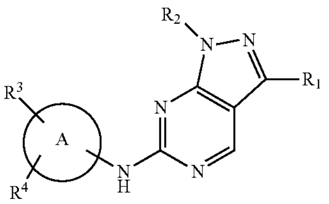

or a pharmaceutically acceptable salt thereof, wherein or a pharmaceutically acceptable salt thereof, wherein $R^1$, $R^2$, $R^3$, $R^4$ and Ring A are as herein defined.

In another aspect, the present disclosure provides a compound represented by Formula (Id):

Formula Id

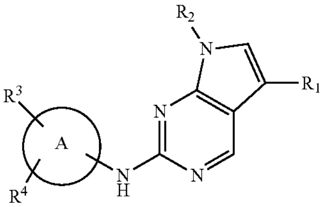

or a pharmaceutically acceptable salt thereof, wherein or a pharmaceutically acceptable salt thereof, wherein $R^1$, $R^2$, $R^3$, $R^4$ and Ring A are as herein defined.

In another aspect, the present disclosure provides a compound represented by Formula (Ie):

Formula Ie

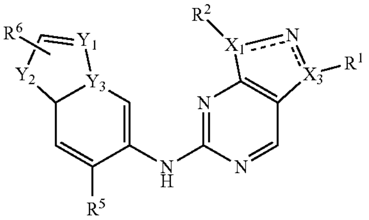

and a pharmaceutically acceptable salt thereof, wherein or a pharmaceutically acceptable salt thereof, wherein $X_1$, $X_3$, $Y_1$, $Y_2$, $Y_3$, $R^1$, $R^2$, $R^5$, and $R^6$ are as herein defined.

In another aspect, the present disclosure provides a pharmaceutical composition comprising one or more compounds of Formula (I), Formula (Ia), Formula (Ib), Formula (Ic), Formula (Id), Formula (Ie), or a pharmaceutically acceptable salts thereof, as an active ingredient.

In another aspect, the present disclosure further provides a compound of Formula (I), or a pharmaceutically acceptable salt thereof, or a pharmaceutical composition of one or more of the foregoing, for use in inhibiting DNA-PK kinase.

In yet another aspect, the present disclosure provides use of the compounds of Formula (I), or a pharmaceutically acceptable salts thereof, or a pharmaceutical composition of one or more of the foregoing in the manufacture of a medicament for inhibiting DNA-PK kinase in a subject.

In another aspect, the present disclosure provides a method for inhibiting DNA-PK kinase, by using one or more compounds of Formula (I), or a pharmaceutically acceptable salts thereof or the pharmaceutical composition of one or more of the foregoing.

In another aspect, the present disclosure provides a method for treating a DNA-PK related disorder (e.g., cancer), by using the compounds of Formula (I), or a pharmaceutically acceptable salts thereof or the pharmaceutical composition of one or more of the foregoing. In a further aspect, the present disclosure provides a compound of Formula (I), or a pharmaceutically acceptable salt thereof, in combination with a second therapeutic agent, preferably an anti-tumor agent.

In another aspect, the present disclosure provides a combined use of a compound of Formula (I), or a pharmaceutically acceptable salt thereof, and a second therapeutic agent, preferably an anti-tumor agent.

DETAILED DESCRIPTION

Compounds

In one aspect, the present disclosure provides compounds of Formula (I):

Formula I

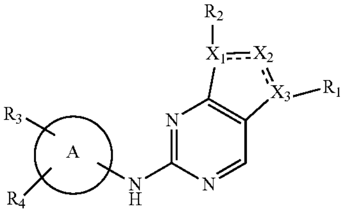

or a pharmaceutically acceptable salt thereof, wherein, $X_1$, $X_2$, and $X_3$ are each independently C or N, provided that at least one of $X_1$, $X_2$, and $X_3$ is N and at least one of $X_1$, $X_2$, and $X_3$ is C;

dash line "__________" means the bond between $X_1$ and $X_2$, and between $X_2$ and $X_3$ can be single or double bonds, provided that at least one of the bonds between $X_1$ and $X_2$, and between $X_2$ and $X_3$ is single bond;

$R^1$ is absent, halogen, or $C_{1-6}$ alkyl, wherein said $C_{1-6}$ alkyl can be optionally mono- or independently multi-substituted by hydroxyl, halogen, or deuterium;

each $R^2$, $R^3$ and $R^4$ is independently selected from absent, halogen, hydroxyl, cyano, $C_{1-6}$ alkyl, $C_{1-6}$ alkoxyl, $-(CH_2)_n$-Q, which can be optionally mono- or independently multi-substituted by deuterium, hydroxyl, amino, cyano, halogen, $C_{1-6}$ alkyl, $C_{1-6}$ haloalkyl, (C≡N)—$C_{1-6}$ alkyl, $C_{1-6}$ alkoxyl, $C_{1-6}$ haloalkoxyl, $C_{3-8}$ cycloalkyl, $C_{3-8}$ cycloalkoxyl, 3-8 membered aryl, or 3-8 membered heterocyclyl, wherein n is 0, 1 or 2, Q is 3-8 membered saturated or unsaturated carbocyclyl, or 3-8 membered saturated or unsaturated heterocyclyl;

Ring A is 5-12 membered aryl, 5-12 membered heteroaryl having 1-5 ring heteroatoms chosen from oxygen, sulfur and nitrogen, 8-10 membered bicyclic ring having 0-5 ring heteroatoms chosen from oxygen, sulfur and nitrogen, wherein Ring A is not phenyl.

In some embodiments, $R^2$ is selected from methyl, ethyl, propyl, butyl, cyclopropyl, cyclobutyl, oxetanyl, cyclopentanyl, tetrahydrofuryl, cyclohexanyl, tetrahydropyranyl, cycloheptanyl, piperidinyl, phenyl, pyridinyl, pyridonyl, oxocanyl, tetrahydropyranyl, dihydropyranyl, spiro[3.3]heptanyl, spiro[2.5]octanyl, bicyclo[1.1.1]pentanyl, bicyclo[3.2.1]octanyl, 8-oxa bicyclo[3.2.1]octan-3-yl, which can be optionally mono- or independently multi-substituted by hydroxyl, cyano, halogen, $C_{1-6}$ alkyl, $C_{1-6}$ haloalkyl, $C_{1-6}$ alkoxyl, $C_{1-6}$ haloalkoxyl, $C_{3-8}$ cycloalkyl, $C_{3-8}$ cycloalkoxyl, 3-8 membered aryl, or 3-8 membered heterocyclyl, which can further be optionally mono- or independently multi-substituted halogen, deuterium, hydroxyl, amino, cyano, $C_{1-6}$ alkyl, $C_{1-6}$ haloalkyl, $C_{1-6}$ alkoxyl, or $C_{1-6}$ haloalkoxyl.

In some embodiments, $R^2$ is selected from:

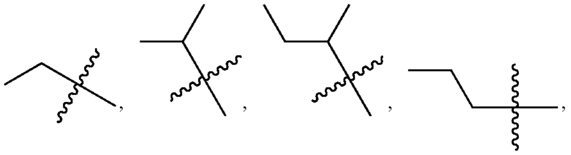
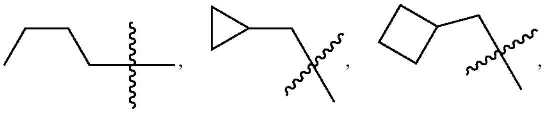
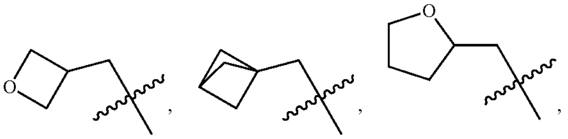
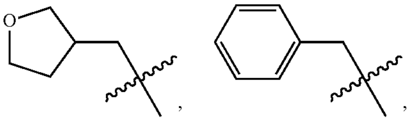
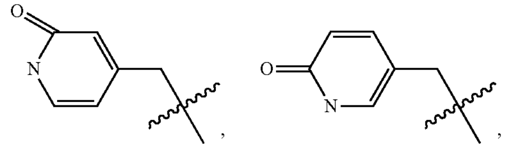
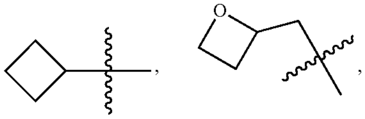
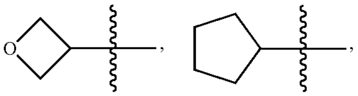
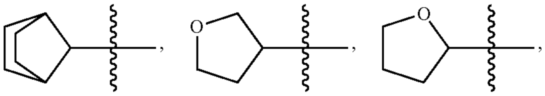
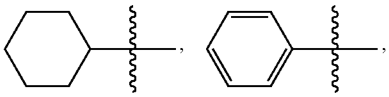
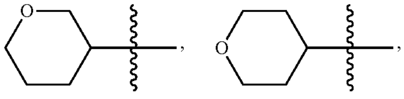
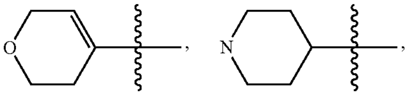

-continued

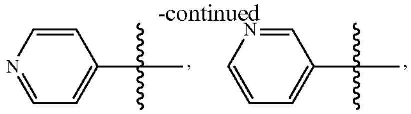
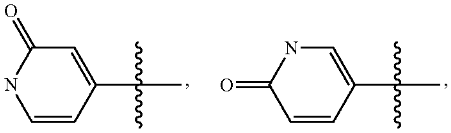
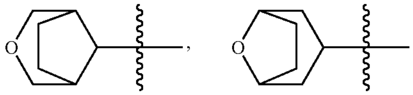
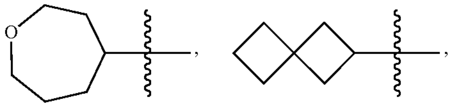
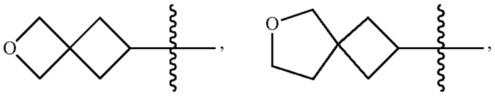
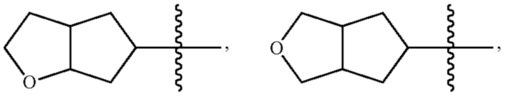
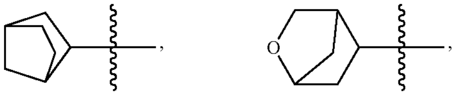
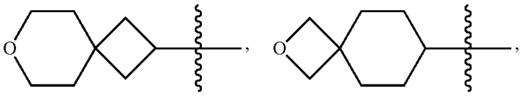
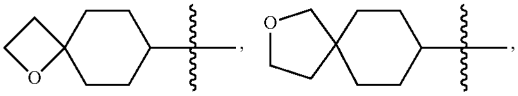 and
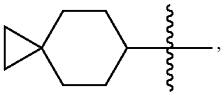

which can be optionally mono- or independently multi-substituted by hydroxyl, cyano, fluoro, chloro, bromo, methyl, ethyl, methoxyl, difluoromethyl, difluoromethoxyl, or trifluoromethoxyl.

In some embodiments, $R^2$ is cyclohexanyl, or tetrahydropyranyl, which can be optionally mono- or independently multi substituted by halogen, $C_{1-6}$ alkyl or $C_{1-6}$ alkoxyl.

In some embodiments, $R^1$ is methyl, ethyl, n-propyl, iso-propyl, n-butyl, sec-butyl, tert-butyl, or isobutyl, which can be optionally mono- or independently multi-substituted by hydroxyl, halogen, or deuterium.

In some embodiments, $R^1$ is methyl, ethyl, tri-fluoromethyl, or tri-deuterium-methyl.

In some embodiments, Ring A is 6 membered heteroaryl having 1 ring heteroatoms nitrogen, 9 membered bicyclic ring having 2-3 ring heteroatoms chosen from oxygen, sulfur and nitrogen, optionally, the 9 membered bicyclic ring is a phenyl- or pyridinyl-fused bicyclic ring, optionally, Ring A is selected from

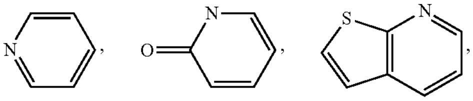

-continued

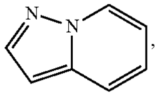, 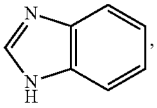, 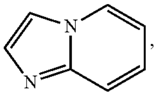,

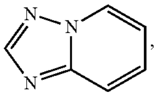, 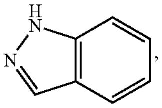, 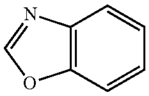 and

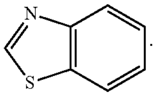.

In some embodiments, each $R^3$ and $R^4$ is independently selected from absent, halogen, hydroxyl, cyano, $C_{1-6}$ alkyl, CN—$C_{1-6}$ alkyl, $C_{1-6}$ haloalkyl, $C_{1-6}$ alkoxyl, $C_{1-6}$ haloalkoxyl, 3 to 8 membered saturated or unsaturated heterocyclyl, wherein said heterocyclyl can optionally be further mono- or independently multi-substituted by $C_{1-3}$ alkyl.

In some embodiments, Ring A is

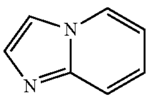 or 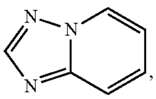, each $R^3$ and $R^4$ is independently selected from absent, methyl, cyano, methoxyl, chloro, cyano-methyl, pyrazolyl, oxazolyl, wherein said pyrazolyl or oxazolyl can optionally be further mono- or independently multi-substituted by $C_{1-3}$ alkyl.

In some embodiments, the compounds provided herein have a structure of Formula Ia Formula Ia

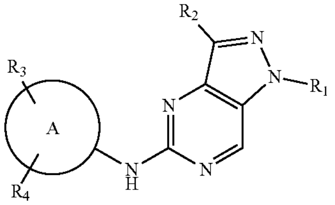

and a pharmaceutically acceptable salt thereof, wherein $R_1$, $R_2$, $R_3$, $R_4$, Ring A are as herein defined.

In some embodiments, the compounds provided herein have a structure of Formula Ib Formula Ib

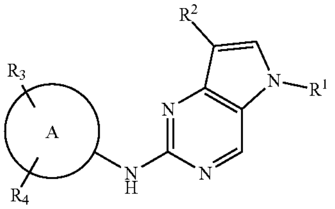

and a pharmaceutically acceptable salt thereof, wherein $R_1$, $R_2$, $R_3$, $R_4$, Ring A are as herein defined.

In some embodiments, the compounds provided herein have a structure of Formula Ic Formula Ic

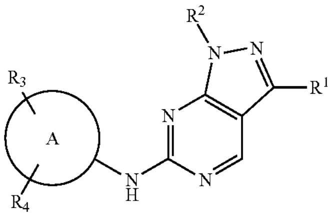

and a pharmaceutically acceptable salt thereof, wherein $R_1$, $R_2$, $R_3$, $R_4$, Ring A are as herein defined.

In some embodiments, the compounds provided herein have a structure of Formula Id Formula Id

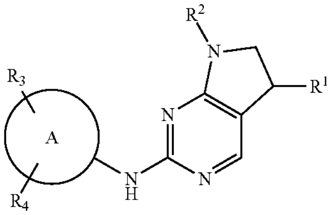

and a pharmaceutically acceptable salt thereof, wherein $R_1$, $R_2$, $R_3$, $R_4$, Ring A are as herein defined.

In some embodiments, the compounds provided herein have a structure of Formula Ie Formula Ie

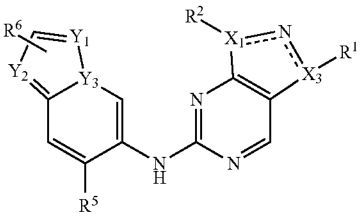

and a pharmaceutically acceptable salt thereof, wherein, one of $X_1$ and $X_3$ is N and the other one is C, dash line "---" means the bond between $X_1$ and N, and between N and $X_3$ can be single or double bonds, provided that at least one of the bonds between $X_1$ and N, and between N and $X_3$ is single bond;

$R^1$ is $C_{1-3}$ alkyl, $R^2$ is cyclopentyl, cyclohexanyl, tetrahydropyranyl or 8-oxabicyclo[3.2.1]octan-3-yl, which can be optionally mono- or independently multi substituted by halogen or $C_{1-3}$ alkoxyl, $Y_1$, $Y_2$, and $Y_3$ are each independently C or N, provided that at least one of $Y_1$, $Y_2$, and $Y_3$ is N;

$R^5$ is halogen or $C_{1-3}$ alkyl, $R^6$ is $C_{1-3}$ alkyl.

In some embodiments, $R^2$ of Formula Ie is un-substituted cyclopentyl, cyclohexanyl, tetrahydropyranyl or 8-oxabicyclo[3.2.1]octan-3-yl, which optionally can be mono- or independently multi substituted by halogen or $C_{1-3}$ alkoxyl.

In some embodiments, $Y_3$ of Formula Ie is N and at least one of $Y_1$ and $Y_2$ is N.

In some embodiments, $R^5$ of Formula Ie is methyl.

Exemplary compounds 1-149 of Formula (I) are set forth in Table 1 below.

TABLE 1

| Exemplary Compounds 1-149 | | |
|---|---|---|
| Example number | structures | Name |
| 1 | 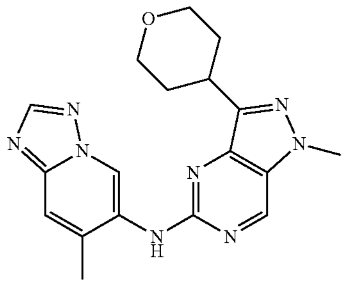 [SMILES: Cc1cc2ncnn2cc1Nc1ncc2c(n1)c(C1CCOCC1)nn2C] | 1-methyl-N-(7-methyl-[1,2,4]triazolo[1,5-a]pyridin-6-yl)-3-(tetrahydro-2H-pyran-4-yl)-1H-pyrazolo[4,3-d]pyrimidin-5-amine |
| 2 | 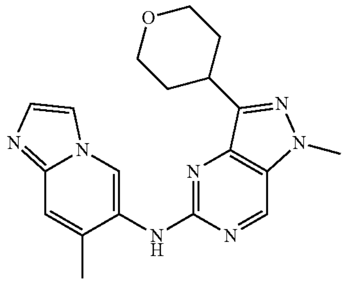 [SMILES: Cc1cc2nccn2cc1Nc1ncc2c(n1)c(C1CCOCC1)nn2C] | 1-methyl-N-(7-methylimidazo[1,2-a]pyridin-6-yl)-3-(tetrahydro-2H-pyran-4-yl)-1H-pyrazolo[4,3-d]pyrimidin-5-amine |
| 3 | 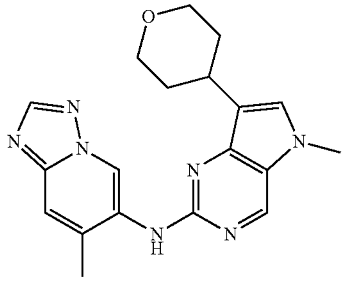 [SMILES: Cc1cc2ncnn2cc1Nc1ncc2c(n1)c(C1CCOCC1)cn2C] | 7-methyl-N-(5-methyl-7-(tetrahydro-2H-pyran-4-yl)-5H-pyrrolo[3,2-d]pyrimidin-2-yl)-[1,2,4]triazolo[1,5-a]pyridin-6-amine |
| 4 | 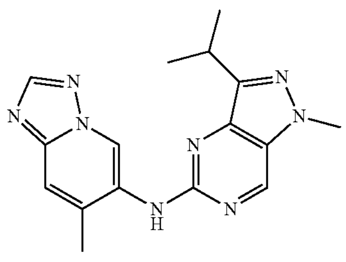 [SMILES: Cc1cc2ncnn2cc1Nc1ncc2c(n1)c(C(C)C)nn2C] | 3-isopropyl-1-methyl-N-(7-methyl-[1,2,4]triazolo[1,5-a]pyridin-6-yl)-1H-pyrazolo[4,3-d]pyrimidin-5-amine |

TABLE 1-continued

Exemplary Compounds 1-149

| Example number | structures | Name |
| --- | --- | --- |
| 5 | 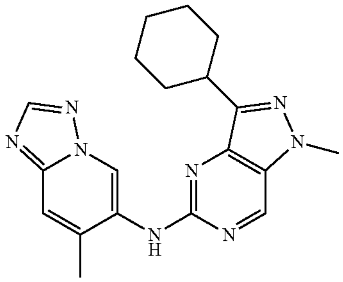 [SMILES: Cc1cc2ncnn2cc1Nc1ncc2c(n1)c(C1CCCCC1)nn2C] | 3-cyclohexyl-1-methyl-N-(7-methyl-[1,2,4]triazolo[1,5-a]pyridin-6-yl)-1H-pyrazolo[4,3-d]pyrimidin-5-amine |
| 6 | 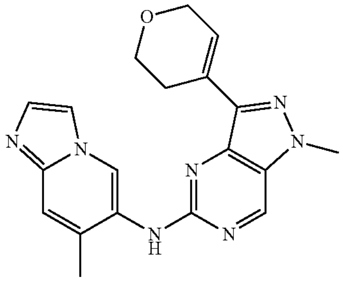 [SMILES: Cc1cc2nccn2cc1Nc1ncc2c(n1)c(C1=CCOCC1)nn2C] | 3-(3,6-dihydro-2H-pyran-4-yl)-1-methyl-N-(7-methylimidazo[1,2-a]pyridin-6-yl)-1H-pyrazolo[4,3-d]pyrimidin-5-amine |
| 7 | 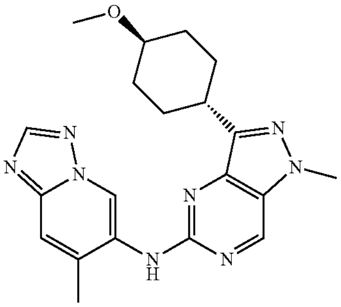 [SMILES: CO[C@H]1CC[C@H](c2nn(C)c3cnc(Nc4cn5ncnc5cc4C)nc32)CC1] | 3-((1r,4r)-4-methoxycyclohexyl)-1-methyl-N-(7-methyl-[1,2,4]triazolo[1,5-a]pyridin-6-yl)-1H-pyrazolo[4,3-d]pyrimidin-5-amine |
| 8 | 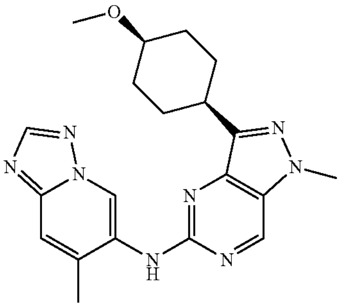 [SMILES: CO[C@H]1CC[C@@H](c2nn(C)c3cnc(Nc4cn5ncnc5cc4C)nc32)CC1] | 3-((1s,4s)-4-methoxycyclohexyl)-1-methyl-N-(7-methyl-[1,2,4]triazolo[1,5-a]pyridin-6-yl)-1H-pyrazolo[4,3-d]pyrimidin-5-amine |
| 9 | 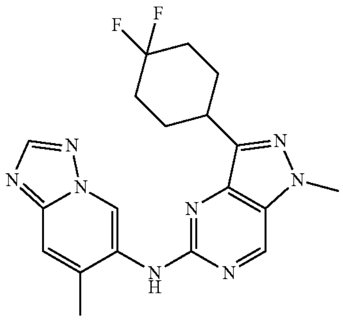 [SMILES: Cc1cc2ncnn2cc1Nc1ncc2c(n1)c(C1CCC(F)(F)CC1)nn2C] | 3-(4,4-difluorocyclohexyl)-1-methyl-N-(7-methyl-[1,2,4]triazolo[1,5-a]pyridin-6-yl)-1H-pyrazolo[4,3-d]pyrimidin-5-amine |

TABLE 1-continued

| Example number | structures | Name |
|---|---|---|
| | Exemplary Compounds 1-149 | |
| 10 | 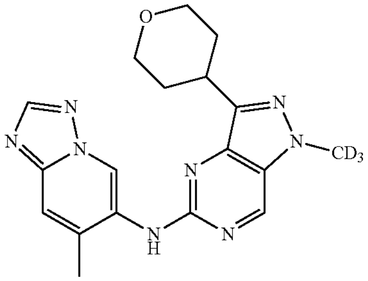 [SMILES: [2H]C([2H])([2H])n1nc(C2CCOCC2)c2nc(Nc3cn4ncnc4cc3C)ncc21] | 1-(methyl-d3)-N-(7-methyl-[1,2,4]triazolo[1,5-a]pyridin-6-yl)-3-(tetrahydro-2H-pyran-4-yl)-1H-pyrazolo[4,3-d]pyrimidin-5-amine |
| 11 | 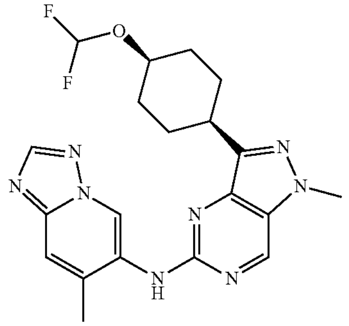 [SMILES: Cc1cc2ncnn2cc1Nc1ncc2c(n1)c([C@H]1CC[C@@H](OC(F)F)CC1)nn2C] | 3-((1s,4s)-4-(difluoromethoxy)cyclohexyl)-1-methyl-N-(7-methyl-[1,2,4]triazolo[1,5-a]pyridin-6-yl)-1H-pyrazolo[4,3-d]pyrimidin-5-amine |
| 12 | 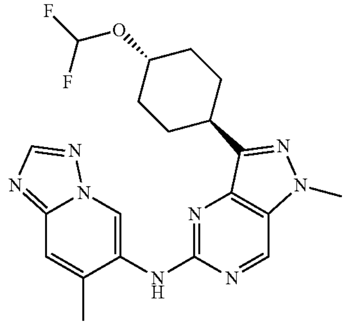 [SMILES: Cc1cc2ncnn2cc1Nc1ncc2c(n1)c([C@H]1CC[C@H](OC(F)F)CC1)nn2C] | 3-((1r,4r)-4-(difluoromethoxy)cyclohexyl)-1-methyl-N-(7-methyl-[1,2,4]triazolo[1,5-a]pyridin-6-yl)-1H-pyrazolo[4,3-d]pyrimidin-5-amine |
| 13 | 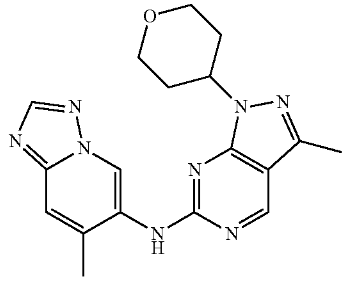 [SMILES: Cc1cc2ncnn2cc1Nc1ncc2c(C)nn(C3CCOCC3)c2n1] | 3-methyl-N-(7-methyl-[1,2,4]triazolo[1,5-a]pyridin-6-yl)-1-(tetrahydro-2H-pyran-4-yl)-1H-pyrazolo[3,4-d]pyrimidin-6-amine |
| 14 | 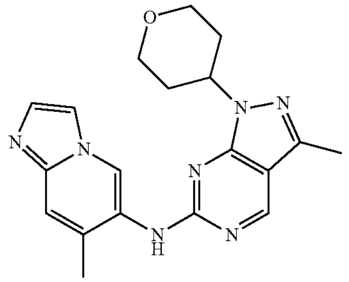 [SMILES: Cc1cc2nccn2cc1Nc1ncc2c(C)nn(C3CCOCC3)c2n1] | 3-methyl-N-(7-methylimidazo[1,2-a]pyridin-6-yl)-1-(tetrahydro-2H-pyran-4-yl)-1H-pyrazolo[3,4-d]pyrimidin-6-amine |

TABLE 1-continued

| Exemplary Compounds 1-149 | | |
|---|---|---|
| Example number | structures | Name |
| 15 | 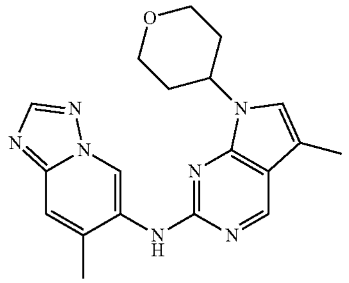 [SMILES: Cc1cc2ncnn2cc1Nc1ncc2c(C)cn(C3CCOCC3)c2n1] | 7-methyl-N-(5-methyl-7-(tetrahydro-2H-pyran-4-yl)-7H-pyrrolo[2,3-d]pyrimidin-2-yl)-[1,2,4]triazolo[1,5-a]pyridin-6-amine |
| 16 | 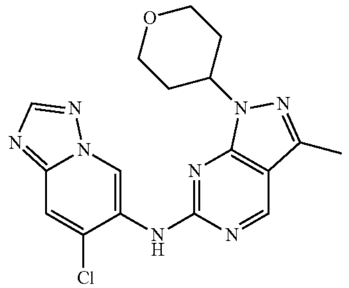 [SMILES: Cc1nn(C2CCOCC2)c2nc(Nc3cn4ncnc4cc3Cl)ncc12] | N-(7-chloro-[1,2,4]triazolo[1,5-a]pyridin-6-yl)-3-methyl-1-(tetrahydro-2H-pyran-4-yl)-1H-pyrazolo[3,4-d]pyrimidin-6-amine |
| 17 | 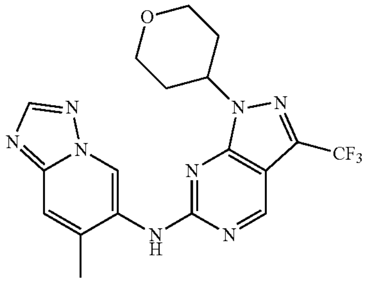 [SMILES: Cc1cc2ncnn2cc1Nc1ncc2c(C(F)(F)F)nn(C3CCOCC3)c2n1] | N-(7-methyl-[1,2,4]triazolo[1,5-a]pyridin-6-yl)-1-(tetrahydro-2H-pyran-4-yl)-3-(trifluoromethyl)-1H-pyrazolo[3,4-d]pyrimidin-6-amine |
| 18 | 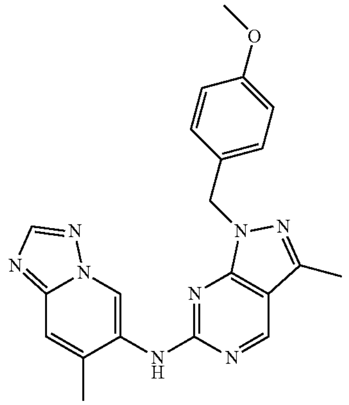 [SMILES: COc1ccc(Cn2nc(C)c3cnc(Nc4cn5ncnc5cc4C)nc32)cc1] | 1-(4-methoxybenzyl)-3-methyl-N-(7-methyl-[1,2,4]triazolo[1,5-a]pyridin-6-yl)-1H-pyrazolo[3,4-d]pyrimidin-6-amine |

TABLE 1-continued

| Example number | structures | Name |
|---|---|---|
| | Exemplary Compounds 1-149 | |
| 19 | 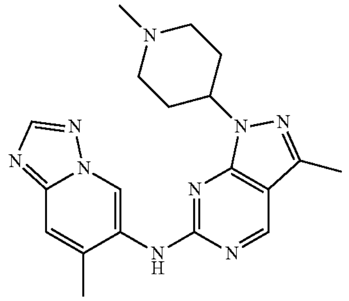 [SMILES: Cc1cc2ncnn2cc1Nc1ncc2c(C)nn(C3CCN(C)CC3)c2n1] | 3-methyl-N-(7-methyl-[1,2,4]triazolo[1,5-a]pyridin-6-yl)-1-(1-methylpiperidin-4-yl)-1H-pyrazolo[3,4-d]pyrimidin-6-amine |
| 20 | 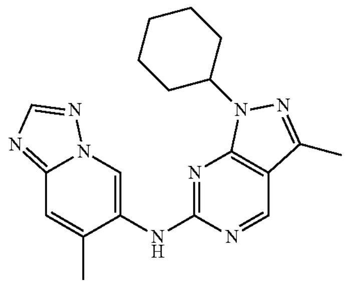 [SMILES: Cc1cc2ncnn2cc1Nc1ncc2c(C)nn(C3CCCCC3)c2n1] | 1-cyclohexyl-3-methyl-N-(7-methyl-[1,2,4]triazolo[1,5-a]pyridin-6-yl)-1H-pyrazolo[3,4-d]pyrimidin-6-amine |
| 21 | 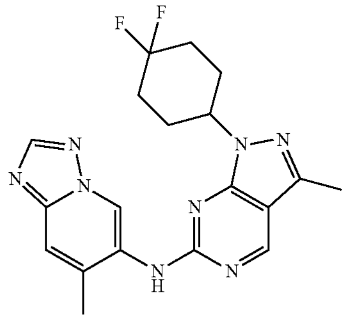 [SMILES: Cc1cc2ncnn2cc1Nc1ncc2c(C)nn(C3CCC(F)(F)CC3)c2n1] | 1-(4,4-difluorocyclohexyl)-3-methyl-N-(7-methyl-[1,2,4]triazolo[1,5-a]pyridin-6-yl)-1H-pyrazolo[3,4-d]pyrimidin-6-amine |
| 22 | 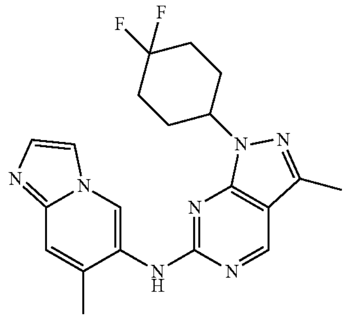 [SMILES: Cc1cc2nccn2cc1Nc1ncc2c(C)nn(C3CCC(F)(F)CC3)c2n1] | 1-(4,4-difluorocyclohexyl)-3-methyl-N-(7-methylimidazo[1,2-a]pyridin-6-yl)-1H-pyrazolo[3,4-d]pyrimidin-6-amine |

TABLE 1-continued

| Exemplary Compounds 1-149 | | |
|---|---|---|
| Example number | structures | Name |
| 23 | 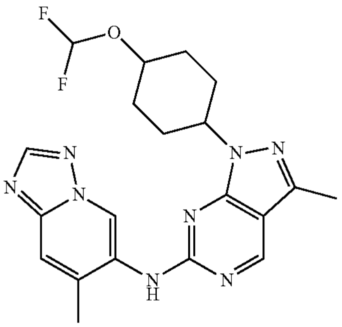 [SMILES: Cc1cc2ncnn2cc1Nc1ncc2c(C)nn(C3CCC(OC(F)F)CC3)c2n1] | 1-(4-(difluoromethoxy)cyclohexyl)-3-methyl-N-(7-methyl-[1,2,4]triazolo[1,5-a]pyridin-6-yl)-1H-pyrazolo[3,4-d]pyrimidin-6-amine |
| 24 | 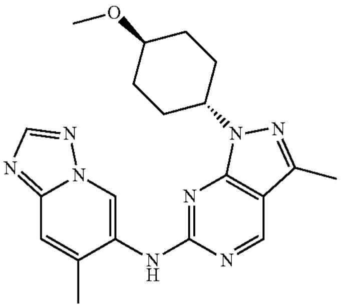 [SMILES: CO[C@H]1CC[C@H](n2nc(C)c3cnc(Nc4cn5ncnc5cc4C)nc32)CC1] | 1-((1r,4r)-4-methoxycyclohexyl)-3-methyl-N-(7-methyl-[1,2,4]triazolo[1,5-a]pyridin-6-yl)-1H-pyrazolo[3,4-d]pyrimidin-6-amine |
| 25 | 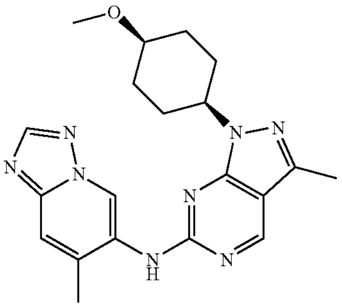 [SMILES: CO[C@H]1CC[C@@H](n2nc(C)c3cnc(Nc4cn5ncnc5cc4C)nc32)CC1] | 1-((1s,4s)-4-methoxycyclohexyl)-3-methyl-N-(7-methyl-[1,2,4]triazolo[1,5-a]pyridin-6-yl)-1H-pyrazolo[3,4-d]pyrimidin-6-amine |
| 26 | 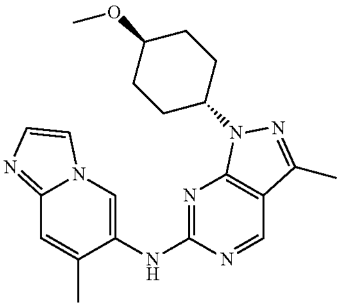 [SMILES: CO[C@H]1CC[C@H](n2nc(C)c3cnc(Nc4cn5ccnc5cc4C)nc32)CC1] | 1-((1r,4r)-4-methoxycyclohexyl)-3-methyl-N-(7-methylimidazo[1,2-a]pyridin-6-yl)-1H-pyrazolo[3,4-d]pyrimidin-6-amine |

TABLE 1-continued

| Exemplary Compounds 1-149 | | |
|---|---|---|
| Example number | structures | Name |
| 27 | 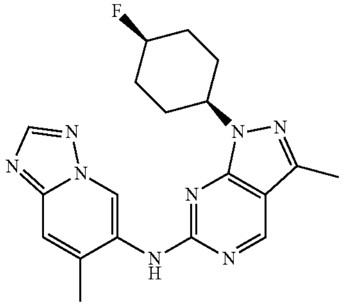 [SMILES: Cc1cc2ncnn2cc1Nc1ncc2c(C)nn([C@H]3CC[C@@H](F)CC3)c2n1] | 1-((1s,4s)-4-fluorocyclohexyl)-3-methyl-N-(7-methyl-[1,2,4]triazolo[1,5-a]pyridin-6-yl)-1H-pyrazolo[3,4-d]pyrimidin-6-amine |
| 28 | 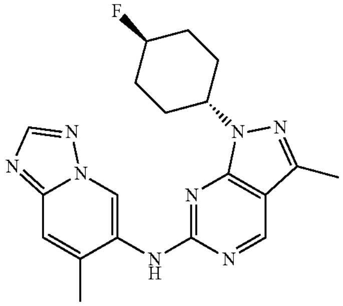 [SMILES: Cc1cc2ncnn2cc1Nc1ncc2c(C)nn([C@H]3CC[C@H](F)CC3)c2n1] | 1-((1r,4r)-4-fluorocyclohexyl)-3-methyl-N-(7-methyl-[1,2,4]triazolo[1,5-a]pyridin-6-yl)-1H-pyrazolo[3,4-d]pyrimidin-6-amine |
| 29 | 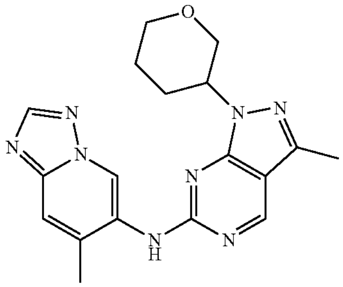 [SMILES: Cc1cc2ncnn2cc1Nc1ncc2c(C)nn(C3CCCOC3)c2n1] | 3-methyl-N-(7-methyl-[1,2,4]triazolo[1,5-a]pyridin-6-yl)-1-(tetrahydro-2H-pyran-3-yl)-1H-pyrazolo[3,4-d]pyrimidin-6-amine (isomer 1) |
| 30 | 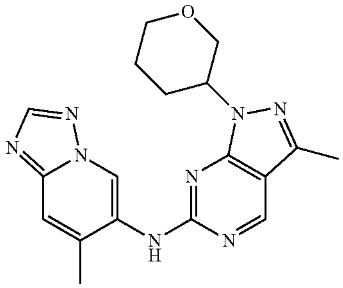 [SMILES: Cc1cc2ncnn2cc1Nc1ncc2c(C)nn(C3CCCOC3)c2n1] | 3-methyl-N-(7-methyl-[1,2,4]triazolo[1,5-a]pyridin-6-yl)-1-(tetrahydro-2H-pyran-3-yl)-1H-pyrazolo[3,4-d]pyrimidin-6-amine (isomer 2) |
| 31 | 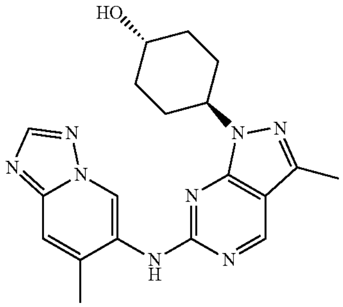 [SMILES: Cc1cc2ncnn2cc1Nc1ncc2c(C)nn([C@H]3CC[C@H](O)CC3)c2n1] | (1r,4r)-4-(3-methyl-6-((7-methyl-[1,2,4]triazolo[1,5-a]pyridin-6-yl)amino)-1H-pyrazolo[3,4-d]pyrimidin-1-yl)cyclohexan-1-ol |

TABLE 1-continued

| Exemplary Compounds 1-149 | | |
|---|---|---|
| Example number | structures | Name |
| 32 | 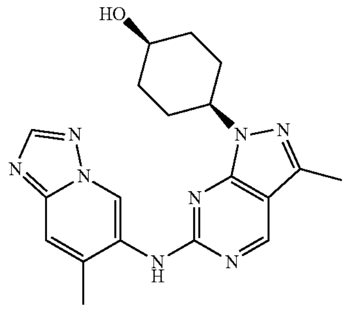 [SMILES: Cc1cc2ncnn2cc1Nc1ncc2c(C)nn([C@H]3CC[C@@H](O)CC3)c2n1] | (1s,4s)-4-(3-methyl-6-((7-methyl-[1,2,4]triazolo[1,5-a]pyridin-6-yl)amino)-1H-pyrazolo[3,4-d]pyrimidin-1-yl)cyclohexan-1-ol |
| 33 | 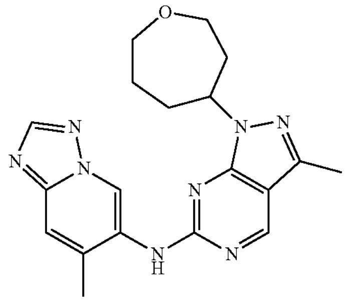 [SMILES: Cc1cc2ncnn2cc1Nc1ncc2c(C)nn(C3CCCOCC3)c2n1] | 3-methyl-N-(7-methyl-[1,2,4]triazolo[1,5-a]pyridin-6-yl)-1-(oxepan-4-yl)-1H-pyrazolo[3,4-d]pyrimidin-6-amine (isomer 1) |
| 34 | 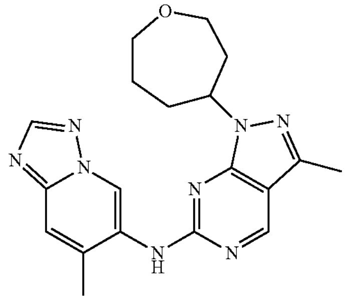 [SMILES: Cc1cc2ncnn2cc1Nc1ncc2c(C)nn(C3CCCOCC3)c2n1] | 3-methyl-N-(7-methyl-[1,2,4]triazolo[1,5-a]pyridin-6-yl)-1-(oxepan-4-yl)-1H-pyrazolo[3,4-d]pyrimidin-6-amine (isomer 2) |
| 35 | 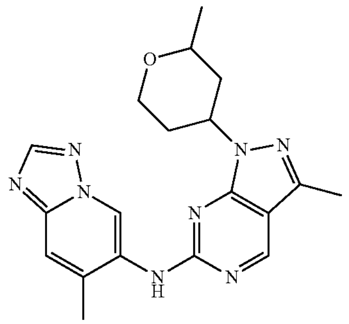 [SMILES: Cc1cc2ncnn2cc1Nc1ncc2c(C)nn(C3CCOC(C)C3)c2n1] | 3-methyl-N-(7-methyl-[1,2,4]triazolo[1,5-a]pyridin-6-yl)-1-(2-methyltetrahydro-2H-pyran-4-yl)-1H-pyrazolo[3,4-d]pyrimidin-6-amine (isomer 1) |

TABLE 1-continued

| Example number | structures | Name |
|---|---|---|
| | Exemplary Compounds 1-149 | |
| 36 | 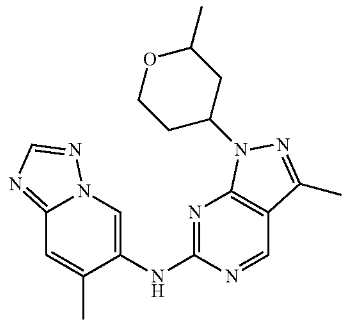 [SMILES: Cc1cc2ncnn2cc1Nc1ncc2c(C)nn(C3CCOC(C)C3)c2n1] | 3-methyl-N-(7-methyl-[1,2,4]triazolo[1,5-a]pyridin-6-yl)-1-(2-methyltetrahydro-2H-pyran-4-yl)-1H-pyrazolo[3,4-d]pyrimidin-6-amine (isomer 2) |
| 37 | 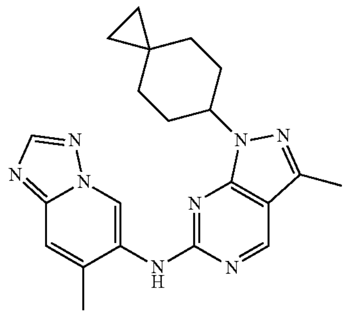 [SMILES: Cc1cc2ncnn2cc1Nc1ncc2c(C)nn(C3CCC4(CC3)CC4)c2n1] | 3-methyl-N-(7-methyl-[1,2,4]triazolo[1,5-a]pyridin-6-yl)-1-(spiro[2.5]octan-6-yl)-1H-pyrazolo[3,4-d]pyrimidin-6-amine |
| 38 | 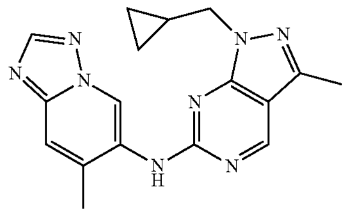 [SMILES: Cc1cc2ncnn2cc1Nc1ncc2c(C)nn(CC3CC3)c2n1] | 1-(cyclopropylmethyl)-3-methyl-N-(7-methyl-[1,2,4]triazolo[1,5-a]pyridin-6-yl)-1H-pyrazolo[3,4-d]pyrimidin-6-amine |
| 39 | 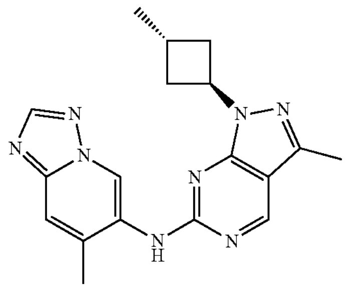 [SMILES: Cc1cc2ncnn2cc1Nc1ncc2c(C)nn([C@H]3C[C@H](C)C3)c2n1] | 3-methyl-N-(7-methyl-[1,2,4]triazolo[1,5-a]pyridin-6-yl)-1-((1r,3r)-3-methylcyclobutyl)-1H-pyrazolo[3,4-d]pyrimidin-6-amine |
| 40 | 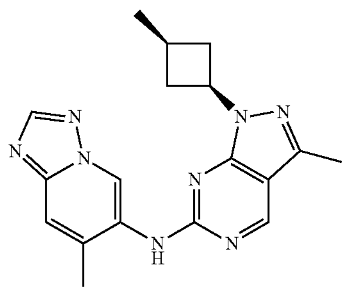 [SMILES: Cc1cc2ncnn2cc1Nc1ncc2c(C)nn([C@H]3C[C@@H](C)C3)c2n1] | 3-methyl-N-(7-methyl-[1,2,4]triazolo[1,5-a]pyridin-6-yl)-1-((1s,3s)-3-methylcyclobutyl)-1H-pyrazolo[3,4-d]pyrimidin-6-amine |

TABLE 1-continued

| Exemplary Compounds 1-149 | | |
|---|---|---|
| Example number | structures | Name |
| 41 | 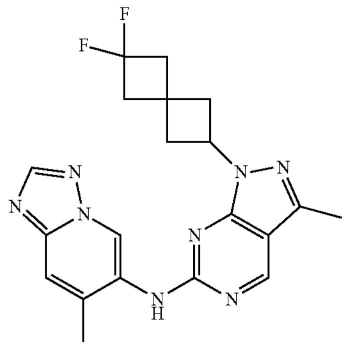 [SMILES: Cc1cc2ncnn2cc1Nc1ncc2c(C)nn(C3CC4(C3)CC(F)(F)C4)c2n1] | 1-(6,6-difluorospiro[3.3]heptan-2-yl)-3-methyl-N-(7-methyl-[1,2,4]triazolo[1,5-a]pyridin-6-yl)-1H-pyrazolo[3,4-d]pyrimidin-6-amine |
| 42 | 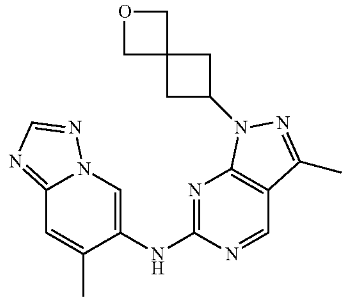 [SMILES: Cc1cc2ncnn2cc1Nc1ncc2c(C)nn(C3CC4(COC4)C3)c2n1] | 3-methyl-N-(7-methyl-[1,2,4]triazolo[1,5-a]pyridin-6-yl)-1-(2-oxaspiro[3.3]heptan-6-yl)-1H-pyrazolo[3,4-d]pyrimidin-6-amine |
| 43 | 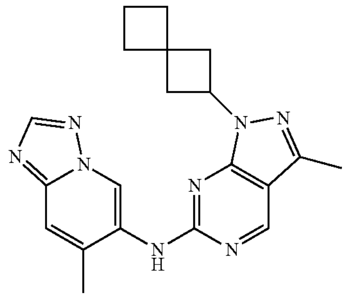 [SMILES: Cc1cc2ncnn2cc1Nc1ncc2c(C)nn(C3CC4(CCC4)C3)c2n1] | 3-methyl-N-(7-methyl-[1,2,4]triazolo[1,5-a]pyridin-6-yl)-1-(spiro[3.3]heptan-2-yl)-1H-pyrazolo[3,4-d]pyrimidin-6-amine |
| 44 | 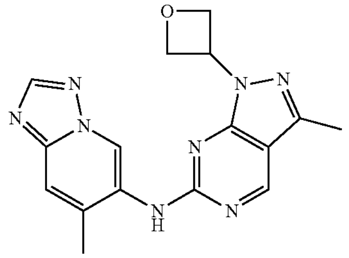 [SMILES: Cc1cc2ncnn2cc1Nc1ncc2c(C)nn(C3COC3)c2n1] | 3-methyl-N-(7-methyl-[1,2,4]triazolo[1,5-a]pyridin-6-yl)-1-(oxetan-3-yl)-1H-pyrazolo[3,4-d]pyrimidin-6-amine |
| 45 | 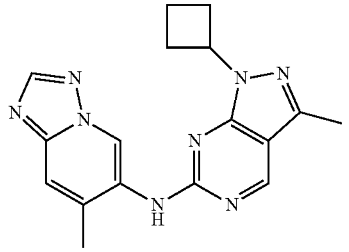 [SMILES: Cc1cc2ncnn2cc1Nc1ncc2c(C)nn(C3CCC3)c2n1] | 1-cyclobutyl-3-methyl-N-(7-methyl-[1,2,4]triazolo[1,5-a]pyridin-6-yl)-1H-pyrazolo[3,4-d]pyrimidin-6-amine |

TABLE 1-continued

| Exemplary Compounds 1-149 | | |
|---|---|---|
| Example number | structures | Name |
| 46 | 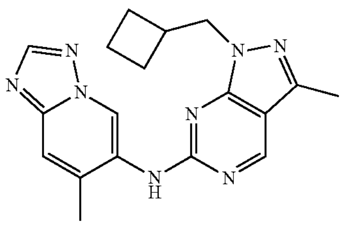 [SMILES: Cc1cc2ncnn2cc1Nc1ncc2c(C)nn(CC3CCC3)c2n1] | 1-(cyclobutylmethyl)-3-methyl-N-(7-methyl-[1,2,4]triazolo[1,5-a]pyridin-6-yl)-1H-pyrazolo[3,4-d]pyrimidin-6-amine |
| 47 | 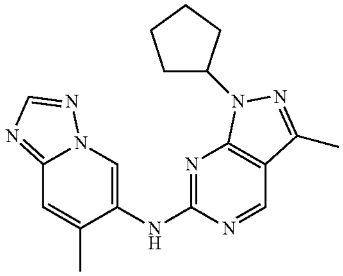 [SMILES: Cc1cc2ncnn2cc1Nc1ncc2c(C)nn(C3CCCC3)c2n1] | 1-cyclopentyl-3-methyl-N-(7-methyl-[1,2,4]triazolo[1,5-a]pyridin-6-yl)-1H-pyrazolo[3,4-d]pyrimidin-6-amine |
| 48 | 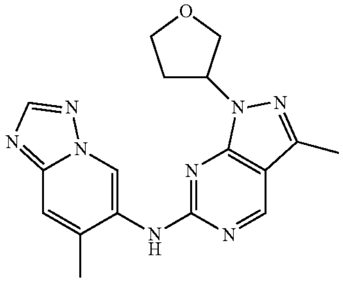 [SMILES: Cc1cc2ncnn2cc1Nc1ncc2c(C)nn(C3CCOC3)c2n1] | 3-methyl-N-(7-methyl-[1,2,4]triazolo[1,5-a]pyridin-6-yl)-1-(tetrahydrofuran-3-yl)-1H-pyrazolo[3,4-d]pyrimidin-6-amine (isomer 1) |
| 49 | 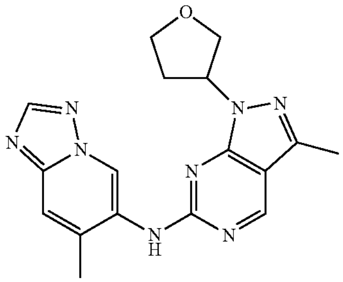 [SMILES: Cc1cc2ncnn2cc1Nc1ncc2c(C)nn(C3CCOC3)c2n1] | 3-methyl-N-(7-methyl-[1,2,4]triazolo[1,5-a]pyridin-6-yl)-1-(tetrahydrofuran-3-yl)-1H-pyrazolo[3,4-d]pyrimidin-6-amine (isomer 2) |
| 50 | 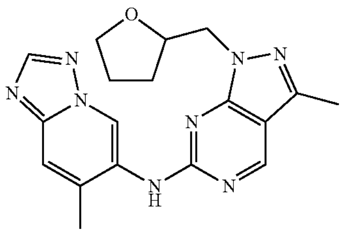 [SMILES: Cc1cc2ncnn2cc1Nc1ncc2c(C)nn(CC3CCCO3)c2n1] | 3-methyl-N-(7-methyl-[1,2,4]triazolo[1,5-a]pyridin-6-yl)-1-((tetrahydrofuran-2-yl)methyl)-1H-pyrazolo[3,4-d]pyrimidin-6-amine (isomer 1) |

TABLE 1-continued

Exemplary Compounds 1-149

| Example number | structures | Name |
|---|---|---|
| 51 | 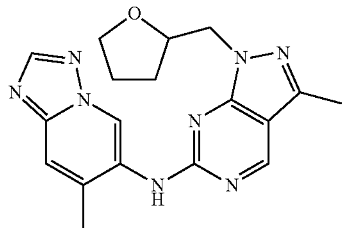 [SMILES: Cc1cc2ncnn2cc1Nc1ncc2c(C)nn(CC3CCCO3)c2n1] | 3-methyl-N-(7-methyl-[1,2,4]triazolo[1,5-a]pyridin-6-yl)-1-((tetrahydrofuran-2-yl)methyl)-1H-pyrazolo[3,4-d]pyrimidin-6-amine (isomer 2) |
| 52 | 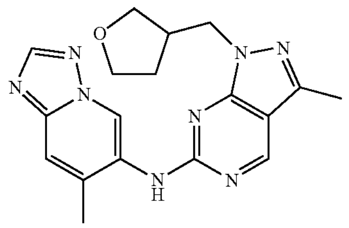 [SMILES: Cc1cc2ncnn2cc1Nc1ncc2c(C)nn(CC3CCOC3)c2n1] | 3-methyl-N-(7-methyl-[1,2,4]triazolo[1,5-a]pyridin-6-yl)-1-((tetrahydrofuran-3-yl)methyl)-1H-pyrazolo[3,4-d]pyrimidin-6-amine (isomer 1) |
| 53 | 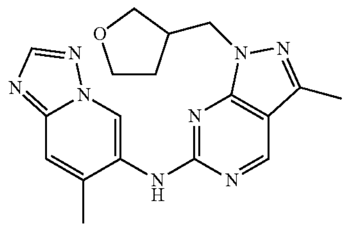 [SMILES: Cc1cc2ncnn2cc1Nc1ncc2c(C)nn(CC3CCOC3)c2n1] | 3-methyl-N-(7-methyl-[1,2,4]triazolo[1,5-a]pyridin-6-yl)-1-((tetrahydrofuran-3-yl)methyl)-1H-pyrazolo[3,4-d]pyrimidin-6-amine (isomer 2) |
| 54 | 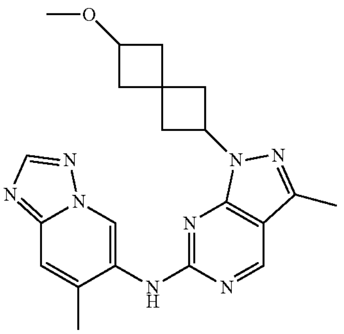 [SMILES: COC1CC2(C1)CC(n1nc(C)c3cnc(Nc4cn5ncnc5cc4C)nc31)C2] | 1-(6-methoxyspiro[3.3]heptan-2-yl)-3-methyl-N-(7-methyl-[1,2,4]triazolo[1,5-a]pyridin-6-yl)-1H-pyrazolo[3,4-d]pyrimidin-6-amine |
| 55 | 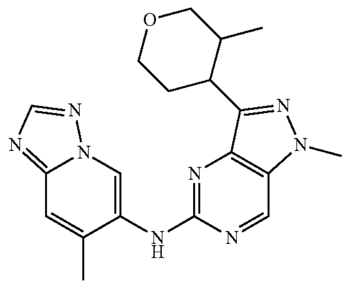 [SMILES: Cc1cc2ncnn2cc1Nc1ncc2c(n1)c(C1CCOCC1C)nn2C] | 1-methyl-N-(7-methyl-[1,2,4]triazolo[1,5-a]pyridin-6-yl)-3-(3-methyltetrahydro-2H-pyran-4-yl)-1H-pyrazolo[4,3-d]pyrimidin-5-amine (isomer 1) |

TABLE 1-continued

| Exemplary Compounds 1-149 | | |
|---|---|---|
| Example number | structures | Name |
| 56 | 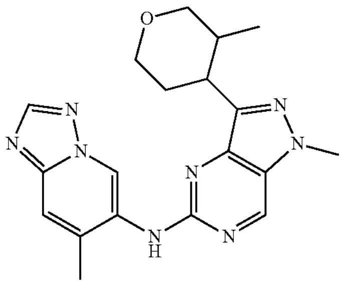 [SMILES: Cc1cc2ncnn2cc1Nc1ncc2c(n1)c(C1CCOCC1C)nn2C] | 1-methyl-N-(7-methyl-[1,2,4]triazolo[1,5-a]pyridin-6-yl)-3-(3-methyltetrahydro-2H-pyran-4-yl)-1H-pyrazolo[4,3-d]pyrimidin-5-amine (isomer 2) |
| 57 | 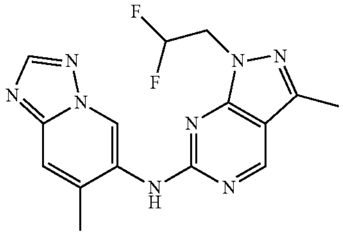 [SMILES: Cc1cc2ncnn2cc1Nc1ncc2c(C)nn(CC(F)F)c2n1] | 1-(2,2-difluoroethyl)-3-methyl-N-(7-methyl-[1,2,4]triazolo[1,5-a]pyridin-6-yl)-1H-pyrazolo[3,4-d]pyrimidin-6-amine |
| 58 | 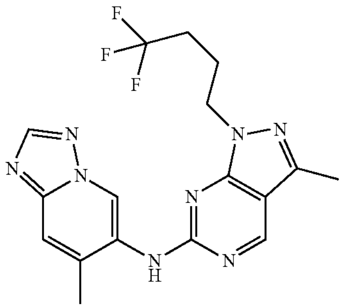 [SMILES: Cc1cc2ncnn2cc1Nc1ncc2c(C)nn(CCCC(F)(F)F)c2n1] | 3-methyl-N-(7-methyl-[1,2,4]triazolo[1,5-a]pyridin-6-yl)-1-(4,4,4-trifluorobutyl)-1H-pyrazolo[3,4-d]pyrimidin-6-amine |
| 59 | 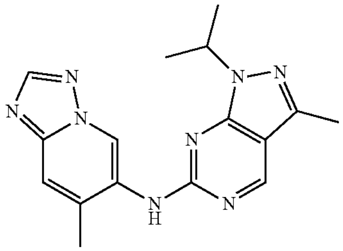 [SMILES: Cc1cc2ncnn2cc1Nc1ncc2c(C)nn(C(C)C)c2n1] | 1-isopropyl-3-methyl-N-(7-methyl-[1,2,4]triazolo[1,5-a]pyridin-6-yl)-1H-pyrazolo[3,4-d]pyrimidin-6-amine |
| 60 | 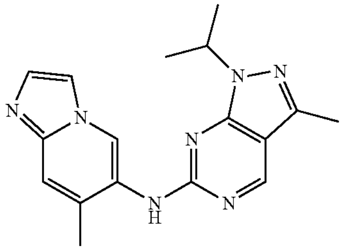 [SMILES: Cc1cc2nccn2cc1Nc1ncc2c(C)nn(C(C)C)c2n1] | 1-isopropyl-3-methyl-N-(7-methylimidazo[1,2-a]pyridin-6-yl)-1H-pyrazolo[3,4-d]pyrimidin-6-amine |

TABLE 1-continued

| Exemplary Compounds 1-149 | | |
|---|---|---|
| Example number | structures | Name |
| 61 | 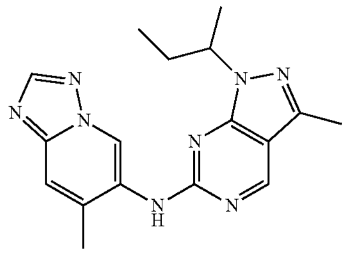 [SMILES: CCC(C)n1nc(C)c2cnc(Nc3cn4ncnc4cc3C)nc21] | 1-(sec-butyl)-3-methyl-N-(7-methyl-[1,2,4]triazolo[1,5-a]pyridin-6-yl)-1H-pyrazolo[3,4-d]pyrimidin-6-amine (isomer 1) |
| 62 | 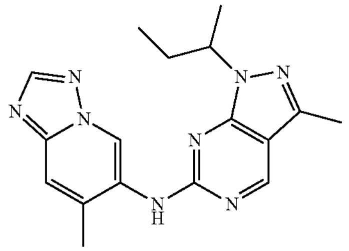 [SMILES: CCC(C)n1nc(C)c2cnc(Nc3cn4ncnc4cc3C)nc21] | 1-(sec-butyl)-3-methyl-N-(7-methyl-[1,2,4]triazolo[1,5-a]pyridin-6-yl)-1H-pyrazolo[3,4-d]pyrimidin-6-amine (isomer 2) |
| 63 | 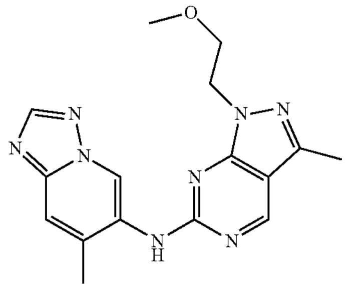 [SMILES: COCCn1nc(C)c2cnc(Nc3cn4ncnc4cc3C)nc21] | 1-(2-methoxyethyl)-3-methyl-N-(7-methyl-[1,2,4]triazolo[1,5-a]pyridin-6-yl)-1H-pyrazolo[3,4-d]pyrimidin-6-amine |
| 64 | 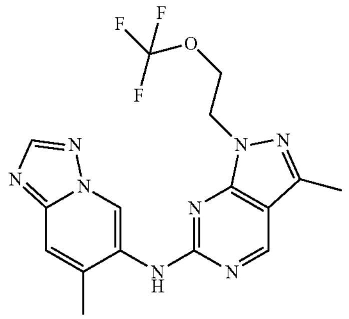 [SMILES: Cc1cc2ncnn2cc1Nc1ncc2c(C)nn(CCOC(F)(F)F)c2n1] | 3-methyl-N-(7-methyl-[1,2,4]triazolo[1,5-a]pyridin-6-yl)-1-(2-(trifluoromethoxy)ethyl)-1H-pyrazolo[3,4-d]pyrimidin-6-amine |
| 65 | 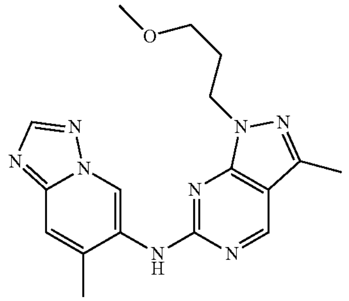 [SMILES: COCCCn1nc(C)c2cnc(Nc3cn4ncnc4cc3C)nc21] | 1-(3-methoxypropyl)-3-methyl-N-(7-methyl-[1,2,4]triazolo[1,5-a]pyridin-6-yl)-1H-pyrazolo[3,4-d]pyrimidin-6-amine |

TABLE 1-continued

| Exemplary Compounds 1-149 | | |
|---|---|---|
| Example number | structures | Name |
| 66 | 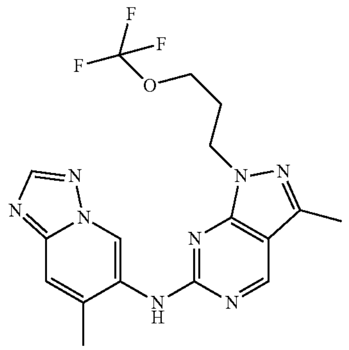 [SMILES: Cc1cc2ncnn2cc1Nc1ncc2c(C)nn(CCCOC(F)(F)F)c2n1] | 3-methyl-N-(7-methyl-[1,2,4]triazolo[1,5-a]pyridin-6-yl)-1-(3-(trifluoromethoxy)propyl)-1H-pyrazolo[3,4-d]pyrimidin-6-amine |
| 67 | 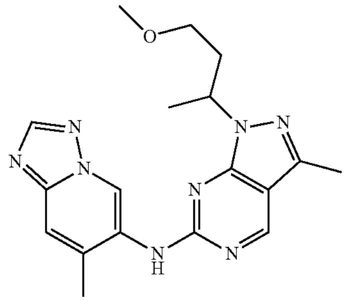 [SMILES: COCCC(C)n1nc(C)c2cnc(Nc3cn4ncnc4cc3C)nc21] | 1-(4-methoxybutan-2-yl)-3-methyl-N-(7-methyl-[1,2,4]triazolo[1,5-a]pyridin-6-yl)-1H-pyrazolo[3,4-d]pyrimidin-6-amine (isomer 1) |
| 68 | 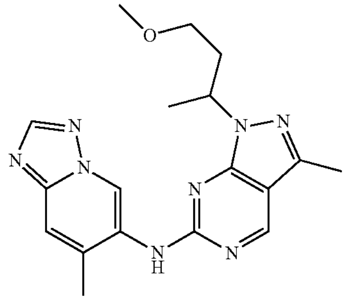 [SMILES: COCCC(C)n1nc(C)c2cnc(Nc3cn4ncnc4cc3C)nc21] | 1-(4-methoxybutan-2-yl)-3-methyl-N-(7-methyl-[1,2,4]triazolo[1,5-a]pyridin-6-yl)-1H-pyrazolo[3,4-d]pyrimidin-6-amine (isomer 2) |
| 69 | 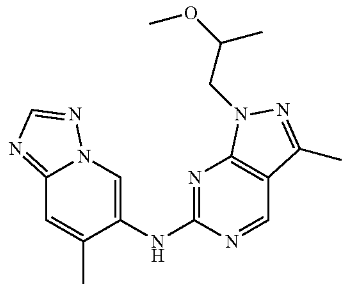 [SMILES: COC(C)Cn1nc(C)c2cnc(Nc3cn4ncnc4cc3C)nc21] | 1-(2-methoxypropyl)-3-methyl-N-(7-methyl-[1,2,4]triazolo[1,5-a]pyridin-6-yl)-1H-pyrazolo[3,4-d]pyrimidin-6-amine (racemate) |

TABLE 1-continued

| Exemplary Compounds 1-149 | | |
|---|---|---|
| Example number | structures | Name |
| 70 | 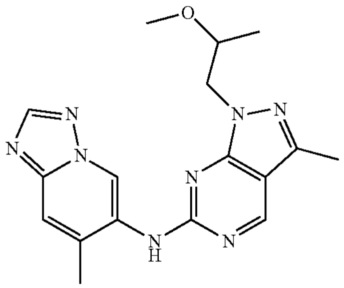 [SMILES: COC(C)Cn1nc(C)c2cnc(Nc3cn4ncnc4cc3C)nc21] | 1-(2-methoxypropyl)-3-methyl-N-(7-methyl-[1,2,4]triazolo[1,5-a]pyridin-6-yl)-1H-pyrazolo[3,4-d]pyrimidin-6-amine (isomer 1) |
| 71 | 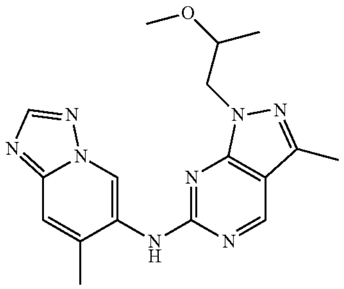 [SMILES: COC(C)Cn1nc(C)c2cnc(Nc3cn4ncnc4cc3C)nc21] | 1-(2-methoxypropyl)-3-methyl-N-(7-methyl-[1,2,4]triazolo[1,5-a]pyridin-6-yl)-1H-pyrazolo[3,4-d]pyrimidin-6-amine (isomer 2) |
| 72 | 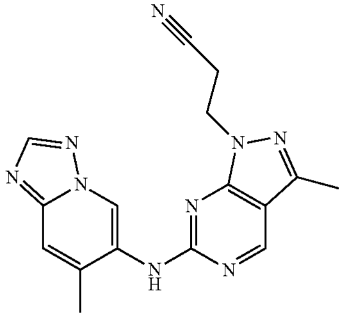 [SMILES: Cc1cc2ncnn2cc1Nc1ncc2c(C)nn(CCC#N)c2n1] | 3-(3-methyl-6-((7-methyl-[1,2,4]triazolo[1,5-a]pyridin-6-yl)amino)-1H-pyrazolo[3,4-d]pyrimidin-1-yl)propanenitrile |
| 73 | 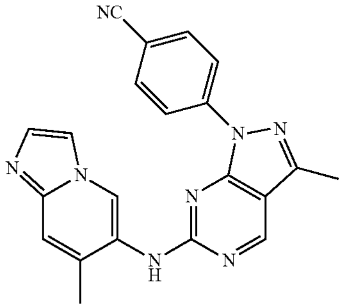 [SMILES: Cc1cc2nccn2cc1Nc1ncc2c(C)nn(-c3ccc(C#N)cc3)c2n1] | 4-(3-methyl-6-((7-methylimidazo[1,2-a]pyridin-6-yl)amino)-1H-pyrazolo[3,4-d]pyrimidin-1-yl)benzonitrile |

TABLE 1-continued

| Exemplary Compounds 1-149 | | |
|---|---|---|
| Example number | structures | Name |
| 79 | 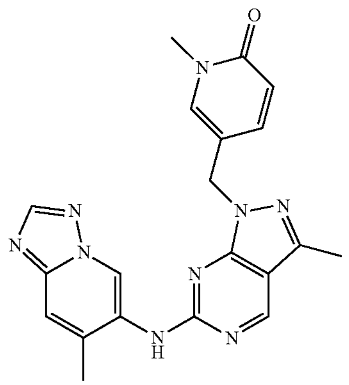 [SMILES: Cc1cc2ncnn2cc1Nc1ncc2c(C)nn(Cc3ccc(=O)n(C)c3)c2n1] | 1-methyl-5-((3-methyl-6-((7-methyl-[1,2,4]triazolo[1,5-a]pyridin-6-yl)amino)-1H-pyrazolo[3,4-d]pyrimidin-1-yl)methyl)pyridin-2(1H)-one |
| 80 | 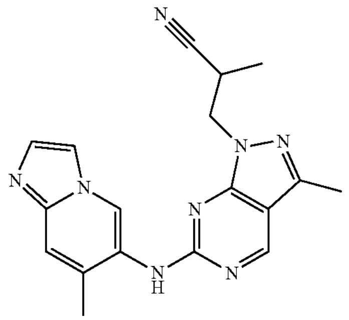 [SMILES: Cc1cc2nccn2cc1Nc1ncc2c(C)nn(CC(C)C#N)c2n1] | 2-methyl-3-(3-methyl-6-((7-methylimidazo[1,2-a]pyridin-6-yl)amino)-1H-pyrazolo[3,4-d]pyrimidin-1-yl)propanenitrile |
| 86 | 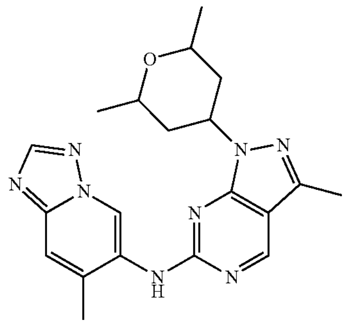 [SMILES: Cc1cc2ncnn2cc1Nc1ncc2c(C)nn(C3CC(C)OC(C)C3)c2n1] | 1-(2,6-dimethyltetrahydro-2H-pyran-4-yl)-3-methyl-N-(7-methyl-[1,2,4]triazolo[1,5-a]pyridin-6-yl)-1H-pyrazolo[3,4-d]pyrimidin-6-amine (isomer 1) |
| 86-1 | 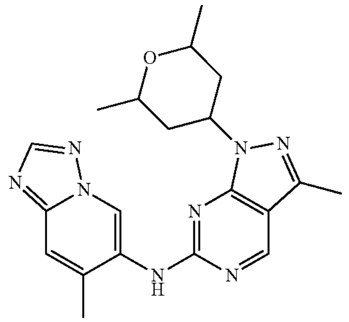 [SMILES: Cc1cc2ncnn2cc1Nc1ncc2c(C)nn(C3CC(C)OC(C)C3)c2n1] | 1-(2,6-dimethyltetrahydro-2H-pyran-4-yl)-3-methyl-N-(7-methyl-[1,2,4]triazolo[1,5-a]pyridin-6-yl)-1H-pyrazolo[3,4-d]pyrimidin-6-amine (isomer 2) |

TABLE 1-continued

| Exemplary Compounds 1-149 | | |
|---|---|---|
| Example number | structures | Name |
| 87 | 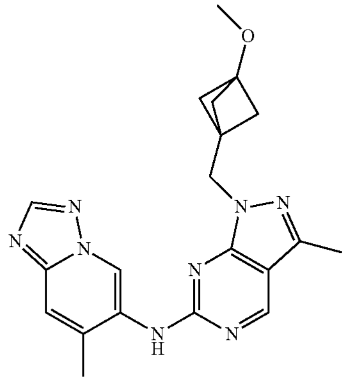 [SMILES: COC12CC(Cn3nc(C)c4cnc(Nc5cn6ncnc6cc5C)nc43)(C1)C2] | 1-((3-methoxybicyclo[1.1.1]pentan-1-yl)methyl)-3-methyl-N-(7-methyl-[1,2,4]triazolo[1,5-a]pyridin-6-yl)-1H-pyrazolo[3,4-d]pyrimidin-6-amine |
| 89 | 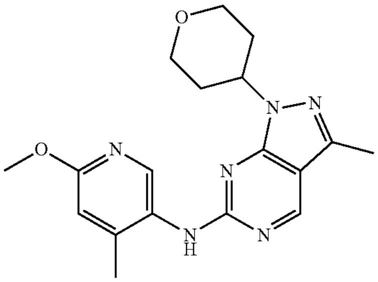 | N-(6-methoxy-4-methylpyridin-3-yl)-3-methyl-1-(tetrahydro-2H-pyran-4-yl)-1H-pyrazolo[3,4-d]pyrimidin-6-amine |
| 90 | 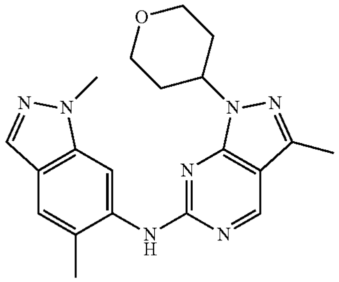 [SMILES: Cc1cc2cnn(C)c2cc1Nc1ncc2c(C)nn(C3CCOCC3)c2n1] | N-(1,5-dimethyl-1H-indazol-6-yl)-3-methyl-1-(tetrahydro-2H-pyran-4-yl)-1H-pyrazolo[3,4-d]pyrimidin-6-amine |
| 91 | 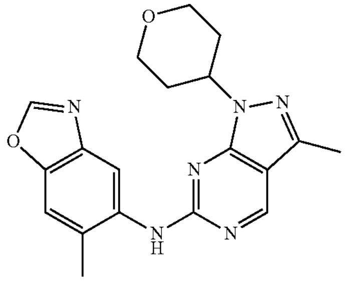 [SMILES: Cc1cc2ocnc2cc1Nc1ncc2c(C)nn(C3CCOCC3)c2n1] | 6-methyl-N-(3-methyl-1-(tetrahydro-2H-pyran-4-yl)-1H-pyrazolo[3,4-d]pyrimidin-6-yl)benzo[d]oxazol-5-amine |
| 92 | 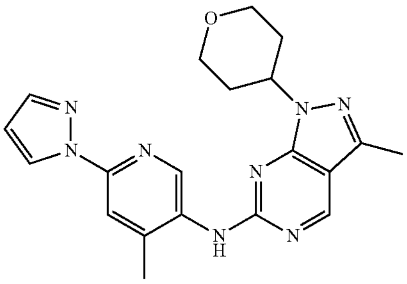 [SMILES: Cc1cc(-n2cccn2)ncc1Nc1ncc2c(C)nn(C3CCOCC3)c2n1] | 3-methyl-N-(4-methyl-6-(1H-pyrazol-1-yl)pyridin-3-yl)-1-(tetrahydro-2H-pyran-4-yl)-1H-pyrazolo[3,4-d]pyrimidin-6-amine |

TABLE 1-continued

| Exemplary Compounds 1-149 | | |
|---|---|---|
| Example number | structures | Name |
| 93 | 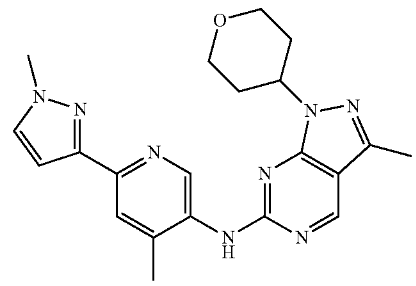 [SMILES: Cc1cc(-c2ccn(C)n2)ncc1Nc1ncc2c(C)nn(C3CCOCC3)c2n1] | 3-methyl-N-(4-methyl-6-(1-methyl-1H-pyrazol-3-yl)pyridin-3-yl)-1-(tetrahydro-2H-pyran-4-yl)-1H-pyrazolo[3,4-d]pyrimidin-6-amine |
| 94 | 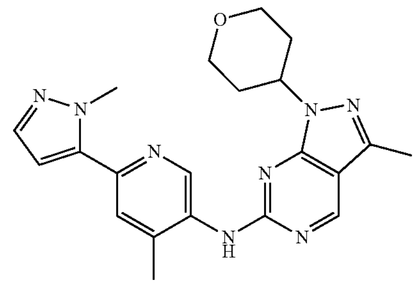 [SMILES: Cc1cc(-c2ccnn2C)ncc1Nc1ncc2c(C)nn(C3CCOCC3)c2n1] | 3-methyl-N-(4-methyl-6-(1-methyl-1H-pyrazol-5-yl)pyridin-3-yl)-1-(tetrahydro-2H-pyran-4-yl)-1H-pyrazolo[3,4-d]pyrimidin-6-amine |
| 95 | 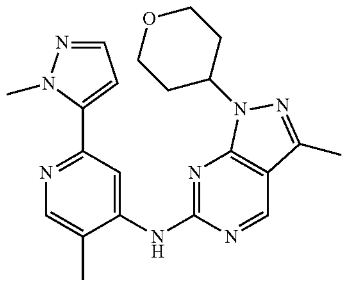 | 3-methyl-N-(5-methyl-2-(1-methyl-1H-pyrazol-5-yl)pyridin-4-yl)-1-(tetrahydro-2H-pyran-4-yl)-1H-pyrazolo[3,4-d]pyrimidin-6-amine |
| 96 | 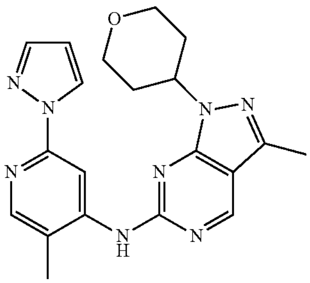 [SMILES: Cc1cnc(-n2cccn2)cc1Nc1ncc2c(C)nn(C3CCOCC3)c2n1] | 3-methyl-N-(5-methyl-2-(1H-pyrazol-1-yl)pyridin-4-yl)-1-(tetrahydro-2H-pyran-4-yl)-1H-pyrazolo[3,4-d]pyrimidin-6-amine |
| 97 | 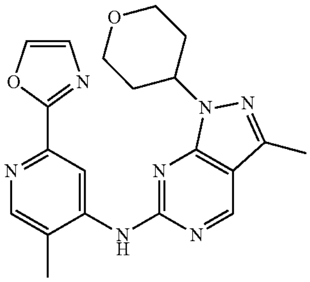 [SMILES: Cc1cnc(-c2ncco2)cc1Nc1ncc2c(C)nn(C3CCOCC3)c2n1] | 3-methyl-N-(5-methyl-2-(oxazol-2-yl)pyridin-4-yl)-1-(tetrahydro-2H-pyran-4-yl)-1H-pyrazolo[3,4-d]pyrimidin-6-amine |

TABLE 1-continued

| Exemplary Compounds 1-149 | | |
|---|---|---|
| Example number | structures | Name |
| 98 | 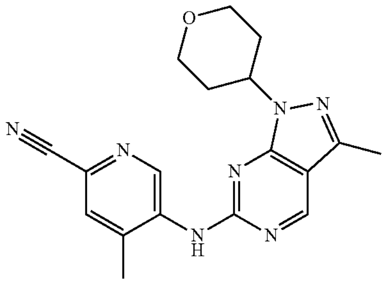 [SMILES: Cc1cc(C#N)ncc1Nc1ncc2c(C)nn(C3CCOCC3)c2n1] | 4-methyl-5-((3-methyl-1-(tetrahydro-2H-pyran-4-yl)-1H-pyrazolo[3,4-d]pyrimidin-6-yl)amino)picolinonitrile |
| 99 | 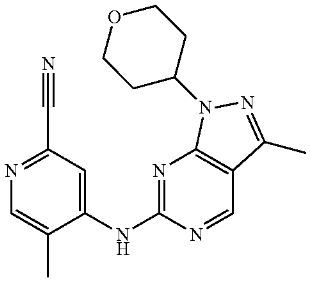 [SMILES: Cc1cnc(C#N)cc1Nc1ncc2c(C)nn(C3CCOCC3)c2n1] | 5-methyl-4-((3-methyl-1-(tetrahydro-2H-pyran-4-yl)-1H-pyrazolo[3,4-d]pyrimidin-6-yl)amino)picolinonitrile |
| 101 | 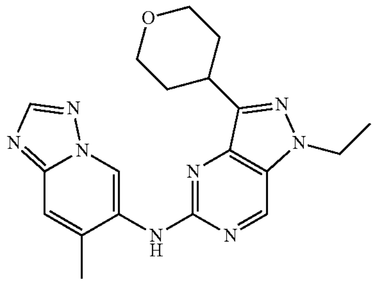 [SMILES: CCn1nc(C2CCOCC2)c2nc(Nc3cn4ncnc4cc3C)ncc21] | 1-ethyl-N-(7-methyl-[1,2,4]triazolo[1,5-a]pyridin-6-yl)-3-(tetrahydro-2H-pyran-4-yl)-1H-pyrazolo[4,3-d]pyrimidin-5-amine |
| 102 | 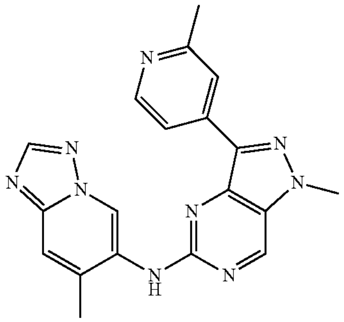 [SMILES: Cc1cc(-c2nn(C)c3cnc(Nc4cn5ncnc5cc4C)nc23)ccn1] | 1-methyl-N-(7-methyl-[1,2,4]triazolo[1,5-a]pyridin-6-yl)-3-(2-methylpyridin-4-yl)-1H-pyrazolo[4,3-d]pyrimidin-5-amine |
| 103 | 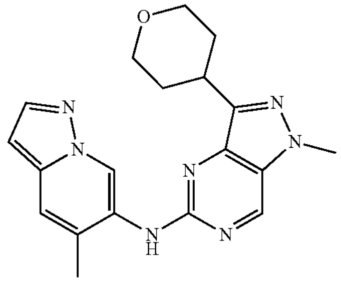 [SMILES: Cc1cc2ccnn2cc1Nc1ncc2c(n1)c(C1CCOCC1)nn2C] | 1-methyl-N-(5-methylpyrazolo[1,5-a]pyridin-6-yl)-3-(tetrahydro-2H-pyran-4-yl)-1H-pyrazolo[4,3-d]pyrimidin-5-amine |

TABLE 1-continued

| Exemplary Compounds 1-149 | | |
|---|---|---|
| Example number | structures | Name |
| 104 | 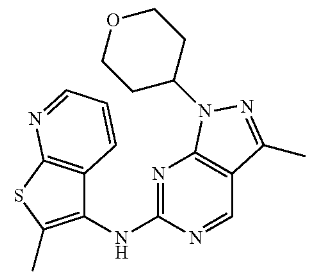 [SMILES: Cc1sc2ncccc2c1Nc1ncc2c(C)nn(C3CCOCC3)c2n1] | 2-methyl-N-(3-methyl-1-(tetrahydro-2H-pyran-4-yl)-1H-pyrazolo[3,4-d]pyrimidin-6-yl)thieno[2,3-b]pyridin-3-amine |
| 105 | 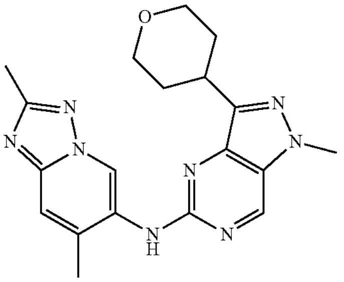 | N-(2,7-dimethyl-[1,2,4]triazolo[1,5-a]pyridin-6-yl)-1-methyl-3-(tetrahydro-2H-pyran-4-yl)-1H-pyrazolo[4,3-d]pyrimidin-5-amine |
| 106 | 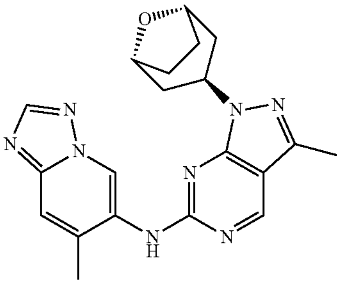 [SMILES: Cc1cc2ncnn2cc1Nc1ncc2c(C)nn([C@H]3C[C@H]4CC[C@@H](C3)O4)c2n1] | 1-((1R,3r,5S)-8-oxabicyclo[3.2.1]octan-3-yl)-3-methyl-N-(7-methyl-[1,2,4]triazolo[1,5-a]pyridin-6-yl)-1H-pyrazolo[3,4-d]pyrimidin-6-amine |
| 107 | 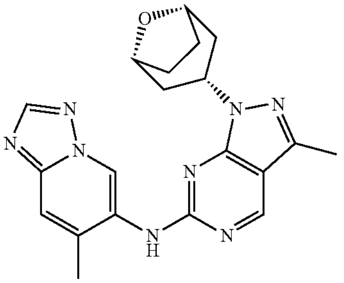 [SMILES: Cc1cc2ncnn2cc1Nc1ncc2c(C)nn([C@@H]3C[C@H]4CC[C@@H](C3)O4)c2n1] | 1-((1R,3s,5S)-8-oxabicyclo[3.2.1]octan-3-yl)-3-methyl-N-(7-methyl-[1,2,4]triazolo[1,5-a]pyridin-6-yl)-1H-pyrazolo[3,4-d]pyrimidin-6-amine |
| 108 | 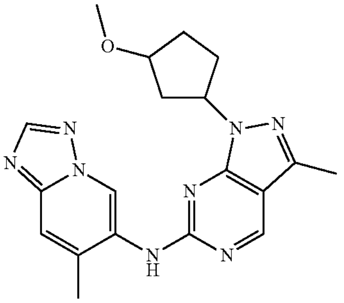 [SMILES: COC1CCC(n2nc(C)c3cnc(Nc4cn5ncnc5cc4C)nc32)C1] | 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (isomer 1) |

TABLE 1-continued

Exemplary Compounds 1-149

| Example number | structures | Name |
| --- | --- | --- |
| 109 | 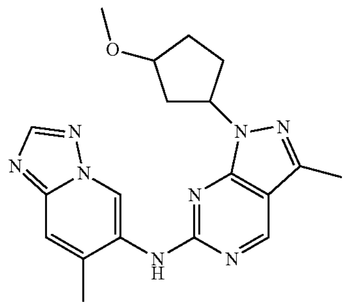 [SMILES: COC1CCC(n2nc(C)c3cnc(Nc4cn5ncnc5cc4C)nc32)C1] | 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (isomer 2) |
| 110 | 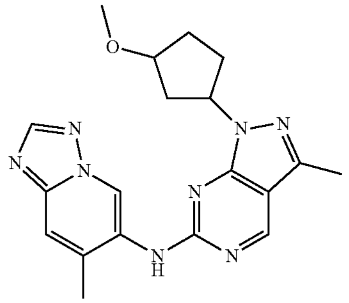 [SMILES: COC1CCC(n2nc(C)c3cnc(Nc4cn5ncnc5cc4C)nc32)C1] | 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (isomer 3) |
| 111 | 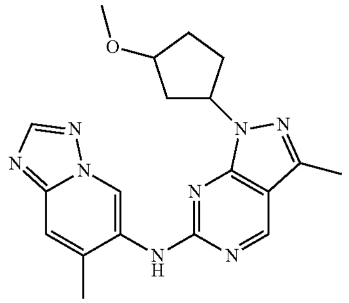 [SMILES: COC1CCC(n2nc(C)c3cnc(Nc4cn5ncnc5cc4C)nc32)C1] | 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (isomer 4) |
| 112 | 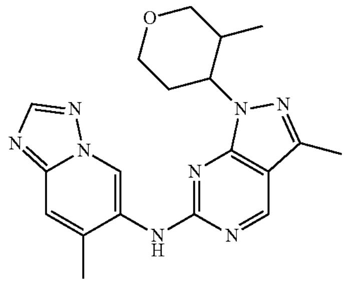 [SMILES: Cc1cc2ncnn2cc1Nc1ncc2c(C)nn(C3CCOCC3C)c2n1] | 3-methyl-N-(7-methyl-[1,2,4]triazolo[1,5-a]pyridin-6-yl)-1-(3-methyltetrahydro-2H-pyran-4-yl)-1H-pyrazolo[3,4-d]pyrimidin-6-amine (isomer 1) |
| 113 | 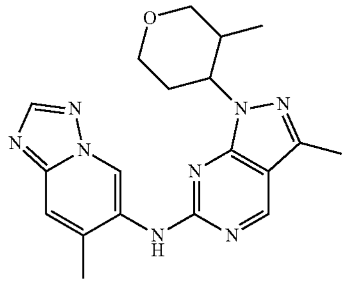 [SMILES: Cc1cc2ncnn2cc1Nc1ncc2c(C)nn(C3CCOCC3C)c2n1] | 3-methyl-N-(7-methyl-[1,2,4]triazolo[1,5-a]pyridin-6-yl)-1-(3-methyltetrahydro-2H-pyran-4-yl)-1H-pyrazolo[3,4-d]pyrimidin-6-amine (isomer 2) |

TABLE 1-continued

| Example number | structures | Name |
|---|---|---|
| | Exemplary Compounds 1-149 | |
| 114 | 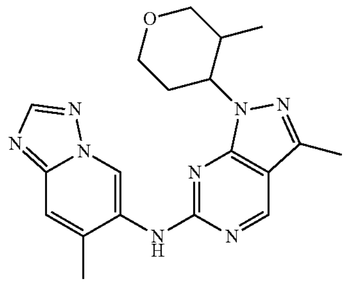 [SMILES: Cc1cc2ncnn2cc1Nc1ncc2c(C)nn(C3CCOCC3C)c2n1] | 3-methyl-N-(7-methyl-[1,2,4]triazolo[1,5-a]pyridin-6-yl)-1-(3-methyltetrahydro-2H-pyran-4-yl)-1H-pyrazolo[3,4-d]pyrimidin-6-amine (isomer 3) |
| 115 | 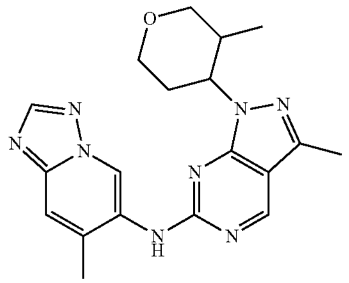 [SMILES: Cc1cc2ncnn2cc1Nc1ncc2c(C)nn(C3CCOCC3C)c2n1] | 3-methyl-N-(7-methyl-[1,2,4]triazolo[1,5-a]pyridin-6-yl)-1-(3-methyltetrahydro-2H-pyran-4-yl)-1H-pyrazolo[3,4-d]pyrimidin-6-amine (isomer 4) |
| 116 | 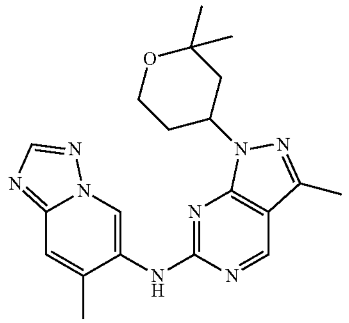 [SMILES: Cc1cc2ncnn2cc1Nc1ncc2c(C)nn(C3CCOC(C)(C)C3)c2n1] | 1-(2,2-dimethyltetrahydro-2H-pyran-4-yl)-3-methyl-N-(7-methyl-[1,2,4]triazolo[1,5-a]pyridin-6-yl)-1H-pyrazolo[3,4-d]pyrimidin-6-amine (isomer 1) |
| 117 | 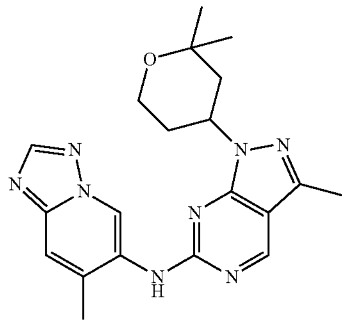 [SMILES: Cc1cc2ncnn2cc1Nc1ncc2c(C)nn(C3CCOC(C)(C)C3)c2n1] | 1-(2,2-dimethyltetrahydro-2H-pyran-4-yl)-3-methyl-N-(7-methyl-[1,2,4]triazolo[1,5-a]pyridin-6-yl)-1H-pyrazolo[3,4-d]pyrimidin-6-amine (isomer 2) |
| 118 | 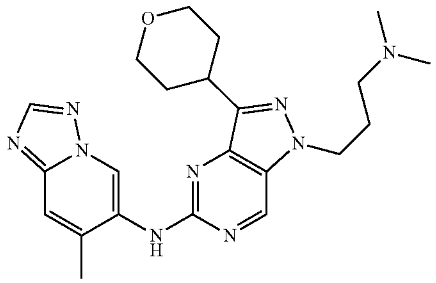 [SMILES: Cc1cc2ncnn2cc1Nc1ncc2c(n1)c(C1CCOCC1)nn2CCCN(C)C] | 1-(3-(dimethylamino)propyl)-N-(7-methyl-[1,2,4]triazolo[1,5-a]pyridin-6-yl)-3-(tetrahydro-2H-pyran-4-yl)-1H-pyrazolo[4,3-d]pyrimidin-5-amine |

TABLE 1-continued

| Exemplary Compounds 1-149 | | |
|---|---|---|
| Example number | structures | Name |
| 119 | 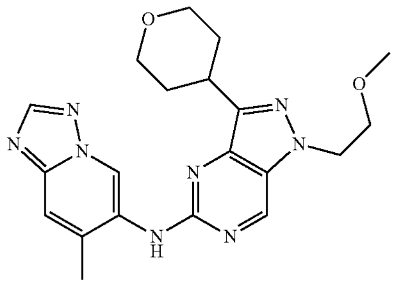 [SMILES: COCCn1nc(C2CCOCC2)c2nc(Nc3cn4ncnc4cc3C)ncc21] | 1-(2-methoxyethyl)-N-(7-methyl-[1,2,4]triazolo[1,5-a]pyridin-6-yl)-3-(tetrahydro-2H-pyran-4-yl)-1H-pyrazolo[4,3-d]pyrimidin-5-amine |
| 120 | 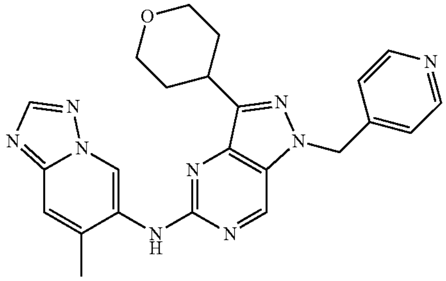 [SMILES: Cc1cc2ncnn2cc1Nc1ncc2c(n1)c(C1CCOCC1)nn2Cc1ccncc1] | N-(7-methyl-[1,2,4]triazolo[1,5-a]pyridin-6-yl)-1-(pyridin-4-ylmethyl)-3-(tetrahydro-2H-pyran-4-yl)-1H-pyrazolo[4,3-d]pyrimidin-5-amine |
| 121 | 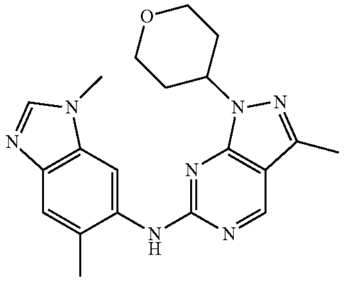 [SMILES: Cc1cc2ncn(C)c2cc1Nc1ncc2c(C)nn(C3CCOCC3)c2n1] | N-(1,5-dimethyl-1H-benzo[d]imidazol-6-yl)-3-methyl-1-(tetrahydro-2H-pyran-4-yl)-1H-pyrazolo[3,4-d]pyrimidin-6-amine |
| 122 | 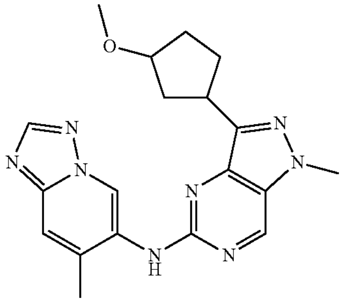 [SMILES: COC1CCC(c2nn(C)c3cnc(Nc4cn5ncnc5cc4C)nc23)C1] | 3-(3-methoxycyclopentyl)-1-methyl-N-(7-methyl-[1,2,4]triazolo[1,5-a]pyridin-6-yl)-1H-pyrazolo[4,3-d]pyrimidin-5-amine |
| 123 | 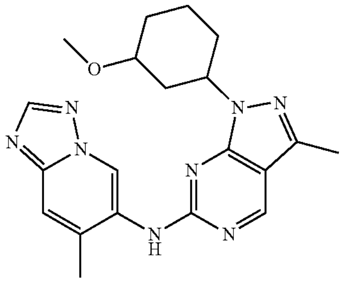 [SMILES: COC1CCCC(n2nc(C)c3cnc(Nc4cn5ncnc5cc4C)nc32)C1] | 1-(3-methoxycyclohexyl)-3-methyl-N-(7-methyl-[1,2,4]triazolo[1,5-a]pyridin-6-yl)-1H-pyrazolo[3,4-d]pyrimidin-6-amine |

TABLE 1-continued

Exemplary Compounds 1-149

| Example number | structures | Name |
| --- | --- | --- |
| 124 | 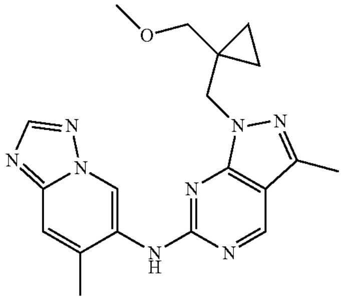 [SMILES: COCC1(Cn2nc(C)c3cnc(Nc4cn5ncnc5cc4C)nc32)CC1] | 1-((1-(methoxymethyl)cyclopropyl)methyl)-3-methyl-N-(7-methyl-[1,2,4]triazolo[1,5-a]pyridin-6-yl)-1H-pyrazolo[3,4-d]pyrimidin-6-amine |
| 125 | 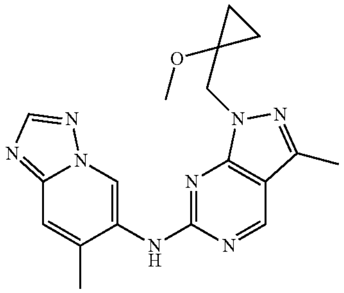 [SMILES: COC1(Cn2nc(C)c3cnc(Nc4cn5ncnc5cc4C)nc32)CC1] | 1-((1-methoxycyclopropyl)methyl)-3-methyl-N-(7-methyl-[1,2,4]triazolo[1,5-a]pyridin-6-yl)-1H-pyrazolo[3,4-d]pyrimidin-6-amine |
| 126 | 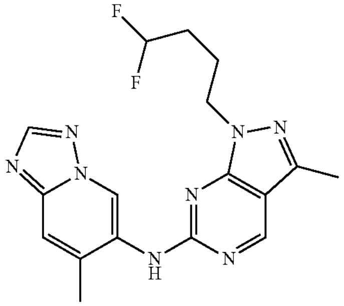 [SMILES: Cc1cc2ncnn2cc1Nc1ncc2c(C)nn(CCCC(F)F)c2n1] | 1-(4,4-difluorobutyl)-3-methyl-N-(7-methyl-[1,2,4]triazolo[1,5-a]pyridin-6-yl)-1H-pyrazolo[3,4-d]pyrimidin-6-amine |
| 127 | 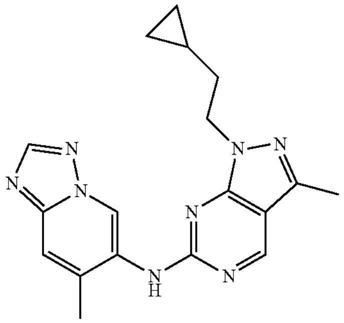 [SMILES: Cc1cc2ncnn2cc1Nc1ncc2c(C)nn(CCC3CC3)c2n1] | 1-(2-cyclopropylethyl)-3-methyl-N-(7-methyl-[1,2,4]triazolo[1,5-a]pyridin-6-yl)-1H-pyrazolo[3,4-d]pyrimidin-6-amine |
| 128 | 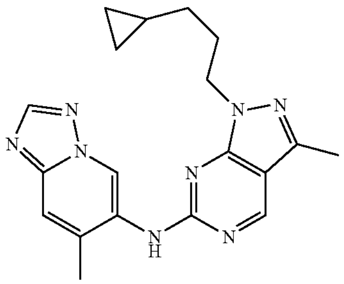 [SMILES: Cc1cc2ncnn2cc1Nc1ncc2c(C)nn(CCCC3CC3)c2n1] | 1-(3-cyclopropylpropyl)-3-methyl-N-(7-methyl-[1,2,4]triazolo[1,5-a]pyridin-6-yl)-1H-pyrazolo[3,4-d]pyrimidin-6-amine |

TABLE 1-continued

| Exemplary Compounds 1-149 | | |
|---|---|---|
| Example number | structures | Name |
| 129 | 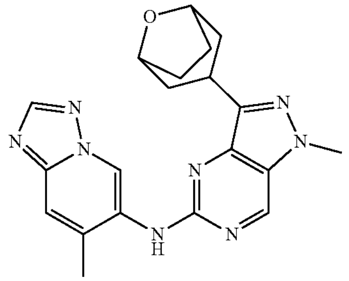 [SMILES: Cc1cc2ncnn2cc1Nc1ncc2c(n1)c(C1CC3CCC(C1)O3)nn2C] | 3-(8-oxabicyclo[3.2.1]octan-3-yl)-1-methyl-N-(7-methyl-[1,2,4]triazolo[1,5-a]pyridin-6-yl)-1H-pyrazolo[4,3-d]pyrimidin-5-amine |
| 130 | 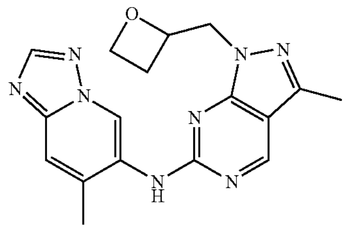 [SMILES: Cc1cc2ncnn2cc1Nc1ncc2c(C)nn(CC3CCO3)c2n1] | 3-methyl-N-(7-methyl-[1,2,4]triazolo[1,5-a]pyridin-6-yl)-1-(oxetan-2-ylmethyl)-1H-pyrazolo[3,4-d]pyrimidin-6-amine |
| 131 | 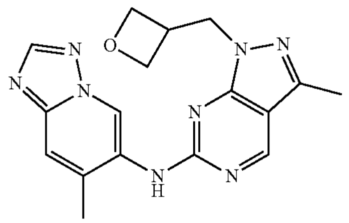 [SMILES: Cc1cc2ncnn2cc1Nc1ncc2c(C)nn(CC3COC3)c2n1] | 3-methyl-N-(7-methyl-[1,2,4]triazolo[1,5-a]pyridin-6-yl)-1-(oxetan-3-ylmethyl)-1H-pyrazolo[3,4-d]pyrimidin-6-amine |
| 132 | 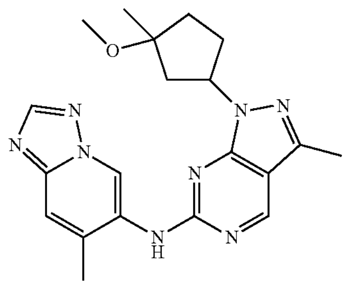 [SMILES: COC1(C)CCC(n2nc(C)c3cnc(Nc4cn5ncnc5cc4C)nc32)C1] | 1-(3-methoxy-3-methylcyclopentyl)-3-methyl-N-(7-methyl-[1,2,4]triazolo[1,5-a]pyridin-6-yl)-1H-pyrazolo[3,4-d]pyrimidin-6-amine |
| 133 | 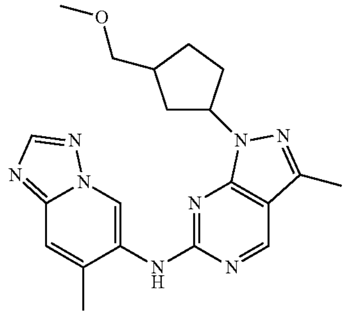 [SMILES: COCC1CCC(n2nc(C)c3cnc(Nc4cn5ncnc5cc4C)nc32)C1] | 1-(3-(methoxymethyl)cyclopentyl)-3-methyl-N-(7-methyl-[1,2,4]triazolo[1,5-a]pyridin-6-yl)-1H-pyrazolo[3,4-d]pyrimidin-6-amine |

TABLE 1-continued

Exemplary Compounds 1-149

| Example number | structures | Name |
| --- | --- | --- |
| 134 | 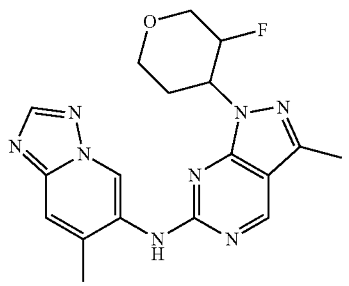 [SMILES: Cc1cc2ncnn2cc1Nc1ncc2c(C)nn(C3CCOCC3F)c2n1] | 1-(3-fluorotetrahydro-2H-pyran-4-yl)-3-methyl-N-(7-methyl-[1,2,4]triazolo[1,5-a]pyridin-6-yl)-1H-pyrazolo[3,4-d]pyrimidin-6-amine |
| 135 | 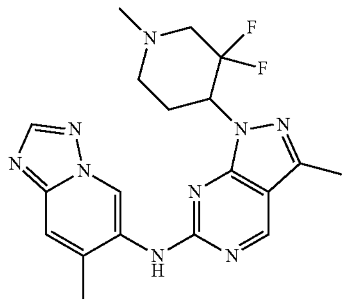 [SMILES: Cc1cc2ncnn2cc1Nc1ncc2c(C)nn(C3CCN(C)CC3(F)F)c2n1] | 1-(3,3-difluoro-1-methylpiperidin-4-yl)-3-methyl-N-(7-methyl-[1,2,4]triazolo[1,5-a]pyridin-6-yl)-1H-pyrazolo[3,4-d]pyrimidin-6-amine |
| 136 | 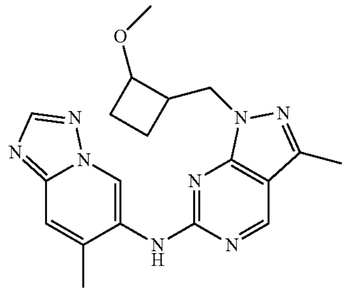 [SMILES: COC1CCC1Cn1nc(C)c2cnc(Nc3cn4ncnc4cc3C)nc21] | 1-((2-methoxycyclobutyl)methyl)-3-methyl-N-(7-methyl-[1,2,4]triazolo[1,5-a]pyridin-6-yl)-1H-pyrazolo[3,4-d]pyrimidin-6-amine |
| 137 | 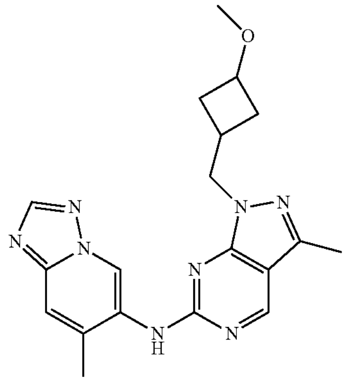 [SMILES: COC1CC(Cn2nc(C)c3cnc(Nc4cn5ncnc5cc4C)nc32)C1] | 1-((3-methoxycyclobutyl)methyl)-3-methyl-N-(7-methyl-[1,2,4]triazolo[1,5-a]pyridin-6-yl)-1H-pyrazolo[3,4-d]pyrimidin-6-amine |

TABLE 1-continued

| Exemplary Compounds 1-149 | | |
|---|---|---|
| Example number | structures | Name |
| 138 | 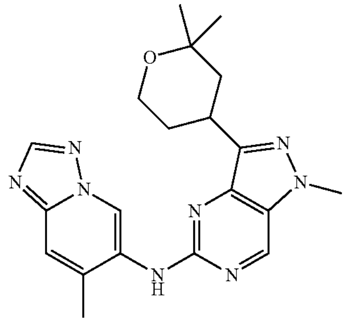 [SMILES: Cc1cc2ncnn2cc1Nc1ncc2c(n1)c(C1CCOC(C)(C)C1)nn2C] | 3-(2,2-dimethyltetrahydro-2H-pyran-4-yl)-1-methyl-N-(7-methyl-[1,2,4]triazolo[1,5-a]pyridin-6-yl)-1H-pyrazolo[4,3-d]pyrimidin-5-amine |
| 139 | 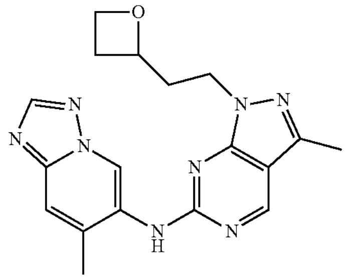 [SMILES: Cc1cc2ncnn2cc1Nc1ncc2c(C)nn(CCC3CCO3)c2n1] | 3-methyl-N-(7-methyl-[1,2,4]triazolo[1,5-a]pyridin-6-yl)-1-(2-(oxetan-2-yl)ethyl)-1H-pyrazolo[3,4-d]pyrimidin-6-amine |
| 140 | 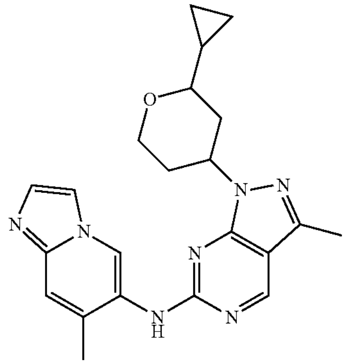 [SMILES: Cc1cc2nccn2cc1Nc1ncc2c(C)nn(C3CCOC(C4CC4)C3)c2n1] | 1-(2-cyclopropyltetrahydro-2H-pyran-4-yl)-3-methyl-N-(7-methylimidazo[1,2-a]pyridin-6-yl)-1H-pyrazolo[3,4-d]pyrimidin-6-amine |
| 141 | 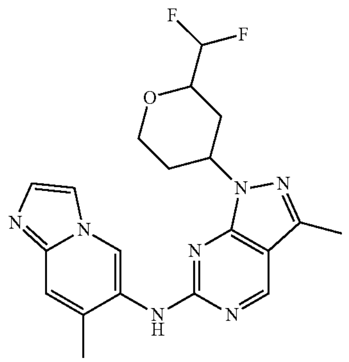 [SMILES: Cc1cc2nccn2cc1Nc1ncc2c(C)nn(C3CCOC(C(F)F)C3)c2n1] | 1-(2-(difluoromethyl)tetrahydro-2H-pyran-4-yl)-3-methyl-N-(7-methylimidazo[1,2-a]pyridin-6-yl)-1H-pyrazolo[3,4-d]pyrimidin-6-amine |

TABLE 1-continued

| Exemplary Compounds 1-149 | | |
|---|---|---|
| Example number | structures | Name |
| 142 | 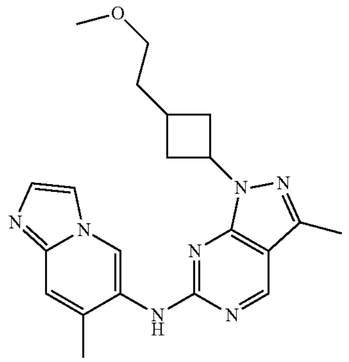 [SMILES: COCCC1CC(n2nc(C)c3cnc(Nc4cn5ccnc5cc4C)nc32)C1] | 1-(3-(2-methoxyethyl)cyclobutyl)-3-methyl-N-(7-methyl-[1,2,4]triazolo[1,5-a]pyridin-6-yl)-1H-pyrazolo[3,4-d]pyrimidin-6-amine |
| 143 | 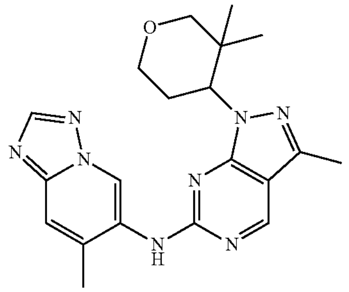 [SMILES: Cc1cc2ncnn2cc1Nc1ncc2c(C)nn(C3CCOCC3(C)C)c2n1] | 1-(3,3-dimethyltetrahydro-2H-pyran-4-yl)-3-methyl-N-(7-methyl-[1,2,4]triazolo[1,5-a]pyridin-6-yl)-1H-pyrazolo[3,4-d]pyrimidin-6-amine |
| 144 | 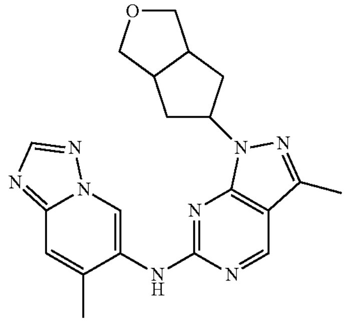 [SMILES: Cc1cc2ncnn2cc1Nc1ncc2c(C)nn(C3CC4COCC4C3)c2n1] | 1-(hexahydro-1H-cyclopenta[c]furan-5-yl)-3-methyl-N-(7-methyl-[1,2,4]triazolo[1,5-a]pyridin-6-yl)-1H-pyrazolo[3,4-d]pyrimidin-6-amine |
| 145 | 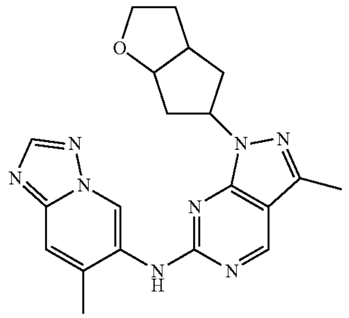 [SMILES: Cc1cc2ncnn2cc1Nc1ncc2c(C)nn(C3CC4CCOC4C3)c2n1] | 1-(hexahydro-2H-cyclopenta[b]furan-5-yl)-3-methyl-N-(7-methyl-[1,2,4]triazolo[1,5-a]pyridin-6-yl)-1H-pyrazolo[3,4-d]pyrimidin-6-amine |

TABLE 1-continued

Exemplary Compounds 1-149

| Example number | structures | Name |
|---|---|---|
| 146 | 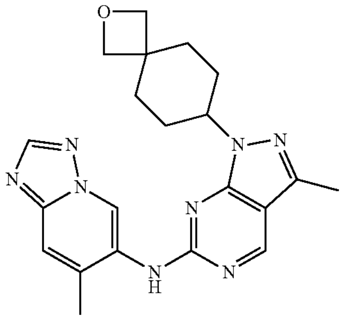 [SMILES: Cc1cc2ncnn2cc1Nc1ncc2c(C)nn(C3CCC4(CC3)COC4)c2n1] | 3-methyl-N-(7-methyl-[1,2,4]triazolo[1,5-a]pyridin-6-yl)-1-(2-oxaspiro[3.5]nonan-7-yl)-1H-pyrazolo[3,4-d]pyrimidin-6-amine |
| 147 | 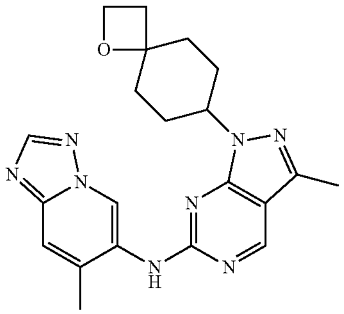 [SMILES: Cc1cc2ncnn2cc1Nc1ncc2c(C)nn(C3CCC4(CCO4)CC3)c2n1] | 3-methyl-N-(7-methyl-[1,2,4]triazolo[1,5-a]pyridin-6-yl)-1-(1-oxaspiro[3.5]nonan-7-yl)-1H-pyrazolo[3,4-d]pyrimidin-6-amine |
| 148 | 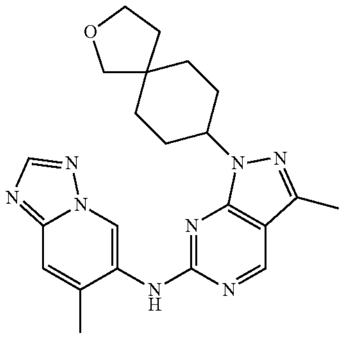 [SMILES: Cc1cc2ncnn2cc1Nc1ncc2c(C)nn(C3CCC4(CCOC4)CC3)c2n1] | 3-methyl-N-(7-methyl-[1,2,4]triazolo[1,5-a]pyridin-6-yl)-1-(2-oxaspiro[4.5]decan-8-yl)-1H-pyrazolo[3,4-d]pyrimidin-6-amine |
| 149 | 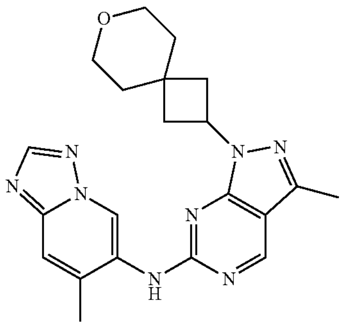 [SMILES: Cc1cc2ncnn2cc1Nc1ncc2c(C)nn(C3CC4(CCOCC4)C3)c2n1] | 3-methyl-N-(7-methyl-[1,2,4]triazolo[1,5-a]pyridin-6-yl)-1-(7-oxaspiro[3.5]nonan-2-yl)-1H-pyrazolo[3,4-d]pyrimidin-6-amine |

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable sub combination.

At various places in the present disclosure, linking substituents are described. Where the structure clearly requires a linking group, the Markush variables listed for that group are understood to be linking groups. For example, if the structure requires a linking group and the Markush group definition for that variable lists "alkyl", then it is understood that the "alkyl" represents a linking alkylene group.

As used herein, the term "substituted", when refers to a chemical group, means the chemical group has one or more hydrogen atoms that is/are removed and replaced by substituents. As used herein, the term "substituent" has the ordinary meaning known in the art and refers to a chemical moiety that is covalently attached to, or if appropriate, fused to, a parent group. As used herein, the term "optionally substituted" or "optionally . . . substituted" means that the chemical group may have no substituents (i.e. unsubstituted) or may have one or more substituents (i.e. substituted). It is to be understood that substitution at a given atom is limited by valency.

As used herein, the term "$C_{i-j}$" indicates a range of the carbon atoms numbers, wherein i and j are integers and the range of the carbon atoms numbers includes the endpoints (i.e. i and j) and each integer point in between, and wherein j is greater than i. For examples, $C_{1-6}$ indicates a range of one to six carbon atoms, including one carbon atom, two carbon atoms, three carbon atoms, four carbon atoms, five carbon atoms and six carbon atoms. In some embodiments, the term "$C_{1-12}$" indicates 1 to 12, including 1 to 10, 1 to 8, 1 to 6, 1 to 5, 1 to 4, 1 to 3 or 1 to 2 carbon atoms.

As used herein, the term "alkyl", whether as part of another term or used independently, refers to a saturated or unsaturated hydrocarbon chain, while the latter may be further subdivided into hydrocarbon chain having at least one double or triple bonds (alkenyl or alkynyl). In some embodiments, alkyl refers to a saturated hydrocarbon chain. The hydrocarbon chain mentioned above may be straight-chain or branched-chain. The term "$C_{i-j}$ alkyl" refers to an alkyl having i to j carbon atoms. Examples of saturated alkyl group include, but are not limited to, methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. Examples of unsaturated alkyl groups include, but are not limited to, ethenyl, n-propenyl, isopropenyl, n-butenyl, sec-butenyl, ethynyl, propyn-1-yl, propyn-2-yl, and the like. Examples of "$C_{1-6}$ alkyl" include, but are not limited to, methyl, ethyl, propyl, isopropyl, n-butyl, iso-butyl and tert-butyl. Examples of "$C_{1-3}$ alkyl" include, but are not limited to, methyl, ethyl, propyl, and isopropyl.

When "alkyl" represents a linking alkylene group, examples of alkylene groups include, but are not limited to, methylene, 1,1-ethylene, 1,2-ethylene, 1,1-propylene, 1,2-propylene, 1,3-propylene, 2,2-propylene, tertbutanylene and the like.

As used herein the term "amino" refers to the group of formula "—$NH_2$".

As used herein, the term "carbamoyl" refers to aminocarbonyl group (i.e., $NH_2$—C(═O)—).

As used herein the term "cyano" refers to the group of formula "—C≡N".

As used herein the terms "halo" and "halogen" refer to fluoro, chloro, bromo or iodo groups.

As used herein the term "hydroxyl" refers to the group of formula "—OH".

As used herein, the term "alkoxy", whether as part of another term or used independently, refers to a group of formula —O-alkyl.

The term "$C_{i-j}$ alkoxy" means that the alkyl moiety of the alkoxy group has i to j carbon atoms. Examples of alkoxy groups include, but are not limited to, methoxyl, ethoxyl, propoxyl (e.g. n-propoxy and isopropoxy), t-butoxy, and the like. Examples of "$C_{1-12}$ alkoxyl" are methoxyl, ethoxyl and propoxyl.

As used herein, the term "hydroxy$C_{1-12}$ alky", refers to a group of formula "—$C_{1-12}$ alkyl-OH", wherein the alkyl moiety of the group has 1 to 12 carbon atoms, and one or more hydroxyl groups may be linked to any carbon atoms in the alkyl moiety. In some embodiments, "$C_{i-j}$ alky-OH" has one hydroxyl group. Examples of "$C_{1-12}$ alkyl-OH" are hydroxymethyl, 1-hydroxyethyl, 2-hydroxyethyl and 1-hydroxyisopropyl.

As used herein, the term "$C_{i-j}$ haloalkyl", refers to a halogen substituted (mono- or multi-substituted) $C_{i-j}$ alkyl group. Examples of "$C_{1-12}$ haloalkyl" are fluoromethyl, difluoromethyl, trifluoromethyl, fluoroethyl, difluoroethyl, trifluoroethyl, chloroethyl and bromoisopropyl.

Examples of "difluoroethyl" are 1,1-difluoroethyl. Examples of "trifluoroethyl" are 2,2,2-trifluoroethyl and 1,2,2-trifluoroethlyl.

Examples of "$C_{i-j}$ haloalkoxyl" are fluoromethoxyl, difluoromethoxyl, or trifluoromethoxyl. Examples of "trifluoroethoxy" are 2,2,2-trifluoroethoxy and 1,2,2-trifluoroethoxy.

As used herein, the term "aryl" or "aromatic", whether as part of another term or used independently, refers to a ring system with alternating double and single bonds between atoms forming rings. In the present disclosure the term "aryl" or "aromatic" also intends to include pseudoaromatic. The term "pseudoaromatic" refers to a ring system which is not strictly aromatic, but which is stabilized by means of delocalization of electrons and behaves in a similar manner to aromatic rings. An aryl or an aromatic group may have mono- or poly-ring(s). Examples of aryl groups include, but are not limited to, phenyl, naphthyl, tetrahydronaphthyl, indanyl and the like.

As used herein, the term "heteroaryl" as used herein refers to aryl which contains at least one ring forming heteroatom selected from O, S, N, P, and the like. Heteroaryl includes but are not limited to, furyl, thienyl, pyridinyl, triazinyl, pyridyl, pyrrolyl, oxazolyl, thiazolyl, imidazolyl, pyrazolyl, isoxazolyl, isothiazolyl, indolizinyl, indolyl, isoindolyl, indolinyl, 1,2,3-oxadiazolyl, 1,2,4-oxadiazolyl, 1,2,4-oxadiazol-5-one, 1,2,3-triazolyl, 1,3,4-thiadiazolyl, pyridazinyl, pyrimidinyl, pyrazinyl, quinazolinyl, isoquinazolinyl, 1,3,5-triazinyl, 1H thieno[2,3-c]pyrazolyl, thieno[2,3-b]furyl, 3H-indolyl, benzo[b]furanyl, benzo[b]thiophenyl, 1H-indazolyl, benzimidazolyl, tetrazolyl, uridinyl, and cytosinyl.

As used herein, the term "carbocyclyl", whether as part of another term or used independently, refers to any ring, including mono- or poly-cyclic ring(s) (e.g. having 2 or 3 fused, bridged or spiro rings), in which all the ring atoms are carbon and which contains at least three ring forming carbon atoms. As used herein, the term "spiro" rings refers to ring systems having two rings connected through one single common atom; the term "fused" rings refers to ring systems having two rings sharing two adjacent atoms; and the term "bridged" rings refers to ring systems with two rings sharing three or more atoms.

In some embodiments, the carbocyclyl may contain 3 to 12 ring forming carbon atoms (i.e. 3-12 membered carbon atoms), 3 to 10 ring forming carbon atoms, 3 to 9 ring forming carbon atoms or 3 to 8 ring forming carbon atoms. Carbocyclyl groups may be saturated, partially unsaturated or fully unsaturated. In some embodiments, the carbocyclyl group may be a saturated cyclic alkyl group. In some embodiments, the carbocyclyl group may be an unsaturated cyclic alkyl group that contains at least one double bond in its ring system. In some embodiments, an unsaturated carbocyclyl group may contains one or more aromatic rings. In some embodiments, one or more ring forming —$CH_2$— group of the saturated or unsaturated carbocyclyl may be replaced by a —C(O)— group.

In some embodiments, the carbocyclyl group is a monocyclic alkyl group. In some embodiments, the carbocyclyl group is a saturated monocyclic alkyl group. Examples of saturated monocyclic alkyl groups include, but are not limited to, cyclopropyl, cyclobutyl, cyclopentyl, cyclohexyl, cycloheptyl, cyclooctyl, cyclopentenyl, cyclohexenyl, and the like.

A 3-8 "membered saturated or unsaturated carbocyclyl" is a saturated, partially unsaturated or fully unsaturated mono- or poly-cyclic ring system having 3 to 8, 3 to 6, or 5 to 8 ring forming carbon atoms respectively, wherein one or more ring forming $—CH_2—$ group can optionally be replaced by a —C(O)— group.

Examples of "3-8 membered saturated or unsaturated carbocyclyl" are $C_{3-6}$ cycloalkyl, cyclohexyl, cyclohexenyl, cyclopentyl, phenyl, naphthyl and bicyclo[1.1.1]pentan-1-yl. Examples of "$C_{3-8}$ cycloalkyl" are cyclopropyl, cyclobutyl, cyclopentyl, cyclohexyl, cycloheptyl, and cyclooctyl. The term "$C_{3-8}$ cycloalkoxyl" refers to the group of formula "$C_{3-8}$ cycloalkyl-O—".

As used herein, the term "heterocyclyl" refers to a carbocyclyl group, wherein one or more (e.g. 1, 2 or 3) ring atoms are replaced by heteroatoms, which include, but are not limited to, O, S, N, P, and the like. In some embodiments, the heterocyclyl is a saturated heterocyclyl. In some embodiments, the heterocyclyl is an unsaturated heterocyclyl having one or more double bonds in its ring system. In some embodiments, the heterocyclyl is a partially unsaturated heterocyclyl. In some embodiments, the heterocyclyl is a fully unsaturated heterocyclyl. In some embodiments, an unsaturated heterocyclyl group may contain one or more aromatic rings. In some embodiments, one or more ring forming $—CH_2—$ group of the heterocyclyl can optionally be replaced by a —C(O)—, a —S—, a —S(O)—, or a $—S(O)_2—$ group. In some embodiments, where the heterocyclyl contains a sulphur in its ring system, said ring forming sulphur atom may be optionally oxidised to form the S-oxides. In some embodiments, the heterocyclyl is linked to the other portion of a compound through its ring forming carbon. In some embodiments, the heterocyclyl is linked to the other portion of a compound through its ring forming nitrogen.

In some embodiments, 3-8 membered saturated or unsaturated mono- or poly-cyclic heterocyclyl having 1, 2, or 3 heteroatoms selected from N, O, or S.

A 3-8 "membered saturated or unsaturated heterocyclyl" is a saturated, partially unsaturated or fully unsaturated mono- or poly-cyclic ring(s) (e.g. having 2 or 3 fused, bridged or spiro rings) system having 3 to 8 ring forming atoms respectively, of which at least one ring forming atom is chosen from nitrogen, sulphur or oxygen, which may, unless otherwise specified, linked to the other portion of a compound through its ring forming carbon or nitrogen, wherein one or more ring forming $—CH_2—$ group of the saturated or unsaturated heterocyclyl may be replaced by a —C(O)—, a —S—, a —S(O)—, or a $—S(O)_2—$ group, and wherein when the heterocyclyl contains a sulphur in its ring system, said ring sulphur atom may be optionally oxidised to form the S-oxides.

Exemplary monocyclic heterocyclyl groups include, but are not limited to oxetanyl, pyranyl, 1,1-dioxothietanylpyrrolidyl, tetrahydrofuryl, tetrahydrothienyl, pyrrolyl, furanyl, thienyl, pyrazolyl, imidazolyl, triazolyl, oxazolyl, thiazolyl, piperidyl, piperidyl, piperazinyl, morpholinyl, pyridinyl, pyrazinyl, pyrimidinyl, pyridazinyl, triazinyl, pyridonyl, pyrimidonyl, pyrazinonyl, pyrimidonyl, pyridazonyl, triazinonyl, and the like.

Examples of spiro heterocyclyl include, but are not limited to, spiropyranyl, spirooxazinyl, and the like. Examples of fused heterocyclyl include, but are not limited to, phenyl fused ring or pyridinyl fused ring, such as quinolinyl, isoquinolinyl, quinoxalinyl, quinolizinyl, quinazolinyl, azaindolizinyl, pteridinyl, chromenyl, isochromenyl, indolyl, isoindolyl, indolizinyl, indazolyl, purinyl, benzofuranyl, isobenzofuranyl, benzimidazolyl, benzothienyl, benzothiazolyl, carbazolyl, phenazinyl, phenothiazinyl, phenanthridinyl, imidazo[1,2-a]pyridinyl, [1,2,4]triazolo[4,3-a]pyridinyl, [1,2,3]triazolo[4,3-a]pyridinyl groups, and the like.

Examples of bridged heterocyclyl include, but are not limited to, morphanyl, hexamethylenetetraminyl, 8-aza-bicyclo[3.2.1]octane, 1-aza-bicyclo[2.2.2]octane, 1,4-diazabicyclo[2.2.2]octane (DABCO), and the like.

The "compound" of present disclosure is intended to encompass all stereoisomers, geometric isomers, and tautomers of the structures depicted unless otherwise specified.

The term "stereoisomer" refers to any of the various stereoisomeric configurations (e.g enantiomers, diastereomers and racemates) of an asymmetric compound (e.g. those having one or more asymmetrically substituted carbon atoms or "asymmetric centers"). Compounds of the present disclosure that contain asymmetric centers can be isolated in optically active (enantiomers or diastereomers) or optically inactive (racemic) forms. The term "enantiomer" includes pairs of stereoisomers that are non-superimposable mirror images of each other. A 1:1 mixture of a pair of enantiomers is a "racemic mixture". The terms "diastereomers" or "diastereoisomers" include stereoisomers that have at least two asymmetric atoms, but which are not mirror images of each other. Certain compounds containing one or more asymmetric centers may give rise to enantiomers, diastereomers or other stereoisomeric forms that may be defined, in terms of absolute configuration, as (R)- or (S)- at each asymmetric center according to the Cahn-Ingold-Prelog R-S system. Resolved compounds whose absolute configuration is unknown can be designated using the term "or" at the asymmetric center. Methods on how to prepare optically active forms from racemic mixtures are known in the art, such as resolution by HPLC or stereoselective synthesis.

The terms "geometric isomers" or "cis and trans isomers" refer to compounds with same formula but their functional groups are rotated into a different orientation in three-dimensional space.

The term "tautomers" include prototropic tautomers that are isomeric protonation states of compounds having the same formula and total charge. Examples of prototropic tautomers include, but are not limited to, ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomers can be in equilibrium or sterically locked into one form by appropriate substitution. Compounds of the present disclosure identified by name or structure as one particular tautomeric form are intended to include other tautomeric forms unless otherwise specified.

The "compound" of the present disclosure is also intended to encompass all isotopes of atoms in the compounds. Isotopes of an atom include atoms having the same atomic number but different mass numbers. For example, unless otherwise specified, hydrogen, carbon, nitrogen, oxygen, phosphorous, sulphur, fluorine, chlorine, bromide or iodine in the "compound" of present disclosure are meant to also include their isotopes such as but are not limited to: $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{19}F$, $^{35}Cl$, $^{37}Cl$, $^{79}Br$, $^{81}Br$, $^{127}I$ and $^{131}I$. In some embodiments, hydrogen includes protium, deuterium and tritium. In some embodiments, the term "substituted by deuterium" or "deuterium substituted" to replace the other isoform of hydrogen (e.g. protium) in the chemical group with deuterium. In some embodiments, carbon includes $^{12}C$ and $^{13}C$. In some embodiments, "compound" of the present disclosure only encompasses the isotopes of hydrogen in the compound. In some embodiments, "compound" of the present disclosure only encompasses the isotopes of atoms in natural abundance.

It is also to be understood that the "compound" of present disclosure can exist in solvated as well as unsolvated forms, such as, for example, hydrated forms, solid forms, and the present disclosure is intended to encompass all such solvated and unsolvated forms.

It is further to be understood that the "compound" of present disclosure can exist in forms of pharmaceutically acceptable salts.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, compounds, materials, compositions, and/or dosage forms that are pharmaceutically acceptable refer to those approved by a regulatory agency (such as U.S. Food and Drug Administration, China Food and Drug Administration or European Medicines Agency) or listed in generally recognized pharmacopoeia (such as U.S. Pharmacopoeia, China Pharmacopoeia or European Pharmacopoeia) for use in animals, and more particularly in humans.

As used herein, "pharmaceutically acceptable salts" refers to derivatives of the compounds of present disclosure wherein the parent compound is modified by converting an existing acidic moiety (e.g. carboxyl and the like) or base moiety (e.g. amine, alkali and the like) to its salt form. In many cases, compounds of present disclosure are capable of forming acid and/or base salts by virtue of the presence of amino and/or carboxyl groups or groups similar thereto. The pharmaceutically acceptable salts are acid and/or base salts that retain biological effectiveness and properties of the parent compound, which typically are not biologically or otherwise undesirable. Suitable pharmaceutically acceptable salts of a compound of the present disclosure includes, for example, an acid-addition salt, which can be derived from for example an inorganic acid (for example, hydrochloric, hydrobromic, sulfuric, nitric, phosphoric acid and the like) or organic acid (for example, formic, acetic, propionic, glycolic, oxalic, maleic, malonic, succinic, fumaric, tartaric, trimesic, citric, lactic, phenylacetic, benzoic, mandelic, methanesulfonic, napadisylic, ethanesulfonic, toluenesulfonic, trifluoroacetic, salicylic, sulfosalicylic acids and the like). In some embodiments, the pharmaceutically acceptable salt of the compound of the present disclosure is a formic acid salt. In some embodiments, the pharmaceutically acceptable salt of the compound of the present disclosure is a TFA salt.

Suitable pharmaceutically acceptable salts of a compound of the present disclosure also include, for example, an base-addition salt, which can be derived from for example an inorganic bases (for example, sodium, potassium, ammonium salts and hydroxide, carbonate, bicarbonate salts of metals from columns I to XII of the periodic table such as calcium, magnesium, iron, silver, zinc, copper and the like) or organic bases (for example, primary, secondary, and tertiary amines, substituted amines including naturally occurring substituted amines, cyclic amines, basic ion exchange resins, and the like). Certain organic amines include but are not limited to isopropylamine, benzathine, cholinate, diethanolamine, diethylamine, lysine, meglumine, piperazine and tromethamine. Those skilled in the art would appreciate that adding acids or bases for forming acid/base-addition salts other than those shown in the examples may also be possible. Lists of additional suitable salts can be found, e.g. in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002). In some embodiments, Suitable pharmaceutically acceptable salts of a compound of the present disclosure is inorganic bases salt.

The present disclosure also includes active intermediates, active metabolites and prodrugs of the compounds of present disclosure. As used herein, an "active intermediate" refer to intermediate compound in the synthetic process, which exhibits the same or essentially the same biological activity as the final synthesized compound.

As used herein, an "active metabolite" refers to a breakdown or end product of a compound of the present disclosure or its salt or prodrug produced through metabolism or biotransformation in the animal or human body, which exhibits the same or essentially the same biological activity as the specified compound. Such metabolites may result from, for example, oxidation, reduction, hydrolysis, amidation, deamidation, esterification, desertification, enzymatic cleavage, and the like, of the administered compound or salt or prodrug.

As used herein, "prodrugs" refer to any compounds or conjugates which release the active parent drug when administered to an animal or human subject. Prodrugs can be prepared by modifying functional groups present in the compounds in such a way that the modifications are cleavable, either in routine manipulation or in vivo, from the parent compounds. Prodrugs include compounds wherein hydroxyl, amino, sulfhydryl, or carboxyl group is bonded to any group that, when administered to a mammalian subject, is cleavable to form a free hydroxyl, amino, sulfhydryl, or carboxyl group respectively. Examples of prodrugs include, but are not limited to, acetate, formate and benzoate derivatives of alcohol and amine functional groups in the compounds of the present disclosure. Preparation and use of prodrugs is discussed in THiguchi and V. Stella, "Pro-drugs as Novel Delivery Systems", Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Disclosed herein are novel compounds or pharmaceutically acceptable salts which can selectively inhibit DNA-PK. The compounds of the presend disclosure, or a pharmaceutically acceptable salt thereof, when compared with other clinically available DNA-PK inhibitors, exhibit certain improved properties e.g. higher BBB penetration (thus making them potentially useful for the treatment of cancers that have metastasised to the CNS, in particular brain metastases and leptomeningeal metastases), better potency etc. They may also possess favourable toxicity profiles, and/or favourable metabolic or pharmacokinetic profiles, in comparison with known DNA-PK inhibitors.

Therefore, such compounds, or a pharmaceutically acceptable salt thereof, may be especially useful in the treatment of cancer, especially those with brain metastasis.

Synthetic Method

Synthesis of the compounds provided herein, including salts, esters, hydrates, or solvates or stereoisomers thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized in China for the purposes of research and potentially submission to regulatory agencies.

The reactions for preparing compounds of the disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety) and normal phase silica chromatography.

Abbreviations as used herein, are defined as follows: "1×" or "×1" for once, "2×" or "×2" for twice, "3×" or "×3" for thrice, "4×" or "×4" for four times, "5×" or "×5" for five times, "° C." for degrees Celsius, "eq" or "eq." for equivalent or equivalents, "g" for gram or grams, "mg" for milligram or milligrams, "L" for liter or liters, "mL" or "ml" for milliliter or milliliters, "μL" for microliter or microliters, "N" for normal, "M" for molar, "mmol" for millimole or millimoles, "min" for minute or minutes, "h" or "hr" for hour or hours, "r.t." or "rt" for room temperature, "atm" for atmosphere, "psi" for pounds per square inch, "conc." for concentrate, "sat" or "sat'd" for saturated, "MS" or "Mass Spec" for mass spectrometry, "ESI" for electrospray ionization mass spectroscopy, "LCMS" for liquid chromatography mass spectrometry, "HPLC" for high pressure liquid chromatography, "RP" for reverse phase, "TLC" or "tlc" for thin layer chromatography, "SM" for starting material, "NMR" for nuclear magnetic resonance spectroscopy, "$^1H$" for proton, "6" for delta, "s" for singlet, "d" for doublet, "t" for triplet, "q" for quartet, "m" for multiplet, "br" for broad, and "Hz" for hertz. "a", "f", "R", "S", "E", and "Z" are stereochemical designations familiar to one skilled in the art.

Pharmaceutical Composition

The present disclosure provides pharmaceutical compositions comprising at least one compound of the present disclosure. In some embodiments, the pharmaceutical composition comprises more than one compounds of the present disclosure. In some embodiments, the pharmaceutical composition comprises one or more compounds of the present disclosure, and a pharmaceutical acceptable carrier.

The pharmaceutically acceptable carriers are conventional medicinal carriers in the art which can be prepared in a manner well known in the pharmaceutical art. In some embodiments, the compounds of the present disclosure may be admixed with pharmaceutically acceptable carrier for the preparation of pharmaceutical composition.

The term "pharmaceutically acceptable carrier" as used herein refers to a pharmaceutically-acceptable material, composition or vehicle, such as a liquid or solid filler, diluent, excipient, solvent or encapsulating material, involved in carrying or transporting a compound provided herein from one location, body fluid, tissue, organ (interior or exterior), or portion of the body, to another location, body fluid, tissue, organ, or portion of the body. Pharmaceutically acceptable carriers can be vehicles, diluents, excipients, or other materials that can be used to contact the tissues of an animal without excessive toxicity or adverse effects. Exemplary pharmaceutically acceptable carriers include, sugars, starch, celluloses, malt, tragacanth, gelatin, Ringer's solution, alginic acid, isotonic saline, buffering agents, and the like. Pharmaceutically acceptable carrier that can be employed in present disclosure includes those generally known in the art, such as those disclosed in "Remington Pharmaceutical Sciences" Mack Pub. Co., New Jersey (1991), which is incorporated herein by reference.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The form of pharmaceutical compositions depends on a number of criteria, including, but not limited to, route of administration, extent of disease, or dose to be administered. The pharmaceutical compositions can be formulated for oral, nasal, rectal, percutaneous, intravenous, or intramuscular administration. For example, dosage forms for nasal administration may conveniently be formulated as aerosols, solutions, drops, gels or dry powders; dosage forms for intranasal administration, may be formulated as a fluid formulation. In accordance to the desired route of administration, the pharmaceutical compositions can be formulated in the form of tablets, capsule, pill, dragee, powder, granule, sachets, cachets, lozenges, suspensions, emulsions, solutions, syrups, aerosols (as a solid or in a liquid medium), spray, omintment, paste, cream, lotion, gel, patche, inhalant, or suppository.

The pharmaceutical compositions can also be formulated to provide quick, sustained or delayed release of the active ingredient after administration to the patient by employing procedures known in the art. In some embodiments, the pharmaceutical composition is formulated in a sustained released form. As used herein, the term "sustained released form" refers to release of the active agent from the pharmaceutical composition so that it becomes available for bio-absorption in the subject, primarily in the gastrointestinal tract of the subject, over a prolonged period of time (extended release), or at a certain location (controlled release). In some embodiments, the prolonged period of time can be about 1 hour to 24 hours, 2 hours to 12 hours, 3 hours to 8 hours, 4 hours to 6 hours, 1 to 2 days or more. In certain embodiments, the prolonged period of time is at least about 4 hours, at least about 8 hours, at least about 12 hours, or at least about 24 hours. The pharmaceutical composition can be formulated in the form of tablet. For example, release rate of the active agent can not only be controlled by dissolution of the active agent in gastrointestinal fluid and subsequent diffusion out of the tablet or pills independent of pH, but can also be influenced by physical processes of disintegration and erosion of the tablet. In some embodiments, polymeric materials as disclosed in "Medical Applications of Controlled Release," Langer and Wise (eds.), CRC Pres., Boca Raton, Florida (1974); "Controlled Drug Bioavailability," Drug Product Design and Performance, Smolen and Ball (eds.), Wiley, New York (1984); Ranger and Peppas, 1983, J MacromolSci. Rev. Macromol Chem. 23:61; see also Levy et al., 1985, Science 228:190; During et al., 1989, Ann. Neurol. 25:351; Howard et al., 1989, J. Neurosurg. 71:105 can be used for sustained release. The above references are incorporated herein by reference in their entirety.

In certain embodiments, the pharmaceutical compositions comprise about 0.0001 mg to about 100 mg of the compounds of the present disclosure (e.g. about 0.0001 mg to about 10 mg, about 0.001 mg to about 10 mg, about 0.01 mg to about 10 mg, about 0.1 mg to about 10 mg, about 0.1 mg to about 5 mg, about 0.1 mg to about 4 mg, about 0.1 mg to about 3 mg, about 0.1 mg to about 2 mg, about 0.1 mg to about 1 mg, about 0.1 mg to about 0.5 mg, about 1 mg to about 10 mg, about 1 mg to about 5 mg, about 5 mg to about 10 mg, about 5 mg to about 20 mg, about 5 mg to about 30 mg, about 5 mg to about 40 mg, about 5 mg to about 50 mg, about 10 mg to about 100 mg, about 20 mg to about 100 mg, about 30 mg to about 100 mg, about 40 mg to about 100 mg, about 50 mg to about 100 mg). Suitable dosages per subject per day can be from about 0.1 mg to about 10 mg, preferably about 0.1 mg to about 5 mg, about 5 mg to about 10 mg, or about 1 mg to about 5 mg.

In certain embodiments, the pharmaceutical compositions can be formulated in a unit dosage form, each dosage containing from about 0.0001 mg to about 10 mg, about 0.001 mg to about 10 mg, about 0.01 mg to about 10 mg, about 0.1 mg to about 10 mg, about 0.1 mg to about 5 mg, about 0.1 mg to about 4 mg, about 0.1 mg to about 3 mg, about 0.1 mg to about 2 mg, about 0.1 mg to about 1 mg, about 0.1 mg to about 0.5 mg, about 1 mg to about 10 mg, about 5 mg to about 10 mg, about 5 mg to about 20 mg, about 5 mg to about 30 mg, about 5 mg to about 40 mg, about 5 mg to about 50 mg, about 10 mg to about 100 mg, about 20 mg to about 100 mg, about 30 mg to about 100 mg, about 40 mg to about 100 mg, about 50 mg to about 100 mg of the compounds of the present disclosure. The term "unit dosage forms" refers to physically discrete units suitable as unitary dosages for human subjects and other mammals, each unit containing a predetermined quantity of active material calculated to produce the desired therapeutic effect, in association with a suitable pharmaceutical carrier.

In some embodiments, the pharmaceutical compositions comprise one or more compounds of the present disclosure as a first active ingredient, and further comprise a second active ingredient. The second active ingredient can be any immunomodulator or anti-tumour agent known in the art, including without limitation, chemotherapeutics, immunotherapeutics, cell signal transduction inhibitors, cell signal transduction inhibitors, alkylating agents, topoisomerase inhibitors, mitosis inhibitors, antihormonal agents, etc. Examples of such immunomodulators or anti-tumour agents are, platinum based chemotherapeutics (e.g., Cisplatin (DDP), Carboplatin (CBP), Sulfato-1,2-diaminocyclohexane platinum (SUP), Nedaplatin, Oxaliplatin (OXA), Laboplatin), Docetaxel, Paclitaxel, Doxorubicin, Etoposide, Mitoxantrone, CTLA-4 inhibitors, anti-CTLA-4 antibodies, PD-1 inhibitors, PD-L1 inhibitors, anti-PD-1/PD-L1 antibodies, CD39 inhibitors, anti-CD39 antibodies, CD73 inhibitors, anti-CD73 antibodies, CCR2 inhibitors, anti-CCR2 antibodies, EGFR inhibitors, CDK 4/6 inhibitors, MELK inhibitors, OX40 agonists, antiandrogen inhibitors, IgG4 isotype antibodies, tyrosine kinase inhibitors, DNA methyltransferase inhibitors, Hsp90 inhibitors, FGFR inhibitors, mTOR inhibitors, aromatase inhibitors, VEGF inhibitors, LHRH antagonists, PI3K inhibitors, AKT inhibitors, aurora kinase inhibitors, MEK inhibitors, HDAC inhibitors, BET inhibitors, PIK3CA inhibitors, proteasome inhibitors, other SERDs, farnesyltransferase inhibitors, VEGF-A antibodies, ErbB3 (Her3) antibodies, proteasome inhibitors, protein kinase Cβ inhibitors, anti-IGF-1R antibodies, anti-HER2 antibodies, SERMs, IGF inhibitors, anti-IgG antibodies and the like. Representative examples of the anti tumour agents for treating cancers or tumors may include, but are not limited to, cisplatin, carboplatin, SHP, nedaplatin, oxaliplatin, laboplatin, docetaxel, paclitaxel, doxorubicin, etoposide, mitoxantrone, vincristine, vinblastine, gemcitabine, cyclophosphamide, chlormabucil, carmustine, methotrexate, fluorouracil, actinomycin, epirubicin, anthracycline, bleomycin, mitomycin-C, irinotecan, topotecan, teniposide interleukin, interferon, tremelimumab, ipilimumab, pembrolizumab, nivolumab, avelumab, durvalumab, atezolizumab, IPH 52, IPH 53, CPI-006, plozalizumab, MLN1202, cetuximab, lapatinib, erlotinib, gefitinib, neratinib, trastuzumab, ado-trastuzumab emtansine, pertuzumab, MCLA-128, anastrazole, raloxifene, G1T38, tamoxifen, goserelin, enzalutamide, vorinostat, entinostat, sunitinib, pazopanib, bevacizumab, ranibizumab, pegaptanib, cediranib, dasatinib, GDC-0980, gedatolisib, alpelisib, BKM120, copanlisib, AZD8835, GDC-0941, taselisib, temsirolimus, everolimus, sapanisertib, AZD5363, MK2206, panitumumab, pembrolizumab, sorafenib, palbociclib, abemaciclib, ribociclib, crizotinib, dovitinib, ruxolitinib, azacitidine, CC-486, HSP90 ganetespib, Debio 1347, erdafitinib, vitusertib, alisertib, selumetinib, GS-5829, GSK525762, MLN9708, GDC-0810, AFP464, tipifarnib, seribantumab, bortezomib, enzastaurin, AVE1642, xentuzumab, dalotuzumab, AMG 479, and the like.

Examples of such anti-tumour agent can also be found in Cancer Principles and Practice of Oncology by V. T. Devita and S. Hellman (editors), 6th edition (Feb. 15, 2001), Lippincott Williams & Wilkins Publishers. A person of ordinary skill in the art would also be able to discern which combinations of agents would be useful based on the particular characteristics of the drugs and the cancer involved.

According to this aspect of the present disclosure, there is provided a combination suitable for use in the treatment of cancer comprising a compound of formula (I) as defined hereinbefore or a pharmaceutically acceptable salt thereof and any one of the immunomodulators or anti tumour agents listed above.

Therefore, in a further aspect of the present disclosure, there is provided a compound of formula (I) or a pharmaceutically acceptable salt thereof in combination with an immunomodulator or chemotherapeutics selected from one listed above.

Herein, where the term "combination" is used, it is to be understood that this refers to simultaneous, separate or sequential administration. In some embodiments, "combination" refers to simultaneous administration. In another aspect of the present disclosure, "combination" refers to separate administration. In a further aspect of the present disclosure, "combination" refers to sequential administration. Where the administration is sequential or separate, the delay in administering the second component should not be such as to lose the beneficial effect of the combination.

According to a further aspect of the present disclosure, there is provided a pharmaceutical composition which comprises a compound of formula (I) or a pharmaceutically acceptable salt thereof in combination with an immunomodulator or anti-tumour agent selected from those listed above, in association with a pharmaceutically acceptable diluent or carrier.

According to a further aspect of the present disclosure, there is provided a pharmaceutical composition which comprises a compound of formula (I) or a pharmaceutically acceptable salt thereof in combination with an immunomodulator or anti-tumour agent selected from one listed above, in association with a pharmaceutically acceptable diluent or carrier for use in producing an immunomodulating or anti-cancer effect.

According to a further aspect of the present disclosure, there is provided a pharmaceutical composition which comprises a compound of formula (I) or a pharmaceutically acceptable salt thereof in combination with an immunomodulator or anti-tumour agent selected from one listed above, in association with a pharmaceutically acceptable diluent or carrier for use in treating DNA-PK related disorder, for example, NSCLC, RCC, prostate cancer, or breast cancer etc.

According to a further aspect of the present present disclosure, there is provided a kit comprising a compound of formula (I) or a pharmaceutically acceptable salt thereof in combination with an immunomodulator or anti-tumour agent selected from one listed above.

According to a further aspect of the present present disclosure, there is provided a kit comprising:

a) a compound of formula (I) or a pharmaceutically acceptable salt thereof in a first unit dosage form;
b) an immunomodulator or anti-tumour agent selected from one listed above in a second unit dosage form; and
c) container for containing said first and second dosage forms.

In addition to their use in therapeutic medicine, the compounds of formula (I), or a pharmaceutically acceptable salt thereof, are also useful as pharmacological tools in the development and standardisation of in vitro and in vivo test systems for the evaluation of the activity or the expression of DNA-PK in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the present disclosure, described herein also apply.

Method for Treatment

The present disclosure provides a method of treating DNA-PK related disorders, comprising administering to a subject an effective amount of one or more compounds, pharmaceutically acceptable salts thereof or the pharmaceutical composition of the present disclosure.

The present disclosure also provides a method of treating DNA-PK related disorders. In certain embodiments, the method comprises administering to a subject an effective amount of one or more compounds, pharmaceutically acceptable salts thereof or the pharmaceutical composition of the present disclosure.

As used herein, the term "DNA-PK related disorders" refers to diseases whose onset or development or both are associated with the expression or activity of DNA-PK. Examples include but are not limited to, hyperproliferative disorder (e.g., cancer).

In some embodiments, the DNA-PK related disorders is cancer, preferably a DNA-PK overexpressing cancer. A "DNA-PK overexpressing cancer" is one which has significantly higher levels of DNA-PK protein in a cancer or tumor cell, compared to a noncancerous cell of the same tissue type. Such overexpression may be caused by gene amplification or by increased transcription or translation. DNA-PK overexpression may be determined in a diagnostic or prognostic assay by evaluating increased levels of the DNA-PK proteins present in a cell (e.g. via an immunohistochemistry assay; IHC). Alternatively, or additionally, one may measure levels of DNA-PK encoding nucleic acid in the cell, e.g. via fluorescent in situ hybridization (FISH; see WO98/45479 published October, 1998), southern blotting, or polymerase chain reaction (PCR) techniques, such as real time quantitative PCR (RT-PCR)(Methods 132: 73-80 (1990)). Aside from the above assays, various in vivo assays are available to one skilled in the art. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

In particular, the cancers include but are not limited to, lung cancer (e.g. non-small cell lung cancer (NSCLC), small cell lung cancer, lung adenocarcinoma, large cell lung cancer, squamous cell lung cancer), renal cell carcinoma (RCC), prostate cancer, breast cancer, ovarian cancer, endometrial cancer, cervical cancer, bone cancer, uterine cancer, colon cancer, leukemia, glioblastoma, melanoma, chondrosarcoma, brain cancer, cholangiocarcinoma, osteosarcoma, lymphoma, adenoma, myeloma, hepatocellular carcinoma, adrenocortical carcinoma, pancreatic cancer, bladder cancer, liver cancer, gastric cancer, colorectal cancer, esophageal cancer, testicular cancer, skin cancer, kidney cancers, mesothelioma, neuroblastoma, thyroid cancer, head and neck cancers, esophageal cancers, eye cancers, nasopharyngeal cancer, or oral cancer. In some embodiments, the cancer is NSCLC, RCC, prostate cancer, or breast cancer. The cancer as mentioned herein can be at any stage, unless otherwise specified. In some embodiments, the cancer is early stage cancer. In some embodiments the cancer is locally advanced cancer. In some embodiments the cancer is locally advanced and/or metastatic cancer. In some embodiments the cancer is invasive cancer. In some embodiments the cancer is a cancer resistant to existing therapies.

As used herein, the terms "treatment", "treat" and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to present or delay their recurrence.

In some embodiments, the one or more compounds, pharmaceutically acceptable salts thereof or the pharmaceutical composition provided herein is administered via a parenteral route or a non-parenteral route. In some embodiments, the one or more compounds pharmaceutically acceptable salts, hydrates, solvates or stereoisomers thereof or the pharmaceutical composition is administered orally, enterally, buccally, nasally, intranasally, transmucosally, epidermally, transdermally, dermally, ophthalmically, pulmonary, rectally, sublingually, vaginally, topically, subcutaneously, intravenously, intramuscularly, intraarterially, intrathecally, intracapsularly, intraorbitally, intracardiacally, intradermally, intraperitoneally, transtracheally, subcuticularly, intra-articularly, subcapsularly, intraspinally, subarachnoidly, or intrasternally.

The compounds provided herein can be administrated in pure form, in a combination with other active ingredients or in the form of pharmaceutically compositions of the present disclosure. In some embodiments, the compounds provided herein can be administered to a subject in need concurrently or sequentially in a combination with one or more anticancer or anti-inflammatory agent(s) known in the art. The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

In some embodiments, the administration is conducted once a day, twice a day, three times a day, or once every two days, once every three days, once every four days, once every five days, once every six days, once a week.

The therapeutically effective amount of a compound or a pharmaceutically acceptable salts thereof as provided herein will depend on various factors known in the art, such as body weight, age, past medical history, present medications, state of health of the subject and potential for cross-reaction, allergies, sensitivities and adverse side-effects, as well as the administration route and extent of disease development. Dosages may be proportionally reduced or increased by one skilled in the art (e.g. physician or veterinarian) as indicated by these and other circumstances or requirements.

In some embodiments, the one or more compounds, pharmaceutically acceptable salts thereof or the pharmaceutical composition provided herein is administered orally. For oral administration, any dose is appropriate that achieves the desired goals. In some embodiments, suitable daily dosages are between about 0.001-100 mg, preferably between 0.1 mg and 5 g, more preferably between 5 mg and 1 g, more preferably between 10 mg and 500 mg, and the administration is conducted once a day, twice a day, three times a day, every day, or 3-5 days a week. In some embodiments, the dose of the one or more compounds, pharmaceutically acceptable salts thereof or the pharmaceutical composition provided herein ranges between about 0.0001 mg, preferably, 0.001 mg, 0.01 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg per day.

Use of Compounds

In certain embodiments, the present disclosure provides use of the compounds, pharmaceutically acceptable salts thereof, or pharmaceutical composition of the present disclosure in the manufacture of medicaments for treating DNA-PK related disorders. In certain embodiments, the DNA-PK related disorders includes cancers.

The compounds and pharmaceutical compositions thereof in the present disclosure can be used in the prevention or treatment of the onset or development of any of DNA-PK related disorders (expression or activities) in mammals especially in human.

In such situation, the present disclosure also provides a method of screening patient suitable for treating with the compounds or pharmaceutical composition of the present disclosure alone or combined with other ingredients (e.g. a second active ingredient, e.g. anti-inflammatory or anticancer agent). The method includes sequencing the tissue samples from patients and detecting the accumulation of DNA-PK in the patient.

EXAMPLES

The followings further explain the general methods of the present disclosure. The compounds of the present disclosure may be prepared by the methods known in the art. The following illustrates the detailed preparation methods of the preferred compounds of the present disclosure. However, they are by no means limiting the preparation methods of the compounds of the present disclosure.

SYNTHETIC EXAMPLES

Synthesis of the compounds provided herein, including pharmaceutically acceptable salts thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized for the purposes of research and potentially submission to regulatory agencies.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g. temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, $3^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g. $^{1}H$ or $^{13}C$), infrared spectroscopy, spectrophotometry (e.g. UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety), and normal phase silica chromatography.

The structures of the compounds in the examples are characterized by nuclear magnetic resonance (NMR) or/and liquid chromatography-mass spectrometry (LC-MS). NMR chemical shift (δ) is given in the unit of $10^{-6}$ (ppm). $^{1}H$-NMR spectra is recorded in dimethyl sulfoxide-d6 (DMSO-d6) or $CDCl_3$ or $CD_3OD$ or $D_2O$ or Acetone_$d_6$ or $CD_3CN$ (from Innochem or Sigma-Aldrich or Cambridge Isotope Lab., Inc.) on Bruker AVANCE NMR (300 MHz or 400 MHz) spectrometers using ICON-NMR (under TopSpin program control) with tetramethylsilane as an internal standard.

MS measurement is carried out using Shimadzu 2020 Mass Spectrometer with an electrospray source at positive and negative ion mode.

High Performance Liquid Chromatography (HPLC) measurement is carried out on Shimadzu LC-20AD systems or Shimadzu LC-20ADXR systems or Shimadzu LC-30AD systems using Shim-pack XR-ODS C18 column (3.0×50 mm, 2.2 m), or Ascentis Express C18 column (2.1×50 mm, 2.7 μm), or Agilent Poroshell HPH-C18 column (3.0×50 mm, 2.7 m).

Thin layer chromatography is carried out using Sinopharm Chemical Reagent Beijing Co., Ltd. and Xinnuo Chemical silica gel plates. The silica gel plates used for thin layer chromatography (TLC) are 175-225 μm. The silica gel plates used for separating and purifying products by TLC are 1.0 mm.

Purified chromatographic column uses the silica gel as the carrier (100~200, 200~300 or 300~400 mesh, produced by Rushanshi Shangbang Xincailiao Co., Ltd. or Rushan Taiyang Desiccant Co., Ltd. etc.), or flash column (reversed phase C18 column 20-45 m, produced by Agela Technologies) in Agela Technologies flash system. The size of columns are adjusted according to the amount of compounds.

The known starting materials of the present disclosure can be synthesized by using or according to the known methods in the art, or can be purchased from Alfa Aesar, TCI, Sigma-Aldrich, Bepharm, Bide pharmatech, PharmaBlock, Enamine, Innochem and JW&Y PharmLab etc.

Unless otherwise specified, the reactions are all carried out under argon or nitrogen atmosphere. Argon or nitrogen atmosphere refers to that the reaction flask is connected to an argon or nitrogen balloon with a volume of about 1 L. Hydrogenation is usually carried out under pressure. Unless otherwise specified, the reaction temperature in the examples is ambient temperature, which is 10° C.~30° C. The reaction progress is monitored by TLC or/and LC-MS. The eluent systems used for the reactions include dichloromethane-methanol system and petroleum ether-ethyl acetate system. The volume ratios of the solvents are adjusted according to the different polarities of compounds.

The elution system of column chromatography used for purifying compounds and eluent system of TLC include dichloromethane-methanol system and petroleum ether-ethyl acetate system. The volume ratios of the solvents are adjusted according to the different polarities of compounds. A small amount of alkaline or acidic agents (0.1%~1%) such as formic acid, or acetic acid, or TFA, or ammonia can be added for adjustment.

Abbreviations for chemicals used in the synthesis of the compounds provided herein are listed below:

| | |
|---|---|
| $(Boc)_2O$ | Di-tert-butyl dicarbonate |
| Brettphos | 2-(Dicyclohexylphosphino)3,6-dimethoxy-2',4',6'-triisopropyl-1,1'-biphenyl |
| $CH_3CN$ | Acetonitrile |
| $Cs_2CO_3$ | Caesium carbonate |
| DCM | Dichloromethane |
| DIEA | N,N-Diisopropylethylamine |
| DMF | N,N-Dimethylformamide |
| DMSO | Dimethyl sulfoxide |
| EtOAc | Ethyl acetate |
| EtOH | Ethanol |
| HATU | 1-[Bis(dimethylamino)methylene]-1H-1,2,3-triazolo[4,5-b]pyridinium 3-oxid hexafluorophosphate |
| $K_2CO_3$ | Potassium carbonate |
| LiOH | Lithium hydroxide |
| MeOH | Methanol |
| 2-MeTHF | 2-Methyltetrahydrofuran |
| $Mg(OTf)_2$ | Magnesium trifluoromethanesulfonate |
| MTBE | Methyl tert-butyl ether |
| $Na_2CO_3$ | Sodium Carbonate |
| NaCl | Sodium chloride |
| $NaHCO_3$ | Sodium bicarbonate |
| NaOH | Sodium hydroxide |
| $Pd(dppf)Cl_2$ | [1,1'-Bis(diphenylphosphino)ferrocene]dichloropalladium(II) |
| PE | Petroleum ether |
| TEA | Triethylamine |
| TFA | Trifluoroacetic acid |
| THF | Tetrahydrofuran |
| TosMIC | toluenesulfonylmethyl isocyanide |

Example 1

Preparation of 1-methyl-N-(7-methyl-[1,2,4]triazolo[1,5-a]pyridin-6-yl)-3-(tetrahydro-2H-pyran-4-yl)-1H-pyrazolo[4,3-d]pyrimidin-5-amine (Ex. 1)

SCHEME 1

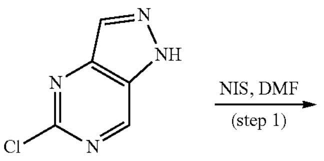

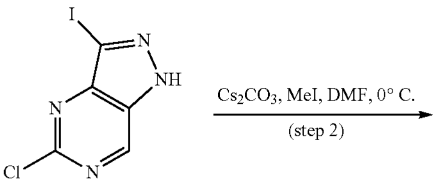

1

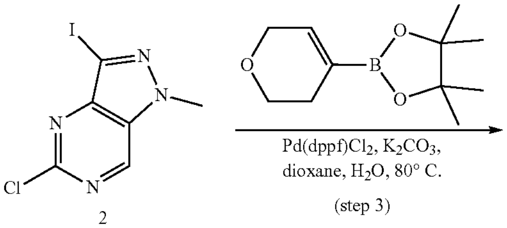

2

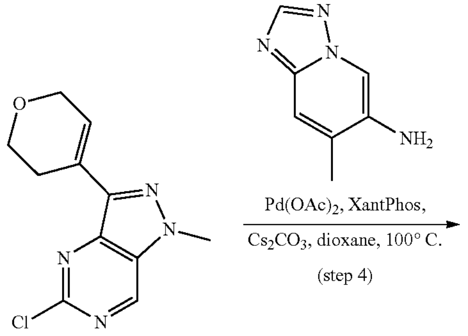

3

-continued

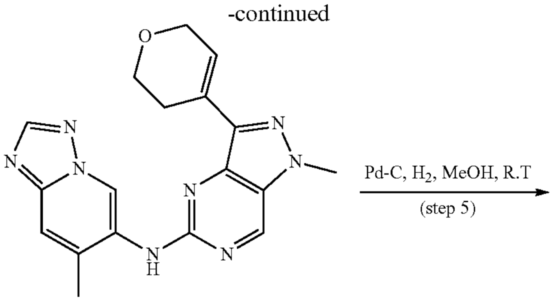

4

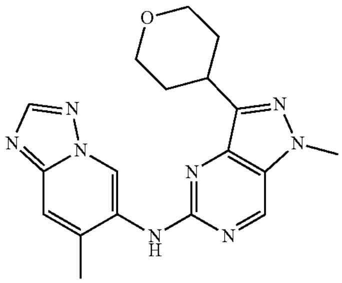

Example 1

Step 1. 5-chloro-3-iodo-1H-pyrazolo[4,3-d]pyrimidine

A mixture of 5-chloro-1H-pyrazolo[4,3-d]pyrimidine (3.00 g, 19.410 mmol, 1.00 equiv) and NIS (7.86 g, 34.936 mmol, 1.80 equiv) in DMF (60.00 mL) was stirred for overnight at 0° C. under air atmosphere. The resulting mixture was extracted with EtOAc (3×150 mL). The combined organic layers were washed with brine (3×200 mL). The combined organic layers were washed with $Na_2S_2O_3$ (3×200 mL), dried over anhydrous $Na_2SO_4$. After filtration, the filtrate was concentrated under reduced pressure. The residue was purified by silica gel column chromatography, eluted with PE/EtOAc (20:1) to afford 5-chloro-3-iodo-1H-pyrazolo[4,3-d]pyrimidine (2.4 g, 44.09%) as a yellow solid. LCMS: m/z (ESI), $[M+H]^+$=281.0.

Step 2. 5-chloro-3-iodo-1-methyl-1H-pyrazolo[4,3-d]pyrimidine

A mixture of $Cs_2CO_3$ (3.49 g, 10.697 mmol, 3 equiv), $CH_3I$ (2.53 g, 17.828 mmol, 5.00 equiv) and 5-chloro-3-iodo-1H-pyrazolo[4,3-d]pyrimidine (1.00 g, 3.566 mmol, 1.00 equiv) in DMF (20.00 mL) was stirred for 1 h at 0° C. under nitrogen atmosphere. The resulting mixture was diluted with water (100 mL) and extracted with EtOAc (3×80 mL). The combined organic layers were washed with brine (3×100 mL), dried over anhydrous $Na_2SO_4$. After filtration, the filtrate was concentrated under reduced pressure. The crude product was re-crystallized from EtOAc/PE (1:5 300 mL) to afford 5-chloro-3-iodo-1-methyl-1H-pyrazolo[4,3-d]pyrimidine (850 mg, 80.95%) as a yellow solid. LCMS: m/z (ESI), $[M+H]^+$=295.0.

Step 3. 5-chloro-3-(3,6-dihydro-2H-pyran-4-yl)-1-methyl-1H-pyrazolo[4,3-d]pyrimidine $K_2CO_3$ (1210.85 mg, 8.761 mmol, 3 equiv), Pd(dppf)$Cl_2$ $CH_2Cl_2$ (476.98 mg, 0.584 mmol, 0.2 equiv), 2-(3,6-dihydro-2H-pyran-4-yl)-4,4,5,5-tetramethyl-1,3,2-dioxaborolane (797.57 mg, 3.797 mmol, 1.3 equiv) and 5-chloro-3-iodo-1-methyl-1H-pyrazolo[4,3-d]pyrimidine (860.00 mg, 2.920 mmol, 1.00 equiv) in dioxane (15.00 mL) and $H_2O$ (3.00 mL) was stirred for 16 hrs at 80° C. under nitrogen atmosphere. The resulting mixture was diluted with water (100 mL). The resulting mixture was extracted with $CH_2Cl_2$/MeOH=12:1 (3×50 mL). The combined organic layers were washed with brine (2×100 mL), dried over anhydrous $Na_2SO_4$. After filtration, the filtrate was concentrated under reduced pressure. The residue was purified by Prep-TLC ($CH_2Cl_2$/MeOH=12:1) to afford 5-chloro-3-(3,6-dihydro-2H-pyran-4-yl)-1-methyl-1H-pyrazolo[4,3-d]pyrimidine (380 mg, 51.90%) as a grey solid. LCMS: m/z (ESI), $[M+H]^+$=251.2.

Step 4. 3-(3,6-dihydro-2H-pyran-4-yl)-1-methyl-N-(7-methyl-[1,2,4]triazolo[1,5-a]pyridin-6-yl)-1H-pyrazolo[4,3-d]pyrimidin-5-amine A mixture of $Cs_2CO_3$ (2599.38 mg, 7.978 mmol, 2.50 equiv), XantPhos (553.94 mg, 0.957 mmol, 0.30 equiv), $Pd(OAc)_2$ (143.29 mg, 0.638 mmol, 0.20 equiv), 7-methyl-[1,2,4]triazolo[1,5-a]pyridin-6-amine (567.40 mg, 3.829 mmol, 1.20 equiv) and 5-chloro-3-(3,6-dihydro-2H-pyran-4-yl)-1-methyl-1H-pyrazolo[4,3-d]pyrimidine (800.00 mg, 3.191 mmol, 1.00 equiv) in dioxane (20.00 mL) was stirred for overnight at 100° C. under nitrogen atmosphere. The resulting mixture was diluted with water (200 mL). The resulting mixture was extracted with $CH_2Cl_2$/MeOH=(12:1) (3×200 mL), dried over anhydrous $Na_2SO_4$. After filtration, the filtrate was concentrated under reduced pressure. The crude product was re-crystallized from EtOAc/PE (1:6 300 mL) to afford 3-(3,6-dihydro-2H-pyran-4-yl)-1-methyl-N-[7-methyl-[1,2,4]triazolo[1,5-a]pyridin-6-yl]-1H-pyrazolo[4,3-d]pyrimidin-5-amine (600 mg, 51.88%) as a brown solid. LCMS: m/z (ESI), $[M+H]^+$=363.3.

Step 5. 1-methyl-N-[7-methyl-[1,2,4]triazolo[1,5-a]pyridin-6-yl]-3-(oxan-4-yl)-1H-pyrazolo [4,3-d]pyrimidin-5-amine. (Ex. 1)

A mixture of Pd/C (47.92 mg, 0.450 mmol, 1.36 equiv) and 3-(3,6-dihydro-2H-pyran-4-yl)-1-methyl-N-[7-methyl-[1,2,4]triazolo[1,5-a]pyridin-6-yl]-1H-pyrazolo[4,3-d]pyrimidin-5-amine (120 mg, 0.331 mmol, 1 equiv) in MeOH (200 mL) and THF (100 mL) was stirred for 2 hours at room temperature under hydrogen atmosphere. The resulting mixture was filtered, the filter cake was washed with MeOH (3×100 mL). The filtrate was concentrated under reduced pressure. The crude product (120 mg) was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; Gradient: 25 B to 51 B in 7 min;) to afford 1-methyl-N-[7-methyl-[1,2,4]triazolo[1,5-a]pyridin-6-yl]-3-(oxan-4-yl)-1H-pyrazolo[4,3-d]pyrimidin-5-amine (55 mg, 45.12%) as a white solid. LCMS: m/z (ESI), $[M+H]^+$=365.2. $^1H$ NMR (300 MHz, DMSO-$d_6$) δ 1.95 (4H, t), 2.42 (3H, d), 3.14-3.30 (1H, m), 3.47 (2H, d), 3.93 (2H, d), 4.04 (3H, s), 7.71 (1H, t), 8.37 (1H, s), 8.84 (1H, s), 9.15 (1H, s), 9.34 (1H, s)

Example 2

Preparation of 1-methyl-N-(7-methyl-[1,2,4]triazolo[1,5-a]pyridin-6-yl)-3-(tetrahydro-2H-pyran-4-yl)-1H-pyrazolo[4,3-d]pyrimidin-5-amine (Ex. 2) and 3-(3,6-dihydro-2H-pyran-4-yl)-1-methyl-N-[7-methylimidazo[1,2-a]pyridin-6-yl]pyrazolo[4,3-d]pyrimidin-5-amine. (Ex. 6)

SCHEME 2

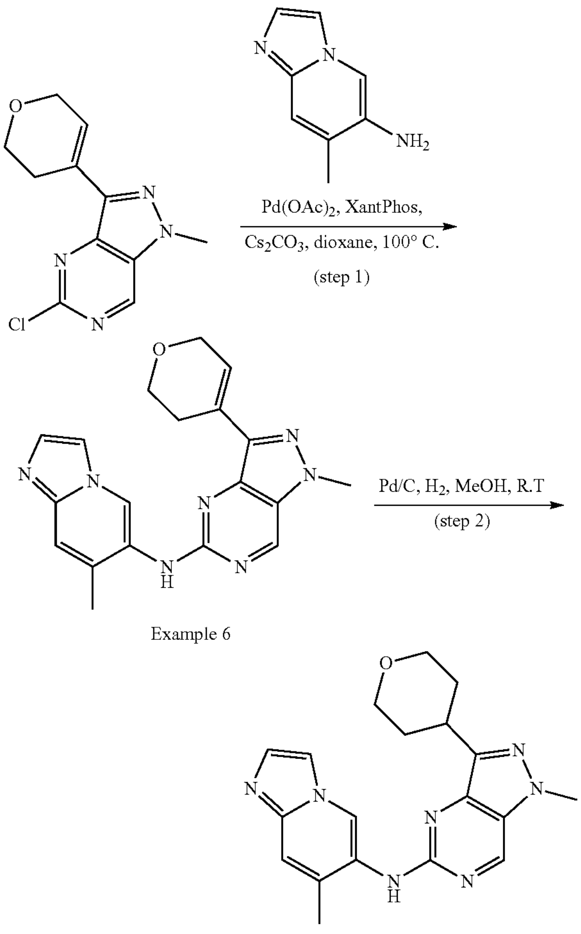

Example 6

Example 2

Step 1. 3-(3,6-dihydro-2H-pyran-4-yl)-1-methyl-N-[7-methylimidazo[1,2-a]pyridin-6-yl]pyrazolo[4,3-d]pyrimidin-5-amine. (Ex. 6)

A mixture of $Cs_2CO_3$ (682.34 mg, 2.094 mmol, 2.5 equiv), XantPhos (96.94 mg, 0.168 mmol, 0.2 equiv), $Pd(OAc)_2$ (37.61 mg, 0.168 mmol, 0.2 equiv), 7-methylimidazo[1,2-a]pyridin-6-amine (147.95 mg, 1.005 mmol, 1.2 equiv) and 5-chloro-3-(3,6-dihydro-2H-pyran-4-yl)-1-methylpyrazolo[4,3-d]pyrimidine (210.00 mg, 0.838 mmol, 1.00 equiv) in dioxane (6.00 mL) was stirred for overnight at 100° C. under nitrogen atmosphere. Desired product could be detected by LCMS. The resulting mixture was filtered, the filter cake was washed with DCM (3×50 mL). The filtrate was concentrated under reduced pressure. The residue was purified by Prep-TLC ($CH_2Cl_2$/MeOH=12:1) to afford crude product. The crude product (170 mg) was purified by Prep-HPLC with the following conditions (Column: XBridge Prep OBD C18 Column, 19*250 mm, 5 um; Mobile Phase A: Water (0.05% $NH_3 \cdot H_2O$), Mobile Phase B: ACN; Flow rate: 60 mL/min; Gradient: 26 B to 36 B in 7 min) to afford 3-(3,6-dihydro-2H-pyran-4-yl)-1-methyl-N-[7-methylimidazo[1,2-a]pyridin-6-yl]pyrazolo[4,3-d]pyrimidin-5-amine (100 mg, 57.65%) as a yellow solid. LCMS: m/z (ESI), $[M+H]^+$=362.2. $^1H$ NMR (300 MHz, DMSO-$d_6$) δ 2.30 (3H, d), 2.58 (2H, s), 3.83 (2H, t), 4.06 (3H, s), 4.25 (2H, d), 7.07-7.12 (1H, m), 7.43 (1H, d), 7.49 (1H, d), 7.84 (1H, t), 8.81 (2H, d), 9.14 (1H, s)

Step 2. 1-methyl-N-[7-methylimidazo[1,2-a]pyridin-6-yl]-3-(oxan-4-yl)pyrazolo[4,3-d]pyrimidin-5-amine. (Ex. 2)

A mixture of Pd/C (70.67 mg, 0.664 mmol, 3.00 equiv) and 3-(3,6-dihydro-2H-pyran-4-yl)-1-methyl-N-[7-methylimidazo[1,2-a]pyridin-6-yl]pyrazolo[4,3-d]pyrimidin-5-amine (80.00 mg, 0.221 mmol, 1.00 equiv) in MeOH (20.00 mL) was stirred for 3 hours at 40° C. under hydrogen atmosphere. Desired product could be detected by LCMS. The resulting mixture was filtered, the filter cake was washed with MeOH (3×10 mL). The filtrate was concentrated under reduced pressure. The crude product (50 mg) was purified by Prep-HPLC with the following conditions (Column: XBridge Prep OBD C18 Column, 19*250 mm, 5 um; Mobile Phase A: Water (0.05% $NH_3 \cdot H_2O$), Mobile Phase B: ACN; Flow rate: 60 mL/min; Gradient: 22 B to 33 B in 7 min; RT1:6.63) to afford 1-methyl-N-[7-methylimidazo[1,2-a]pyridin-6-yl]-3-(oxan-4-yl)pyrazolo[4,3-d]pyrimidin-5-amine (20 mg, 24.61%) as a yellow solid. LCMS: m/z (ESI), $[M+H]^+$=364.2. $^1H$ NMR (300 MHz, DMSO-$d_6$) δ 1.96 (4H, d), 2.28 (3H, d), 3.21 (1H, t), 3.47 (2H, d), 3.93 (2H, d), 4.03 (3H, s), 7.42 (1H, q), 7.49 (1H, d), 7.81 (1H, t), 8.69 (1H, s), 8.84 (1H, s), 9.09 (1H, s)

Example 3

Preparation of 7-methyl-N-(5-methyl-7-(tetrahydro-2H-pyran-4-yl)-5H-pyrrolo[3,2-d]pyrimidin-2-yl)-[1,2,4]triazolo[1,5-a]pyridin-6-amine (Ex. 3)

SCHEME 3

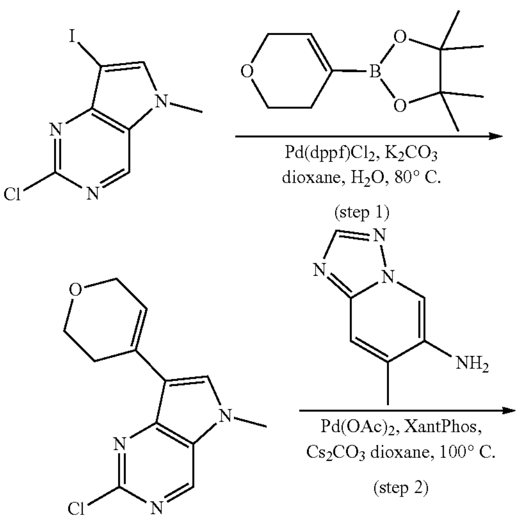

1

-continued

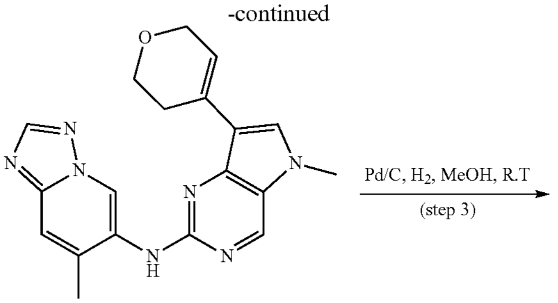

2

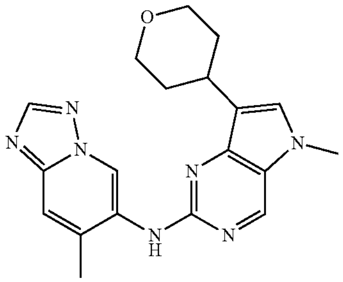

Example 3

Step 1. 2-chloro-7-(3,6-dihydro-2H-pyran-4-yl)-5-methyl-5H-pyrrolo[3,2-d]pyrimidine A mixture of 2-chloro-7-iodo-5-methylpyrrolo[3,2-d]pyrimidine (300.00 mg, 1.022 mmol, 1.00 equiv), 2-(3,6-dihydro-2H-pyran-4-yl)-4,4,5,5-tetramethyl-1,3,2-dioxaborolane (279.16 mg, 1.329 mmol, 1.30 equiv), Pd(dppf)$Cl_2$ (149.59 mg, 0.204 mmol, 0.2 equiv) and $K_2CO_3$ (423.81 mg, 3.067 mmol, 3 equiv) in dioxane (6.00 mL) and $H_2O$ (1.20 mL) was stirred for 3 hs at 80° C. under nitrogen atmosphere. The resulting mixture was concentrated under reduced pressure. The residue was purified by Prep-TLC (PE/EtOAc 1:3) to afford 2-chloro-7-(3,6-dihydro-2H-pyran-4-yl)-5-methylpyrrolo[3,2-d]pyrimidine (196 mg, 76.79%) as a brown solid. LCMS: m/z (ESI), $[M+H]^+$=250.2.

Step 2. 7-(3,6-dihydro-2H-pyran-4-yl)-5-methyl-N-[7-methyl-[1,2,4]triazolo[1,5-a]pyridin-6-yl]pyrrolo[3,2-d]pyrimidin-2-amine A mixture of 2-chloro-7-(3,6-dihydro-2H-pyran-4-yl)-5-methylpyrrolo[3,2-d]pyrimidine (196.00 mg, 0.785 mmol, 1.00 equiv), 7-methyl-[1,2,4]triazolo[1,5-a]pyridin-6-amine (139.56 mg, 0.942 mmol, 1.20 equiv), Pd$(AcO)_2$ (35.25 mg, 0.157 mmol, 0.20 equiv), XantPhos (136.25 mg, 0.235 mmol, 0.30 equiv) and $Cs_2CO_3$ (639.37 mg, 1.962 mmol, 2.50 equiv) in dioxane (3.00 mL) was stirred for 3 hs at 100° C. under nitrogen atmosphere. The resulting mixture was concentrated under vacuum. The residue was purified by Prep-TLC ($CH_2Cl_2$/MeOH=10:1) to afford 7-(3,6-dihydro-2H-pyran-4-yl)-5-methyl-N-[7-methyl-[1,2,4]triazolo[1,5-a]pyridin-6-yl]pyrrolo[3,2-d]pyrimidin-2-amine (170 mg, 59.93%) as a yellow solid. LCMS: m/z (ESI), $[M+H]^+$=362.3.

Step 3. 7-methyl-N-(5-methyl-7-(tetrahydro-2H-pyran-4-yl)-5H-pyrrolo[3,2-d]pyrimidin-2-yl)-[1,2,4]triazolo[1,5-a]pyridin-6-amine (Ex. 3)

A mixture of 7-(3,6-dihydro-2H-pyran-4-yl)-5-methyl-N-[7-methyl-[1,2,4]triazolo[1,5-a]pyridin-6-yl]pyrrolo[3,2-d]

pyrimidin-2-amine (170.00 mg, 0.470 mmol, 1.00 equiv) and Pd/C (250.29 mg, 2.352 mmol, 5.00 equiv) in MeOH (20.00 mL) and THF (50.00 mL) was stirred for overnight at room temperature under hydrogen atmosphere. The resulting mixture was filtered, the filter cake was washed with MeOH (5×30 mL). The filtrate was concentrated under reduced pressure to afford crude product. The crude product (100 mg) was purified by Prep-HPLC with the following conditions (Column: XBridge Prep OBD C18 Column, 19*250 mm, 5 um; Mobile Phase A: Water (0.05% $NH_3 \cdot H_2O$), Mobile Phase B: ACN; Flow rate: 25 mL/min; Gradient: 30 B to 45 B in 7 min; RT1:6.02) to afford 5-methyl-N-[7-methyl-[1,2,4]triazolo[1,5-a]pyridin-6-yl]-7-(oxan-4-yl)pyrrolo[3,2-d]pyrimidin-2-amine (29 mg, 16.96%) as a white solid. LCMS: m/z (ESI), $[M+H]^+$=364.3. $^1$H NMR (300 MHz, DMSO-$d_6$) δ 1.76 (2H, d), 1.88-2.01 (2H, m), 2.46 (3H, d), 3.02 (1H, t), 3.47 (2H, td), 3.80 (3H, s), 3.88-4.05 (2H, m), 7.51 (1H, s), 7.61-7.75 (1H, m), 8.33 (2H, d), 8.74 (1H, s), 9.49 (1H, s)

Example 4

Preparation of 3-isopropyl-1-methyl-N-(7-methyl-[1,2,4]triazolo[1,5-a]pyridin-6-yl)-1H-pyrazolo[4,3-d]pyrimidin-5-amine (Ex. 4)

SCHEME 4

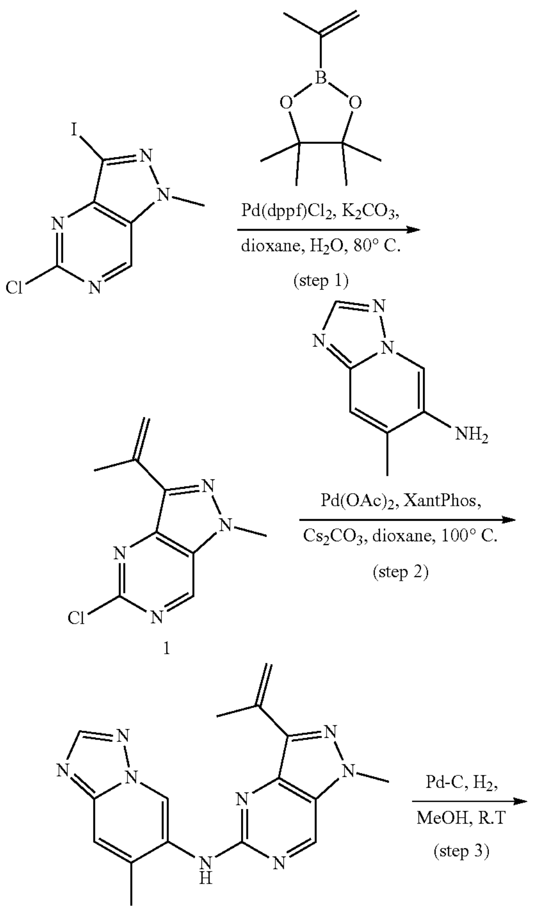

1

2

-continued

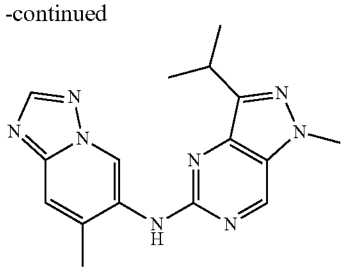

Example 4

Step 1. 5-chloro-1-methyl-3-(prop-1-en-2-yl)-1H-pyrazolo[4,3-d]pyrimidine

A mixture of Pd(dppf)$Cl_2$ (124.24 mg, 0.170 mmol, 0.2 equiv), $K_2CO_3$ (293.33 mg, 2.122 mmol, 2.5 equiv), 4,4,5,5-tetramethyl-2-(prop-1-en-2-yl)-1,3,2-dioxaborolane (213.99 mg, 1.273 mmol, 1.5 equiv) and 5-chloro-3-iodo-1-methylpyrazolo[4,3-d]pyrimidine (250.00 mg, 0.849 mmol, 1.00 equiv) in dioxane (5.00 mL) and $H_2O$ (1.00 mL) was stirred for 2 hours at 80° C. under nitrogen atmosphere. Desired product could be detected by LCMS. The resulting mixture was concentrated under reduced pressure. The residue was purified by Prep-TLC (PE/EtOAc 1:3) to afford 5-chloro-1-methyl-3-(prop-1-en-2-yl)pyrazolo[4,3-d]pyrimidine (130 mg, 73.39%) as a pink solid. LCMS: m/z (ESI), $[M+H]^+$=209.6. $^1$H NMR (300 MHz, DMSO-$d_6$) δ 2.22 (3H, t), 4.18 (3H, s), 5.50 (1H, p), 6.43 (1H, d), 9.45 (1H, s)

Step 2. 1-methyl-N-(7-methyl-[1,2,4]triazolo[1,5-a]pyridin-6-yl)-3-(prop-1-en-2-yl)-1H-pyrazolo[4,3-d]pyrimidin-5-amine A mixture of $Cs_2CO_3$ (468.47 mg, 1.438 mmol, 2.5 equiv), XantPhos (66.56 mg, 0.115 mmol, 0.2 equiv), $Pd(AcO)_2$ (25.82 mg, 0.115 mmol, 0.2 equiv), 7-methyl-[1,2,4]triazolo[1,5-a]pyridin-6-amine (127.82 mg, 0.863 mmol, 1.50 equiv) and 5-chloro-1-methyl-3-(prop-1-en-2-yl)pyrazolo[4,3-d]pyrimidine (120.00 mg, 0.575 mmol, 1.00 equiv) in dioxane (4.00 mL) was stirred for 3 hours at 100° C. under nitrogen atmosphere. Desired product could be detected by LCMS. The resulting mixture was concentrated under reduced pressure. The residue was purified by Prep-TLC ($CH_2Cl_2$/MeOH=15:1) to afford 1-methyl-N-[7-methyl-[1,2,4]triazolo[1,5-a]pyridin-6-yl]-3-(prop-1-en-2-yl)pyrazolo[4,3-d]pyrimidin-5-amine (90 mg, 48.85%) as a yellow solid. LCMS: m/z (ESI), $[M+H]^+$=321.3. $^1$H NMR (300 MHz, DMSO-$d_6$) δ 2.18 (3H, s), 2.45 (3H, d), 4.09 (3H, d), 5.33 (1H, d), 6.35 (1H, d), 7.70-7.78 (1H, m), 8.38 (1H, s), 8.96 (1H, s), 9.22 (1H, s), 9.37 (1H, s)

Step 3. 3-isopropyl-1-methyl-N-(7-methyl-[1,2,4]triazolo[1,5-a]pyridin-6-yl)-1H-pyrazolo[4,3-d]pyrimidin-5-amine (Ex. 4)

A mixture of Pd/C (89.69 mg, 0.843 mmol, 3 equiv) and 1-methyl-N-[7-methyl-[1,2,4]triazolo[1,5-a]pyridin-6-yl]-3-(prop-1-en-2-yl)pyrazolo[4,3-d]pyrimidin-5-amine (90.00 mg, 0.281 mmol, 1.00 equiv) in MeOH (10.00 mL) was stirred for overnight at room temperature under hydrogen atmosphere. Desired product could be detected by LCMS. The resulting mixture was filtered, the filter cake was washed with MeOH (4×50 mL). The filtrate was concentrated under reduced pressure. The residue was purified by Prep-TLC ($CH_2Cl_2$: MeOH 12:1) to afford crude product. The crude product (80 mg) was purified by Prep-HPLC with the following conditions (Column: XBridge Prep OBD C18 Column, 19*250 mm, 5 um; Mobile Phase A: Water (0.05% $NH_3 \cdot H_2O$), Mobile Phase B: MeOH; Flow rate: 25 mL/min; Gradient 58 B to 70 B in 7 min; RT1 5.57) to afford 3-isopropyl-1-methyl-N-[7-methyl-[1,2,4]triazolo[1,5-a]pyridin-6-yl]pyrazolo[4,3-d]pyrimidin-5-amine (50 mg, 54.66%) as a white solid. LCMS: m/z (ESI), $[M+H]^+$=323.2. $^1$H NMR (300 MHz, DMSO-$d_6$) δ 1.39 (6H, d), 2.45 (3H, d), 3.18-3.34 (1H, m), 4.04 (3H, s), 7.69-7.75 (1H, m), 8.37 (1H, s), 8.79 (1H, s), 9.16 (1H, s), 9.44 (1H, s)

Example 5

Preparation of 3-cyclohexyl-1-methyl-N-(7-methyl-[1,2,4]triazolo[1,5-a]pyridin-6-yl)-1H-pyrazolo[4,3-d]pyrimidin-5-amine (Ex. 5)

SCHEME 5

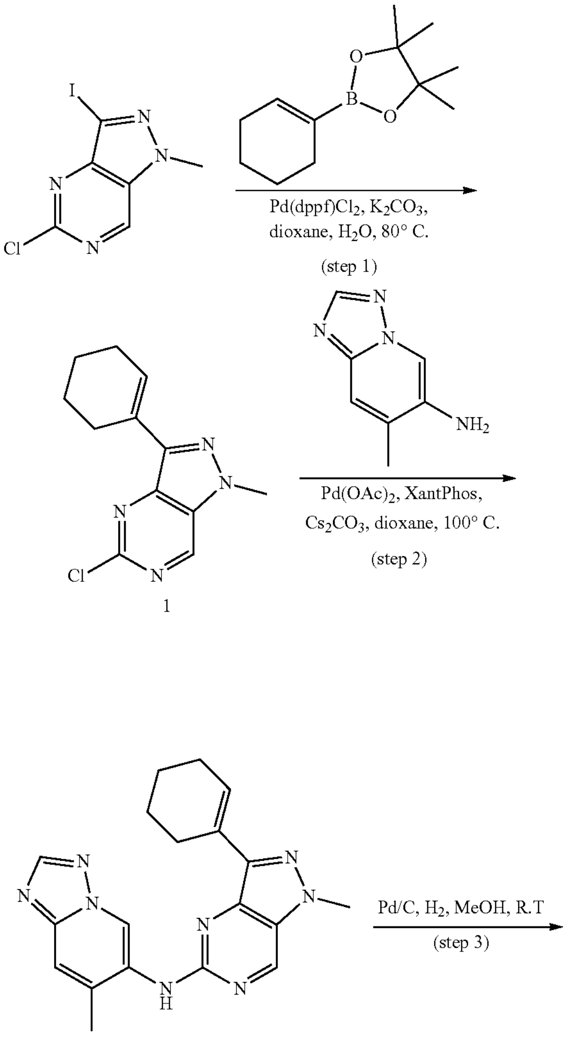

2

-continued

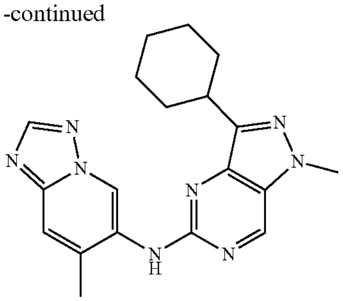

Example 5

Step 1. 5-chloro-3-(cyclohex-1-en-1-yl)-1-methyl-1H-pyrazolo[4,3-d]pyrimidine $K_2CO_3$ (293.33 mg, 2.122 mmol, 2.50 equiv), 2-(cyclohex-1-en-1-yl)-4,4,5,5-tetramethyl-1,3,2-dioxaborolane (265.01 mg, 1.273 mmol, 1.50 equiv) and 5-chloro-3-iodo-1-methylpyrazolo[4,3-d]pyrimidine (250.00 mg, 0.849 mmol, 1.00 equiv) in dioxane (5.00 mL) and $H_2O$ (1.00 mL) was stirred for 2 hrs at 80° C. under nitrogen atmosphere. Desired product could be detected by LCMS. The resulting mixture was concentrated under reduced pressure. The residue was purified by Prep-TLC (PE/EtOAc 1:2) to afford 5-chloro-3-(cyclohex-1-en-1-yl)-1-methylpyrazolo[4,3-d]pyrimidine (150 mg, 71.04%) as a pink solid. LCMS: m/z (ESI), $[M+H]^+$=249.3. $^1$H NMR (300 MHz, DMSO-$d_6$) δ 1.61-1.80 (4H, m), 2.29 (2H, s), 2.54 (2H, s), 4.14 (3H, s), 7.17-7.27 (1H, m), 9.40 (1H, s)

Step 2. 3-(cyclohex-1-en-1-yl)-1-methyl-N-(7-methyl-[1,2,4]triazolo[1,5-a]pyridin-6-yl)-1H-pyrazolo[4,3-d]pyrimidin-5-amine A mixture of $Cs_2CO_3$ (458.51 mg, 1.407 mmol, 2.5 equiv), XantPhos (65.14 mg, 0.113 mmol, 0.2 equiv), $Pd(AcO)_2$ (25.28 mg, 0.113 mmol, 0.2 equiv), 7-methyl-[1,2,4]triazolo[1,5-a]pyridin-6-amine (125.11 mg, 0.844 mmol, 1.5 equiv) and 5-chloro-3-(cyclohex-1-en-1-yl)-1-methylpyrazolo[4,3-d]pyrimidine (140.00 mg, 0.563 mmol, 1.00 equiv) in dioxane (4.00 mL) was stirred for 3 hours at 100° C. under nitrogen atmosphere. Desired product could be detected by LCMS. The resulting mixture was concentrated under reduced pressure. The residue was purified by Prep-TLC ($CH_2Cl_2$/MeOH=15:1) to afford 3-(cyclohex-1-en-1-yl)-1-methyl-N-[7-methyl-[1,2,4]triazolo[1,5-a]pyridin-6-yl]pyrazolo[4,3-d]pyrimidin-5-amine (140 mg, 69.00%) as a yellow solid. LCMS: m/z (ESI), $[M+H]^+$=361.3. $^1$H NMR (300 MHz, DMSO-$d_6$) δ 1.61-1.83 (4H, m), 2.17-2.33 (4H, m), 2.46 (3H, d), 4.06 (3H, s), 7.21 (1H, s), 7.73 (1H, s), 8.38 (1H, s), 8.88 (1H, s), 9.19 (1H, s), 9.46 (1H, s)

Step 3. 3-cyclohexyl-1-methyl-N-(7-methyl-[1,2,4]triazolo[1,5-a]pyridin-6-yl)-1H-pyrazolo[4,3-d]pyrimidin-5-amine (Ex. 5)

A solution of 3-(cyclohex-1-en-1-yl)-1-methyl-N-[7-methyl-[1,2,4]triazolo[1,5-a]pyridin-6-yl]pyrazolo[4,3-d]pyrimidin-5-amine (160.00 mg, 0.444 mmol, 1.00 equiv) and Pd/C (236.21 mg, 2.220 mmol, 5.00 equiv) in THF (40.00 mL) and MeOH (80.00 mL) was stirred for 3 days at room temperature under hydrogen atmosphere. The precipitated solids were collected by filtration and washed with MeOH (5x30 mL). The resulting mixture was concentrated under reduced pressure. The crude product (150 mg) was purified by Prep-HPLC with the following conditions (Column: XBridge Prep OBD C18 Column, 30x150 mm 5 um; Mobile Phase A: Water (0.05% $NH_3 \cdot H_2O$), Mobile Phase B: ACN; Flow rate: 60 mL/min; Gradient: 40 B to 50 B in 7 min; RT1:6.55) to afford 3-cyclohexyl-1-methyl-N-[7-methyl-[1,2,4]triazolo[1,5-a]pyridin-6-yl]pyrazolo[4,3-d]pyrimidin-5-amine (17.41 mg, 10.82%) as a white solid. LCMS: m/z (ESI), $[M+H]^+$=363.2. $^1H$ NMR (300 MHz, DMSO-$d_6$) δ 1.33 (3H, d), 1.76 (5H, d), 2.00 (2H, d), 2.46 (3H, d), 2.88-3.05 (1H, m), 4.04 (3H, s), 7.72 (1H, t), 8.38 (1H, s), 8.78 (1H, s), 9.15 (1H, s), 9.51 (1H, s)

Example 8

Preparation of 3-((1r,4r)-4-methoxycyclohexyl)-1-methyl-N-(7-methyl-[1,2,4]triazolo[1,5-a]pyridin-6-yl)-1H-pyrazolo[4,3-d]pyrimidin-5-amine (Ex. 7) and 3-((1s,4s)-4-methoxycyclohexyl)-1-methyl-N-(7-methyl-[1,2,4]triazolo[1,5-a]pyridin-6-yl)-1H-pyrazolo[4,3-d]pyrimidin-5-amine (Ex. 8)

SCHEME 8

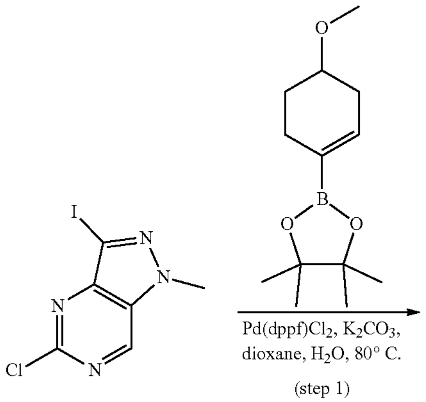

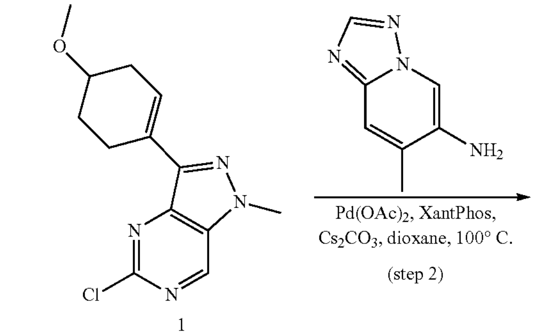

1

-continued

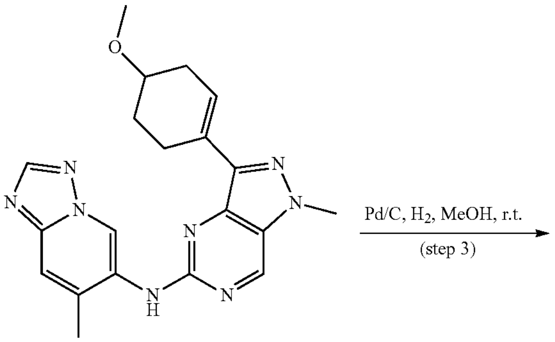

2

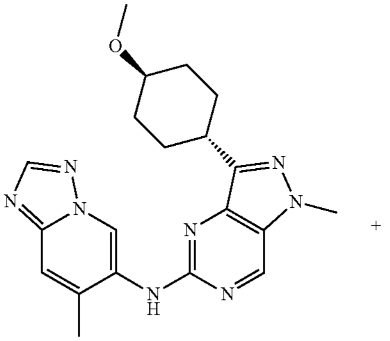

Example 7

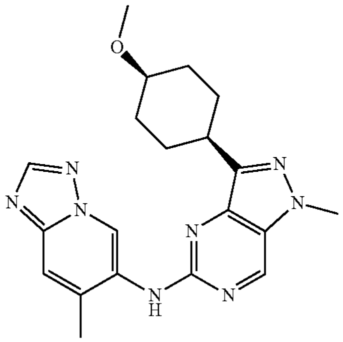

Example 8

Step 1. 5-chloro-3-(4-methoxycyclohex-1-en-1-yl)-1-methyl-1H-pyrazolo[4,3-d]pyrimidine A mixture of $K_2CO_3$ (234.66 mg, 1.698 mmol, 2.5 equiv), Pd(dppf)$Cl_2$ $CH_2Cl_2$ (110.93 mg, 0.136 mmol, 0.2 equiv), 2-(4-methoxycyclohex-1-en-1-yl)-4,4,5,5-tetramethyl-1,3,2-dioxaborolane (194.07 mg, 0.815 mmol, 1.2 equiv) and 5-chloro-3-iodo-1-methylpyrazolo[4,3-d]pyrimidine (200.00 mg, 0.679 mmol, 1.00 equiv) in dioxane (5.00 mL) and $H_2O$ (1.00 mL) was stirred for 2 hours at 80° C. under nitrogen atmosphere. The resulting mixture was concentrated under reduced pressure. The residue was purified by Prep-TLC (PE/EtOAc 1:2) to afford 5-chloro-3-(4-methoxycyclohex-1-en-1-yl)-1-methylpyrazolo[4,3-d]pyrimidine (175 mg, 92.44%) as a white solid. LCMS: m/z (ESI), $[M+H]^+$=279.3. $^1H$ NMR (300 MHz, $CDCl_3$) δ 1.89 (2H, d), 2.11 (1H, m), 2.33 (1H, t), 2.66 (1H, m), 2.88 (1H, d), 3.43 (3H, s), 3.60 (1H, d), 4.12 (3H, s), 7.27 (1H, d), 8.89 (1H, s)

Step 2. 3-(4-methoxycyclohex-1-en-1-yl)-1-methyl-N-(7-methyl-[1,2,4]triazolo[1,5-a]pyridin-6-yl)-1H-pyrazolo[4,3-d]pyrimidin-5-amine A mixture of $Cs_2CO_3$ (496.78 mg, 1.525 mmol, 2.5 equiv), XantPhos (70.58 mg, 0.122 mmol, 0.2 equiv), $Pd(AcO)_2$ (27.39 mg, 0.122 mmol, 0.2 equiv), 7-methyl-[1,2,4]triazolo[1,5-a]pyridin-6-amine (99.40 mg, 0.671 mmol, 1.1 equiv) and 5-chloro-3-(4-methoxycyclohex-1-en-1-yl)-1-methylpyrazolo[4,3-d]pyrimidine (170.00 mg, 0.610 mmol, 1.00 equiv) in dioxane (5.00 mL) was stirred for 3 hours at 100° C. under nitrogen atmosphere. The resulting mixture was concentrated under reduced pressure. The residue was purified by Prep-TLC ($CH_2Cl_2$/MeOH=12:1) to afford 3-(4-methoxycyclohex-1-en-1-yl)-1-methyl-N-[7-methyl-[1,2,4]triazolo[1,5-a]pyridin-6-yl]pyrazolo[4,3-d]pyrimidin-5-amine (100 mg, 41.99%) as a yellow solid. LCMS: m/z (ESI), $[M+H]^+$=392.4. $^1H$ NMR (300 MHz, DMSO-$d_6$) δ 1.67 (1H, d), 2.00 (1H, s), 2.27 (1H, m), 2.46 (3H, d), 2.72 (1H, d), 3.17 (2H, d), 3.33 (3H, s), 3.53 (1H, s), 4.07 (3H, s), 7.08 (1H, s), 7.73 (1H, s), 8.39 (1H, s), 8.91 (1H, s), 9.19 (1H, s), 9.43 (1H, s)

Step 3. 3-((1r,4r)-4-methoxycyclohexyl)-1-methyl-N-(7-methyl-[1,2,4]triazolo[1,5-a]pyridin-6-yl)-1H-pyrazolo[4,3-d]pyrimidin-5-amine (Ex. 7) and 3-((1s,4s)-4-methoxycyclohexyl)-1-methyl-N-(7-methyl-[1,2,4]triazolo[1,5-a]pyridin-6-yl)-1H-pyrazolo[4,3-d]pyrimidin-5-amine (Ex. 8)

A mixture of Pd/C (65.41 mg, 0.615 mmol, 3 equiv) and 3-(4-methoxycyclohex-1-en-1-yl)-1-methyl-N-[7-methyl-[1,2,4]triazolo[1,5-a]pyridin-6-yl]pyrazolo[4,3-d]pyrimidin-5-amine (80.00 mg, 0.205 mmol, 1.00 equiv) in MeOH (150.00 mL) and THF (80.00 mL) was stirred for overnight at room temperature under hydrogen atmosphere. The resulting mixture was filtered, the filter cake was washed with MeOH (3×50 mL). The filtrate was concentrated under reduced pressure. The residue was purified by Prep-TLC ($CH_2Cl_2$/MeOH=12:1) to afford crude product. The crude product (80 mg) was purified by Prep-HPLC with the following conditions (Column: XBridge Prep OBD C18 Column, 19*250 mm, 5 um; Mobile Phase A: Water (0.05% $NH_3 \cdot H_2O$), Mobile Phase B: ACN; Flow rate: 25 mL/min; Gradient: 37 B to 41 B in 7 min; RT1:5.30/5.92) to afford 3-((1r,4r)-4-methoxycyclohexyl)-1-methyl-N-(7-methyl-[1,2,4]triazolo[1,5-a]pyridin-6-yl)-1H-pyrazolo[4,3-d]pyrimidin-5-amine (Ex. 7, 60 mg, 22.73%) as a white solid. LCMS: m/z (ESI), $[M+H]^+$=393.3. $^1H$ NMR (400 MHz, DMSO-$d_6$) δ 1.28 (2H, q), 1.83 (2H, q), 2.09 (4H, t), 2.43 (3H, d), 2.95 (1H, t), 3.30 (4H, m), 4.04 (3H, s), 7.73 (1H, s), 8.38 (1H, s), 8.81 (1H, s), 9.16 (1H, s), 9.51 (1H, s);

3-((1s,4s)-4-methoxycyclohexyl)-1-methyl-N-(7-methyl-[1,2,4]triazolo[1,5-a]pyridin-6-yl)-1H-pyrazolo[4,3-d]pyrimidin-5-amine (Ex. 8, 10 mg, 12.19%) as a white solid. LCMS: m/z (ESI), $[M+H]^+$=393.2. $^1H$ NMR (300 MHz, DMSO-$d_6$) δ 1.57 (2H, t), 1.76 (2H, m), 1.86 (2H, m), 2.04 (2H, q), 2.43 (3H, d), 3.05 (1H, m), 3.20 (3H, s), 3.42 (1H, s), 4.04 (3H, s), 7.72 (1H, s), 8.37 (1H, s), 8.80 (1H, s), 9.14 (1H, s), 9.34 (1H, s).

Example 9

Preparation of 3-(4,4-difluorocyclohexyl)-1-methyl-N-(7-methyl-[1,2,4]triazolo[1,5-a]pyridin-6-yl)-1H-pyrazolo[4,3-d]pyrimidin-5-amine (Ex. 9)

SCHEME 9

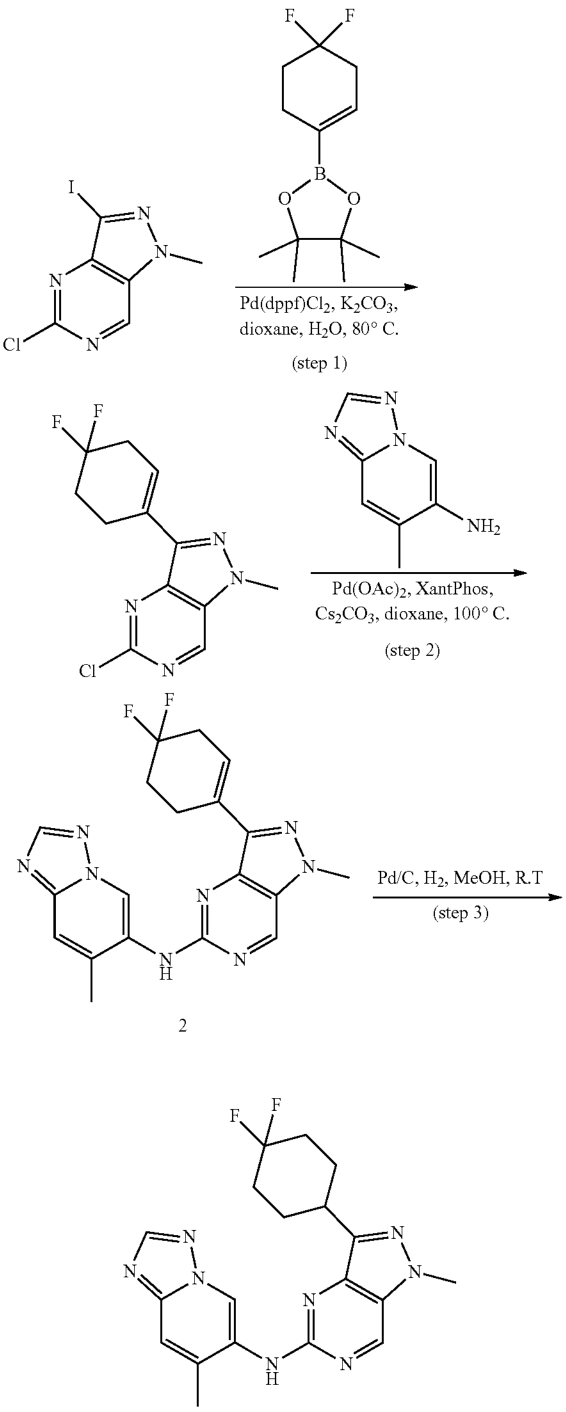

2

Example 9

Step 1. 5-chloro-3-(4,4-difluorocyclohex-1-en-1-yl)-1-methyl-1H-pyrazolo[4,3-d]pyrimidine A mixture of 5-chloro-3-iodo-1-methylpyrazolo[4,3-d]pyrimidine (200.00 mg, 0.679 mmol, 1.00 equiv), 2-(4,4-difluorocyclohex-1-en-1-yl)-4,4,5,5-tetramethyl-1,3,2-dioxaborolane (198.93 mg, 0.815 mmol, 1.20 equiv), Pd(dppf)$Cl_2$ (99.39 mg, 0.136 mmol, 0.2 equiv) and $K_2CO_3$ (234.66 mg, 1.698 mmol, 2.5 equiv) in dioxane (3.00 mL) and $H_2O$ (0.60 mL) was stirred for 2 hs at 80° C. under nitrogen atmosphere. The resulting mixture was concentrated under vacuum. The residue was purified by Prep-TLC (PE/EtOAc 2:3) to afford 5-chloro-3-(4,4-difluorocyclohex-1-en-1-yl)-1-methylpyrazolo[4,3-d]pyrimidine (100 mg, 51.72%) as a yellow solid. LCMS: m/z (ESI), $[M+H]^+$=285.3.

Step 2. 3-(4,4-difluorocyclohex-1-en-1-yl)-1-methyl-N-(7-methyl-[1,2,4]triazolo[1,5-a]pyridin-6-yl)-1H-pyrazolo[4,3-d]pyrimidin-5-amine A mixture of 5-chloro-3-(4,4-difluorocyclohex-1-en-1-yl)-1-methylpyrazolo[4,3-d]pyrimidine (100.00 mg, 0.351 mmol, 1.00 equiv), 7-methyl-[1,2,4]triazolo[1,5-a]pyridin-6-amine (62.45 mg, 0.421 mmol, 1.20 equiv), $Pd(OAc)_2$ (15.77 mg, 0.070 mmol, 0.20 equiv), XantPhos (60.97 mg, 0.105 mmol, 0.30 equiv) and $Cs_2CO_3$ (286.12 mg, 0.878 mmol, 2.50 equiv) in dioxane (2.50 mL) was stirred for 2 hs at 100° C. under nitrogen atmosphere. The resulting mixture was concentrated under reduced pressure. The residue was purified by Prep-TLC ($CH_2Cl_2$/MeOH=12:1) to afford 3-(4,4-difluorocyclohex-1-en-1-yl)-1-methyl-N-[7-methyl-[1,2,4]triazolo[1,5-a]pyridin-6-yl]pyrazolo[4,3-d]pyrimidin-5-amine (110 mg, 79.00%) as a white solid. LCMS: m/z (ESI), $[M+H]^+$=397.3.

Step 3. 3-(4,4-difluorocyclohexyl)-1-methyl-N-(7-methyl-[1,2,4]triazolo[1,5-a]pyridin-6-yl)-1H-pyrazolo[4,3-d]pyrimidin-5-amine (Ex. 9)

A mixture of 3-(4,4-difluorocyclohex-1-en-1-yl)-1-methyl-N-[7-methyl-[1,2,4]triazolo[1,5-a]pyridin-6-yl]pyrazolo[4,3-d]pyrimidin-5-amine (130.00 mg, 0.328 mmol, 1.00 equiv) and Pd/C (174.50 mg, 1.640 mmol, 5.00 equiv) in MeOH (60.00 mL) and THF (30.00 mL) was stirred for 5 hs at 30° C. under hydrogen atmosphere. The resulting mixture was filtered, the filter cake was washed with $CH_2Cl_2$ (3×40 mL). The filtrate was concentrated under reduced pressure. The residue was purified by Prep-TLC ($CH_2Cl_2$/MeOH=12:1). The crude product (70 mg) was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; Gradient: 34 B to 48 B in 7 min; RT1:5.97) to afford 3-(4,4-difluorocyclohexyl)-1-methyl-N-[7-methyl-[1,2,4]triazolo[1,5-a]pyridin-6-yl]pyrazolo[4,3-d]pyrimidin-5-amine (17 mg, 13.01%) as a pink solid. LCMS: m/z (ESI), $[M+H]^+$=399.3. $^1H$ NMR (300 MHz, MeOD-$d_4$) δ 1.80-2.22 (8H, m), 2.49 (3H, d), 3.22 (1H, s), 4.03 (3H, s), 7.58 (1H, t), 8.27 (1H, s), 8.98 (1H, s), 9.62 (1H, s)

Example 10

Preparation of 1-(methyl-$d_3$)—N-(7-methyl-[1,2,4]triazolo[1,5-a]pyridin-6-yl)-3-(tetrahydro-2H-pyran-4-yl)-1H-pyrazolo[4,3-d]pyrimidin-5-amine (Ex. 10)

SCHEME 10

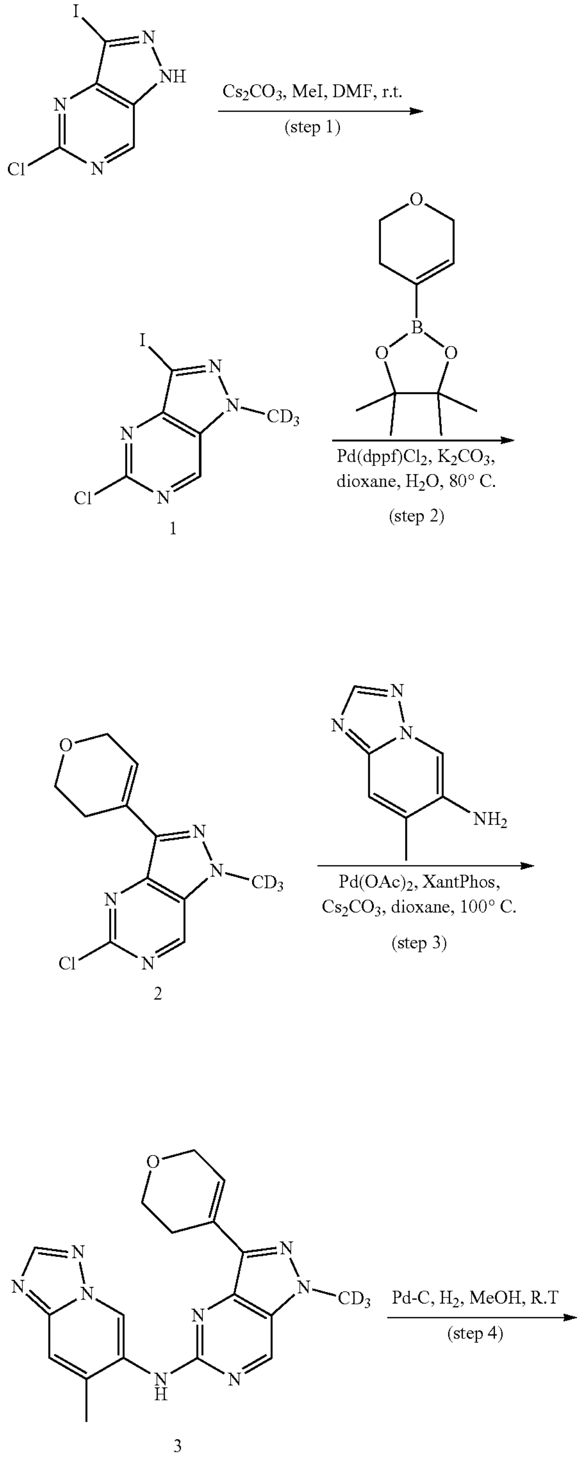

-continued

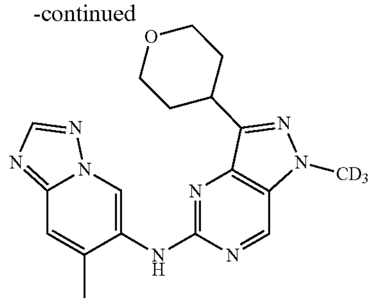

Example 10

Step 1. 5-chloro-3-iodo-1-(methyl-$d_3$)-1H-pyrazolo[4,3-d]pyrimidine

A mixture of $Cs_2CO_3$ (1045.60 mg, 3.209 mmol, 3 equiv), $CD_3I$ (775.31 mg, 5.349 mmol, 5 equiv) and 5-chloro-3-iodo-1H-pyrazolo[4,3-d]pyrimidine (300.00 mg, 1.070 mmol, 1.00 equiv) in DMF (6.00 mL) was stirred for 1 h at 0° C. under nitrogen atmosphere. Desired product could be detected by LCMS. The resulting mixture was diluted with water (50 mL). The resulting mixture was extracted with EtOAc (3×50 mL). The combined organic layers were washed with Sat. brine (3×50 mL) and $Na_2S_2O_3$ (3×50 mL) and dried over anhydrous $Na_2SO_4$. After filtration, the filtrate was concentrated under reduced pressure to afford 5-chloro-3-iodo-1-(methyl-$d_3$)-1H-pyrazolo[4,3-d]pyrimidine (260 mg, 81.70%) as a pink solid. LCMS: m/z (ESI), $[M+H]^+$=298.0. $^1$H NMR (400 MHz, DMSO-$d_6$) δ 9.45 (1H, s).

Step 2. 5-chloro-3-(3,6-dihydro-2H-pyran-4-yl)-1-(methyl-$d_3$)-1H-pyrazolo[4,3-d]pyrimidine A mixture of $K_2CO_3$ (313.58 mg, 2.269 mmol, 2.5 equiv), Pd(dppf)$Cl_2$ $CH_2Cl_2$ (148.23 mg, 0.182 mmol, 0.2 equiv), 2-(3,6-dihydro-2H-pyran-4-yl)-4,4,5,5-tetramethyl-1,3,2-dioxaborolane (228.79 mg, 1.089 mmol, 1.2 equiv) and 5-chloro-3-iodo-1-(methyl-$d_3$)-1H-pyrazolo[4,3-d]pyrimidine (270.00 mg, 0.908 mmol, 1.00 equiv) in dioxane (5.00 mL) and water (1.00 mL) was stirred for 2 hours at 80° C. under nitrogen atmosphere. Desired product could be detected by LCMS. The resulting mixture was concentrated under reduced pressure. The residue was purified by Prep-TLC (hexane/EtOAc 1:2) to afford 5-chloro-3-(3,6-dihydro-2H-pyran-4-yl)-1-(methyl-$d_3$)-1H-pyrazolo[4,3-d]pyrimidine (100 mg, 43.43%) as a pink solid. LCMS: m/z (ESI), $[M+H]^+$=254.2. $^1$H NMR (400 MHz, DMSO-$d_6$) δ 2.62 (2H, m), 3.86 (2H, t), 4.33 (2H, q), 7.18 (1H, t), 9.43 (1H, s)

Step 3. 3-(3,6-dihydro-2H-pyran-4-yl)-1-(methyl-$d_3$)—N-(7-methyl-[1,2,4]triazolo[1,5-a]pyridin-6-yl)-1H-pyrazolo[4,3-d]pyrimidin-5-amine A mixture of $Cs_2CO_3$ (385.28 mg, 1.182 mmol, 3 equiv), XantPhos (45.61 mg, 0.079 mmol, 0.2 equiv), Pd$(OAc)_2$ (17.70 mg, 0.079 mmol, 0.2 equiv), 7-methyl-[1,2,4]triazolo[1,5-a]pyridin-6-amine (70.08 mg, 0.473 mmol, 1.20 equiv) and 5-chloro-3-(3,6-dihydro-2H-pyran-4-yl)-1-(methyl-$d_3$)-1H-pyrazolo[4,3-d]pyrimidine (100.00 mg, 0.394 mmol, 1.00 equiv) in dioxane (3.00 mL) was stirred for 2 h at 100° C. under nitrogen atmosphere. Desired product could be detected by LCMS. The resulting mixture was concentrated under reduced pressure. The residue was purified by Prep-TLC ($CH_2Cl_2$/MeOH=12:1) to afford 3-(3,6-dihydro-2H-pyran-4-yl)-1-(methyl-$d_3$)—N-(7-methyl-[1,2,4]triazolo[1,5-a]pyridin-6-yl)-1H-pyrazolo[4,3-d]pyrimidin-5-amine (100 mg, 69.43%) as a yellow solid. LCMS: m/z (ESI), $[M+H]^+$=366.3. $^1$H NMR (400 MHz, DMSO-$d_6$) δ 2.44 (2H, d), 2.61 (3H, s), 3.17 (1H, d), 3.85 (2H, t), 4.26 (2H, q), 7.72 (1H, s), 8.38 (1H, s), 8.94 (1H, s), 9.20 (1H, s), 9.37 (1H, s).

Step 4. 1-(methyl-$d_3$)—N-(7-methyl-[1,2,4]triazolo[1,5-a]pyridin-6-yl)-3-(tetrahydro-2H-pyran-4-yl)-1H-pyrazolo[4,3-d]pyrimidin-5-amine. (Ex. 10)

A mixture of Pd/C (87.37 mg, 0.821 mmol, 3 equiv) and 3-(3,6-dihydro-2H-pyran-4-yl)-1-(methyl-$d_3$)—N-(7-methyl-[1,2,4]triazolo[1,5-a]pyridin-6-yl)-1H-pyrazolo[4,3-d]pyrimidin-5-amine (100.00 mg, 0.274 mmol, 1.00 equiv) in MeOH (10.00 mL) and THF (10.00 mL) was stirred for 2 h at 35° C. under hydrogen atmosphere. Desired product could be detected by LCMS. The resulting mixture was filtered, the filter cake was washed with MeOH (3×30 mL) and DCM (3×30 mL). The filtrate was concentrated under reduced pressure. The residue was purified by Prep-TLC ($CH_2Cl_2$/MeOH=12:1) to afford crude product. The crude product (40 mg) was purified by Prep-HPLC with the following conditions (Column: XBridge Prep OBD C18 Column, 19*250 mm, 5 um; Mobile Phase A: Water (0.05% $NH_3 \cdot H_2O$), Mobile Phase B: ACN; Flow rate: 60 mL/min; Gradient: 15 B to 35 B in 7 min; RT1:6.4) to afford 1-(methyl-$d_3$)—N-(7-methyl-[1,2,4]triazolo[1,5-a]pyridin-6-yl)-3-(tetrahydro-2H-pyran-4-yl)-1H-pyrazolo[4,3-d]pyrimidin-5-amine (10 mg, 9.85%) as a white solid. LCMS: m/z (ESI), $[M+H]^+$=368.2. $^1$H NMR (400 MHz, DMSO-$d_6$) δ 1.94 (4H, d), 2.43 (3H, d), 3.24 (1H, d), 3.48 (2H, m), 3.93 (2H, m), 7.71 (1H, s), 8.37 (1H, s), 8.81 (1H, s), 9.15 (1H, s), 9.33 (1H, s).

Example 11/12

Preparation of 1-methyl-N-[7-methyl-[1,2,4]triazolo[1,5-a]pyridin-6-yl]-3-[(1s,4s)-4-(difluoromethoxy)cyclohexyl]pyrazolo[4,3-d]pyrimidin-5-amine (Ex. 11) and 1-methyl-N-[7-methyl-[1,2,4]triazolo[1,5-a]pyridin-6-yl]-3-[(1r,4r)-4-(difluoromethoxy)cyclohexyl]pyrazolo[4,3-d]pyrimidin-5-amine (Ex. 12)

SCHEME 11/12

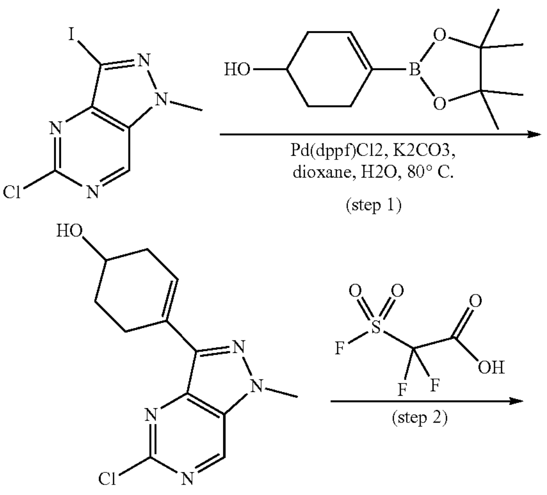

1

-continued

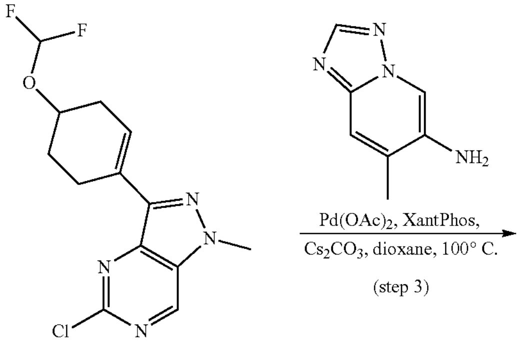

2

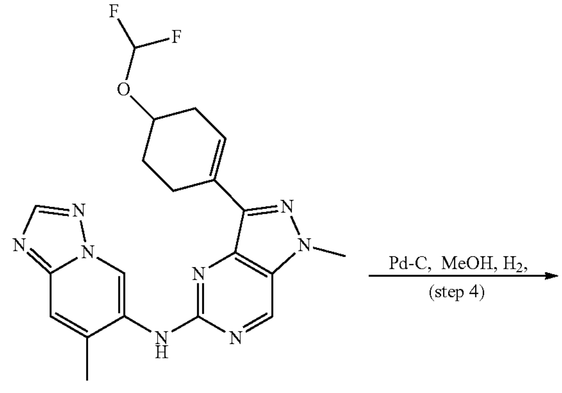

3

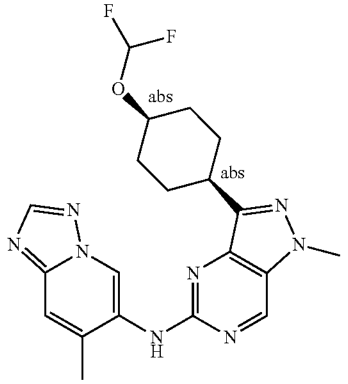

Example 11

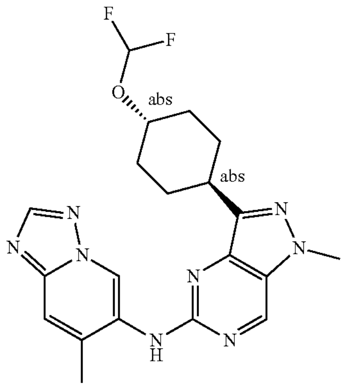

Example 12

Step 1. 4-(5-chloro-1-methyl-1H-pyrazolo[4,3-d]pyrimidin-3-yl)cyclohex-3-en-1-ol Into a 40 mL vial were added 5-chloro-3-iodo-1-methylpyrazolo[4,3-d]pyrimidine (500.00 mg, 1.698 mmol, 1.00 equiv), and 4-(4,4,5,5-tetramethyl-1,3,2-dioxaborolan-2-yl)cyclohex-3-en-1-ol (570.78 mg, 2.547 mmol, 1.50 equiv), $Pd(dppf)Cl_2$ (248.47 mg, 0.340 mmol, 0.20 equiv), $K_2CO_3$ (938.64 mg, 6.792 mmol, 4 equiv), dioxane (10.00 mL) and $H_2O$ (2.00 mL) at room temperature. Then the mixture was stirred at 80° C. under nitrogen atmosphere for 3 h. The resulting mixture was concentrated under vacuum. The residue was purified by Prep-TLC (PE:EA=1:4) to afford 4-[5-chloro-1-methylpyrazolo[4,3-d]pyrimidin-3-yl]cyclohex-3-en-1-ol (253 mg, 56.29%) as a yellow solid. LCMS: m/z (ESI), $[M+H]^+$=265.2.

Step 2. 5-chloro-3-(4-(difluoromethoxy)cyclohex-1-enyl)-1-methyl-1H-pyrazolo[4,3-d]pyrimidine Into a 40 mL vial were added 4-[5-chloro-1-methylpyrazolo[4,3-d]pyrimidin-3-yl]cyclohex-3-en-1-ol (253.00 mg, 0.956 mmol, 1.00 equiv), CuI (63.71 mg, 0.335 mmol, 0.35 equiv), MeCN (10.00 mL) at 50° C. and 2,2-difluoro-2-(fluorosulfonyl)acetic acid (510.61 mg, 2.867 mmol, 3.00 equiv) was added dropwise the mixture. Then the mixture was stirred at 50° C. under air atmosphere for 3 h. The resulting mixture was diluted with water (10 mL). The aqueous layer was extracted with DCM (3x30 mL). The resulting mixture was diluted with DCM (5 mL). The resulting mixture was filtered, the filter cake was washed with DCM (10 mL*3). The filtrate was concentrated under reduced pressure. The residue was purified by Prep-TLC (PE/EtOAc 1:1) to afford 5-chloro-3-[4-(difluoromethoxy)cyclohex-1-en-1-yl]-1-methylpyrazolo[4,3-d]pyrimidine (180 mg, 47.87%) as a yellow solid. LCMS: m/z (ESI), $[M+H]^+$=315.2.

Step 3. 3-(4-(difluoromethoxy)cyclohex-1-enyl)-1-methyl-N-(7-methyl-[1,2,4]triazolo[1,5-a]pyridin-6-yl)-1H-pyrazolo[4,3-d]pyrimidin-5-amine Into a 40 mL vial were added 5-chloro-3-[4-(difluoromethoxy)cyclohex-1-en-1-yl]-1-methylpyrazolo[4,3-d]pyrimidine (180.00 mg, 0.572 mmol, 1.00 equiv), and 7-methyl-[1,2,4]triazolo[1,5-a]pyridin-6-amine (101.69 mg, 0.686 mmol, 1.20 equiv), $Pd(OAc)_2$ (38.52 mg, 0.172 mmol, 0.30 equiv), XantPhos (99.28 mg, 0.172 mmol, 0.30 equiv), $Cs_2CO_3$ (559.05 mg, 1.716 mmol, 3.00 equiv) and dioxane (10.00 mL) at room temperature. Then the mixture was stirred at 70° C. under nitrogen atmosphere for 3 h. The resulting mixture was concentrated under vacuum. The residue was purified by Prep-TLC (DCM:MeOH 15:1) to afford 3-[4-(difluoromethoxy)cyclohex-1-en-1-yl]-1-methyl-N-[7-methyl-[1,2,4]triazolo[1,5-a]pyridin-6-yl]pyrazolo[4,3-d]pyrimidin-5-amine (135 mg, 55.35%) as a yellow solid. LCMS: m/z (ESI), $[M+H]^+$=427.1. $^1H$ NMR (400 MHz, $CDCl_3$) δ 1.97-2.23 (3H, m), 2.55 (4H, s), 2.68-2.87 (2H, m), 2.98 (1H, d), 4.11 (3H, s), 4.54-4.62 (1H, m), 6.35 (1H, t), 7.00 (1H, s), 7.61 (1H, s), 8.29 (1H, s), 8.82 (1H, s), 9.90 (1H, s)

Step 4. Preparation of 1-methyl-N-[7-methyl-[1,2,4]triazolo[1,5-a]pyridin-6-yl]-3-[(1s,4s)-4-(difluoromethoxy)cyclohexyl]pyrazolo[4,3-d]pyrimidin-5-amine (Ex. 11) and 1-methyl-N-[7-methyl-[1,2,4]triazolo[1,5-a]pyridin-6-yl]-3-[(1r,4r)-4-(difluoromethoxy)cyclohexyl]pyrazolo[4,3-d]pyrimidin-5-amine (Ex. 12)

To a stirred mixture of 3-[4-(difluoromethoxy)cyclohex-1-en-1-yl]-1-methyl-N-[7-methyl-[1,2,4]triazolo[1,5-a]

pyridin-6-yl]pyrazolo[4,3-d]pyrimidin-5-amine (135.00 mg, 0.317 mmol, 1.00 equiv) in MeOH (20 mL) were added Pd/C (168.45 mg, 1.583 mmol, 5.00 equiv) under air atmosphere. The resulting mixture was stirred for 4 h at 40° C. under hydrogen atmosphere. The resulting mixture was filtered, and the filter cake was washed with DCM (8×100 mL). The filtrate was concentrated under reduced pressure to afford crude solid. The crude product was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; Gradient: 34 B to 54 B in 7 min; RT1:5.93) to afford solid. Then the product was purified by Prep-HPLC with the following conditions (Column: CHIRALPAK IG, 2*25 cm, 5 um; Mobile Phase A: Hex: DCM=3:1, Mobile Phase B: EtOH; Flow rate: 20 mL/min; Gradient: 10 B to 10 B in 15 min; RT1:10; RT2:11;) to afford 1-methyl-N-[7-methyl-[1,2,4]triazolo[1,5-a]pyridin-6-yl]-3-[(1s,4s)-4-(difluoromethoxy)cyclohexyl]pyrazolo[4,3-d]pyrimidin-5-amine (Ex. 11, 15 mg, 50.00%) as a white solid and 1-methyl-N-[7-methyl-[1,2,4]triazolo[1,5-a]pyridin-6-yl]-3-[(1r,4r)-4-(difluoromethoxy)cyclohexyl]pyrazolo [4,3-d]pyrimidin-5-amine (Ex. 12, 5 mg, 16.67%) as a white solid.

(Ex. 11) LCMS: m/z (ESI), $[M+H]^+$=429.3. $^1H$ NMR (300 MHz, DMSO-$d_6$) δ 1.87 (2H, d), 1.97 (4H, d), 2.09 (2H, d), 2.43 (3H, s), 3.07 (1H, d), 4.04 (3H, s), 4.37 (1H, s), 6.69 (1H, t), 7.70 (1H, s), 8.36 (1H, s), 8.79 (1H, s), 9.14 (1H, s), 9.33 (1H, s);

(Ex. 12) LCMS: m/z (ESI), $[M+H]^+$=429.3. $^1H$ NMR (300 MHz, MeOD-$d_4$) δ 1.59-1.71 (2H, m), 1.95-2.09 (2H, m), 2.15-2.20 (4H, m), 2.55 (3H, s), 3.05-3.14 (1H, m), 4.09 (3H, s), 4.20-4.27 (1H, m), 6.71 (1H, t), 7.64 (1H, s), 8.31 (1H, s), 9.03 (1H, s), 9.85 (1H, s).

Example 13

Preparation of 3-methyl-N-(7-methyl-[1,2,4]triazolo[1,5-a]pyridin-6-yl)-1-(tetrahydro-2H-pyran-4-yl)-1H-pyrazolo[3,4-d]pyrimidin-6-amine (Ex. 13)

SCHEME 13

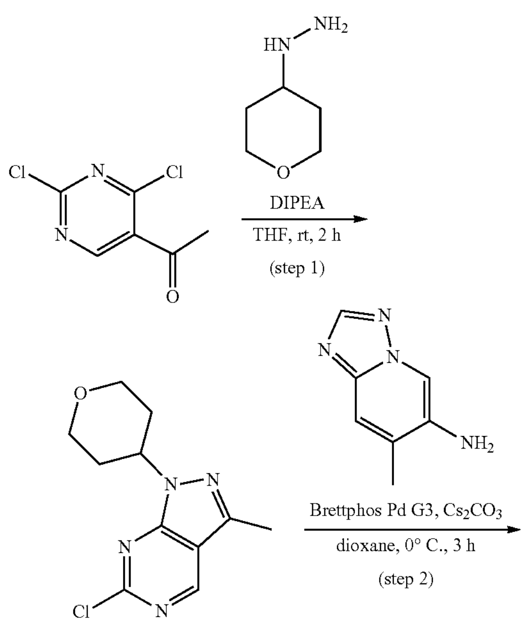

-continued

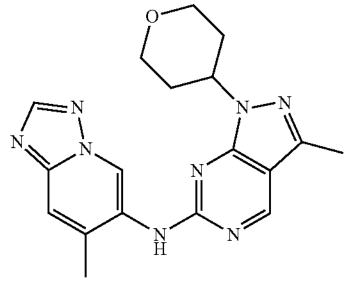

Example 13

Step 1. 6-chloro-3-methyl-1-(tetrahydro-2H-pyran-4-yl)-1H-pyrazolo[3,4-d]pyrimidine To a stirred mixture of 1-(2,4-dichloropyrimidin-5-yl) ethanone (500.00 mg, 2.618 mmol, 1.00 equiv) and DIPEA (1353.26 mg, 10.471 mmol, 4.00 equiv) in THF (5.00 mL) was added oxan-4-ylhydrazine (364.89 mg, 3.141 mmol, 1.20 equiv) in portions at room temperature under nitrogen atmosphere. And the mixture was stirred for 2 h at room temperature under nitrogen atmosphere. The resulting mixture was extracted with EtOAc (3×50 mL). The combined organic layers were washed with water (3×10 mL), dried over anhydrous $Na_2SO_4$. After filtration, the filtrate was concentrated under reduced pressure. The residue was purified by Prep-TLC (PE/EtOAc 2:1) to afford 6-chloro-3-methyl-1-(oxan-4-yl)pyrazolo[3,4-d]pyrimidine (350 mg, 52.91%) as a yellow solid. LCMS: m/z (ESI), $[M+H]^+$=253.2

Step 2. 3-methyl-N-(7-methyl-[1,2,4]triazolo[1,5-a]pyridin-6-yl)-1-(tetrahydro-2H-pyran-4-yl)-1H-pyrazolo[3,4-d]pyrimidin-6-amine (Ex. 13)

To a stirred mixture of 6-chloro-3-methyl-1-(oxan-4-yl)-1H-pyrazolo[3,4-d]pyrimidine (200 mg, 0.791 mmol, 1 equiv), $Cs_2CO_3$ (644.68 mg, 1.979 mmol, 2.5 equiv) and 7-methyl-[1,2,4]triazolo[1,5-a]pyridin-6-amine (140.72 mg, 0.950 mmol, 1.2 equiv) in dioxane (20 mL) was added BrettPhos Pd $G_3$ (143.49 mg, 0.158 mmol, 0.2 equiv) in portions at room temperature under nitrogen atmosphere. And the mixture was stirred for 3 h at 100° C. under nitrogen atmosphere. The resulting mixture was extracted with EtOAc (3×50 mL). The combined organic layers were washed with water (3×50 mL), dried over anhydrous $Na_2SO_4$. After filtration, the filtrate was concentrated under reduced pressure. The crude product was purified by Prep-HPLC with the following conditions (Column: X select CSH OBD Column 30×150 mm 5 um n; Mobile Phase A: Water (0.05% TFA), Mobile Phase B: ACN; Flow rate: 60 mL/min; Gradient: 18% B to 29% B in 7 min; $t_R$: 6.30 min) to afford 3-methyl-N-[7-methyl-[1,2,4]triazolo[1,5-a]pyridin-6-yl]-1-(oxan-4-yl)-1H-pyrazolo[3,4-d]pyrimidin-6-amine (74 mg, 25.66%) as a white solid. LCMS: m/z (ESI), $[M+H]^+$=365.3 $^1H$ NMR (DMSO-$d_6$, 300 MHz) δ 1.7-1.9 (2H, m), 2.0-2.2 (2H, m), 2.4-2.5 (6H, m), 3.4 (2H, td), 3.9-4.1 (2H, m), 4.5-4.7 (1H, m), 7.8 (1H, s), 8.6 (1H, s), 8.9 (1H, s), 9.3 (1H, s), 9.3 (1H, s)

Example 14

Preparation of 3-methyl-N-(7-methylimidazo[1,2-a]pyridin-6-yl)-1-(tetrahydro-2H-pyran-4-yl)-1H-pyrazolo[3,4-d]pyrimidin-6-amine (Ex. 14)

SCHEME 14

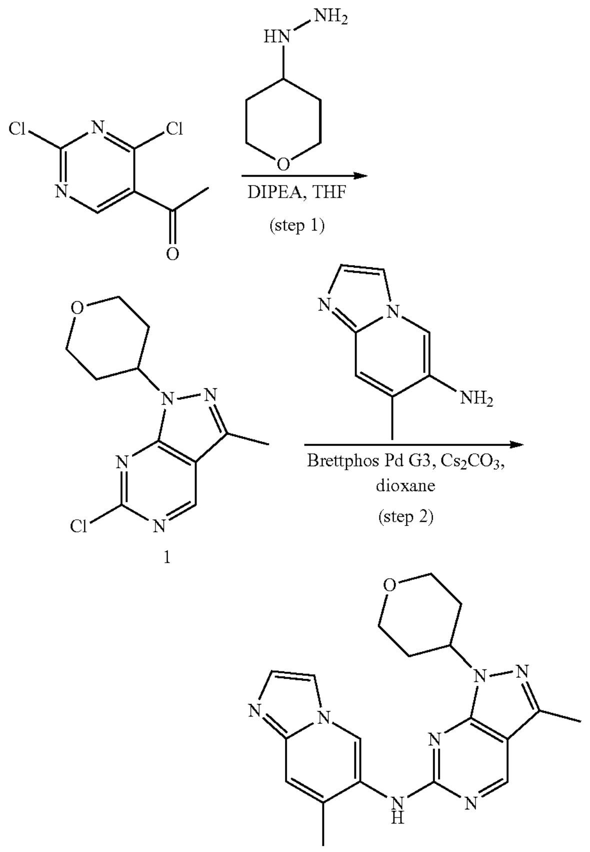

1

Example 14

Step 1. 6-chloro-3-methyl-1-(tetrahydro-2H-pyran-4-yl)-1H-pyrazolo[3,4-d]pyrimidine A solution of 1-(2,4-dichloropyrimidin-5-yl)ethanone (250.00 mg, 1.309 mmol, 1.00 equiv) and oxan-4-ylhydrazine (182.45 mg, 1.571 mmol, 1.20 equiv), DIPEA (338.32 mg, 2.618 mmol, 2.00 equiv) in THF (10.00 mL) was stirred for 2 h at 0° C. under nitrogen atmosphere. The resulting mixture was extracted with EtOAc (20 mL×3). The combined organic layers were washed with brine (10 mL×3), dried over anhydrous $Na_2SO_4$. After filtration, the filtrate was concentrated under reduced pressure. The residue was purified by Prep-TLC (PE/EtOAc 5:1) to afford 6-chloro-3-methyl-1-(oxan-4-yl)pyrazolo[3,4-d]pyrimidine (230 mg, 69.54%) as a white solid. LCMS: m/z (ESI), $[M+H]^+$=253.2.

Step 2. 3-methyl-N-(7-methylimidazo[1,2-a]pyridin-6-yl)-1-(tetrahydro-2H-pyran-4-yl)-1H-pyrazolo[3,4-d]pyrimidin-6-amine (Ex. 14)

A mixture of 7-methylimidazo[1,2-a]pyridin-6-amine (139.78 mg, 0.950 mmol, 1.50 equiv) and 6-chloro-3-methyl-1-(oxan-4-yl)pyrazolo[3,4-d]pyrimidine (160 mg, 0.633 mmol, 1.00 equiv), BrettPhos Pd $G_3$ (57.40 mg, 0.063 mmol, 0.10 equiv), $Cs_2CO_3$ (412.59 mg, 1.266 mmol, 2.00 equiv) in dioxane (5.00 mL) was stirred for 3 h at 100° C. under nitrogen atmosphere. The residue was purified by silica gel column chromatography, eluted with $CH_2Cl_2$/MeOH=(10:1) to afford crude product. The crude product was purified by Prep-HPLC to afford crude solid. The crude product was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; Gradient: 17 B to 37 B in 7 min; RT1:6.75) to afford 3-methyl-N-[7-methylimidazo[1,2-a]pyridin-6-yl]-1-(oxan-4-yl)pyrazolo[3,4-d]pyrimidin-6-amine (140 mg, 60.84%) as off-white solid. LCMS: m/z (ESI), $[M+H]^+$=364.1, $^1$H NMR (DMSO-$d_6$, 300 MHz) δ1.79 (2H, d), 2.02-2.18 (2H, m), 2.23 (3H, d), 2.42 (3H, s), 3.44 (2H, dd), 3.94 (2H, dd), 4.62 (1H, dd), 7.42 (1H, s), 7.48 (1H, d), 7.84 (1H, s), 8.69 (1H, s), 8.85 (1H, s), 9.04 (1H, s)

Example 15

Preparation of 7-methyl-N-(5-methyl-7-(tetrahydro-2H-pyran-4-yl)-7H-pyrrolo[2,3-d]pyrimidin-2-yl)-[1,2,4]triazolo[1,5-a]pyridin-6-amine (Ex. 15)

SCHEME 15

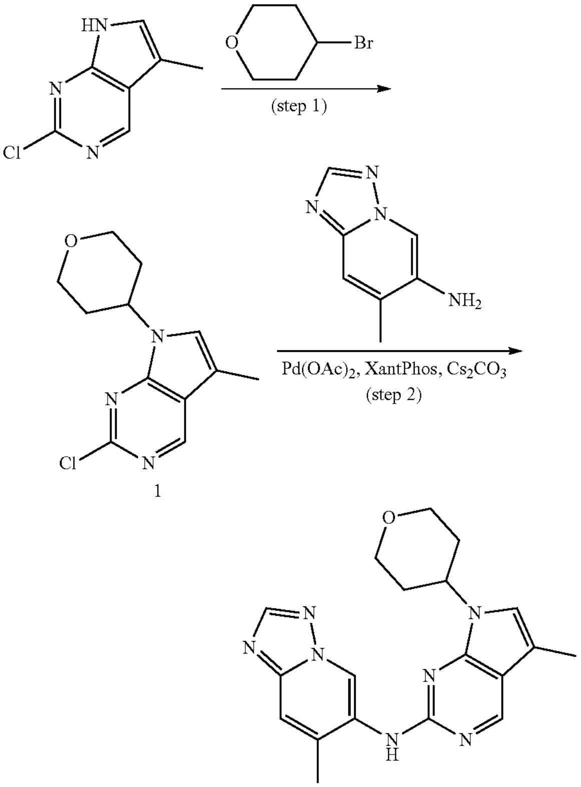

1

Example 15

Step 1. 2-chloro-5-methyl-7-(tetrahydro-2H-pyran-4-yl)-7H-pyrrolo[2,3-d]pyrimidine A mixture of 2-chloro-5-methyl-7H-pyrrolo[2,3-d]pyrimidine (400.00 mg, 2.387 mmol, 1.00 equiv), 4-bromooxane (3.94 g, 23.874 mmol, 10.00 equiv) and $K_2CO_3$ (824.62 mg, 5.967 mmol, 2.50 equiv) in DMSO (50.00 mL, 12.922 mmol) was stirred for overnight at 120° C. under nitrogen atmosphere. The resulting mixture was diluted with water (150 mL). The resulting mixture was extracted with EtOAc (3×50 mL). The combined organic layers were washed with brine (3×30 mL), dried over anhydrous $Na_2SO_4$. After filtration, the filtrate was concentrated under reduced pressure. The residue was purified by Prep-TLC ($CH_2Cl_2$/MeOH=10:1). The crude product (70 mg) was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; Gradient: 28 B to 48 B in 7 min; RT1:5.80) to afford 2-chloro-5-methyl-7-(oxan-4-yl) pyrrolo[2,3-d]pyrimidine (40 mg, 6.66%) as a yellow solid.

Step 2. 7-methyl-N-(5-methyl-7-(tetrahydro-2H-pyran-4-yl)-7H-pyrrolo[2,3-d]pyrimidin-2-yl)-[1,2,4]triazolo[1,5-a]pyridin-6-amine (Ex. 15)

A mixture of 2-chloro-5-methyl-7-(oxan-4-yl)pyrrolo[2,3-d]pyrimidine (30.00 mg, 0.119 mmol, 1.00 equiv), 7-methyl-[1,2,4]triazolo[1,5-a]pyridin-6-amine (21.19 mg, 0.143 mmol, 1.20 equiv), $Pd(AcO)_2$ (5.35 mg, 0.024 mmol, 0.20 equiv), XantPhos (20.69 mg, 0.036 mmol, 0.30 equiv) and $Cs_2CO_3$ (97.08 mg, 0.298 mmol, 2.50 equiv) in dioxane (1.50 mL) was stirred for 2 hs at 100° C. under nitrogen atmosphere. The resulting mixture was concentrated under vacuum. The residue was purified by Prep-TLC ($CH_2Cl_2$/MeOH=12:1) to afford crude product. The crude product (40 mg) was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; Gradient: 26 B to 46 B in 7 min; RT1:6.37) to afford 5-methyl-N-[7-methyl-[1,2,4]triazolo[1,5-a]pyridin-6-yl]-7-(oxan-4-yl) pyrrolo[2,3-d]pyrimidin-2-amine (6 mg, 13.85%) as a white solid. LCMS: m/z (ESI), $[M+H]^+$=364.3. 1H NMR (300 MHz, MeOD-$d_4$) δ 1.79-1.91 (2H, m), 1.95-2.14 (2H, m), 2.24 (3H, d), 2.43 (3H, d), 3.47 (2H, td), 3.93-4.05 (2H, m), 4.55-4.72 (1H, m), 7.18 (1H, d), 7.58-7.74 (1H, m), 8.37 (1H, s), 8.62 (2H, d), 9.32 (1H, s)

Example 16

Preparation of N-(7-chloro-[1,2,4]triazolo[1,5-a]pyridin-6-yl)-3-methyl-1-(tetrahydro-2H-pyran-4-yl)-1H-pyrazolo[3,4-d]pyrimidin-6-amine (Ex. 16)

SCHEME 16

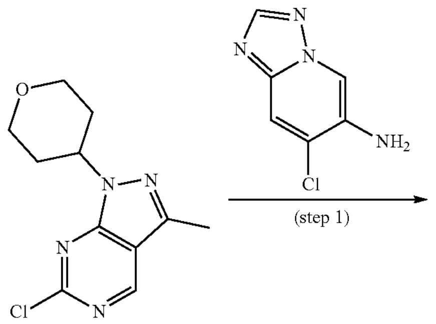

-continued

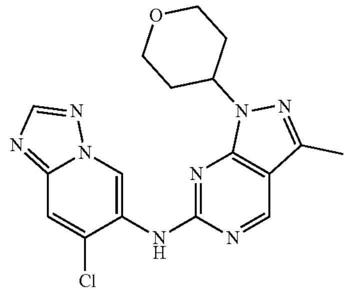

Example 16

Step 1. N-(7-chloro-[1,2,4]triazolo[1,5-a]pyridin-6-yl)-3-methyl-1-(tetrahydro-2H-pyran-4-yl)-1H-pyrazolo[3,4-d]pyrimidin-6-amine (Ex. 16)

A mixture of 7-chloro-[1,2,4]triazolo[1,5-a]pyridin-6-amine (50.00 mg, 0.297 mmol, 1.00 equiv), 6-chloro-3-methyl-1-(oxan-4-yl)pyrazolo[3,4-d]pyrimidine (74.95 mg, 0.297 mmol, 1.00 equiv), $Pd(AcO)_2$ (13.32 mg, 0.059 mmol, 0.2 equiv), XantPhos (51.48 mg, 0.089 mmol, 0.3 equiv) and $Cs_2CO_3$ (241.59 mg, 0.741 mmol, 2.5 equiv) in dioxane (4.00 mL) was stirred for 2 hs at 100° C. under nitrogen atmosphere. The resulting mixture was concentrated under vacuum. The residue was purified by Prep-TLC ($CH_2Cl_2$/MeOH=12:1). The crude product (90 mg) was purified by Prep-HPLC with the following conditions (Column: XBridge Prep OBD C18 Column, 19*250 mm, 5 um; Mobile Phase A: Water (0.05% $NH_3 \cdot H_2O$), Mobile Phase B: ACN; Flow rate: 25 mL/min; Gradient: 30 B to 40 B in 7 min; RT1:6.62) to afford N-[7-chloro-[1,2,4]triazolo[1,5-a]pyridin-6-yl]-3-methyl-1-(oxan-4-yl)pyrazolo[3,4-d]pyrimidin-6-amine (32.77 mg, 28.71%) as a white solid. LCMS: m/z (ESI), $[M+H]^+$=385.2. $^1H$ NMR (300 MHz, DMSO-$d_6$) δ 1.84 (2H, d), 2.13 (2H, dd), 2.46 (3H, s), 3.39-3.57 (2H, m), 3.97 (2H, dd), 4.54-4.77 (1H, m), 8.23 (1H, s), 8.57 (1H, s), 8.93 (1H, s), 9.36 (2H, d).

Example 17

Preparation of N-(7-methyl-[1,2,4]triazolo[1,5-a]pyridin-6-yl)-1-(tetrahydro-2H-pyran-4-yl)-3-(trifluoromethyl)-1H-pyrazolo[3,4-d]pyrimidin-6-amine (Ex. 17)

SCHEME 17

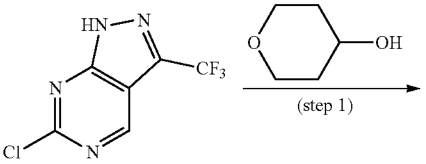

-continued

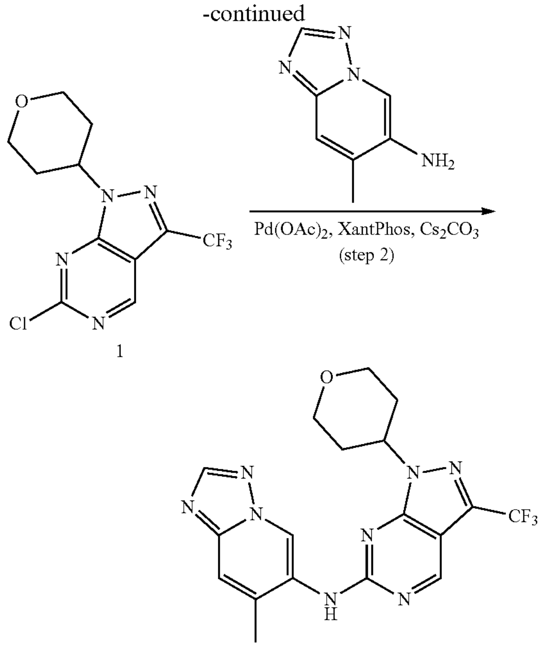

Example 17

Step 1. 6-chloro-1-(tetrahydro-2H-pyran-4-yl)-3-(trifluoromethyl)-1H-pyrazolo[3,4-d]pyrimidine To a stirred mixture of 6-chloro-3-(trifluoromethyl)-1H-pyrazolo[3,4-d]pyrimidine (340.00 mg, 1.528 mmol, 1.00 equiv), oxan-4-ol (624.11 mg, 6.111 mmol, 4.00 equiv) and $PPh_3$ (1442.48 mg, 5.500 mmol, 3.60 equiv) in THF (2.50 mL) was added DIAD (1112.07 mg, 5.500 mmol, 3.60 equiv) dropwise at 0° C. under nitrogen atmosphere. The resulting mixture was extracted with EtOAc (3×20 mL), dried over anhydrous $Na_2SO_4$. After filtration, the filtrate was concentrated under reduced pressure. The residue was purified by Prep-TLC ($CH_2Cl_2$/MeOH=10:1) to afford 6-chloro-1-(tetrahydro-2H-pyran-4-yl)-3-(trifluoromethyl)-1H-pyrazolo[3,4-d]pyrimidine (370 mg, 78.98%) as a white solid. LCMS: m/z (ESI), $[M+H]^+$=307.3.

Step 2. N-(7-methyl-[1,2,4]triazolo[1,5-a]pyridin-6-yl)-1-(tetrahydro-2H-pyran-4-yl)-3-(trifluoromethyl)-1H-pyrazolo[3,4-d]pyrimidin-6-amine (Ex. 17)

A mixture of 6-chloro-1-(oxan-4-yl)-3-(trifluoromethyl) pyrazolo[3,4-d]pyrimidine (70.00 mg, 0.228 mmol, 1.00 equiv), 7-methyl-[1,2,4]triazolo[1,5-a]pyridin-6-amine (33.82 mg, 0.228 mmol, 1.00 equiv), $Pd(AcO)_2$ (10.25 mg, 0.046 mmol, 0.20 equiv), XantPhos (39.62 mg, 0.068 mmol, 0.30 equiv) and $Cs_2CO_3$ (185.93 mg, 0.571 mmol, 2.50 equiv) in dioxane (3.00 mL) was stirred for 3 hs at 70° C. under nitrogen atmosphere. The resulting mixture was concentrated under vacuum. The residue was purified by Prep-TLC ($CH_2Cl_2$/MeOH=12:1). The crude product (90 mg) was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; Gradient: 30 B to 50 B in 7 min; RT1:6.67) to afford N-[7-methyl-[1,2,4]triazolo [1,5-a]pyridin-6-yl]-1-(oxan-4-yl)-3-(trifluoromethyl)pyrazolo[3,4-d]pyrimidin-6-amine (54.44 mg, 53.86%) as a white solid. LCMS: m/z (ESI), $[M+H]^+$=419.2. $^1H$ NMR (300 MHz, DMSO-$d_6$) δ 1.77-2.01 (2H, m), 2.01-2.24 (2H, m), 2.39 (3H, d), 3.40-3.59 (2H, m), 3.98 (2H, d), 4.82 (1H, t), 7.78 (1H, d), 8.44 (1H, s), 9.13 (2H, d), 9.69 (1H, s)

Example 18

Preparation of 1-(4-methoxybenzyl)-3-methyl-N-(7-methyl-[1,2,4]triazolo[1,5-a]pyridin-6-yl)-1H-pyrazolo[3,4-d]pyrimidin-6-amine (Ex. 18)

SCHEME 18

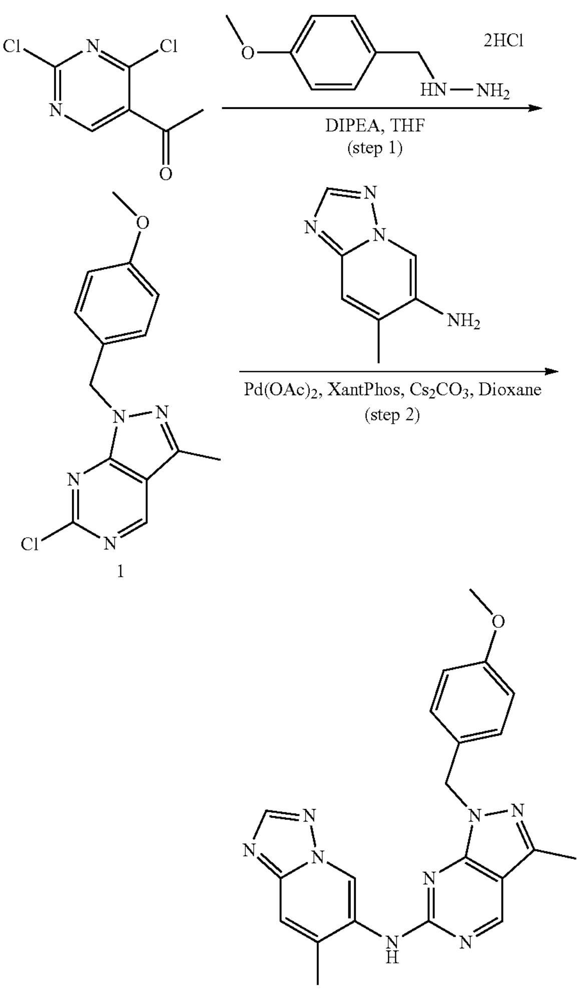

Example 18

Step 1. 6-chloro-1-(4-methoxybenzyl)-3-methyl-1H-pyrazolo[3,4-d]pyrimidine

To a stirred mixture of 1-(2,4-dichloropyrimidin-5-yl) ethanone (640.00 mg, 3.351 mmol, 1.00 equiv) and DIPEA (433.04 mg, 3.351 mmol, 1.00 equiv) in THF were added [(4-methoxyphenyl)methyl]hydrazine (764.93 mg, 5.026 mmol, 1.50 equiv) dropwise at 0° C. under air atmosphere. The resulting mixture was stirred for 2 h at room temperature under air atmosphere. The resulting mixture was concentrated under reduced pressure. The residue was purified by Prep-TLC (PE:EA 1:1) to afford 6-chloro-1-[(4-methoxyphenyl)methyl]-3-methylpyrazolo[3,4-d]pyrimidine (623 mg, 64.40%) as a yellow solid. LCMS: m/z (ESI), $[M+H]^+$=289.2. $^1H$ NMR (300 MHz, $CDCl_3$) δ2.58 (3H, s), 3.77 (3H, s), 5.47 (2H, s), 6.82-6.87 (2H, m), 7.30-7.35 (2H, m), 8.90 (1H, s)

Step 2. 1-(4-methoxybenzyl)-3-methyl-N-(7-methyl-[1,2,4]triazolo[1,5-a]pyridin-6-yl)-1H-pyrazolo[3,4-d]pyrimidin-6-amine (Ex. 18)

To a stirred mixture of 6-chloro-1-[(4-methoxyphenyl)methyl]-3-methylpyrazolo[3,4-d]pyrimidine (100.00 mg, 0.346 mmol, 1.00 equiv) and 7-methyl-[1,2,4]triazolo[1,5-a]pyridin-6-amine (76.97 mg, 0.519 mmol, 1.50 equiv) in dioxane (5 mL) were added $Cs_2CO_3$ (338.53 mg, 1.039 mmol, 3.00 equiv) and XantPhos (40.08 mg, 0.069 mmol, 0.20 equiv), $Pd(AcO)_2$ (15.55 mg, 0.069 mmol, 0.20 equiv) dropwise at room temperature under air atmosphere. The resulting mixture was stirred for 2 h at 80° C. under nitrogen atmosphere. The resulting mixture was concentrated under reduced pressure. The residue was purified by Prep-TLC ($CH_2Cl_2$/MeOH=10:1) to afford a yellow solid. The crude product (70 mg) was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; Gradient: 26 B to 46 B in 7 min; RT1:7.07) to afford 1-[(4-methoxyphenyl)methyl]-3-methyl-N-[7-methyl-[1,2,4]triazolo[1,5-a]pyridin-6-yl]pyrazolo[3,4-d]pyrimidin-6-amine (20 mg, 28.57%) as a white solid. LCMS: m/z (ESI), $[M+H]^+$=401.2. $^1H$ NMR (400 MHz, DMSO-$d_6$) δ 2.38 (3H, s), 2.44 (3H, s), 3.71 (3H, s), 5.24 (2H, s), 6.85-6.88 (2H, m), 7.18 (2H, t), 7.77 (1H, s), 8.43 (1H, s), 8.95 (1H, s), 9.22 (2H, d)

Example 20

Preparation of 1-cyclohexyl-3-methyl-N-(7-methyl-[1,2,4]triazolo[1,5-a]pyridin-6-yl)-1H-pyrazolo[3,4-d]pyrimidin-6-amine (Ex. 20)

SCHEME 20

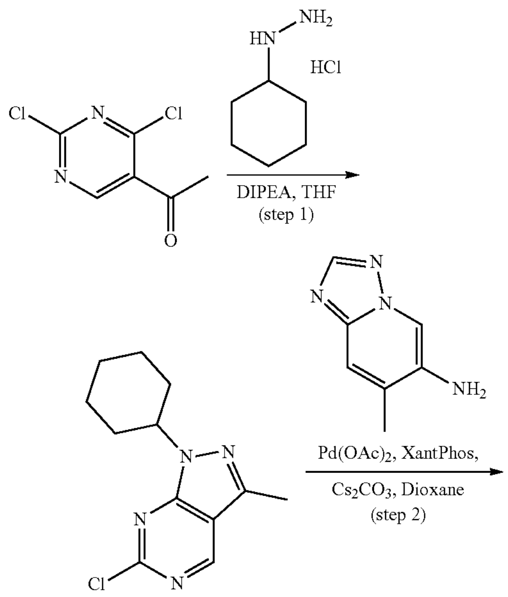

1

-continued

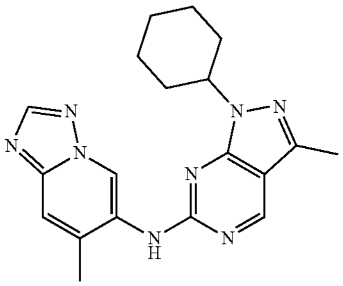

Example 20

Step 1. 6-chloro-1-cyclohexyl-3-methyl-1H-pyrazolo[3,4-d]pyrimidine

To a stirred mixture of 1-(2,4-dichloropyrimidin-5-yl)ethanone (180.00 mg, 0.942 mmol, 1.00 equiv) and DIPEA (487.17 mg, 3.769 mmol, 4.00 equiv) in THF (10 mL) was added cyclohexylhydrazine hydrochloride (184.56 mg, 1.225 mmol, 1.30 equiv) in portions at 0° C. under air atmosphere. The resulting mixture was stirred for 2 h at 25° C. under air atmosphere. The resulting mixture was concentrated under vacuum. The residue was purified by Prep-TLC (PE/EA 1:2) to afford 6-chloro-1-cyclohexyl-3-methylpyrazolo[3,4-d]pyrimidine (145 mg, 61.37%) as a yellow solid. LCMS: m/z (ESI), $[M+H]^+$=251.2. $^1H$ NMR (300 MHz, $CDCl_3$) δ 1.42-1.48 (2H, m), 1.51-1.55 (2H, m), 1.99-2.08 (6H, m), 2.60 (3H, s), 4.66-4.76 (1H, m), 8.90 (1H, s)

Step 2. 1-cyclohexyl-3-methyl-N-(7-methyl-[1,2,4]triazolo[1,5-a]pyridin-6-yl)-1H-pyrazolo [3,4-d]pyrimidin-6-amine (Ex. 20)

To a stirred mixture of 6-chloro-1-cyclohexyl-3-methylpyrazolo[3,4-d]pyrimidine (120.00 mg, 0.479 mmol, 1.00 equiv) and 7-methyl-[1,2,4]triazolo[1,5-a]pyridin-6-amine (106.37 mg, 0.718 mmol, 1.5 equiv) in dioxane (6 mL) were added $Cs_2CO_3$ (467.81 mg, 1.436 mmol, 3 equiv) and XantPhos (55.39 mg, 0.096 mmol, 0.2 equiv), $Pd(AcO)_2$ (21.49 mg, 0.096 mmol, 0.2 equiv) in portions at room temperature under air atmosphere. The resulting mixture was stirred for 2 h at 80° C. under nitrogen atmosphere. The resulting mixture was concentrated under vacuum. The residue was purified by Prep-TLC ($CH_2Cl_2$/MeOH=10:1) to afford crude solid. The crude product (80 mg) was purified by Prep-HPLC with the following conditions (Column: XBridge Prep OBD C18 Column, 30*150 mm 5 um; Phase A: Water (0.05% $NH_3 \cdot H_2O$), Mobile Phase B: ACN; Flow rate: 60 mL/min; Gradient: % B; 254; 220 nm; RT1: 6.50) to afford 1-cyclohexyl-3-methyl-N-[7-methyl-[1,2,4]triazolo[1,5-a]pyridin-6-yl]pyrazolo[3,4-d]pyrimidin-6-amine (60 mg, 34.59%) as a white solid. LCMS: m/z (ESI), $[M+H]^+$=363.2. $^1H$ NMR (300 MHz, DMSO-$d_6$) δ 1.23-1.38 (3H, m), 1.67 (1H, d), 1.81-1.97 (6H, m), 2.41-2.44 (6H, m), 4.36-4.43 (1H, m), 7.74 (1H, s), 8.41 (1H, s), 8.91 (1H, s), 9.15 (1H, s), 9.22 (1H, s).

Example 21

Preparation of 1-(4,4-difluorocyclohexyl)-3-methyl-N-(7-methyl-[1,2,4]triazolo[1,5-a]pyridin-6-yl)-1H-pyrazolo[3,4-d]pyrimidin-6-amine (Ex. 21)

SCHEME 21

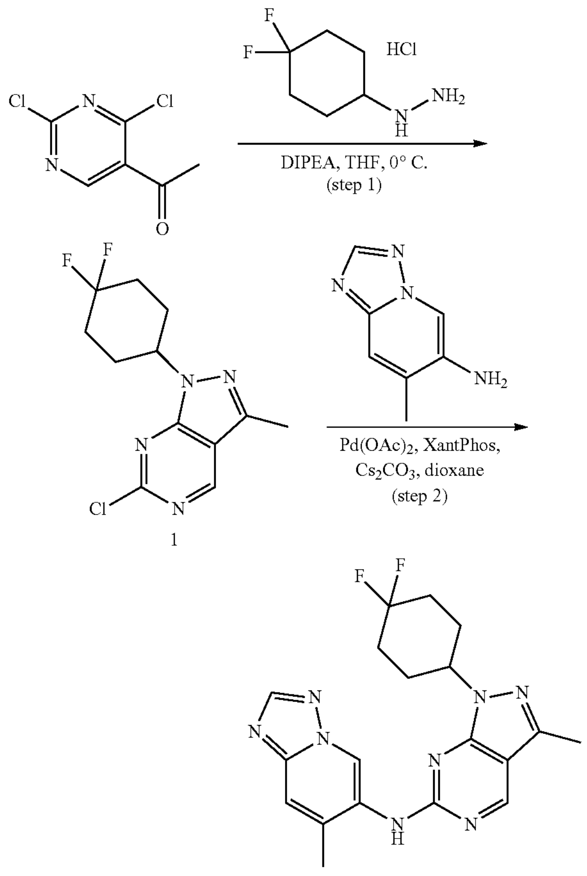

Example 21

Step 1. 6-chloro-1-(4,4-difluorocyclohexyl)-3-methyl-1H-pyrazolo[3,4-d]pyrimidine A mixture of DIPEA (338.32 mg, 2.618 mmol, 5 equiv), (4,4-difluorocyclohexyl)hydrazine (86.48 mg, 0.576 mmol, 1.10 equiv) and 1-(2,4-dichloropyrimidin-5-yl)ethanone (100.00 mg, 0.524 mmol, 1.00 equiv) in THF (5.00 mL) was stirred for 3 hrs at 0° C. under nitrogen atmosphere. The resulting mixture was concentrated under reduced pressure. The residue was purified by Prep-TLC (hexane/EtOAc 1:1) to afford 6-chloro-1-(4,4-difluorocyclohexyl)-3-methylpyrazolo[3,4-d]pyrimidine (80 mg, 53.30%) as a white solid. LCMS: m/z (ESI), $[M+H]^+$=287.3. $^1$H NMR (300 MHz, $CDCl_3$) δ 2.03 (4H, d), 2.35 (4H, d), 2.60 (3H, s), 4.85 (1H, t), 8.92 (1H, s).

Step 2. 1-(4,4-difluorocyclohexyl)-3-methyl-N-(7-methyl-[1,2,4]triazolo[1,5-a]pyridin-6-yl)-1H-pyrazolo[3,4-d]pyrimidin-6-amine (Ex. 21)

A mixture of $Cs_2CO_3$ (227.28 mg, 0.698 mmol, 2.5 equiv), XantPhos (32.29 mg, 0.056 mmol, 0.2 equiv), $Pd(AcO)_2$ (12.53 mg, 0.056 mmol, 0.2 equiv), 7-methyl-[1,2,4]triazolo[1,5-a]pyridin-6-amine (45.48 mg, 0.307 mmol, 1.1 equiv) and 6-chloro-1-(4,4-difluorocyclohexyl)-3-methylpyrazolo[3,4-d]pyrimidine (80.00 mg, 0.279 mmol, 1.00 equiv) in dioxane (3.00 mL) was stirred for 2 hrs at 100° C. under nitrogen atmosphere. The resulting mixture was concentrated under reduced pressure. The residue was purified by Prep-TLC ($CH_2Cl_2$/MeOH=12:1) to afford crude product. The crude product (100 mg) was purified by Prep-HPLC with the following conditions (Column: XBridge Prep OBD C18 Column, 19*250 mm, 5 um; Mobile Phase A: Water (0.05% $NH_3 \cdot H_2O$), Mobile Phase B: ACN; Flow rate: 60 mL/min; Gradient: 31 B to 51 B in 7 min; RT1: 6.30) to afford 1-(4,4-difluorocyclohexyl)-3-methyl-N-[7-methyl-[1,2,4]triazolo[1,5-a]pyridin-6-yl]pyrazolo[3,4-d]pyrimidin-6-amine (80 mg, 71.96%) as a white solid. LCMS: m/z (ESI), $[M+H]^+$=399.3. $^1$H NMR (300 MHz, DMSO-$d_6$) δ 1.99 (3H, s), 2.15 (5H, s), 2.38 (3H, d), 2.45 (3H, s), 4.62 (1H, s), 7.75 (1H, d), 8.42 (1H, s), 8.93 (1H, s), 9.13 (1H, s), 9.22 (1H, s).

Example 22

Preparation of 1-(4,4-difluorocyclohexyl)-3-methyl-N-(7-methylimidazo[1,2-a]pyridin-6-yl)-1H-pyrazolo[3,4-d]pyrimidin-6-amine (Ex. 22)

SCHEME 22

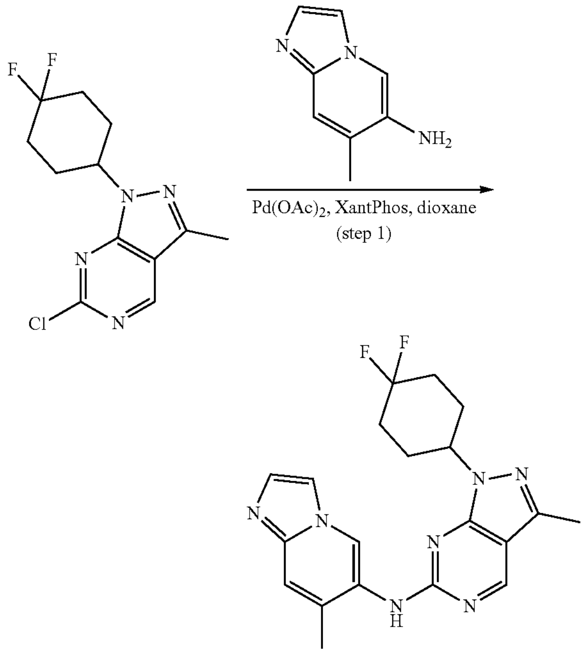

Example 22

Step 1. 1-(4,4-difluorocyclohexyl)-3-methyl-N-(7-methylimidazo[1,2-a]pyridin-6-yl)-1H-pyrazolo[3,4-d]pyrimidin-6-amine (Ex. 22)

A mixture of 6-chloro-1-(4,4-difluorocyclohexyl)-3-methylpyrazolo[3,4-d]pyrimidine (67.00 mg, 0.234 mmol, 1.00 equiv), 7-methylimidazo[1,2-a]pyridin-6-amine (68.79 mg, 0.467 mmol, 2 equiv), $Pd(AcO)_2$ (10.49 mg, 0.047 mmol, 0.20 equiv), XantPhos (40.56 mg, 0.070 mmol, 0.30 equiv) and $Cs_2CO_3$ (190.35 mg, 0.584 mmol, 2.50 equiv) in dioxane (5.00 mL) was stirred for 2 hs at 80° C. under nitrogen atmosphere. The resulting mixture was concentrated under vacuum. The residue was purified by Prep-TLC ($CH_2Cl_2$/MeOH=12:1). The crude product (50 mg) was purified by Prep-HPLC with the following conditions (Column: XBridge Prep OBD C18 Column, 30×150 mm 5 um; Mobile Phase A: Water (10 MMOL/L $NH_4HCO_3$+0.1% $NH_3 \cdot H_2O$), Mobile Phase B: ACN; Flow rate: 60 mL/min; Gradient: 38 B to 50 B in 7 min; RT1:5.63) to afford 1-(4,4-difluorocyclohexyl)-3-methyl-N-[7-methylimidazo[1,2-a]pyridin-6-yl]pyrazolo[3,4-d]pyrimidin-6-amine (20 mg) as a white solid. LCMS: m/z (ESI), $[M+H]^+$=398.2. $^1H$ NMR (300 MHz, DMSO-$d_6$) δ 1.95 (3H, d), 2.15 (5H, d), 2.26 (3H, d), 2.44 (3H, s), 4.62 (1H, s), 7.44 (1H, s), 7.50 (1H, d), 7.86 (1H, t), 8.72 (1H, s), 8.88 (1H, s), 9.02 (1H, s)

Example 26

Preparation of 1-((1r,4r)-4-methoxycyclohexyl)-3-methyl-N-(7-methylimidazo[1,2-a]pyridin-6-yl)-1H-pyrazolo[3,4-d]pyrimidin-6-amine (Ex. 26)

SCHEME 26

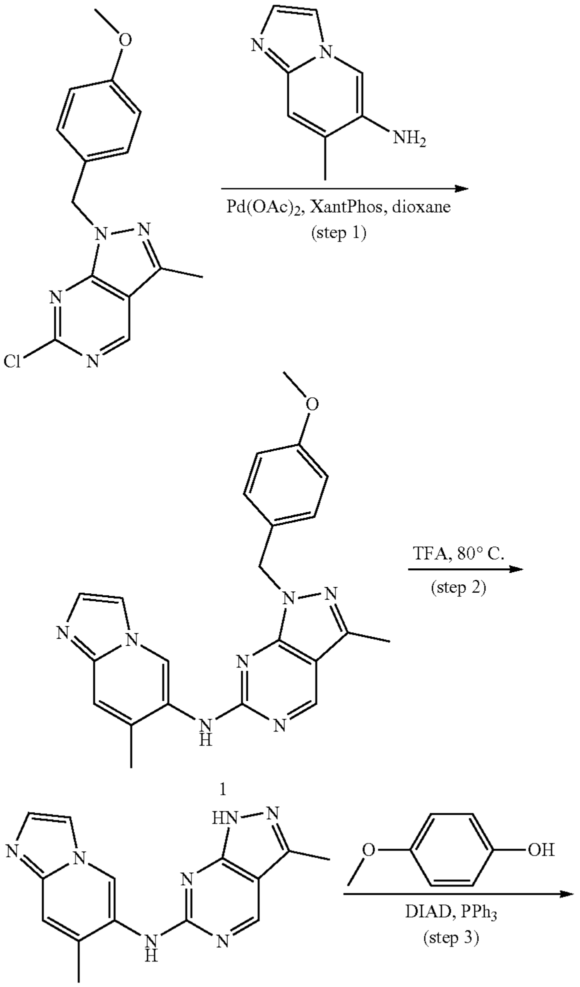

1

2

-continued

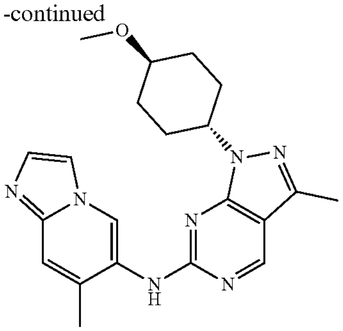

Example 26

Step 1. 1-(4-methoxybenzyl)-3-methyl-N-(7-methylimidazo[1,2-a]pyridin-6-yl)-1H-pyrazolo [3,4-d] pyrimidin-6-amine A mixture of 6-chloro-1-[(4-methoxyphenyl)methyl]-3-methylpyrazolo[3,4-d]pyrimidine (200.00 mg, 0.693 mmol, 1.00 equiv), 7-methylimidazo[1,2-a]pyridin-6-amine (152.92 mg, 1.039 mmol, 1.50 equiv), XantPhos (120.24 mg, 0.208 mmol, 0.30 equiv), $Pd(AcO)_2$ (31.10 mg, 0.139 mmol, 0.20 equiv) and $Cs_2CO_3$ (564.21 mg, 1.732 mmol, 2.50 equiv) in dioxane (3 mL) was stirred for 2 hs at 80° C. under nitrogen atmosphere. The resulting mixture was concentrated under reduced pressure. The residue was purified by Prep-TLC ($CH_2Cl_2$/MeOH=12:1) to afford 1-[(4-methoxyphenyl)methyl]-3-methyl-N-[7-methylimidazo[1,2-a]pyridin-6-yl]pyrazolo[3,4-d]pyrimidin-6-amine (200 mg, 72.28%) as a yellow solid. LCMS: m/z (ESI), $[M+H]^+$=400.3.

Step 2. 3-methyl-N-(7-methylimidazo[1,2-a]pyridin-6-yl)-1H-pyrazolo[3,4-d]pyrimidin-6-amine A solution of 1-[(4-methoxyphenyl)methyl]-3-methyl-N-[7-methylimidazo[1,2-a]pyridin-6-yl]pyrazolo[3,4-d]pyrimidin-6-amine (190.00 mg, 0.476 mmol, 1.00 equiv) and TFA (70.00 mL, 613.910 mmol, 1981.34 equiv) was stirred for 2 days at 80° C. under air atmosphere. The resulting mixture was concentrated under vacuum. The resulting mixture was diluted with DCM (10 mL). The mixture was adjusted to pH 8 with saturated $NaHCO_3$ (aq.) by filtration and washed with DCM (2×3 mL). The precipitated solids were collected to afford 3-methyl-N-[7-methylimidazo[1,2-a]pyridin-6-yl]-1H-pyrazolo[3,4-d]pyrimidin-6-amine (160 mg, 80.00%), LCMS: m/z (ESI), $[M+H]^+$=280.2

Step 3. 1-((1r,4r)-4-methoxycyclohexyl)-3-methyl-N-(7-methylimidazo[1,2-a]pyridin-6-yl)-1H-pyrazolo[3,4-d]pyrimidin-6-amine (Ex. 26)

A mixture of 3-methyl-N-[7-methylimidazo[1,2-a]pyridin-6-yl]-1H-pyrazolo[3,4-d]pyrimidin-6-amine (150.00 mg, 0.537 mmol, 1.00 equiv), 4-methoxycyclohexan-1-ol (174.79 mg, 1.343 mmol, 2.50 equiv) and $PPh_3$ (422.58 mg, 1.611 mmol, 3.00 equiv) in THF (2.50 mL) was stirred for 20 min at 0° C. under nitrogen atmosphere then DIAD (325.78 mg, 1.611 mmol, 3.00 equiv) was added, and the mixture was stirred for 2 hs at 70° C. The resulting mixture was concentrated under reduced pressure. The residue was purified by Prep-TLC ($CH_2Cl_2$/EtOAc=12:1) to afford crude solid. The crude product (60.00 mg) was purified by Prep- HPLC with the following conditions (Column: XBridge Prep OBD C18 Column, 30×150 mm 5 um; Mobile Phase A: Water (10 MMOL/L $NH_4HCO_3$+0.1% $NH_3 \cdot H_2O$), Mobile Phase B: ACN; Flow rate: 60 mL/min; Gradient: 29 B to 39 B in 9 min; RT1:6.22, 7.43) to afford 3-methyl-N-[7-methylimidazo[1,2-a]pyridin-6-yl]-1-[(1r,4r)-4-methoxycyclohexyl]pyrazolo[3,4-d]pyrimidin-6-amine (16 mg, 26.67%) as a white solid. LCMS: m/z (ESI), $[M+H]^+$=392.2. $^1H$ NMR (300 MHz, MeOD-$d_4$) δ 1.31-1.46 (2H, m), 2.00 (2H, s), 2.03-2.14 (2H, m), 2.21 (2H, d), 2.39 (3H, d), 2.50 (3H, s), 3.23 (1H, d), 3.38 (3H, s), 4.51 (1H, t), 7.46 (1H, s), 7.54 (1H, d), 7.80 (1H, s), 8.82 (2H, s).

Example 27

Preparation of 1-((1s,4s)-4-fluorocyclohexyl)-3-methyl-N-(7-methyl-[1,2,4]triazolo[1,5-a]pyridin-6-yl)-1H-pyrazolo[3,4-d]pyrimidin-6-amine (Ex. 27) and 1-((1r,4r)-4-fluorocyclohexyl)-3-methyl-N-(7-methyl-[1,2,4]triazolo[1,5-a]pyridin-6-yl)-1H-pyrazolo[3,4-d]pyrimidin-6-amine (Ex. 28)

SCHEME 27

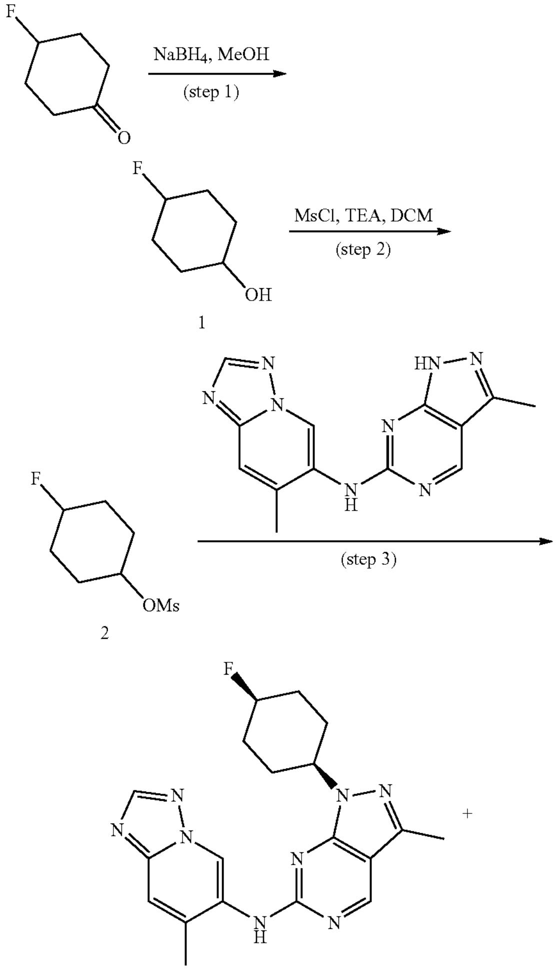

-continued

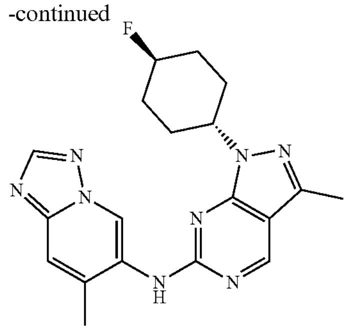

Example 28

Step 1. 4-fluorocyclohexane-1-ol

To a stirred mixture of 4-fluorocyclohexan-1-one (1.00 g, 8.611 mmol, 1.00 equiv) and MeOH (100.00 mL) was added $NaBH_4$ (0.98 mg, 0.026 mmol, 3.0 equiv) in portions at 0° C. The resulting mixture was stirred for 16 h at room temperature. The reaction was quenched with water at 0° C. The resulting mixture was concentrated under reduced pressure. The resulting mixture was diluted with water (50 mL). The resulting mixture was extracted with $CH_2Cl_2$ (3×50 mL). The combined organic layers were washed with brine, dried over anhydrous $Na_2SO_4$. After filtration, the filtrate was concentrated under reduced pressure to afford 4-fluorocyclohexan-1-ol (800 mg, 78.63%) as light yellow solid. $^1$HNMR (300 MHz, DMSO-$d_6$) δ 1.52-1.56 (5H, m), 1.88-1.90 (3H, m), 3.54-3.57 (1H, m), 4.55-4.58 (1H, m), 4.70-4.72 (1H, m)

Step 2. 4-fluorocyclohexyl methanesulfonate

To a stirred mixture of 4-fluorocyclohexan-1-ol (400.00 mg, 3.385 mmol, 1.00 equiv) and TEA (1027.74 mg, 10.156 mmol, 3.00 equiv) in DCM (10.00 mL) was added methanesulfonyl chloride (581.66 mg, 5.078 mmol, 1.5 equiv) dropwise at 0 degrees C. The resulting mixture was stirred for 2 hours at room temperature. The resulting mixture was diluted with water (50 mL). The resulting mixture was extracted with $CH_2Cl_2$ (3×50 mL). The combined organic layers were washed with brine, dried over anhydrous $Na_2SO_4$. After filtration, the filtrate was concentrated under reduced pressure. The resulting mixture was concentrated under reduced pressure to afford 4-fluorocyclohexyl methanesulfonate (650 mg, 97.84%) as a light yellow solid. The crude product was used in the next step directly without further purification.

$^1$HNMR (300 MHz, DMSO-$d_6$) δ 1.52-1.90 (8H, m), 3.22 (3H, s), 4.60-4.78 (2H, m)

Step 3. 1-((1s,4s)-4-fluorocyclohexyl)-3-methyl-N-(7-methyl-[1,2,4]triazolo[1,5-a]pyridin-6-yl)-1H-pyrazolo[3,4-d]pyrimidin-6-amine (Ex. 27) and 1-((1r,4r)-4-fluorocyclohexyl)-3-methyl-N-(7-methyl-[1,2,4]triazolo[1,5-a]pyridin-6-yl)-1H-pyrazolo[3,4-d]pyrimidin-6-amine (Ex. 28)

A mixture of 3-methyl-N-[7-methyl-[1,2,4]triazolo[1,5-a]pyridin-6-yl]-1H-pyrazolo[3,4-d]pyrimidin-6-amine (150.00 mg, 0.535 mmol, 1.00 equiv), 4-fluorocyclohexyl methanesulfonate (1050.18 mg, 5.352 mmol, 10.00 equiv) and $Cs_2CO_3$ (523.09 mg, 1.605 mmol, 3.00 equiv) in DMF (20.00 mL) was stirred for 16 h at 110° C. under nitrogen atmosphere. The resulting mixture was diluted with water (20 mL). The resulting mixture was extracted with EtOAc (3×20 mL). The combined organic layers were washed with brine, dried over anhydrous $Na_2SO_4$. After filtration, the filtrate was concentrated under reduced pressure. The crude product (100 mg) was purified by Prep-HPLC with the following conditions (Column: XBridge Prep OBD C18 Column, 30×150 mm 5 um; Mobile Phase A: Water (0.05% $NH_3$·$H_2O$), Mobile Phase B: ACN; Flow rate: 60 mL/min; Gradient: 39 B to 59 B in 7 min; RT1:6.4) to afford:

1-((1s,4s)-4-fluorocyclohexyl)-3-methyl-N-(7-methyl-[1,2,4]triazolo[1,5-a]pyridin-6-yl)-1H-pyrazolo[3,4-d]pyrimidin-6-amine (Ex. 27, 6.8 mg, 3.34%) as a white solid. LCMS: m/z (ESI), $[M+H]^+$=381.2. $^1$HNMR (300 MHz, DMSO-$d_6$) δ 1.66-1.68 (1H, m), 1.75 (3H, d), 2.04-2.06 (2H, m), 2.18-2.19 (2H, m), 2.38 (3H, d), 2.45 (3H, s), 4.50-4.53 (1H, m), 4.81-4.93 (1H, s), 7.73 (1H, s), 8.40 (1H, s), 8.91 (1H, s), 9.15 (2H, d); 1-((1r,4r)-4-fluorocyclohexyl)-3-methyl-N-(7-methyl-[1,2,4]triazolo[1,5-a]pyridin-6-yl)-1H-pyrazolo[3,4-d]pyrimidin-6-amine (Ex. 28, 18.8 mg, 9.23%) as a white solid. LCMS: m/z (ESI), $[M+H]^+$=381.2. $^1$HNMR (400 MHz, DMSO-$d_6$) δ 1.63-1.65 (2H, m), 1.92-1.96 (4H, m), 2.00-2.04 (2H, m), 2.14 (3H, s), 2.41 (3H, s), 4.47-4.49 (1H, m), 4.61-4.65 (1H, m), 7.74 (1H, s), 8.41 (1H, s), 8.91 (1H, s), 9.19 (2H, d).

Example 42

Preparation of 3-methyl-N-(7-methyl-[1,2,4]triazolo[1,5-a]pyridin-6-yl)-1-(2-oxaspiro[3.3]heptan-6-yl)-1H-pyrazolo[3,4-d]pyrimidin-6-amine (Ex. 42)

SCHEME 42

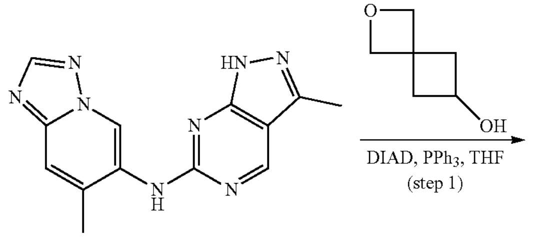

-continued

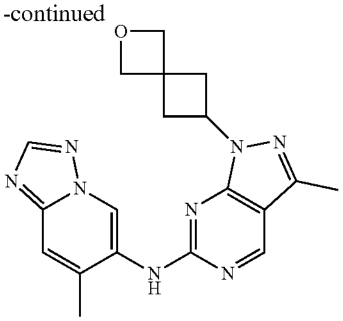

Example 42

Step 1. 3-methyl-N-(7-methyl-[1,2,4]triazolo[1,5-a]pyridin-6-yl)-1-(2-oxaspiro[3.3]heptan-6-yl)-1H-pyrazolo[3,4-d]pyrimidin-6-amine (Ex. 42)

To a stirred mixture of 3-methyl-N-[7-methyl-[1,2,4]triazolo[1,5-a]pyridin-6-yl]-1H-pyrazolo[3,4-d]pyrimidin-6-amine (70.00 mg, 0.250 mmol, 1.00 equiv) and 2-oxaspiro[3.3]heptan-6-ol (57.01 mg, 0.499 mmol, 2.00 equiv) and $PPh_3$ (196.51 mg, 0.749 mmol, 3.00 equiv) in THF (10 mL) were added DIAD (151.50 mg, 0.749 mmol, 3.00 equiv) in portions at 0° C. under $N_2$ atmosphere. The resulting mixture was stirred for 2 h at 70° C. under nitrogen atmosphere. The resulting mixture was concentrated under vacuum. The residue was purified by Prep-TLC (DCM/MeOH=15:1) to afford crude solid. The crude product (80 mg) was purified by Prep-HPLC with the following conditions (Column: XBridge Prep OBD C18 Column, 30×150 mm 5 um; Mobile Phase A: Water (10 MMOL/L $NH_4HCO_3$+0.1% $NH_3$·$H_2O$), Mobile Phase B: ACN; Flow rate: 60 mL/min; Gradient: 26 B to 36 B in 7 min; RT1:5.88) to afford 3-methyl-N-[7-methyl-[1,2,4]triazolo[1,5-a]pyridin-6-yl]-1-[2-oxaspiro[3.3]heptan-6-yl]pyrazolo[3,4-d]pyrimidin-6-amine (40 mg, 50.00%) as a white solid. LCMS: m/z (ESI), $[M+H]^+$=337.3. $^1$H NMR (300 MHz, DMSO-$d_6$) δ 2.37 (3H, s), 2.44 (3H, s), 2.65-2.80 (4H, m), 4.45 (2H, s), 4.64 (2H, s), 4.84-4.89 (1H, m), 7.76 (1H, s), 8.42 (1H, s), 8.92 (1H, s), 9.13 (1H, s), 9.18 (1H, s).

The following compounds in table 2 below are synthesized by the similar method descried in example 42.

TABLE 2

| Example number | Structures | LCMS | NMR |
|---|---|---|---|
| 19 | 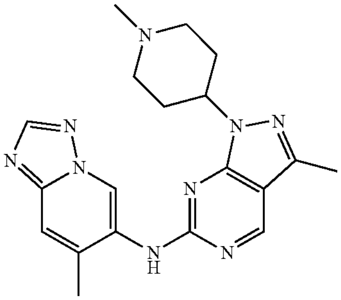 [SMILES: Cc1cc2ncnn2cc1Nc1ncc2c(C)nn(C3CCN(C)CC3)c2n1] | 378.2 | $^1$H NMR (300 MHz, DMSO-$d_6$) δ 1.70-1.75 (2H, m), 1.95-2.15 (4H, m), 2.22 (3H, d), 2.27-2.45 (6H, m), 2.73-2.90 (2H, m), 4.33-4.42 (1H, m), 7.75 (1H, s), 8.42 (1H, s), 8.91 (s, 1H), 9.18 (2H, s) |

TABLE 2-continued
| Example number | Structures | LCMS | NMR |
|---|---|---|---|
| 23 | 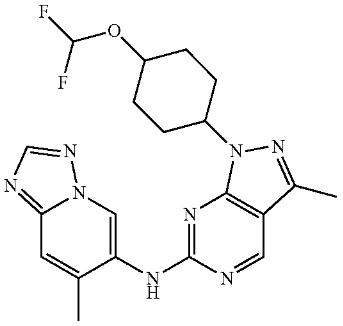 [SMILES: Cc1cc2ncnn2cc1Nc1ncc2c(C)nn(C3CCC(OC(F)F)CC3)c2n1] | 429.2 | $^1$H NMR (300 MHz, DMSO-$d_6$) δ 1.50-1.63 (2H, m), 1.93-2.11 (6H, m), 2.40 (3H, s), 2.44 (3H, s), 4.13-4.20 (1H, m), 4.42-4.49 (1H, m), 6.48-6.99 (1H.m), 7.74 (1H, s), 8.41 (1H, s), 8.92 (1H, s), 9.21 (2H, d) |
| 24 | 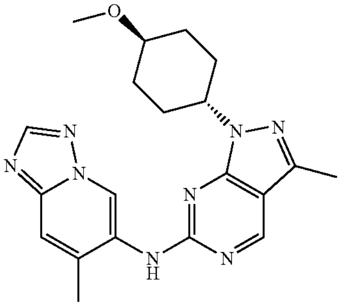 [SMILES: CO[C@H]1CC[C@H](n2nc(C)c3cnc(Nc4cn5ncnc5cc4C)nc32)CC1] | 393.3 | $^1$H NMR (400 MHz, DMSO-$d_6$) δ 1.19-1.35 (2H, m), 1.91-1.98 (4H, m), 2.01-2.12 (2H, m), 2.40 (3H, s), 2.44 (3H, s), 3.18-3.24 (1H, m), 3.26 (3H, s), 4.38-4.44 (1H, m), 7.73 (1H, s), 8.40 (1H, s), 8.91 (1H, s), 9.16 (1H, s), 9.22 (1H, s) |
| 25 | 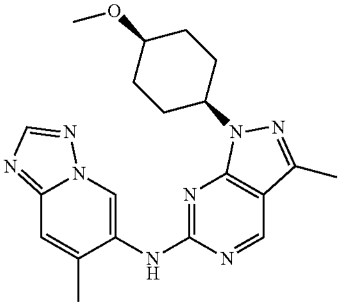 [SMILES: CO[C@H]1CC[C@@H](n2nc(C)c3cnc(Nc4cn5ncnc5cc4C)nc32)CC1] | 393.3 | $^1$H NMR (400 MHz, DMSO-$d_6$) δ 1.40-1.58 (2H, m), 1.63 (2H, t), 1.98 (2H, t), 209-2.19 (2H, m), 2.38 (3H, s), 2.44 (3H, s), 3.21 (3H, s), 3.42 (1H, s), 4.41-4.47 (1H, m), 7.73 (1H, s), 8.40 (1H, s), 8.90 (1H, s), 9.15 (2H, s) |
| 31 | 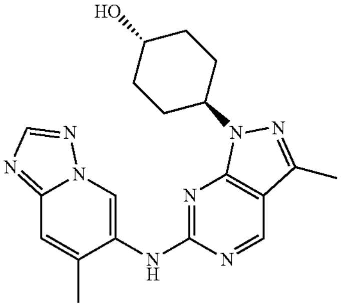 [SMILES: Cc1cc2ncnn2cc1Nc1ncc2c(C)nn([C@H]3CC[C@H](O)CC3)c2n1] | 379.3 | $^1$H NMR (300 MHz, DMSO-$d_6$) δ 1.17-1.51 (2H, m), 1.83-2.07 (6H, m), 2.41 (3H, s), 2.43 (3H, s), 3.52 (1H, d), 4.34-4.43 (1H, m), 4.63 (1H, s), 7.74 (1H, s), 8.40 (1H, s), 8.90 (1H, d), 9.14 (1H, s), 9.21 (1H, s) |
| 32 | 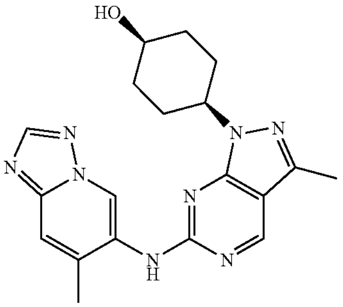 [SMILES: Cc1cc2ncnn2cc1Nc1ncc2c(C)nn([C@H]3CC[C@@H](O)CC3)c2n1] | 379.3 | $^1$H NMR (300 MHz, DMSO-$d_6$) δ 1.56-1.63 (4H, m), 1.77-1.81 (2H, m), 2.07-2.37 (2H, m), 2.39 (3H, s), 2.45 (3H, s), 3.87 (1H, d), 4.38-4.46 (2H, m), 7.73 (1H, s), 8.40 (1H, s), 8.90 (1H, d), 9.12 (1H, s), 9.18 (1H, s) |

TABLE 2-continued
| Example number | Structures | LCMS | NMR |
|---|---|---|---|
| 33 | 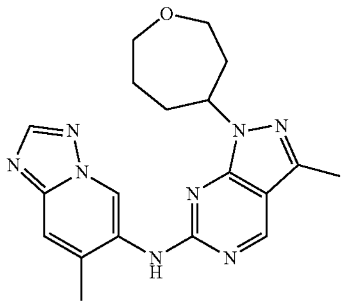 [SMILES: Cc1cc2ncnn2cc1Nc1ncc2c(C)nn(C3CCCOCC3)c2n1] | 379.3 | $^1$HNMR (300 MHz, MeOD-$d_4$) δ 1.91 (2H, m), 2.04-2.12 (2H, m), 2.37-2.41 (2H, m), 2.51 (6H, d), 3.82-3.85 (4H, m), 4.87 (1H, t), 7.66-7.69 (1H, m), 8.34 (1H, s), 8.86 (1H, s), 9.43 (1H, s). (isomer 1) |
| 34 | 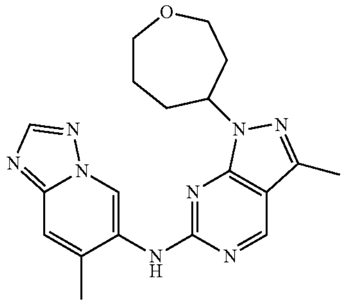 [SMILES: Cc1cc2ncnn2cc1Nc1ncc2c(C)nn(C3CCCOCC3)c2n1] | 379.3 | $^1$HNMR (300 MHz, MeOD-$d_4$) δ 1.91-1.93 (2H, m), 2.04-2.14 (2H, m), 2.33-2.37 (2H, m), 2.51 (6H, s), 3.82-3.85 (4H, m), 4.85 (1H, dd), 7.66 (1H, s), 8.34 (1H, s), 8.87 (1H, s), 9.43 (1H, s), (isomer 2) |
| 35 | 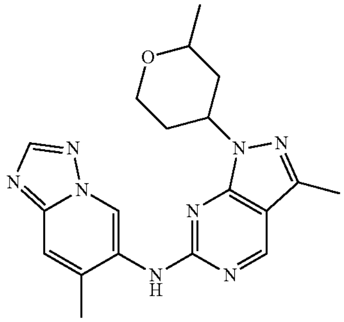 [SMILES: Cc1cc2ncnn2cc1Nc1ncc2c(C)nn(C3CCOC(C)C3)c2n1] | 379.3 | $^1$HNMR (300 MHz, DMSO-$d_6$) δ 1.05 (3H, d), 1.67-1.69 (1H, m), 1.93-1.96 (1H, m), 2.13 (2H, d), 2.36-2.39 (3H, m), 2.45 (3H, s), 3.71 (1H, d), 3.82 (1H, d), 4.01 (1H, s), 4.82 (1H, d), 7.72 (1H, s), 8.39 (1H, s), 8.92 (1H, s), 9.15 (2H, d). (isomer 1) |
| 36 | 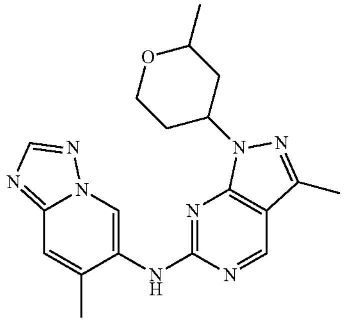 [SMILES: Cc1cc2ncnn2cc1Nc1ncc2c(C)nn(C3CCOC(C)C3)c2n1] | 379.3 | $^1$HNMR (300 MHz, DMSO-$d_6$) δ 1.05 (3H, d), 1.66-1.69 (1H, m), 2.03-2.08 (1H, m), 2.13-2.16 (2H, m), 2.37 (3H, d), 2.45-2.47 (3H, m), 3.71 (1H, d), 3.81-3.84 (1H, m), 4.00-4.05 (1H, s), 4.80 (1H, d), 7.72 (1H, s), 8.39 (1H, s), 8.92 (1H, s), 9.15 (2H, d). (isomer 2) |
| 50 | 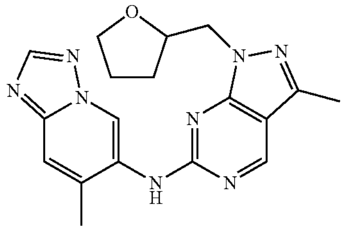 [SMILES: Cc1cc2ncnn2cc1Nc1ncc2c(C)nn(CC3CCCO3)c2n1] | 365.3 | $^1$H NMR (300 MHz, DMSO-$d_6$) δ 1.82-1.93 (4H, m), 2.40 (3H, s), 2.45 (3H, s), 3.55-3.76 (2H, m), 4.01-4.27 (3H, m), 7.74 (1H, s), 8.40 (1H, s), 8.94 (1H, s), 9.21 (2H, d). (isomer 1) |

TABLE 2-continued
| Example number | Structures | LCMS | NMR |
|---|---|---|---|
| 51 | 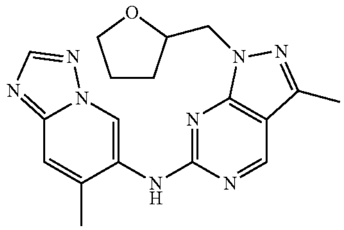 [SMILES: Cc1cc2ncnn2cc1Nc1ncc2c(C)nn(CC3CCCO3)c2n1] | 365.2 | $^1$H NMR (300 MHz, DMSO-$d_6$) δ 1.84-1.93 (4H, m), 2.40 (3H, s), 2.45 (3H, s), 3.55-3.77 (2H, m), 4.02-4.27 (3H, m), 7.74 (1H, s), 8.40 (1H, s), 8.94 (1H, s), 9.21 (2H, d). (isomer 2) |
| 52 | 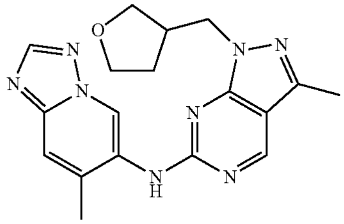 [SMILES: Cc1cc2ncnn2cc1Nc1ncc2c(C)nn(CC3CCOC3)c2n1] | 365.2 | $^1$H NMR (300 MHz, DMSO-$d_6$) δ 1.56-1.67 (1H, m), 1.83-1.94 (1H, m), 2.39 (3H, s), 2.45 (3H, s), 2.66-2.80 (1H, m), 3.50 (1H, d), 3.57-3.76 (3H, m), 4.03-4.16 (2H, m), 7.75 (1H, s), 8.41 (1H, s), 8.94 (1H, d), 9.18 (1H, s), 9.21 (1H, s) (isomer 1) |
| 53 | 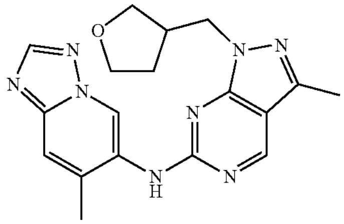 [SMILES: Cc1cc2ncnn2cc1Nc1ncc2c(C)nn(CC3CCOC3)c2n1] | 365.2 | $^1$H NMR (300 MHz, DMSO-$d_6$) δ 1.56-1.67 (1H, m), 1.83-1.94 (1H, m), 2.39 (3H, s), 2.45 (3H, s), 2.66-2.80 (1H, m), 3.50 (1H, d), 3.57-3.76 (3H, m), 4.03-4.16 (2H, m), 7.75 (1H, s), 8.41 (1H, s), 8.94 (1H, d), 9.18 (1H, s), 9.21 (1H, s) (isomer 2) |
| 54 | 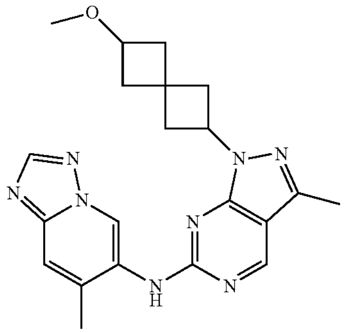 [SMILES: COC1CC2(C1)CC(n1nc(C)c3cnc(Nc4cn5ncnc5cc4C)nc31)C2] | 405.3 | $^1$H NMR (300 MHz, DMSO-$d_6$) δ 1.85 (1H, d), 1.92 (1H, d), 2.01-2.14 (1H, m), 2.28-2.44 (9H, m), 2.61-2.69 (2H, m), 3.28 (3H, d), 3.73 (1H, t), 4.92 (1H, t), 7.75 (1H, s), 8.41 (1H, s), 8.91 (1H, s), 9.14 (1H, s), 9.17 (1H, s). |
| 55 | 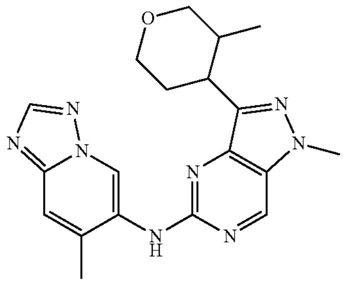 [SMILES: Cc1cc2ncnn2cc1Nc1ncc2c(n1)c(C1CCOCC1C)nn2C] | 379.3 | $^1$H NMR (300 MHz, DMSO-$d_6$) δ 0.52 (3H, d), 1.74 (1H, d), 2.06-2.31 (2H, m), 2.36 (3H, d), 2.45 (3H, s), 3.07 (1H, t), 3.43 (1H, t), 3.82-4.00 (2H, m), 4.14-4.27 (1H, m), 7.69-7.76 (1H, m), 8.39 (1H, s), 8.91 (1H, s), 9.15 (2H, d) (isomer 1) |

TABLE 2-continued
| Example number | Structures | LCMS | NMR |
|---|---|---|---|
| 56 | 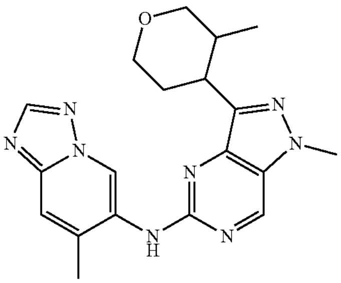 [SMILES: Cc1cc2ncnn2cc1Nc1ncc2c(n1)c(C1CCOCC1C)nn2C] | 379.3 | $^1$H NMR (300 MHz, DMSO-$d_6$) δ 0.70 (3H, d), 1.74-1.91 (1H, m), 2.23 (1H, dd), 2.37 (4H, d), 2.44 (3H, s), 3.44-3.65 (2H, m), 3.72 (1H, dd), 4.05 (1H, dt), 4.79 (1H, dt), 7.72 (1H, s), 8.39 (1H, s), 8.93 (1H, s), 9.17 (2H, s) (isomer 2) |
| 66 | 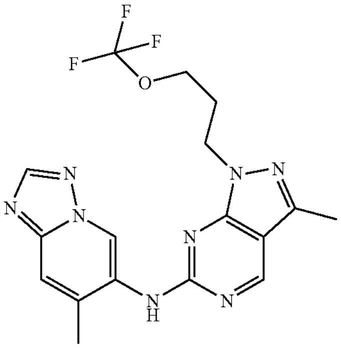 [SMILES: Cc1cc2ncnn2cc1Nc1ncc2c(C)nn(CCCOC(F)(F)F)c2n1] | 407.2 | $^1$H NMR (300 MHz, DMSO-$d_6$) δ 2.14-2.22 (2H, m), 2.38 (3H, s), 2.45 (3H, s), 4.04 (2H, t), 4.22 (2H, t), 7.73 (1H, s), 8.40 (1H, s), 8.94 (1H, s), 9.14 (1H, s), 9.22 (1H, s) |
| 67 | 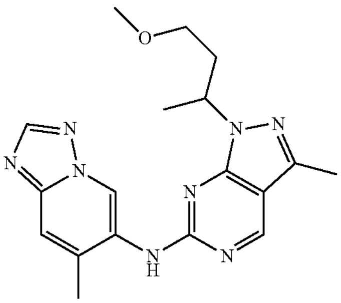 [SMILES: COCCC(C)n1nc(C)c2cnc(Nc3cn4ncnc4cc3C)nc21] | 367.3 | $^1$H NMR (300 MHz, DMSO-$d_6$) δ 1.45 (3H, s), 1.80-2.13 (2H, m), 2.40 (3H, s), 2.46 (3H, s), 2.97-3.04 (1H, m), 3.09 (3H, s), 3.15-3.22 (1H, m), 4.74-4.81 (1H, m), 7.74 (1H, s), 8.40 (1H, s), 8.93 (1H, s), 9.14 (1H, s), 9.22 (1H, s) (isomer 1) |
| 68 | 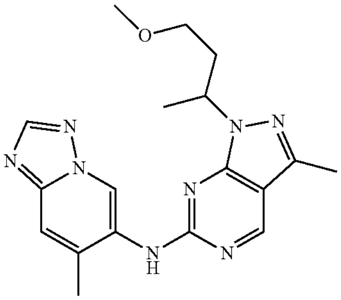 [SMILES: COCCC(C)n1nc(C)c2cnc(Nc3cn4ncnc4cc3C)nc21] | 367.3 | $^1$H NMR (300 MHz, DMSO-$d_6$) δ 1.45 (3H, s), 1.80-2.15 (2H, m), 2.41 (3H, s), 2.46 (3H, s), 2.97-3.04 (1H, m), 3.09 (3H, s), 3.15-3.22 (1H, m), 4.74-4.81 (1H, m), 7.74 (1H, s), 8.40 (1H, s), 8.93 (1H, s), 91.4 (1H, s), 9.22 (1H, s) (isomer 2) |
| 69 | 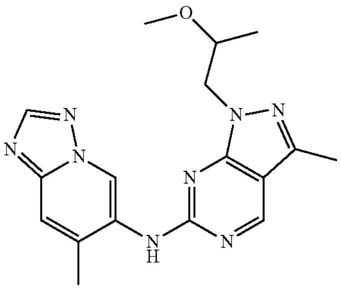 [SMILES: COC(C)Cn1nc(C)c2cnc(Nc3cn4ncnc4cc3C)nc21] | 353.2 | $^1$H NMR (DMSO-$d_6$, 400 MHz) δ 1.07 (3H, t), 2.40 (3H, s), 2.45 (3H, s), 3.16 (3H, d), 3.75-3.81 (1H, m), 4.01-4.06 (1H, m), 4.14-4.24 (1H, m), 7.74 (1H, s), 8.40 (1H, d), 8.94 (1H, d), 9.20 (2H, d), (racemate) |

TABLE 2-continued

| Example number | Structures | LCMS | NMR |
|---|---|---|---|
| 70 | 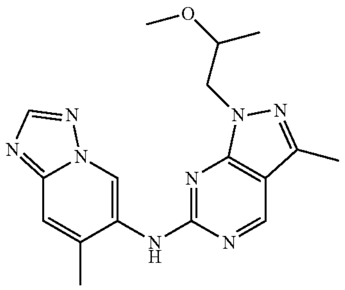 [SMILES: COC(C)Cn1nc(C)c2cnc(Nc3cn4ncnc4cc3C)nc21] | 353.3 | $^1H$ NMR (400 MHz, DMSO-$d_6$) δ 1.08 (3H, d), 2.40 (3H, d), 2.46 (3H, s), 3.16 (3H, s), 3.75-3.80 (1H, m), 4.05 (1H, d), 4.20 (1H, d), 7.75 (1H, m), 8.41 (1H, s), 8.95 (1H, s), 9.22 (2H, d) (isomer 1) |
| 71 | 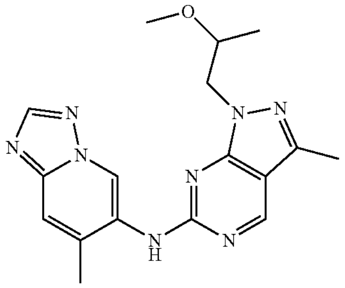 [SMILES: COC(C)Cn1nc(C)c2cnc(Nc3cn4ncnc4cc3C)nc21] | 353.3 | $^1H$ NMR (400 MHz, DMSO-$d_6$) δ 1.07 (3H, d), 2.40 (3H, d), 2.45 (3H, m), 3.16 (3H, s), 3.75-3.80 (1H, m), 4.04 (1H, d), 4.19 (1H, d), 7.74 (1H, s), 8.41 (1H, s), 8.94 (1H, m), 9.21 (2H, d). (isomer 2) |

Example 37

Preparation of 3-methyl-N-(7-methyl-[1,2,4]triazolo[1,5-a]pyridin-6-yl)-1-(spiro[2.5]octan-6-yl)-1H-pyrazolo[3,4-d]pyrimidin-6-amine (Ex. 37)

SCHEME 37

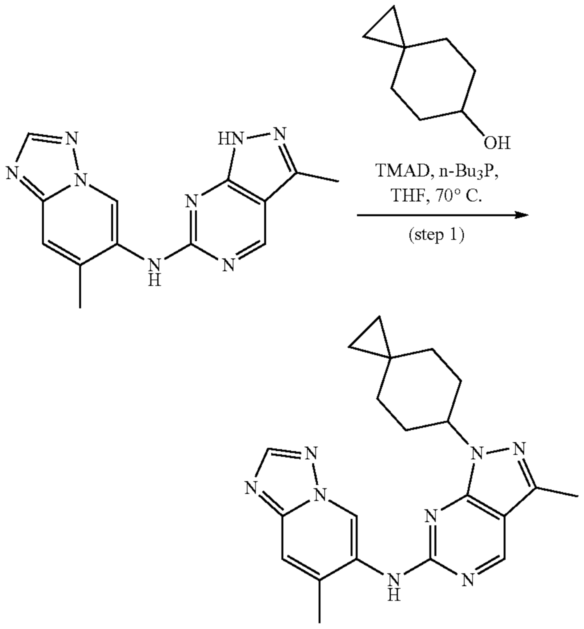

Example 37

Step 1. 3-methyl-N-(7-methyl-[1,2,4]triazolo[1,5-a]pyridin-6-yl)-1-(spiro[2.5]octan-6-yl)-1H-pyrazolo[3,4-d]pyrimidin-6-amine (Ex. 37)

A mixture of TMAD (276.43 mg, 1.605 mmol, 3.00 equiv), n-$Bu_3P$ (324.81 mg, 1.605 mmol, 3.00 equiv), spiro[2.5]octan-6-ol (202.61 mg, 1.605 mmol, 3.00 equiv) and 3-methyl-N-[7-methyl-[1,2,4]triazolo[1,5-a]pyridin-6-yl]-1H-pyrazolo[3,4-d]pyrimidin-6-amine (150.00 mg, 0.535 mmol, 1.00 equiv) in THF (25.00 mL) was stirred for 2 h at 70 degrees C. under nitrogen atmosphere. The resulting mixture was diluted with water (100 mL). The resulting mixture was extracted with $CH_2Cl_2$ (3×50 mL), dried over anhydrous $Na_2SO_4$. After filtration, the filtrate was concentrated under reduced pressure. The crude product was re-crystallized from MeOH (20 mL) to afford crude product. The crude product (60 mg) was purified by Prep-HPLC with the following conditions (Column: XBridge Prep OBD C18 Column, 19*250 mm, 5 um; Mobile Phase A: Water (0.05% $NH_3 \cdot H_2O$), Mobile Phase B: MeOH; Flow rate: 25 mL/min; Gradient 58 B to 70 B in 7 min) to afford 3-methyl-N-[7-methyl-[1,2,4]triazolo[1,5-a]pyridin-6-yl]-1-[spiro[2.5]octan-6-yl]pyrazolo[3,4-d]pyrimidin-6-amine (30 mg, 14.29%) as a white solid. LCMS: m/z (ESI), $[M+H]^+$=389.3. $^1H$ NMR (400 MHz, DMSO-$d_6$) δ 0.20 (2H, d), 0.33 (2H, d), 0.98 (2H, d), 1.84 (4H, in), 2.08 (2H, in), 2.39 (3H, d), 2.45 (3H, s), 4.45 (1H, d), 7.74 (1H, s), 8.40 (1H, s), 8.91 (1H, s), 9.16 (2H, d)

The following compounds in table 3 below are synthesized by the similar method descried in example 37.

TABLE 3

| Example number | Structures | LCMS | NMR |
|---|---|---|---|
| 39 | 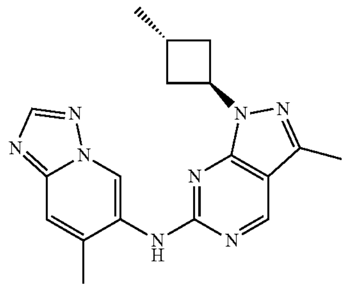 [SMILES: Cc1cc2ncnn2cc1Nc1ncc2c(C)nn([C@H]3C[C@H](C)C3)c2n1] | 349.3 | $^1$H NMR (DMSO-d$_4$, 300 MHz) δ 1.27 (3H, d), 2.02-2.10 (2H, m), 2.40 (3H, s), 2.47 (3H, s), 2.72-2.82 (2H, m), 3.32 (1H, s), 5.14-5.25 (1H, m), 7.74 (1H, s), 8.41 (1H, s), 8.93 (1H, s), 9.16 (1H, s), 9.22 (1H, s) |
| 40 | 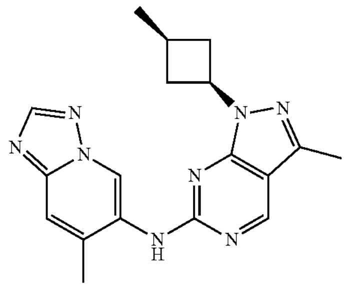 [SMILES: Cc1cc2ncnn2cc1Nc1ncc2c(C)nn([C@H]3C[C@@H](C)C3)c2n1] | 349.3 | $^1$H NMR (Methanol-d$_4$, 300 MHz) δ 1.13 (3H, d), 2.27-2.39 (3H, m), 2.47-2.65 (8H, m), 4.93-5.07 (1H, m), 7.69 (1H, s), 8.37 (1H, s), 8.90 (1H, d), 9.44 (1H, s) |

Example 43

Preparation of 3-methyl-N-(7-methyl-[1,2,4]triazolo[1,5-a]pyridin-6-yl)-1-(spiro[3.3]heptan-2-yl)-1H-pyrazolo[3,4-d]pyrimidin-6-amine (Ex. 43)

SCHEME 43

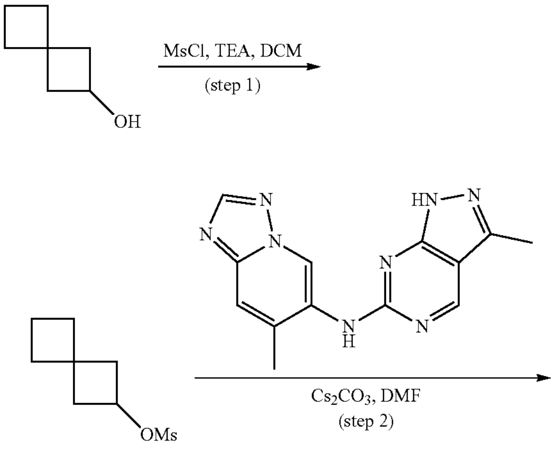

1

-continued

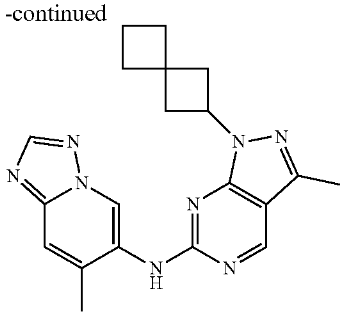

Example 43

Step 1. spiro[3.3]heptan-2-yl methanesulfonate

To a stirred mixture of spiro[3.3]heptan-2-ol (300.00 mg, 2.674 mmol, 1.00 equiv) and TEA (811.89 mg, 8.023 mmol, 3.00 equiv) in DCM (50.00 mL) was added methanesulfonyl chloride (459.50 mg, 4.012 mmol, 1.50 equiv) dropwise at 0° C. under nitrogen atmosphere. The resulting mixture was diluted with water (20 mL). The resulting mixture was extracted with $CH_2Cl_2$ (3×20 mL). The combined organic layers were washed with brine, dried over anhydrous $Na_2SO_4$. After filtration, the filtrate was concentrated under reduced pressure. This gave spiro[3.3]heptan-2-yl methanesulfonate (500 mg, 98.26%) as a light yellow oil.

Step 2. 3-methyl-N-(7-methyl-[1,2,4]triazolo[1,5-a] pyridin-6-yl)-1-(spiro[3.3]heptan-2-yl)-1H-pyrazolo [3,4-d]pyrimidin-6-amine (Ex. 43)

A mixture of 3-methyl-N-[7-methyl-[1,2,4]triazolo[1,5-a] pyridin-6-yl]-1H-pyrazolo[3,4-d]pyrimidin-6-amine (100.00 mg, 0.357 mmol, 1.00 equiv), spiro[3.3]heptan-2-yl methanesulfonate (678.78 mg, 3.568 mmol, 10.00 equiv) and $Cs_2CO_3$ (348.73 mg, 1.070 mmol, 3.00 equiv) in DMF (20.00 mL) was stirred for 16 h at 100° C. under nitrogen atmosphere. The resulting mixture was diluted with water (40 mL). The resulting mixture was extracted with EtOAc (3×100 mL). The combined organic layers were washed with brine, dried over anhydrous $Na_2SO_4$. After filtration, the filtrate was concentrated under reduced pressure. The crude product was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; Gradient: 39 B to 59 B in 7 min; RT1:6.4) to afford 3-methyl-N-[7-methyl-[1,2,4]triazolo[1,5-a]pyridin-6-yl]-1-[spiro[3.3]heptan-2-yl]pyrazolo[3,4-d]pyrimidin-6-amine (31.8 mg, 23.80%) as a white solid. LCMS: m/z (ESI), [M+H]+=375.3. $^1$HNMR (400 MHz, DMSO-$d_6$) δ 1.81-1.95 (2H, m), 1.89-1.91 (2H, m), 2.09-2.11 (2H, m), 2.42 (8H, d), 2.59-2.63 (2H, m), 4.89-4.93 (1H, m), 7.76 (1H, s), 8.42 (1H, s), 8.92 (1H, s), 9.17 (2H, d)

Example 44

Preparation of 3-methyl-N-(7-methyl-[1,2,4]triazolo [1,5-a]pyridin-6-yl)-1-(oxetan-3-yl)-1H-pyrazolo[3, 4-d]pyrimidin-6-amine (Ex. 44)

SCHEME 44

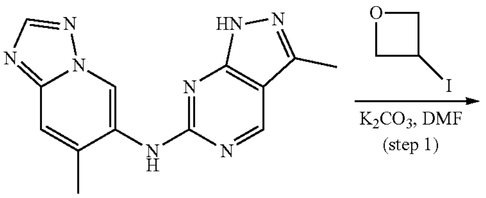

-continued

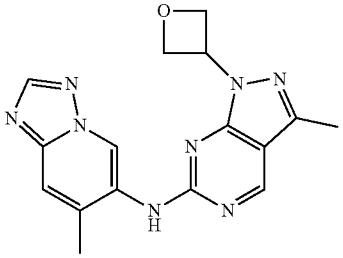

Example 44

Step 1. 3-methyl-N-(7-methyl-[1,2,4]triazolo[1,5-a] pyridin-6-yl)-1-(oxetan-3-yl)-1H-pyrazolo[3,4-d] pyrimidin-6-amine (Ex. 44)

To a stirred mixture of 3-methyl-N-[7-methyl-[1,2,4]triazolo[1,5-a]pyridin-6-yl]-1H-pyrazolo[3,4-d]pyrimidin-6-amine (80.00 mg, 0.285 mmol, 1.00 equiv) and 3-iodooxetane (78.76 mg, 0.428 mmol, 1.50 equiv) in DMF (10 mL) were added $K_2CO_3$ (118.34 mg, 0.856 mmol, 3.00 equiv) at room temperature under air atmosphere. The resulting mixture was stirred for 2 h at 80° C. under air atmosphere. The resulting mixture was concentrated under reduced pressure. The residue was purified by Prep-TLC ($CH_2Cl_2$: MEOH 12:1) to afford crude product. The crude product (100 mg) was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; Gradient: 12 B to 32 B in 7 min; RT1:6.62) to afford 3-methyl-N-[7-methyl-[1,2,4]triazolo[1,5-a]pyridin-6-yl]-1-(oxetan-3-yl)pyrazolo[3,4-d]pyrimidin-6-amine (Ex. 44, 40 mg, 41.67%) as a white solid. LCMS: m/z (ESI), $[M+H]^+$=337.2. $^1$H NMR (300 MHz, DMSO-$d_6$) δ 2.38 (3H, s), 2.49 (3H, s), 4.89-5.02 (4H, m), 5.72 (1H, t), 7.75 (1H, s), 8.42 (1H, s), 8.96 (1H, s), 9.15 (1H, s), 9.27 (1H, s)

The following compounds in table 4 below are synthesized by the similar method descried in example 44.

TABLE 4

| Example number | structures | LCMS | NMR |
|---|---|---|---|
| 38 | 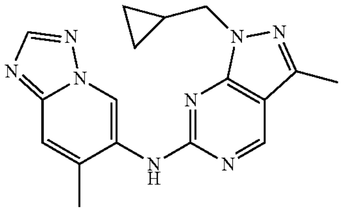 [SMILES: Cc1cc2ncnn2cc1Nc1ncc2c(C)nn(CC3CC3)c2n1] | 335.3 | $^1$H NMR (300 MHz, DMSO-$d_6$) δ 0.32 (2H, t), 0.47 (2H, m), 1.21 (1H, t), 2.39 (3H, d), 2.45 (3H, s), 3.98 (2H, d), 7.74 (1H, s), 8.40 (1H, s), 8.93 (1H, s), 9.17 (2H, s) |

TABLE 4-continued
| Example number | structures | LCMS | NMR |
|---|---|---|---|
| 45 | 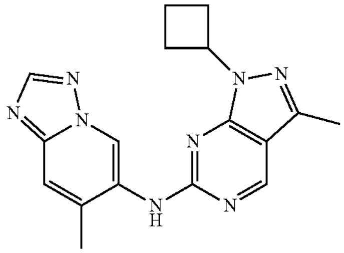 [SMILES: Cc1cc2ncnn2cc1Nc1ncc2c(C)nn(C3CCC3)c2n1] | 335.3 | $^1$H NMR (300 MHz, DMSO-$d_6$) δ 1.82 (2H, dd), 2.25-2.40 (5H, m), 2.44 (3H, s), 2.56-2.71 (2H, m), 5.01 (1H, t), 7.72 (1H, s), 8.38 (1H, s), 8.90 (1H, s), 9.12 (1H, s), 9.19 (1H, s) |
| 46 | 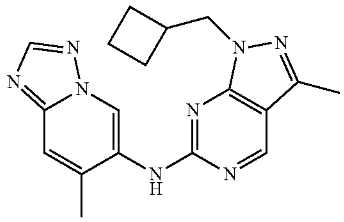 | 349.3 | $^1$H NMR (300 MHz, DMSO-$d_6$) δ 1.74-1.86 (4H, m), 1.92-1.97 (2H, m), 2.40 (3H, s), 2.44 (3H, s), 2.77 (1H, dd), 4.14 (2H, d), 7.74 (1H, s), 8.40 (1H, s), 8.92 (1H, s), 9.14 (1H, s), 9.21 (1H, s) |
| 47 | 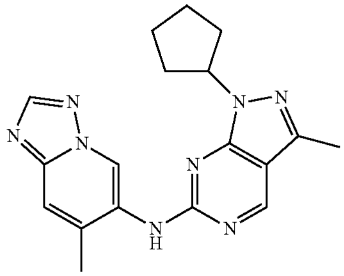 [SMILES: Cc1cc2ncnn2cc1Nc1ncc2c(C)nn(C3CCCC3)c2n1] | 349.2 | $^1$H NMR (300 MHz, DMSO-$d_6$) δ 1.65-1.78 (2H, m), 1.81-1.87 (2H, m), 1.92-2.05 (4H, m), 2.39 (3H, s), 2.45 (3H, s), 4.88-4.95 (1H, m), 7.74 (1H, s), 8.40 (1H, s), 8.91 (1H, s), 9.14 (1H, s), 9.18 (1H, s). |
| 48 | 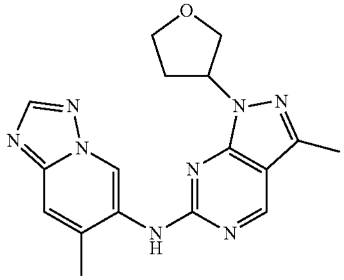 [SMILES: Cc1cc2ncnn2cc1Nc1ncc2c(C)nn(C3CCOC3)c2n1] | 351.2 | $^1$H NMR (300 MHz, DMSO-$d_6$) δ 2.33 (2H, d), 2.38 (3H, d), 3.46 (3H, s), 3.81-3.88 (2H, m), 3.95-4.04 (2H, m), 5.15-5.23 (1H, m), 7.75 (1H, s), 8.41 (1H, s), 8.94 (1H, s), 9.18 (1H, s), 9.22 (1H, s), (isomer 1) |
| 49 | 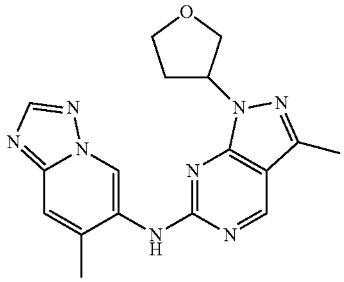 [SMILES: Cc1cc2ncnn2cc1Nc1ncc2c(C)nn(C3CCOC3)c2n1] | 351.2 | $^1$H NMR (300 MHz, DMSO-$d_6$) δ 2.23-2.39 (5H, m), 3.45 (3H, s), 3.78-3.88 (2H, m), 3.95-4.04 (2H, m), 5.15-5.23 (1H, m), 7.75 (1H, s), 8.41 (1H, s), 8.94 (1H, s), 9.17 (1H, s), 9.22 (1H, s) (isomer 2) |
| 57 | 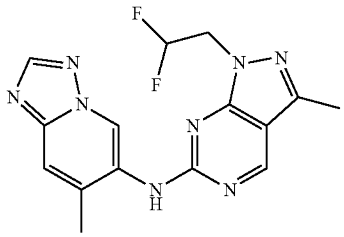 [SMILES: Cc1cc2ncnn2cc1Nc1ncc2c(C)nn(CC(F)F)c2n1] | 345.2 | $^1$H NMR (300 MHz, DMSO-$d_6$) δ 2.38 (3H, s), 2.45 (3H, t), 4.46-4.60 (2H, m), 6.20-6.58 (1H, m), 7.73 (1H, s), 8.39 (1H, s), 8.96 (1H, s), 9.14 (1H, s), 9.31 (1H, s) |

TABLE 4-continued
| Example number | structures | LCMS | NMR |
|---|---|---|---|
| 58 | 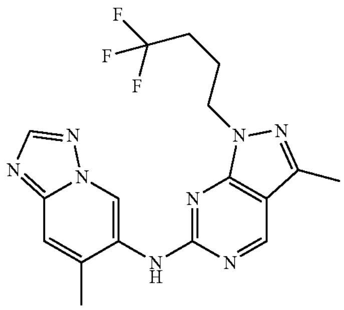 [SMILES: Cc1cc2ncnn2cc1Nc1ncc2c(C)nn(CCCC(F)(F)F)c2n1] | 391.2 | $^1$H NMR (DMSO-$d_6$, 300 MHz) δ 1.98-2.06 (2H, m), 2.22-2.34 (2H, m), 2.38 (3H, s), 2.46 (3H, s), 4.19 (2H, t), 7.74 (1H, s), 8.41 (1H, s), 8.95 (1H, s), 9.14 (1H, s), 9.22 (1H, s) |
| 61 | 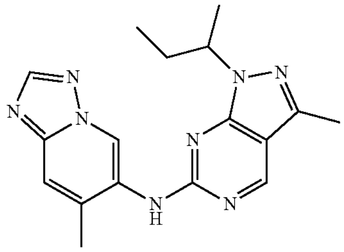 [SMILES: CCC(C)n1nc(C)c2cnc(Nc3cn4ncnc4cc3C)nc21] | 337.3 | $^1$H NMR (300 MHz, DMSO-$d_6$) δ 0.62-0.80 (3H, m), 1.38 (3H, d), 1.71-1.93 (2H, m), 2.39 (3H, s), 2.45 (3H, s), 4.48-4.55 (1H, m), 7.74 (1H, s), 8.40 (1H, s), 8.93 (1H, d), 9.14 (1H, s), 9.19 (1H, s) (isomer 1) |
| 62 | 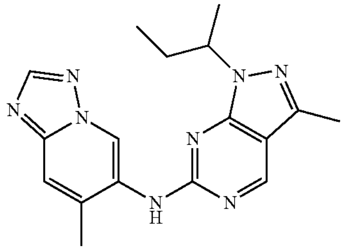 [SMILES: CCC(C)n1nc(C)c2cnc(Nc3cn4ncnc4cc3C)nc21] | 337.3 | $^1$H NMR (300 MHz, DMSO-$d_6$) δ 0.62-0.82 (3H, m), 1.38 (3H, d), 1.71-1.93 (2H, m), 2.39 (3H, s), 2.45 (3H, s), 4.48-4.55 (1H, m), 7.74 (1H, s), 8.40 (1H, s), 8.93 (1H, d), 9.14 (1H, s), 9.19 (1H, s) (isomer 2) |
| 63 | 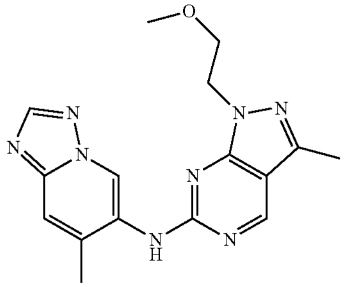 [SMILES: COCCn1nc(C)c2cnc(Nc3cn4ncnc4cc3C)nc21] | 339.2 | $^1$H NMR (300 MHz, DMSO-$d_6$) δ 2.39 (3H, s), 2.45 (3H, s), 3.18 (3H, s), 3.72 (2H, t), 4.26 (2H, t), 7.75 (1H, s), 8.41 (1H, s), 8.93 (1H, s), 9.19 (2H, s) |
| 64 | 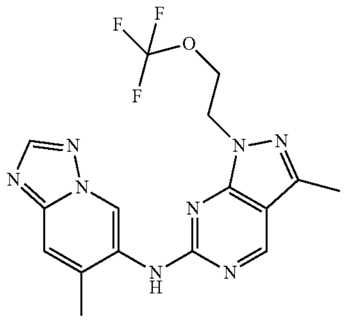 [SMILES: Cc1cc2ncnn2cc1Nc1ncc2c(C)nn(CCOC(F)(F)F)c2n1] | 393.2 | $^1$H NMR (300 MHz, DMSO-$d_6$) δ 2.38 (3H, d), 2.47 (3H, s), 4.45 (4H, dd), 7.75 (1H, t), 8.41 (1H, s), 8.96 (1H, s), 9.13 (1H, s), 9.26 (1H, s) |

TABLE 4-continued

| Example number | structures | LCMS | NMR |
|---|---|---|---|
| 65 | 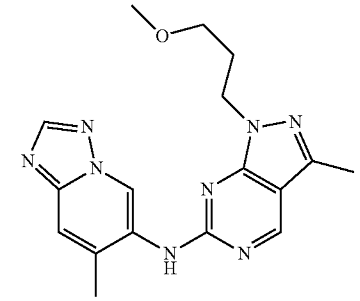 [SMILES: COCCCn1nc(C)c2cnc(Nc3cn4ncnc4cc3C)nc21] | 353.2 | $^1$H NMR (300 MHz, DMSO-$d_6$) δ 1.95-2.03 (2H, m), 2.40 (3H, s), 2.45 (3H, s), 3.14 (3H, s), 3.22 (2H, t), 4.17 (2H, t), 7.74 (1H, s), 8.40 (1H, s), 8.93 (1H, s), 9.17 (1H, s), 9.20 (1H, s). |

Example 59

Preparation of 1-isopropyl-3-methyl-N-(7-methyl-[1,2,4]triazolo[1,5-a]pyridin-6-yl)-1H-pyrazolo[3,4-d]pyrimidin-6-amine (Ex. 59)

SCHEME 59

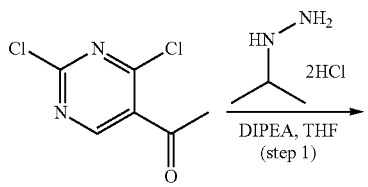

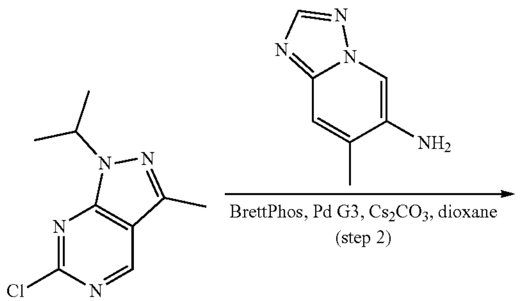

1

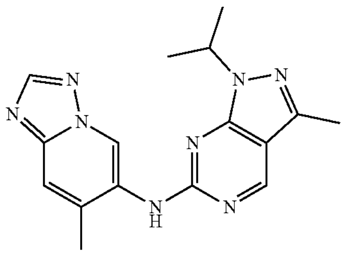

Example 59

Step 1. 6-chloro-1-isopropyl-3-methyl-1H-pyrazolo[3,4-d]pyrimidine

To a stirred mixture of 1-(2,4-dichloropyrimidin-5-yl) ethanone (150.00 mg, 0.785 mmol, 1.00 equiv) and DIPEA (54.13 mg, 0.419 mmol, 4.00 equiv) in THF were added isopropylhydrazine (15.26 mg, 0.136 mmol, 1.30 equiv) dropwise at 0° C. under air atmosphere. The resulting mixture was stirred for 2 h at room temperature under air atmosphere. The resulting mixture was concentrated under vacuum. The residue was purified by Prep-TLC (PE:EA 1:1) to afford 6-chloro-1-isopropyl-3-methylpyrazolo[3,4-d]pyrimidine (120 mg, 72.53%) as a yellow solid. LCMS: m/z (ESI), $[M+H]^+$=211.2. H NMR (300 MHz, $CDCl_3$) δ1.54 (6H, d), 2.61 (3H, s), 5.12 (1H, dd), 8.90 (1H, s)

Step 2. 1-isopropyl-3-methyl-N-(7-methyl-[1,2,4]triazolo[1,5-a]pyridin-6-yl)-1H-pyrazolo [3,4-d]pyrimidin-6-amine (Ex. 59)

To a stirred mixture of 6-chloro-1-isopropyl-3-methylpyrazolo[3,4-d]pyrimidine (120.00 mg, 0.570 mmol, 1.00 equiv) and 7-methylimidazo[1,2-a]pyridin-6-amine (108.99 mg, 0.740 mmol, 1.30 equiv) in dioxane (10 mL) were added XantPhos (65.92 mg, 0.114 mmol, 0.20 equiv), $Pd(AcO)_2$ (25.58 mg, 0.114 mmol, 0.20 equiv) and $Cs_2CO_3$ (556.77 mg, 1.709 mmol, 3.00 equiv) at room temperature under air atmosphere. The resulting mixture was stirred for 2 h at 60° C. under nitrogen atmosphere. The resulting mixture was concentrated under vacuum. The residue was purified by Prep-TLC ($CH_2Cl_2$/MeOH=10:1) to afford crude product. The crude product (100 mg) was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; RT1:6.67) to afford 1-isopropyl-3-methyl-N-[7-methyl-[1,2,4]triazolo[1,5-a]pyridin-6-yl]pyrazolo[3,4-d]pyrimidin-6-amine (62 mg, 33.76%) as a white solid. LCMS: m/z (ESI), $[M+H]^+$=323.4. $^1$H NMR (300 MHz, DMSO-$d_6$) δ 1.41 (6H, d), 2.40 (3H, d), 2.45 (3H, s), 4.73-4.82 (1H, m), 7.74 (1H, s), 8.41 (1H, s), 8.92 (1H, s), 9.16 (1H, s), 9.19 (1H, s)

Example 60

Preparation of 1-isopropyl-3-methyl-N-(7-methylimidazo[1,2-a]pyridin-6-yl)-1H-pyrazolo [3,4-d] pyrimidin-6-amine (Ex. 60)

SCHEME 60

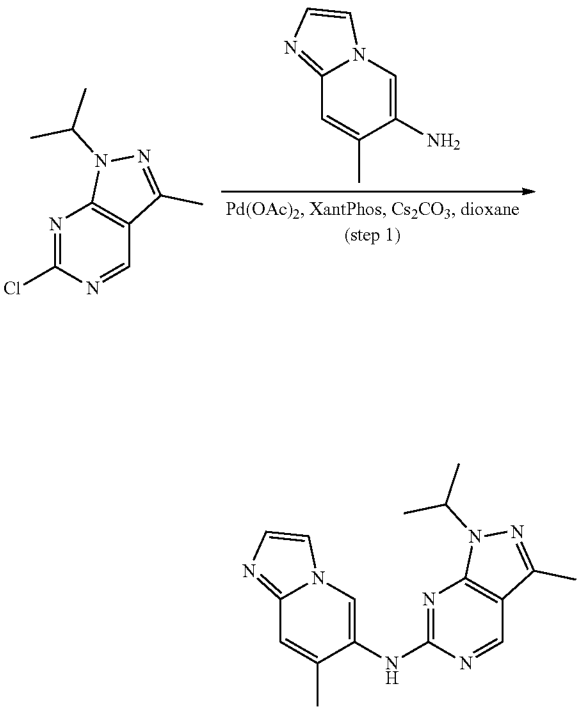

Example 60

Step 1. 1-isopropyl-3-methyl-N-(7-methylimidazo [1,2-a]pyridin-6-yl)-1H-pyrazolo[3,4-d]pyrimidin-6-amine (Ex. 60)

A mixture of 6-chloro-1-isopropyl-3-methylpyrazolo[3,4-d]pyrimidine (80.00 mg, 0.380 mmol, 1.00 equiv), 7-methylimidazo[1,2-a]pyridin-6-amine (67.07 mg, 0.456 mmol, 1.20 equiv), $Pd(AcO)_2$ (17.05 mg, 0.076 mmol, 0.20 equiv), XantPhos (65.92 mg, 0.114 mmol, 0.30 equiv) and $Cs_2CO_3$ (309.32 mg, 0.949 mmol, 2.50 equiv) in dioxane (10.00 mL) was stirred for 3 hs at 100° C. under nitrogen atmosphere. The resulting mixture was concentrated under vacuum. The residue was purified by Prep-TLC ($CH_2Cl_2$/MeOH=10:1). The crude product (100 mg) was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; Gradient: 21 B to 41 B in 7 min; RT1:7.02) to afford 1-isopropyl-3-methyl-N-[7-methylimidazo[1,2-a] pyridin-6-yl]pyrazolo[3,4-d]pyrimidin-6-amine (55.77 mg, 45.70%) as a white solid. LCMS: m/z (ESI), $[M+H]^+$=322.2. $^1$H NMR (300 MHz, DMSO-$d_6$) δ 1.38 (6H, d), 2.25 (3H, d), 2.44 (3H, s), 4.67-4.89 (1H, m), 7.47 (2H, dd), 7.87 (1H, t), 8.67 (1H, s), 8.86 (1H, s), 9.03 (1H, s)

Example 72

Preparation of 3-(3-methyl-6-((7-methyl-[1,2,4]triazolo[1,5-a]pyridin-6-yl)amino)-1H-pyrazolo[3,4-d] pyrimidin-1-yl)propanenitrile (Ex. 72)

SCHEME 72

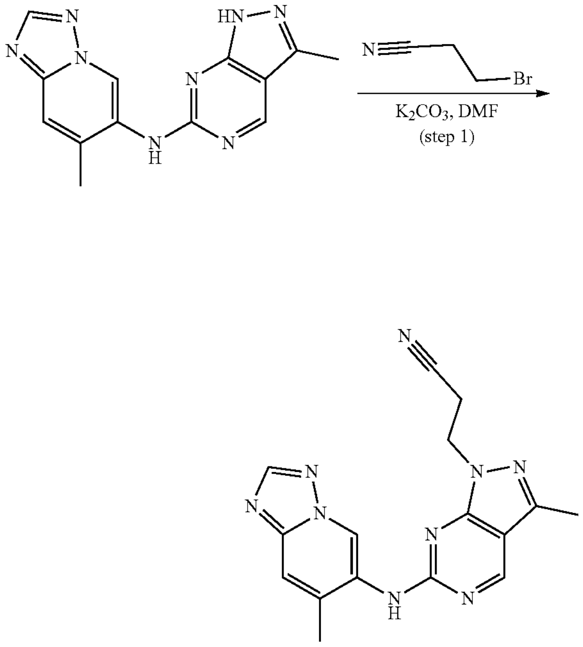

Example 72

Step 1. 3-(3-methyl-6-((7-methyl-[1,2,4]triazolo[1,5-a]pyridin-6-yl)amino)-1H-pyrazolo[3,4-d]pyrimidin-1-yl)propanenitrile (Ex. 72)

To a stirred mixture of 3-methyl-N-[7-methyl-[1,2,4]triazolo[1,5-a]pyridin-6-yl]-1H-pyrazolo[3,4-d]pyrimidin-6-amine (70.00 mg, 0.250 mmol, 1.00 equiv) and propanenitrile, 3-bromo-(66.92 mg, 0.499 mmol, 2.00 equiv) in DMF (10 mL) was added $K_2CO_3$ (103.55 mg, 0.749 mmol, 3.00 equiv). The resulting mixture was stirred for 2 h at 80° C. under air atmosphere. The resulting mixture was concentrated under vacuum. The residue was purified by Prep-TLC (DCM:MeOH=15:1) to afford crude solid. The crude product was purified by Prep-HPLC with the following conditions (Column: XBridge Prep OBD C18 Column, 30×150 mm 5 um; Mobile Phase A: Water (0.05% $NH_3 \cdot H_2O$), Mobile Phase B: ACN; Flow rate: 60 mL/min; Gradient: 8 B to 28 B in 7 min; RT1:7.70) to afford 3-[3-methyl-6-([7-methyl-[1,2,4]triazolo[1,5-a]pyridin-6-yl]amino)pyrazolo [3,4-d]pyrimidin-1-yl]propanenitrile (40 mg, 48.05%) as a white solid. LCMS: m/z (ESI), $[M+H]^+$=334.3. $^1$H NMR (300 MHz, DMSO-$d_6$) δ 2.39 (3H, s), 2.47 (3H, s), 3.08 (2H, t), 4.36 (2H, t), 7.75 (1H, s), 8.41 (1H, s), 8.97 (1H, s), 9.17 (1H, s), 9.29 (1H, s).

The following compounds in table 5 below are synthesized by the similar method descried in example 72.

TABLE 5
| Example number | structures | LCMS | NMR |
|---|---|---|---|
| 29 | 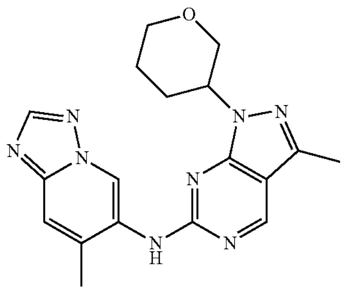 [SMILES: Cc1cc2ncnn2cc1Nc1ncc2c(C)nn(C3CCCOC3)c2n1] | 365.3 | $^1$H NMR (300 MHz, DMSO-$d_6$) δ 1.75-1.81 (2H, m), 1.98-2.12 (1H, m), 2.16-2.28 (1H, m), 2.40 (3H, s), 2.44 (3H, s), 3.35-3.40 (1H, m), 3.65 (1H, t), 3.83-3.92 (2H, m), 4.44-4.54 (1H, m), 7.75 (1H, s), 8.41 (1H, s), 8.93 (1H, s), 9.21 (2H, d). Isomer 1 |
| 30 | 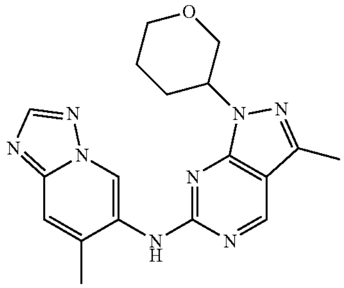 [SMILES: Cc1cc2ncnn2cc1Nc1ncc2c(C)nn(C3CCCOC3)c2n1] | 365.2 | $^1$H NMR (300 MHz, DMSO-$d_6$) δ 1.75-1.81 (2H, m), 2.02-2.15 (1H, m), 2.18-2.28 (1H, m), 2.40 (3H, s), 2.44 (3H, s), 3.35-3.40 (1H, m), 3.65 (1H, t), 3.83-3.92 (2H, m), 4.46-4.53 (1H, m), 7.75 (1H, s), 8.41 (1H, s), 8.93 (1H, s), 9.21 (2H, s). Isomer 2 |
| 41 | 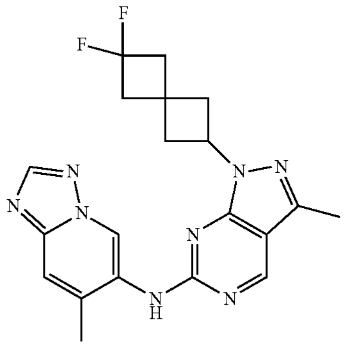 [SMILES: Cc1cc2ncnn2cc1Nc1ncc2c(C)nn(C3CC4(C3)CC(F)(F)C4)c2n1] | 411.3 | $^1$H NMR (DMSO-$d_6$, 300 MHz) δ 2.38 (3H, d), 2.45 (3H, s), 2.51-2.61 (4H, m), 2.62-2.83 (4H, m), 4.99 (1H, p), 7.72-7.79 (1H, m), 8.42 (1H, s), 8.92 (1H, s), 9.16 (2H, d) |
| 72 | 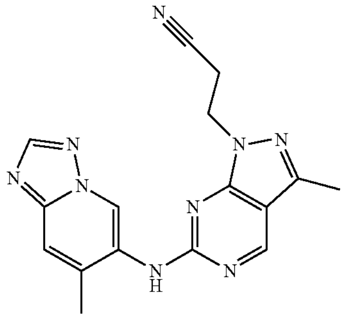 [SMILES: Cc1cc2ncnn2cc1Nc1ncc2c(C)nn(CCC#N)c2n1] | 334.3 | $^1$H NMR (300 MHz, DMSO-$d_6$) δ 2.39 (3H, s), 2.47 (3H, s), 3.08 (2H, t), 4.36 (2H, t), 7.75 (1H, s), 8.41 (1H, s), 8.97 (1H, s), 9.17 (1H, s), 9.29 (1H, s). |

Example 73

Preparation of 4-(3-methyl-6-(7-methylimidazo[1,2-a]pyridin-6-ylamino)-1H-pyrazolo[3,4-d]pyrimidin-1-yl)benzonitrile (Ex. 73)

Scheme 73

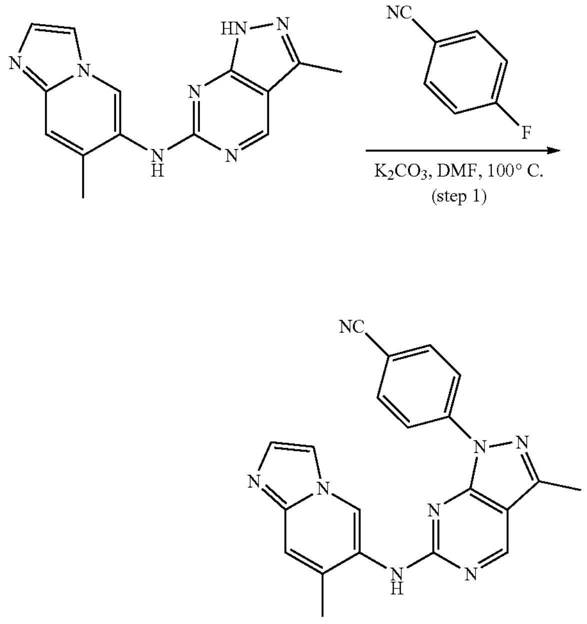

Example 73

Step 1. 4-(3-methyl-6-(7-methylimidazo[1,2-a]pyridin-6-ylamino)-1H-pyrazolo[3,4-d]pyrimidin-1-yl)benzonitrile (Ex. 73')

A mixture of 7-methyl-N-[3-methyl-1H-pyrazolo[3,4-d]pyrimidin-6-yl]-[1,2,4]triazolo[1,5-a]pyridin-6-amine (150.00 mg, 0.535 mmol, 1.00 equiv), benzonitrile, 4-fluoro-(97.57 mg, 0.806 mmol, 1.50 equiv), benzonitrile (97.22 mg, 0.803 mmol, 1.50 equiv) and $K_2CO_3$ (221.88 mg, 1.605 mmol, 3.0 equiv) in DMF (50.00 mL) was stirred for 16 h at 100 degrees C. The resulting mixture was concentrated under reduced pressure. The residue was purified by Prep-TLC ($CH_2Cl_2$/MeOH=10:1) to afford 4-[3-methyl-6-([7-methyl-[1,2,4]triazolo[1,5-a]pyridin-6-yl]amino)pyrazolo[3,4-d]pyrimidin-1-yl]benzonitrile (40 mg, crude) as a light yellow solid. The crude product (40 mg) was purified by Prep-HPLC with the following conditions (Column: XBridge Shield RP18 OBD Column, 19*250 mm, 10 um; Mobile Phase A: Water (10 MMOL/L $NH_4HCO_3$+0.1% $NH_3{\cdot}H_2O$), Mobile Phase B: ACN; Flow rate: 20 mL/min; Gradient: 36 B to 46 B in 7 min; RT1:5.73) to afford 4-[3-methyl-6-([7-methylimidazo[1,2-a]pyridin-6-yl]amino)pyrazolo[3,4-d]pyrimidin-1-yl]benzonitrile (8.8 mg, 4.31%) as a white solid. LCMS: m/z (ESI), $[M+H]^+$=381.3. $^1$HNMR (300 MHz, $CDCl_3$) δ 2.45 (3H, d), 2.62 (3H, s), 7.08 (1H, s), 7.54 (2H, s), 7.65 (1H, s), 7.75 (2H, d), 8.42-8.44 (2H, m), 8.85 (1H, s), 9.06 (1H, d).

Example 89

Preparation of 6-methoxy-4-methyl-N-[3-methyl-1-(oxan-4-yl)pyrazolo[3,4-d]pyrimidin-6-yl]pyridin-3-amine Scheme 89

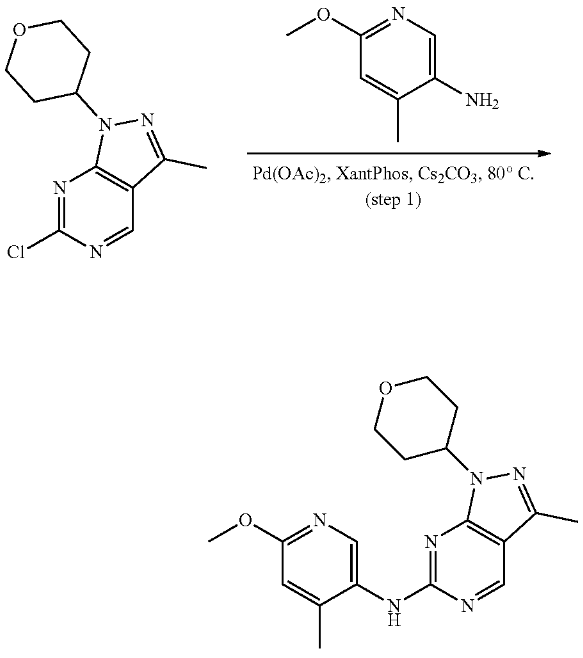

Example 89

Step 1. 6-methoxy-4-methyl-N-[3-methyl-1-(oxan-4-yl)pyrazolo[3,4-d]pyrimidin-6-yl]pyridin-3-amine (Ex. 89)

A mixture of 6-chloro-3-methyl-1-(oxan-4-yl)pyrazolo[3,4-d]pyrimidine (80.00 mg, 0.317 mmol, 1.00 equiv), 6-methoxy-4-methylpyridin-3-amine (52.49 mg, 0.380 mmol, 1.20 equiv), $Pd(AcO)_2$ (14.22 mg, 0.063 mmol, 0.20 equiv), XantPhos (54.95 mg, 0.095 mmol, 0.30 equiv) and $Cs_2CO_3$ (257.87 mg, 0.791 mmol, 2.50 equiv) in dioxane (2.50 mL) was stirred for 2 h at 80° C. under nitrogen atmosphere. The resulting mixture was concentrated under vacuum. The residue was purified by Prep-TLC ($CH_2Cl_2$/MeOH 15:1) to afford a crude solid. The crude product (100 mg) was purified by Prep-HPLC with the following conditions (Column: XBridge Shield RP18 OBD Column, 30*150 mm, 5 um; Mobile Phase A: Water (0.05% $NH_3H_2O$), Mobile Phase B: ACN; Flow rate: 60 mL/min; Gradient: 25 B to 55 B in 7 min; 254; 220 nm; RT1:5.20) to afford 6-methoxy-4-methyl-N-[3-methyl-1-(oxan-4-yl)pyrazolo[3,4-d]pyrimidin-6-yl]pyridin-3-amine (70 mg, 62.39%) as a white solid. LCMS: m/z (ESI), $[M+H]^+$=355.2. $^1$H-NMR (300 MHz, DMSO-$d_6$) δ 1.79 (2H, d), 1.99-2.20 (5H, m), 2.42 (3H, s), 3.43-3.56 (2H, m), 3.83 (3H, s), 3.96 (2H, dd), 4.58 (1H, t), 6.74 (1H, s), 8.11 (1H, s), 8.82 (1H, s), 8.98 (1H, s).

Example 106

Preparation of 1-((1R,3r,5S)-8-oxa-bicyclo[3.2.1]octan-3-yl)-3-methyl-N-(7-methyl-[1,2,4]triazolo[1,5-a]pyridin-6-yl)-1H-pyrazolo[3,4-d]pyrimidin-6-amine Scheme 106

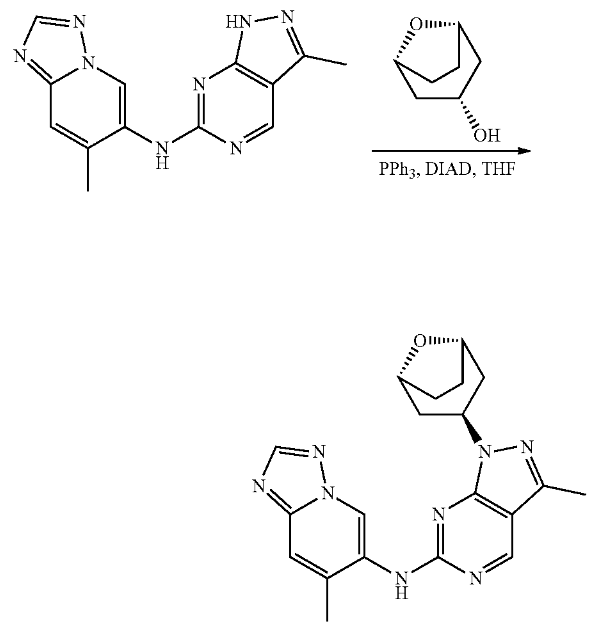

Example 106

Step 1. 1-((1R,3r,5S)-8-oxa-bicyclo[3.2.1]octan-3-yl)-3-methyl-N-(7-methyl-[1,2,4]triazolo [1,5-a]pyridin-6-yl)-1H-pyrazolo[3,4-d]pyrimidin-6-amine To a stirred mixture of 3-methyl-N-[7-methyl-[1,2,4]triazolo[1,5-a]pyridin-6-yl]-1H-pyrazolo[3,4-d]pyrimidin-6-amine (100.00 mg, 0.357 mmol, 1.00 equiv), (1R,3S,5S)-8-oxabicyclo[3.2.1]octan-3-ol (137.18 mg, 1.070 mmol, 3.00 equiv) and $PPh_3$ (280.72 mg, 1.070 mmol, 3 equiv) in THF (10.00 mL) was added DIAD (216.42 mg, 1.070 mmol, 3 equiv) dropwise at 0° C. under nitrogen atmosphere. The resulting mixture was stirred for 2 h at 70° C. under nitrogen atmosphere. The resulting mixture was concentrated under vacuum. The residue was purified by Prep-TLC ($CH_2Cl_2$/MeOH 12:1) to afford crude solid. The crude product was purified by Prep-HPLC with the following conditions (Column: XBridge Prep OBD C18 Column, 30×150 mm 5 um; Mobile Phase A: Water (0.05% $NH_3H_2O$), Mobile Phase B: ACN; Flow rate: 60 mL/min; Gradient: 37 B to 57 B in 7 min) to afford 3-methyl-N-[7-methyl-[1,2,4]triazolo[1,5-a]pyridin-6-yl]-1-[(1R,3R,5S)-8-oxabicyclo[3.2.1]octan-3-yl]pyrazolo[3,4-d]pyrimidin-6-amine (Ex. 106, 50 mg, 50.00%) as a white solid. LCMS: m/z (ESI), $[M+H]^+$=391.3. $^1H$ NMR (300 MHz, DMSO-$d_6$) δ 1.74 (4H, s), 2.22-2.45 (10H, m), 4.35 (2H, s), 4.63 (1H, s), 7.75 (1H, s), 8.41 (1H, s), 8.93 (1H, s), 9.17 (1H, s), 9.21 (1H, s).

Example 107

Preparation of 1-((1R,3s,5S)-8-oxa-bicyclo[3.2.1]octan-3-yl)-3-methyl-N-(7-methyl-[1,2,4]triazolo[1,5-a]pyridin-6-yl)-1H-pyrazolo[3,4-d]pyrimidin-6-amine Scheme 107

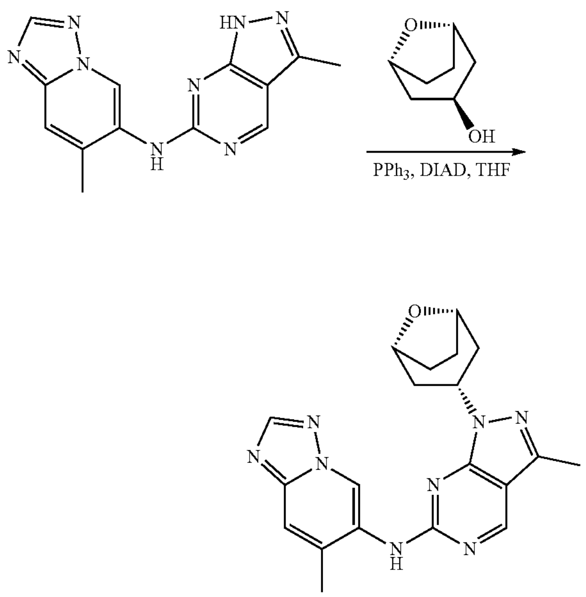

Example 107

Step 1. 1-((1R,3s,5S)-8-oxa-bicyclo[3.2.1]octan-3-yl)-3-methyl-N-(7-methyl-[1,2,4]triazolo [1,5-a]pyridin-6-yl)-1H-pyrazolo[3,4-d]pyrimidin-6-amine To a stirred mixture of 3-methyl-N-[7-methyl-[1,2,4]triazolo[1,5-a]pyridin-6-yl]-1H-pyrazolo[3,4-d]pyrimidin-6-amine (80.00 mg, 0.285 mmol, 1.00 equiv), (1R,3R,5S)-8-oxabicyclo[3.2.1]octan-3-ol (109.75 mg, 0.856 mmol, 3.00 equiv) and $PPh_3$ (224.58 mg, 0.856 mmol, 3.00 equiv) in THF (16.00 mL) was added DIAD (173.14 mg, 0.856 mmol, 3.00 equiv) dropwise at 0° C. under nitrogen atmosphere. The resulting mixture was stirred for 2 h at 70° C. under nitrogen atmosphere. The resulting mixture was concentrated under vacuum. The residue was purified by Prep-TLC ($CH_2Cl_2$/MeOH 12:1) to afford crude solid. The crude product was purified by Prep-HPLC with the following conditions (Column: XBridge Prep OBD C18 Column, 30×150 mm 5 um; Mobile Phase A: Water (0.05% $NH_3H_2O$), Mobile Phase B: ACN; Flow rate: 60 mL/min; Gradient: 37 B to 50 B in 7 min) to afford 1-((1R,3s,5S)-8-oxa-bicyclo[3.2.1]octan-3-yl)-3-methyl-N-(7-methyl-[1,2,4]triazolo[1,5-a]pyridin-6-yl)-1H-pyrazolo[3,4-d]pyrimidin-6-amine (Ex. 107, 45 mg, 45.00%) as a white solid. LCMS: m/z (ESI), $[M+H]^+$=391.4. $^1H$ NMR (300 MHz, DMSO-$d_6$) δ 1.78-1.94 (6H, m), 2.07-2.25 (2H, m), 2.42 (3H. s), 2.45 (3H, s), 4.44 (2H, s), 4.88-4.96 (1H, m), 7.73 (1H, s), 8.41 (1H, s), 8.92 (1H, s), 9.18 (1H, s), 9.29 (1H, s).

Example 108/109/110/111

1-(3-methoxycyclopentyl)-3-methyl-N-(7-methyl-[1,2,4]triazolo[1,5-a]pyridin-6-yl)-1H-pyrazolo[3,4-d]pyrimidin-6-amine (Ex. 108, isomer 1)/1-(3-methoxycyclopentyl)-3-methyl-N-(7-methyl-[1,2,4]triazolo[1,5-a]pyridin-6-yl)-1H-pyrazolo[3,4-d]pyrimidin-6-amine (Ex. 109, isomer 2)/1-(3-methoxycyclopentyl)-3-methyl-N-(7-methyl-[1,2,4]triazolo[1,5-a]pyridin-6-yl)-1H-pyrazolo[3,4-d]pyrimidin-6-amine (Ex. 110, isomer 3)/1-(3-methoxycyclopentyl)-3-methyl-N-(7-methyl-[1,2,4]triazolo[1,5-a]pyridin-6-yl)-1H-pyrazolo[3,4-d]pyrimidin-6-amine (Ex. 111, isomer 4)

Scheme 108-111

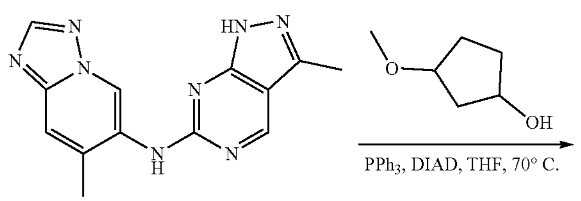

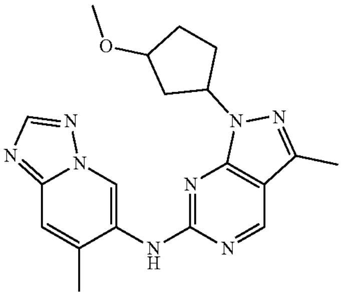

+

Example 108
isomer 1

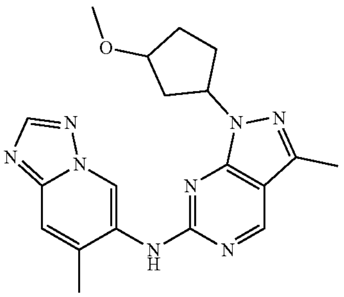

+

Example 109
isomer 2

-continued

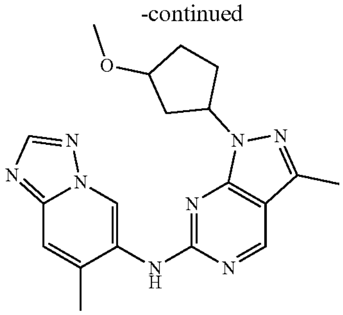

+

Example 110
isomer 3

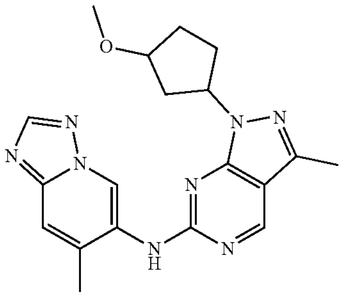

Example 111
isomer 4

Step 1. Preparation of 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (mixtures of 108/109) and Preparation of 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (mixtures of 110/111)

To a stirred mixture of 3-methyl-N-[7-methyl-[1,2,4]triazolo[1,5-a]pyridin-6-yl]-1H-pyrazolo[3,4-d]pyrimidin-6-amine (220.00 mg, 0.785 mmol, 1.00 equiv), $PPh_3$ (617.59 mg, 2.355 mmol, 3.00 equiv) and 3-methoxycyclopentane-1-ol (273.52 mg, 2.355 mmol, 3.00 equiv) in THF (20.00 mL) was added DIAD (476.13 mg, 2.355 mmol, 3.00 equiv) in THF (3 mL) dropwise 10 min at 0° C. The resulting mixture was stirred for 2 h at 70° C. under nitrogen atmosphere. The resulting mixture was concentrated under reduced pressure. The residue was purified by Prep-TLC ($CH_2Cl_2$/MeOH 10:1) to afford 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (150 mg) as a light yellow solid. The crude product (150 mg) was purified by Prep-HPLC with the following conditions (Column: YMC-Actus Triart C18, 30*250.5 um; Mobile Phase A: Water (0.05% $NH_3H_2O$), Mobile Phase B: ACN; Flow rate: 60 mL/min; Gradient: 34 B to 46 B in 8.5 min) to afford 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (mixtures of Ex. 108/109, 25 mg, 16.67%) as a white solid. LCMS: m/z (ESI), $[M+H]^+$=379.3. $^1$HNMR (400 MHz, DMSO-$d_6$) δ 1.81-1.85 (2H, m), 1.98-2.02 (2H, m), 2.09-2.11 (1H, m), 2.38-2.41 (4H, m), 2.45 (3H, s), 3.18 (3H, s), 3.83-3.85 (1H, m), 4.85-4.89 (1H, m), 7.74 (1H, s), 8.40 (1H, s), 8.91 (1H, s), 9.14 (2H, s), and 1-(3-methoxy-cyclopentyl)-3-methyl-N-(7-methyl-[1,2,4]triazolo[1,5-a]pyridin-6-yl)-1H-pyrazolo[3,4-d]pyrimidin-6-amine (mixtures of Ex. 110/111, 80 mg, 53.33%) as a white solid. LCMS: m/z (ESI), $[M+H]^+$=379.3. $^1$HNMR (400 MHz, DMSO-$d_6$) δ 1.61-1.63 (1H, m), 1.82-1.98 (1H, m), 2.38-2.41 (4H, m), 2.39 (3H, s), 2.45 (3H, s), 3.18 (3H, s), 3.93-3.96 (1H, m), 5.00-5.06 (1H, m), 7.74 (1H, s), 8.40 (1H, s), 8.91 (1H, s), 9.15 (2H, d).

Step 2. Preparation of 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (Ex. 108, isomer 1)/1-(3-methoxycyclopentyl)-3-methyl-N-(7-methyl-[1,2,4]triazolo[1,5-a]pyridin-6-yl)-1H-pyrazolo[3,4-d]pyrimidin-6-amine (Ex. 109, isomer 2)

The mixtures of Ex. 108/109 (25 mg) was purified by chiral-Prep-HPLC with the following conditions (Column: CHIRALPAK AD-H, 2.0 cm I.D.*25 cm L; Mobile Phase A: Hex (8 mmol/L $NH_3$·MeOH)—HPLC, Mobile Phase B: IPA—HPLC; Flow rate: 40 mL/min; Gradient: 20 B to 20 B in 18 min) to afford 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (Ex. 108, 4.5 mg, 18.00%) (isomer 1) as a white solid. LCMS: m/z (ESI), $[M+H]^+$=379.3. $^1$HNMR (400 MHz, DMSO-$d_6$) δ 1.81-1.85 (2H, m), 1.98-2.01 (2H, m), 2.06-2.09 (1H, m), 2.38-2.43 (4H, m), 2.45 (3H, s), 3.18 (3H, s), 3.80-3.85 (1H, m), 4.82-4.87 (1H, m), 7.74 (1H, s), 8.40 (1H, s), 8.91 (1H, s), 9.14 (2H, s) and 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (Ex. 109, 3.8 mg, 12.00%) (isomer 2) as a white solid. LCMS: m/z (ESI), $[M+H]^+$=379.3. $^1$HNMR (400 MHz, DMSO-$d_6$) δ 1.81-1.83 (2H, m), 1.97-2.01 (2H, m), 2.10-2.12 (1H, m), 2.37-2.43 (4H, m), 2.45 (3H, s), 3.18 (3H, s), 3.81-3.85 (1H, m), 4.80-4.89 (1H, m), 7.73 (1H, s), 8.40 (1H, s), 8.91 (1H, s), 9.14 (2H, s).

Step 4. 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (Ex. 110, isomer 3)/1-(3-methoxycyclopentyl)-3-methyl-N-(7-methyl-[1,2,4]triazolo[1,5-a]pyridin-6-yl)-1H-pyrazolo[3,4-d]pyrimidin-6-amine (Ex. 111, isomer 4)

The mixtures of Ex. 110/111 (80 mg) was purified by Prep-HPLC with the following conditions (Column: CHIRALPAK AD-H, 2.0 cm I.D.*25 cm L; Mobile Phase A: Hex (8 mmol/L $NH_3$·MeOH)—HPLC, Mobile Phase B: IPA—HPLC; Flow rate: 40 mL/min; Gradient: 30 B to 30 B in 12 min) to afford 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (Ex. 110, 39.1 mg, 48.87%) (isomer 3) as a white solid. LCMS: m/z (ESI), $[M+H]^+$=379.3. $^1$HNMR (400 MHz, DMSO-$d_6$) δ 1.67-1.69 (1H, m), 1.93-1.99 (1H, m), 2.10-2.15 (4H, m), 2.39 (3H, s), 2.44 (3H, s), 3.16 (3H, s), 3.94 (1H, s), 5.00-5.08 (1H, m), 7.74 (1H, s), 8.40 (1H, s), 8.91 (1H, s), 9.16 (2H, d) and 1-(3-methoxycyclopentyl)-3-methyl-N-(7-methyl-[1,2,4]triazolo[1,5-a]pyridin-6-yl)-1H-pyrazolo[3,4-d]pyrimidin-6-amine (Ex. 111, 35.2 mg) (isomer 4) as a white solid. LCMS: m/z (ESI), $[M+H]^+$=379.3. $^1$HNMR (400 MHz, DMSO-$d_6$) δ 1.65-1.69 (1H, m), 1.93-1.97 (1H, m), 2.09-2.14 (4H, m), 2.39 (3H, d), 2.44 (3H, s), 3.15 (3H, s), 3.93-3.96 (1H, m), 5.00-5.08 (1H, m), 7.74 (1H, s), 8.41 (1H, s), 8.91 (1H, s), 9.16 (2H, d).

Ex. 112/113/114/115

Preparation of 3-methyl-N-(7-methyl-[1,2,4]triazolo[1,5-a]pyridin-6-yl)-1-(3-methyltetrahydro-2H-pyran-4-yl)-1H-pyrazolo[3,4-d]pyrimidin-6-amine (Ex. 112, isomer 1)/3-methyl-N-(7-methyl-[1,2,4]triazolo[1,5-a]pyridin-6-yl)-1-(3-methyltetrahydro-2H-pyran-4-yl)-1H-pyrazolo[3,4-d]pyrimidin-6-amine (Ex. 113, isomer 2)/3-methyl-N-(7-methyl-[1,2,4]triazolo[1,5-a]pyridin-6-yl)-1-(3-methyltetrahydro-2H-pyran-4-yl)-1H-pyrazolo[3,4-d]pyrimidin-6-amine (Ex. 114, isomer 3)/3-methyl-N-(7-methyl-[1,2,4]triazolo[1,5-a]pyridin-6-yl)-1-(3-methyltetrahydro-2H-pyran-4-yl)-1H-pyrazolo[3,4-d]pyrimidin-6-amine (Ex. 115, isomer 4)

Scheme 112-115

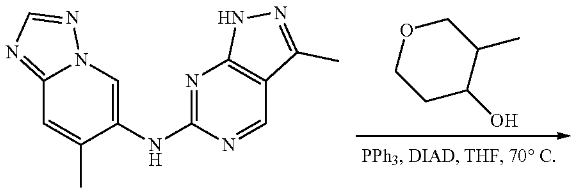

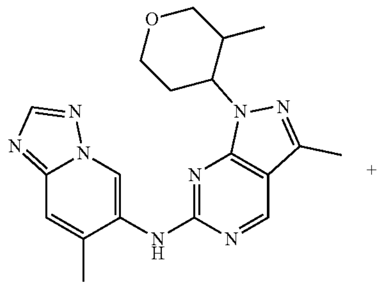

Ex. 112
isomer 1

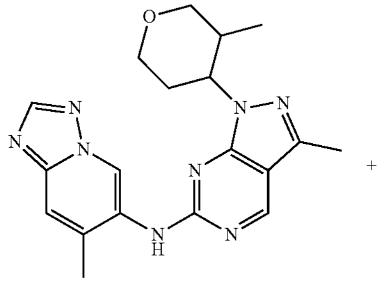

Ex. 113
isomer 2

-continued

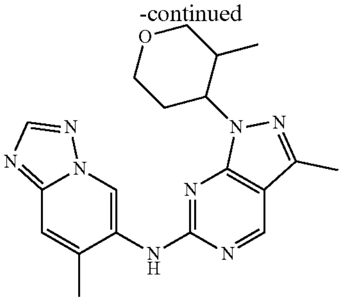

+

Ex. 114
isomer 3

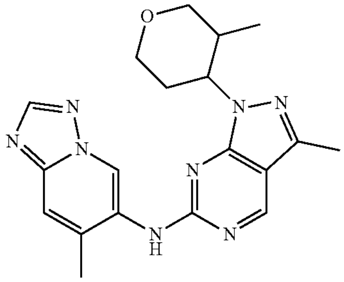

Ex. 115
isomer 4

Step 1. 3-methyl-N-[7-methyl-[1,2,4]triazolo[1,5-a] pyridin-6-yl]-1-[3-methyloxan-4-yl]pyrazolo[3,4-d] pyrimidin-6-amine (mixtures of Ex. 112/113) and 3-methyl-N-[7-methyl-[1,2,4]triazolo[1,5-a]pyridin-6-yl]-1-[3-methyloxan-4-yl]pyrazolo[3,4-d]pyrimidin-6-amine (mixtures of Ex. 114/115)

A mixture of 3-methyl-N-[7-methyl-[1,2,4]triazolo[1,5-a] pyridin-6-yl]-1H-pyrazolo[3,4-d]pyrimidin-6-amine (200.00 mg, 0.714 mmol, 1.00 equiv), 3-methyloxan-4-ol (248.65 mg, 2.141 mmol, 3.00 equiv) and $PPh_3$ (561.45 mg, 2.141 mmol, 3.00 equiv) in THF (10.00 mL) at 0° C. was stirred, and DIAD (432.85 mg, 2.141 mmol, 3.00 equiv) was dropwise added under nitrogen atmosphere at 70° C. was stirred for 2 hs. The resulting mixture was concentrated under reduced pressure. The residue was purified by Prep_TLC ($CH_2Cl_2$/MeOH 15:1) to afford crude solid. The crude product (120 mg) was purified by Prep-HPLC with the following conditions (Column: XBridge Shield RP18 OBD Column, 30*150 mm, 5 um; Mobile Phase A: Water (0.05% $NH_3H_2O$), Mobile Phase B: ACN; Flow rate: 60 mL/min; Gradient: 18 B to 48 B in 7 min) to afford 3-methyl-N-[7-methyl-[1,2,4]triazolo[1,5-a]pyridin-6-yl]-1-[3-methyl-oxan-4-yl]pyrazolo[3,4-d]pyrimidin-6-amine (mixtures of Ex. 112/113, 30 mg, 25.00%) as a white solid. LCMS: m/z (ESI), $[M+H]^+$=379.3. 4 HNMR (400 MHz, DMSO-$d_6$) δ 0.52 (3H, d), 1.74 (2H, d), 2.06-2.31 (1H, m), 2.36 (3H, d), 2.45 (3H, s), 3.07 (1H, t), 3.43 (1H, t), 3.82-4.00 (2H, m), 4.14-4.27 (1H, m), 7.69-7.76 (1H, m), 8.39 (1H, s), 8.91 (1H, s), 9.15 (2H, d) and 3-methyl-N-[7-methyl-[1,2,4] triazolo[1,5-a]pyridin-6-yl]-1-[-3-methyloxan-4-yl]pyrazolo[3,4-d]pyrimidin-6-amine (mixtures of Ex. 114/115, 70 mg, 57.75%) as a white solid. LCMS: m/z (ESI), $[M+H]^+$=379.3. 4 HNMR (400 MHz, DMSO-$d_6$) δ 0.70 (3H, d), 1.74-1.91 (1H, m), 2.23 (1H, d), 2.37 (4H, d), 2.44 (3H, s), 3.44-3.65 (2H, m), 3.72 (1H, dd), 4.05 (1H, dt), 4.79 (1H, dt), 7.72 (1H, s), 8.39 (1H, s), 8.93 (1H, s), 9.17 (2H, s)

Step 2. 3-methyl-N-(7-methyl-[1,2,4]triazolo[1,5-a] pyridin-6-yl)-1-(3-methyltetrahydro-2H-pyran-4-yl)-1H-pyrazolo[3,4-d]pyrimidin-6-amine (Ex. 112, isomer 1) and 3-methyl-N-(7-methyl-[1,2,4]triazolo [1,5-a]pyridin-6-yl)-1-(3-methyltetrahydro-2H-pyran-4-yl)-1H-pyrazolo[3,4-d]pyrimidin-6-amine (Ex. 113, isomer 2)

The crude product 3-methyl-N-(7-methyl-[1,2,4]triazolo [1,5-a]pyridin-6-yl)-1-(3-methyltetrahydro-2H-pyran-4-yl)-1H-pyrazolo[3,4-d]pyrimidin-6-amine (mixtures of Ex. 112/113, 30.00 mg, 0.079 mmol, 1.00 equiv)) was purified by Prep-CHIRAL-HPLC with the following conditions (Column: CHIRALPAK IE-3, 4.6*50 mm 3 um; Mobile Phase A: Hex (0.1% DEA): EtOH=50:50) to afford 3-methyl-N-(7-methyl-[1,2,4]triazolo[1,5-a]pyridin-6-yl)-1-(3-methyl-tetrahydro-2H-pyran-4-yl)-1H-pyrazolo[3,4-d]pyrimidin-6-amine (Ex. 112, isomer 1, 12.22 mg, 40.73%) as a white solid. LCMS: m/z (ESI), [M+H]+=379.3. $^1$HNMR (400 MHz, DMSO-$d_6$) δ 0.52 (3H, d), 1.74 (2H, d), 2.06-2.31 (1H, m), 2.36 (3H, d), 2.45 (3H, s), 3.07 (1H, t), 3.43 (1H, t), 3.82-4.00 (2H, m), 4.14-4.27 (1H, m), 7.69-7.76 (1H, m), 8.39 (1H, s), 8.91 (1H, s), 9.15 (2H, d) and 3-methyl-N-(7-methyl-[1,2,4]triazolo [1,5-a]pyridin-6-yl)-1-(3-methyltetrahydro-2H-pyran-4-yl)-1H-pyrazolo[3,4-d]pyrimidin-6-amine (Ex. 113, isomer 2, 8.37 mg, 27.90%) as a white solid. LCMS: m/z (ESI), $[M+H]^+$=379.3. $^1$HNMR (400 MHz, DMSO-$d_6$) δ 0.52 (3H, d), 1.74 (2H, d), 2.06-2.31 (1H, m), 2.36 (3H, d), 2.45 (3H, s), 3.07 (1H, t), 3.43 (1H, t), 3.82-4.00 (2H, m), 4.14-4.27 (1H, m), 7.69-7.76 (1H, m), 8.39 (1H, s), 8.91 (1H, s), 9.15 (2H, d)

Step 3. 3-methyl-N-(7-methyl-[1,2,4]triazolo[1,5-a] pyridin-6-yl)-1-(3-methyltetrahydro-2H-pyran-4-yl)-1H-pyrazolo[3,4-d]pyrimidin-6-amine (Ex. 114, isomer 3) and 3-methyl-N-(7-methyl-[1,2,4]triazolo [1,5-a]pyridin-6-yl)-1-(3-methyltetrahydro-2H-pyran-4-yl)-1H-pyrazolo[3,4-d]pyrimidin-6-amine (Ex. 115, isomer 4)

The crude product 3-methyl-N-(7-methyl-[1,2,4]triazolo [1,5-a]pyridin-6-yl)-1-(3-methyl tetrahydro-2H-pyran-4-yl)-1H-pyrazolo[3,4-d]pyrimidin-6-amine (mixtures of Ex. 114/115, 70.00 mg, 0.185 mmol, 1.00 equiv)) was purified by Prep-CHIRAL-HPLC with the following conditions (Column: CHIRALPAK IE-3, 4.6*50 mm 3 um; Mobile Phase A: Hex (0.1% DEA): EtOH=50:50) to afford 3-methyl-N-(7-methyl-[1,2,4]triazolo[1,5-a]pyridin-6-yl)-1-(3-methyltetrahydro-2H-pyran-4-yl)-1H-pyrazolo[3,4-d] pyrimidin-6-amine (Ex. 114, isomer 3, 32.98 mg, 47.11%) as a white solid. LCMS: m/z (ESI), $[M+H]^+$=379.3. 1H NMR (300 MHz, DMSO-$d_6$) δ 0.70 (3H, d), 1.74-1.91 (1H, m), 2.23 (1H, d), 2.37 (4H, d), 2.44 (3H, s), 3.44-3.65 (2H, m), 3.72 (1H, d), 4.05 (1H, t), 4.79 (1H, t), 7.72 (1H, s), 8.39 (1H, s), 8.93 (1H, s), 9.17 (2H, s), and 3-methyl-N-(7-methyl-[1,2,4]triazolo[1,5-a]pyridin-6-yl)-1-(3-methyltetrahydro-2H-pyran-4-yl)-1H-pyrazolo[3,4-d]pyrimidin-6-amine (Ex. 115, isomer 4, 33.45 mg, 41.39%) as a white solid. LCMS: m/z (ESI), $[M+H]^+$=379.3. $^1$H NMR (300 MHz, DMSO-$d_6$) δ 0.70 (3H, d), 1.74-1.91 (1H, m), 2.23 (1H, d), 2.37 (4H, d), 2.44 (3H, s), 3.44-3.65 (2H, m), 3.72 (1H, d), 4.05 (1H, t), 4.79 (1H, t), 7.72 (1H, s), 8.39 (1H, s), 8.93 (1H, s), 9.17 (2H, s)

Example 116/117

Preparation of 1-(2,2-dimethyltetrahydro-2H-pyran-4-yl)-3-methyl-N-(7-methyl-[1,2,4]triazolo[1,5-a]pyridin-6-yl)-1H-pyrazolo[3,4-d]pyrimidin-6-amine (Example 116, isomer 1) and 1-(2,2-dimethyltetrahydro-2H-pyran-4-yl)-3-methyl-N-(7-methyl-[1,2,4]triazolo[1,5-a]pyridin-6-yl)-1H-pyrazolo[3,4-d]pyrimidin-6-amine (Example 117, isomer 2)

Scheme 116

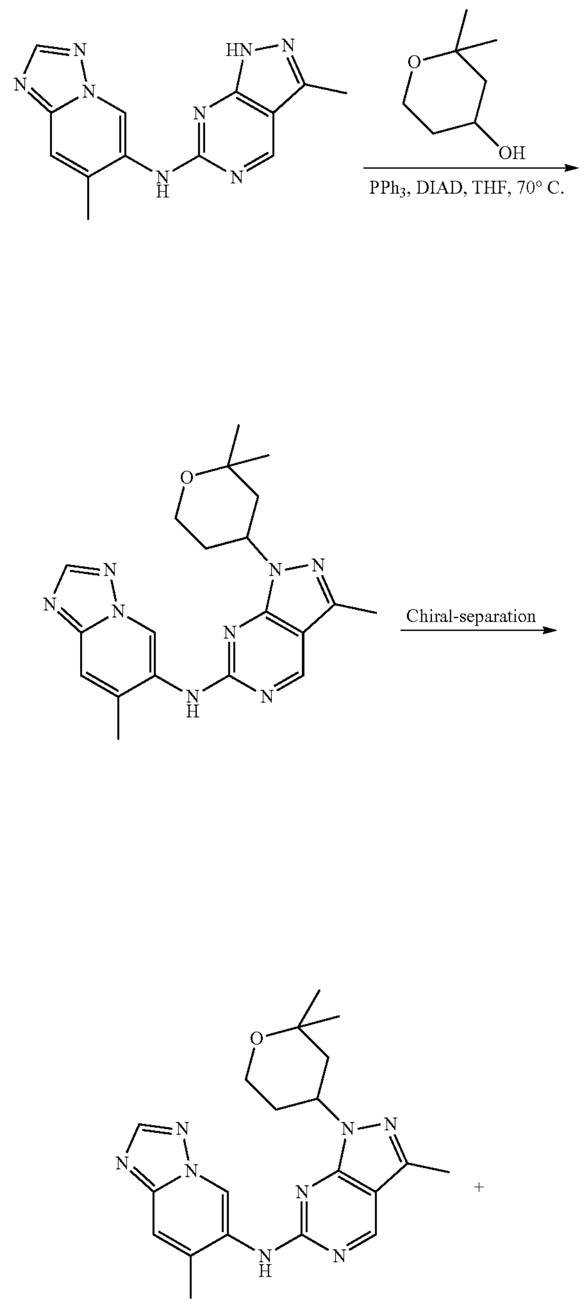

isomer 1
Example 116

-continued

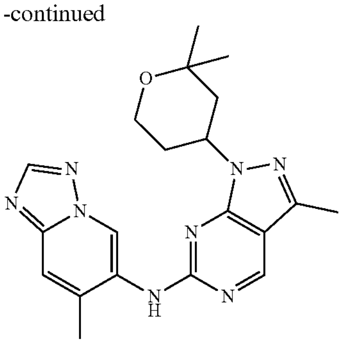

isomer 2
Example 117

Step 1. 1-(2,2-dimethyltetrahydro-2H-pyran-4-yl)-3-methyl-N-(7-methyl-[1,2,4]triazolo[1,5-a]pyridin-6-yl)-1H-pyrazolo[3,4-d]pyrimidin-6-amine Into a 250 mL round-bottom flask were added 2,2-dimethyloxan-4-ol (627.03 mg, 4.816 mmol, 3.00 equiv) and 3-methyl-N-[7-methyl-[1,2,4]triazolo[1,5-a]pyridin-6-yl]-1H-pyrazolo[3,4-d]pyrimidin-6-amine (450.00 mg, 1.605 mmol, 1.00 equiv), $PPh_3$ (1263.26 mg, 4.816 mmol, 3.00 equiv) in THF (60.00 mL) at 0° C. Solution of DIAD (973.90 mg, 4.816 mmol, 3.00 equiv) in THF (10 mL) was added to the above solution dropwise at 0° C. under $N_2$ and stirred at rt for 3 min. The reaction mixture was continued to stir at 70° C. for 2 h. The resulting mixture was concentrated under reduced pressure. The resulting mixture was diluted with DCM (20 mL) and filtered, the filter cake was washed with DCM (2×5 mL). The filtrate was concentrated under reduced pressure. The residue was purified by Prep-TLC ($CH_2Cl_2$/MeOH 15:1) to afford a crude product. The crude product (250 mg) was purified by Prep-HPLC with the following conditions (Column: YMC-Actus Triart C18, 30*250.5 um; Mobile Phase A: Water (0.05% $NH_3H_2O$), Mobile Phase B: ACN; Flow rate: 60 mL/min; Gradient: 37 B to 57 B in 7 min) to afford 1-[2,2-dimethyloxan-4-yl]-3-methyl-N-[7-methyl-[1,2,4]triazolo[1,5-a]pyridin-6-yl]pyrazolo[3,4-d]pyrimidin-6-amine (170 mg, 26.98%) as a white solid. LCMS: m/z (ESI), $[M+H]^+$=393.2

Step 2. 1-(2,2-dimethyltetrahydro-2H-pyran-4-yl)-3-methyl-N-(7-methyl-[1,2,4]triazolo[1,5-a]pyridin-6-yl)-1H-pyrazolo[3,4-d]pyrimidin-6-amine (Example 116, isomer1)/1-(2,2-dimethyltetrahydro-2H-pyran-4-yl)-3-methyl-N-(7-methyl-[1,2,4]triazolo[1,5-a]pyridin-6-yl)-1H-pyrazolo[3,4-d]pyrimidin-6-amine (Example 117, isomer 2)

The crude product (170 mg) was purified by Chiral-Prep-HPLC with the following conditions (Column: CHIRALPAK-AD-H-UL001, 20*250 mm, 5 um; Mobile Phase A: Hex (8 mmol/L $NH_3$·MeOH)—HPLC, Mobile Phase B: IPA—HPLC; Flow rate: 20 mL/min; Gradient: 25 B to 25 B in 15 min; RT1:10.12; RT2:11.691) to afford rel-1-[(4R)-2,2-dimethyloxan-4-yl]-3-methyl-N-[7-methyl-[1,2,4]triazolo[1,5-a]pyridin-6-yl]pyrazolo[3,4-d]pyrimidin-6-amine (Example 116, isomer 1) (70 mg, 41.18%) LCMS: m/z (ESI), $[M+H]^+$=393.3. $^1H$-NMR (400 MHz, DMSO-$d_6$) δ 1.21 (6H, d), 1.80 (2H, dd), 1.89 (1H, t), 2.05 (1H, qd), 2.35-2.48 (6H, m), 3.66-3.81 (2H, m), 4.75-4.95 (1H, m), 7.74 (1H, d), 8.40 (1H, s), 8.92 (1H, s), 9.20 (2H, d); and rel-1-[(4R)-2, 2-dimethyloxan-4-yl]-3-methyl-N-[7-methyl-[1,2,4]triazolo[1,5-a]pyridin-6-yl]pyrazolo[3,4-d]pyrimidin-6-amine (Example 117, isomer 2) (70 mg, 41.18%) as a white solid, LCMS: m/z (ESI), $[M+H]^+$=393.3. $^1$H-NMR (400 MHz, DMSO-$d_6$) δ 1.21 (6H, d), 1.80 (2H, dd), 1.89 (1H, t), 2.05 (1H, qd), 2.35-2.48 (6H, m), 3.66-3.81 (2H, m), 4.75-4.95 (1H, m), 7.74 (1H, d), 8.40 (1H, s), 8.92 (1H, s), 9.20 (2H, d).

BIOLOGICAL EXAMPLES

Exemplary compounds disclosed herein have been characterized in one or more of the following biological assays.

Biological Example 1

Enzymatic Assay

The inhibitory activity of compounds against DNA-PK was determined by TR-FRET measuring a fluorescent labelled peptide substrate converting to a phosphorylated product. All assays were performed in black Greiner 384 well low volume plates (Greiner), in a total reaction volume of 6 μL and 0.5% (v/v) final DMSO concentration. Full length human DNAPK protein, Fluorescein-P53 (Ser15) Peptide Substrate (Fluorescein-EPPLSQEAFADLWKK) and LanthaScreen™ Tb-anti-phospho-p53 [pSer15] Antibody Kit were purchased from Thermo Fisher Scientific. Initially DNA-PK protein was incubated with compound for 30 minutes at room temperature in reaction buffer (50 mM HEPES pH 7.5, 0.01% Brij-35, 10 mM MgCl2, 1 mM EGTA, 1 mM DTT, 10 μg/ml Calf Thymus DNA). The reaction was then initiated by the addition of ATP and Fluorescein-P53 (Ser15) Peptide Substrate. The kinase reaction (10 μM ATP, 1.6 μM peptide substrate) was quenched after 60 minutes by the addition of 6 μl of stop buffer containing 20 mM EDTA, 4 nM Tb anti-phospho-p53 [Serl5] Antibody. The reaction was incubated for a further hour and the plates were read on Spark 20M (Tecan). Data was analyzed and the concentration of compound producing 50% inhibition of the respective kinase ($IC_{50}$) was calculated using four-parameter logistic fit with XLfit. DNA-PK inhibition activities of exemplary compounds are shown in Table 5 below. It can been seen that compounds of the present disclosure have demonstrated potent DNA-PK inhibitory activity.

TABLE 5

DNA-PK enzymatic activity

| Example number | DNA-PK $IC_{50}$ (nM) | Example number | DNA-PK $IC_{50}$ (nM) |
|---|---|---|---|
| 1 | 0.8 | 46 | 3.3 |
| 2 | 1.4 | 47 | 1.7 |
| 3 | 10.2 | 48 | 1.8 |
| 4 | 1.6 | 49 | 1.7 |
| 5 | 0.4 | 50 | 7.0 |
| 6 | 1.6 | 51 | 12.0 |
| 7 | 0.8 | 52 | 10.8 |
| 8 | 0.7 | 53 | 7.2 |
| 9 | 0.7 | 54 | 1.5 |
| 10 | 1.7 | 55 | 2.5 |
| 11 | 0.7 | 56 | 1.1 |
| 12 | 1.1 | 57 | 12.2 |
| 13 | 3.9 | 58 | 2.2 |
| 14 | 1.6 | 59 | 4.5 |
| 15 | 35.2 | 60 | 13.5 |
| 16 | 8.4 | 61 | 3.5 |
| 17 | 5.2 | 62 | 5.1 |
| 18 | 2.6 | 63 | 36.0 |
| 19 | 25.9 | 64 | 3.6 |
| 20 | 1.3 | 65 | 8.0 |
| 21 | 1.4 | 66 | 2.0 |
| 22 | 1.3 | 67 | 27.0 |
| 23 | 0.7 | 68 | 65.3 |
| 24 | 0.4 | 69 | 8.8 |
| 25 | 1.8 | 70 | 4.3 |
| 26 | 3.0 | 71 | 6.4 |
| 27 | 1.0 | 72 | 1.8 |
| 28 | 1.3 | 73 | 1.3 |
| 29 | 2.0 | 80 | 2.1 |
| 30 | 15.7 | 86 | 2.4 |
| 31 | 1.8 | 86-1 | 3 |
| 32 | 1.9 | 89 | 6.2 |
| 33 | 1.5 | 102 | 0.9 |
| 34 | 1.2 | 106 | 0.9 |
| 35 | 2.8 | 107 | 1.3 |
| 36 | 1.4 | 108 | 1.9 |
| 37 | 0.9 | 109 | 4 |
| 38 | 11.1 | 110 | 1.8 |
| 39 | 2.1 | 111 | 1.1 |
| 40 | 4.2 | 112 | 3.7 |
| 41 | 1.4 | 113 | 3.2 |
| 42 | 7.5 | 114 | 1.7 |
| 43 | 1.5 | 115 | 1.9 |
| 44 | 24.0 | 116 | 1.6 |
| 45 | 4.3 | 117 | 1.8 |

Biological Example 2

Metabolic Stability Assay (Rat Hepatocyte Clint)

Viability of cryopreserved hepatocytes was determined using trypan blue and the cell conc. was adjusted to 106 cells per mL with buffer. 1 μM compound (in Acetonitrile; 0.01% DMSO) was incubated with 250 μL of hepatocytecells (1 million cells per mL) in a 96 deep well plate. Reaction was stopped at different time points (0, 0.5, 5, 15, 30, 45, 60, 80, 100 and 120 min) by addition of 3 volumes of chilled acetonitrile to 20 μL of reaction mixture and centrifuged at 4° C. for 15 min. 40 μL of supernatant was diluted to 200 μL with pure water and analyzed using LC-MS/MS.

In vitro hepatocyte clearance was estimated based on determination of elimination half-life ($T_{1/2}$) of compounds disappearance from their initial concentrations. Peak area ratios of each compound (test or control) to IS was calculated. Drug elimination rate constant k (min−1), $T_{1/2}$ (min), and in vitro intrinsic clearance $CL_{int}$ (μL/min/E6) was calculated according to the following equations:

$$k = -\text{slope}$$

$$T_{1/2} = 0.693/k$$

$$CL_{int} = k/C_{hep}$$

Where $C_{hep}$ (cells×$\mu L^{-1}$) is the cell concentration in the incubation system.

Data are shown as below in Table 6.

Metabolic Stability Assay (Human Microsomal Clint)

1 μM compound was incubated with 1 mg/mL of microsomes (Pooled HLM with 20 mg/ml protein cone) at 37° C. in 250 μL of buffer (100 mM phosphate buffer, pH-7.4) containing 1 mM NADPH solution. 20 μL of incubation mix was quenched with 5 volumes chilled acetonitrile at different time points 0, 0.5, 5, 10, 15, 20 and 30 min in a fresh 96 well plate. The quench plate was centrifuged at 4000 rpm for 15 min. 40 μL of supernatant was diluted to 200 μL with pure water and analyzed using LC-MS/MS.

In vitro intrinsic clearance of the drugs in the microsome $CL_{int}$ (μl/min/mg) was calculated in the similar manner as the $CL_{int}$ in the hepatocyte. Data are also shown as below in Table 6.

MDCKII-MDR1-BCRP Efflux Assay

The apical-to-basolateral (A-B) and basolateral-to-apical (B-A) transport of compound in HBSS (25 mM HEPES, pH 7.4) was measured across MDCKII-MDR1-BCRP cell monolayers. Incubations were performed at approximately 37° C. for 120 min, with functionality of the test system being confirmed using 5 μM digoxin as a positive control substrate. Transport of 5 μM compound and control compound were determined by quantifying substrate concentration in the incubation medium of donor compartment at the beginning of the incubation period, and both donor and receiver compartments at the end of the incubation period. The data was used to calculate the apparent permeability (Papp). All incubations were performed in triplicate and integrity of the cell monolayers was confirmed using the marker Lucifer yellow.

The permeability coefficient Pexact (cm/s) was calculated using the equation:

$$Papp = (dCr/dt) \times Vr/(A \times C0)$$

$$Pexact = -(Vd \times Vr)/(Vd + Vr)/A/t \times \ln(1 - (Vd + Vr) \times Cr/(Vd \times Cd + Vr \times Cr))$$

The Pexact ratio was calculated using the equation:

$$\text{Efflux Ratio} = Pexact \text{ or } Papp(BA)/Pexact \text{ or } Papp(AB)$$

The efflux ratio was calculated using the equation:

$$Pexact \text{ or } Papp \text{ ratio} = Pexact \text{ or } Papp(+\text{inhibitor})/Pexact \text{ or } Papp(-\text{inhibitor})$$

Where dCr/dt is the cumulative concentration of compound in the receiver chamber as a function of time (μM/s); Vr is the solution volume in the receiver chamber (0.1 mL on the apical side, 0.3 mL on the basolateral side); A is the surface area for the transport, i.e. 0.11 cm2 for the area of the monolayer; CO is the initial concentration in the donor chamber (μM). Data are shown in table 6 below.

TABLE 6

In vitro metabolic stability and efflux ratio

| Example number | Rat hepatocyte $CL_{int}$ (μl/min/ $10^{-6}$ cells) | Human liver microsomal $CL_{int}$ (μl/min/mg) | MDCK-Mdr1-BCRP efflux ratio |
|---|---|---|---|
| 1 | 5.4 | 19.8 | 5.9 |
| 2 | 3.0 | 12.7 | 3.3 |
| 3 | 9.8 | 39.7 | 3.1 |
| 4 | 10.7 | 47.3 | 0.9 |

TABLE 6-continued

In vitro metabolic stability and efflux ratio

| Example number | Rat hepatocyte $CL_{int}$ (μl/min/ $10^{-6}$ cells) | Human liver microsomal $CL_{int}$ (μl/min/mg) | MDCK-Mdr1-BCRP efflux ratio |
|---|---|---|---|
| 5 | 22.8 | 134.6 | 0.8 |
| 6 | 6.8 | 35.5 | 4.9 |
| 7 | 7.5 | 75.1 | 2.3 |
| 8 | 20.7 | 233.5 | 1.7 |
| 9 | 11.3 | 135.4 | 1.3 |
| 10 | 6.8 | 17.2 | 7.2 |
| 11 | 190.4 | >300 | 1.8 |
| 12 | 70.3 | 108.7 | 2.1 |
| 13 | <1 | 12.9 | 2.8 |
| 14 | 1.7 | 9.9 | 2.3 |
| 15 | 14.6 | 69.6 | 0.8 |
| 16 | 11.8 | 26.4 | 0.8 |
| 17 | 7.2 | 54.7 | 1.5 |
| 18 | 31.7 | 153.0 | 1.1 |
| 19 | 6.8 | 4.3 | 13.1 |
| 20 | 52.0 | 117.1 | 0.8 |
| 21 | 10.0 | 101.6 | 1.3 |
| 22 | 40.9 | 114.8 | |
| 23 | 21.2 | 115.4 | 0.9 |
| 24 | 5.5 | 72.3 | 1.4 |
| 25 | 17.7 | 209.4 | 1.3 |
| 26 | 13.6 | 133.8 | 4.2 |
| 27 | 10.8 | 41.4 | |
| 28 | 14.1 | 70.0 | |
| 29 | 13.3 | 24.5 | 1.6 |
| 30 | 4.5 | 17.7 | 1.2 |
| 31 | 12.4 | 6.6 | 31.2 |
| 32 | 11.5 | 9.1 | 9.4 |
| 33 | 11.3 | 41.5 | 3.0 |
| 34 | 12.7 | 31.4 | 3.5 |
| 35 | 21.7 | 55.4 | 1.7 |
| 36 | 11.6 | 51.5 | 2.1 |
| 37 | 71.1 | 200.5 | 0.6 |
| 38 | 15.3 | 34.2 | 1.4 |
| 39 | 153.3 | 151.1 | 0.9 |
| 40 | 144.4 | 125.3 | 0.9 |
| 41 | 65.5 | 216.3 | 1.5 |
| 42 | 34.2 | 19.5 | 4.8 |
| 43 | 16.9 | 173.3 | |
| 44 | 1.9 | 8.8 | 4.3 |
| 45 | 64.0 | 70.0 | |
| 46 | 60.9 | 104.9 | |
| 47 | 43.3 | 89.7 | |
| 48 | <1 | 11.1 | 3.6 |
| 49 | <1 | 8.7 | 3.4 |
| 50 | 2.1 | 12.2 | 2.7 |
| 51 | <1 | 20.9 | 1.9 |
| 52 | 4.9 | 14.1 | 3.2 |
| 53 | 5.0 | 15.2 | 2.4 |
| 57 | 4.2 | 20.9 | 1.6 |
| 58 | 32.9 | 70.8 | 1.9 |
| 59 | 5.5 | 20.2 | 0.7 |
| 60 | 22.7 | 20.4 | 0.7 |
| 61 | 5.2 | 34.5 | |
| 62 | 11.7 | 42.4 | |
| 63 | 5.3 | 5.5 | 2.4 |
| 64 | 38.6 | 50.8 | |
| 65 | 13.3 | 17.1 | 2.0 |
| 66 | 15.3 | 120.1 | 1.9 |
| 67 | 8.3 | 103.8 | |
| 68 | 37.0 | 201.9 | |
| 69 | 6.3 | 13.6 | 3.0 |
| 72 | 1.0 | 5.9 | 7.5 |
| 80 | 9.3 | 23.5 | 19 |
| 86 | 33.4 | >300 | 1.4 |
| 86-1 | 42.7 | >300 | 0.9 |
| 89 | 9.6 | 10.1 | 0.8 |
| 102 | 32.0 | 15.0 | 14 |
| 106 | 17.6 | 68.9 | 2.1 |
| 107 | 4.5 | 13.9 | 2.7 |
| 108 | 17.2 | 89.0 | 2 |
| 109 | 11.9 | 87.2 | 2 |
| 110 | 17.4 | 64.8 | 1.7 |
| 111 | 17.0 | 68.5 | 1.8 |

TABLE 6-continued

| In vitro metabolic stability and efflux ratio | | | |
|---|---|---|---|
| Example number | Rat hepatocyte $CL_{int}$ (µl/min/$10^{-6}$ cells) | Human liver microsomal $CL_{int}$ (µl/min/mg) | MDCK-Mdr1-BCRP efflux ratio |
| 112 | 7.8 | 47.0 | 3.5 |
| 113 | 8.2 | 60.5 | 4 |
| 114 | 8.5 | 50.4 | 2 |
| 115 | 7.7 | 53.5 | 2 |
| 116 | 9.6 | 71.1 | 2 |
| 117 | 9.1 | 50.4 | 1.8 |

Biological Example 3

Brain-Blood-Barrier Penetration Assay

It is believed that Kp,uu, the relationship between concentrations of unbound drug in brain and in plasma, is the key to prediction of CNS action and should be the main parameter measured and optimized for in drug discovery (Di L et al., Journal of Medicinal Chemistry [2013], 56: 2-12).

In vitro plasma and brain binding assay was carried out by using equilibrium dialysis method with semi-permeable membrane. Plasma and diluted brain homogenate (1:4 with DPBS pH7.4) were spiked with 5 µM test compound (in triplicate) and dialyzed against equal volume of 150 µL 100 mM PBS buffer (pH7.4) at 37° C. for 18 hours in a slowly rotated plate. At the end of incubation, a 50 µL aliquot from the receiver side and a 5 µL from the donor chamber were taken. The 5 µL sample was further diluted with 45 µL of blank plasma or brain homogenate. Paired samples were matrix-matched with either buffer or blank plasma/brain homogenate and mixed for 2 min, and then precipitated with 150 µL cold acetonitrile with 100 ng/mL tolbutamide as internal standard. After centrifuging at 4000 rpm for 20 min, supernatant was diluted with 0.1% formic acid aqueous solution and analyzed for LC/MS/MS (API 4000, Applied Biosystems, Foster City). Unbound fraction (fu) of test compound in the brain homogenate and diluted plasma were calculated by the ratio of the buffer side response to the brain homogenate/plasma side response, and unbound fraction (fu,pl and fu,br) of test compound in non-diluted plasma and tissue were calculated from measured fu in homogenate and plasma with the following equation: fu,bl (fu,br)=(1/D)/[(1/fu−1)+1/D)]. D is dilution factor.

A Short oral absorption (SOA) model is an in-vivo screening model to identify brain penetration of a compound. Six male Han Wistar rats purchased from Beijing Vital River were orally dosed with the compound at 10 mg/kg in 1% methylcellulose At 0.5, 1, 2, 4, 7 and 16 hour post-dose, cerebral spinal fluid (CSF) was collected from cisterna magna. Plasma samples will be processed for plasma by centrifugation at approximately 4° C., 3,000 g within half an hour of collection. Plasma samples will be removed to a labeled tube and stored at −80 degree until analysis. Brain tissue was harvested and homogenized in 3× volume of 100 mM phosphate buffered saline (pH7.4). All samples were stored at ~−70° C. prior to LC/MS/MS analysis.

Standards were prepared by spiking blank plasma, brain homogenate and artificial CSF covering 0.5 to 500 ng/mL. Homogenized brain tissue along with plasma samples were precipitated by adding 3-fold volume of cold acetonitrile containing internal standard (40 ng/mL Dexamethasone and 40 ng/mL Diclofenac), and 10 µL of CSF samples were precipitated with 100 µL of cold acetonitrile containing internal standard. After 2 min vortex and 5 min centrifugation at 14,000 rpm, supernatant was analyzed by LC/MS/MS (API 4000, Applied Biosystems, Foster City). Two sets of standard curves were run at the beginning and end of each batch from plasma sample analysis. For brain and CSF samples, one standard curve was analyzed along with test samples.

Total brain levels, expressed as brain/plasma ratio (Kp) were measured by AUCbrain/AUCplasma in rodents after oral administration. Free fraction of test compound in biological matrix was determined by in vitro plasma and brain binding assay. Kp,uu was calculated by the following equation: Kp,uu=AUC (brain)/AUC (plasma)×(fu,brain/fu.plasma). Data are shown in table 7.

TABLE 7

| Kp, uu (brain) data | |
|---|---|
| Example number | Kp, uu (brain) |
| 1 | 0.17 |
| 2 | 0.14 |
| 7 | 0.10 |
| 21 | 0.08 |
| 24 | 0.10 |
| 34 | 0.24 |
| 106 | 0.19 |
| 107 | 0.30 |
| 110 | 0.25 |
| 111 | 0.36 |

While the present disclosure has been particularly shown and described with reference to specific embodiments (some of which are preferred embodiments), it should be understood by those skilled in the art that various changes in form and detail may be made therein without departing from the spirit and scope of the present disclosure as disclosed herein.

What is claimed is:

1. A compound of Formula Ia, Ib or Ic:

Formula Ia

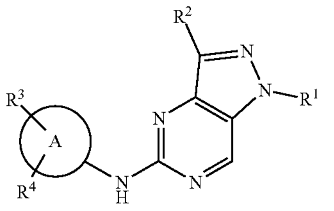

Formula Ib

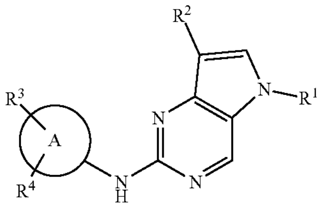

Formula Ic

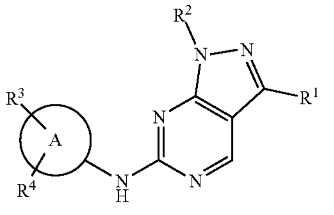

and a pharmaceutically acceptable salt thereof, wherein, $R^1$ is $C_{1-6}$ alkyl, wherein said $C_{1-6}$ alkyl can be optionally mono- or independently multi-substituted by hydroxyl, halogen, or deuterium;

$R^2$ is selected from $C_{1-6}$ alkyl, $C_{1-6}$ alkoxyl, —$(CH_2)_n$-Q, which can be optionally mono- or independently multi-substituted by deuterium, hydroxyl, amino, cyano, halogen, $C_{1-6}$ alkyl, $C_{1-6}$ haloalkyl, (C=N)—$C_{1-6}$ alkyl, $C_{1-6}$ alkoxyl, $C_{1-6}$ haloalkoxyl, $C_{3-8}$ cycloalkyl, $C_{3-8}$ cycloalkoxyl, 3-8 membered aryl, or 3-8 membered heterocyclyl, wherein n is 0, 1 or 2, Q in $R^2$ is 3-8 membered saturated or unsaturated carbocyclyl, or 3-8 membered saturated or unsaturated heterocyclyl;

$R^3$ is selected from halogen, hydroxyl, $C_{1-6}$ alkyl or $C_{1-6}$ alkoxyl;

$R^4$ is selected from absent, cyano, $C_{1-6}$ alkyl, $C_{1-6}$ alkoxyl, —$(CH_2)_n$-Q, wherein the $C_{1-6}$ alkyl, $C_{1-6}$ alkoxyl or —$(CH_2)_n$-Q can be optionally mono- or independently multi-substituted by deuterium, hydroxyl, $C_{1-6}$ alkyl, $C_{1-6}$ alkoxyl, $C_{1-6}$ haloalkoxyl, wherein n is 0, 1 or 2, Q in $R^4$ is 3-8 unsaturated heterocyclyl;

Ring A is 6 membered heteroaryl having I nitrogen, or 9 membered bicyclic ring having 2-3 ring heteroatoms chosen from oxygen, sulfur and nitrogen.

2. The compound of claim 1, having a structure of Formula Ia

Formula Ia

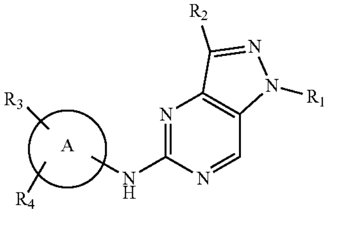

and a pharmaceutically acceptable salt thereof.

3. The compound of claim 1, having a structure of Formula Ib

Formula Ib

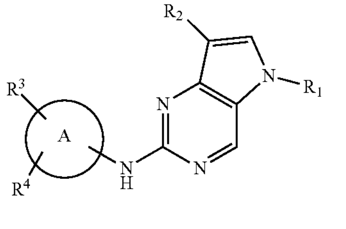

and a pharmaceutically acceptable salt thereof.

4. The compound of claim 1, having a structure of Formula Ic

Formula Ic

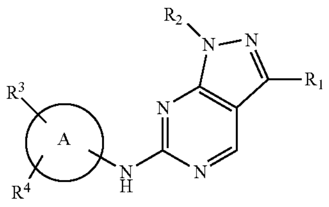

and a pharmaceutically acceptable salt thereof.

5. The compound of claim 1, wherein $R^2$ is selected from methyl, ethyl, propyl, butyl, cyclopropyl, cyclobutyl, oxetanyl, cyclopentanyl, tetrahydrofuryl, cyclohexanyl, cycloheptanyl, piperidinyl, phenyl, pyridinyl, pyridonyl, oxocanyl, tetrahydropyranyl, dihydropyranyl, spiro[3.3]heptanyl, spiro[2.5]octanyl, bicyclo[1.1.1]pentanyl, bicyclo[3.2.1]octanyl, 8-oxa bicyclo[3.2.1]octan-3-yl, which can be optionally mono- or independently multi-substituted by hydroxyl, cyano, halogen, $C_{1-6}$ alkyl, $C_{1-6}$ haloalkyl, $C_{1-6}$ alkoxyl, $C_{1-6}$ haloalkoxyl, $C_{3-8}$ cycloalkyl, $C_{1-6}$ cycloalkoxyl, 3-8 membered aryl, or 3-8 membered heterocyclyl, which can further be optionally mono- or independently multi-substituted halogen, deuterium, hydroxyl, amino, cyano, $C_{1-6}$ alkyl, $C_{1-6}$ haloalkyl, $C_{1-6}$ alkoxyl, or $C_{1-6}$ haloalkoxyl.

6. The compound of claim 1, wherein $R^2$ is selected from:

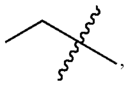, 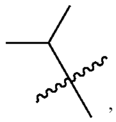, 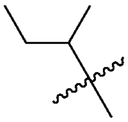, 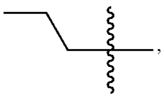, 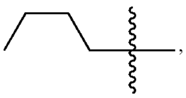, 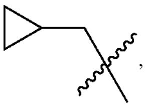, 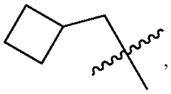, 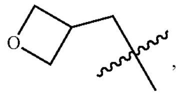, 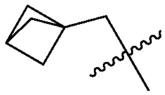, 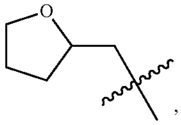, 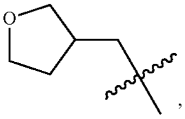, 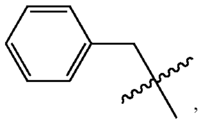, 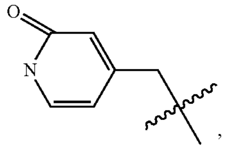, 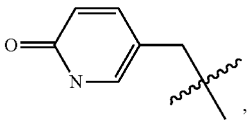, 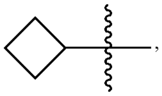, 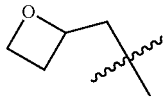, 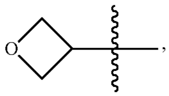, 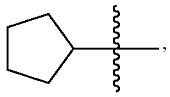, -continued

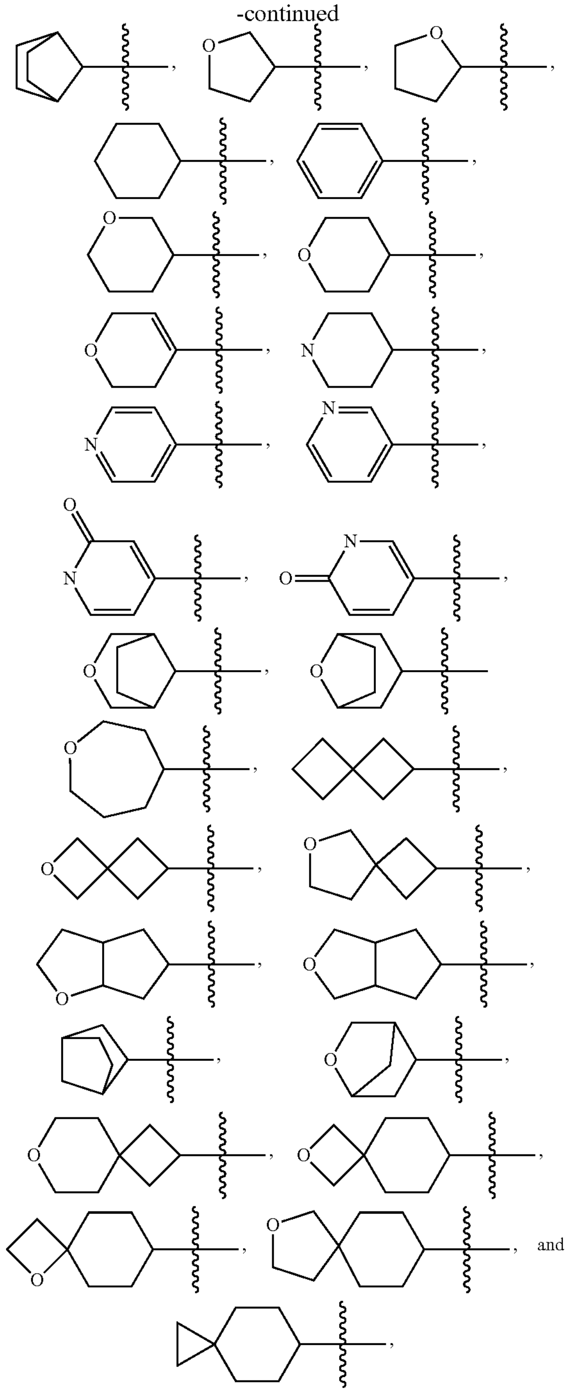

and which can be optionally mono- or independently multi-substituted by hydroxyl, cyano, fluoro, chloro, bromo, methyl, ethyl, methoxyl, difluoromethyl, difluoromethoxyl, or trifluoromethoxyl.

7. The compound of claim 1, wherein $R^2$ is cyclohexanyl, or tetrahydropyranyl, which can be optionally mono- or independently multi substituted by halogen, $C_{1-6}$ alkyl or $C_{1-6}$ alkoxyl.

8. The compound of claim 1, wherein $R^1$ is methyl, ethyl, n-propyl, iso-propyl, n-butyl, sec-butyl, tert-butyl, or isobutyl, which can be optionally mono- or independently multi-substituted by hydroxyl, halogen, or deuterium.

9. The compound of claim 1, wherein $R^1$ is methyl, ethyl, tri-fluoro-methyl, or tri-deuterium-methyl.

10. The compound of claim 1, wherein Ring A is a phenyl- or pyridinyl-fused bicyclic ring.

11. The compound of claim 1, wherein $R^3$ is selected from $C_{1-6}$ alkyl or $C_{1-6}$ alkoxyl, and/or $R^4$ is selected from absent, cyano, $C_{1-6}$ alkyl, $C_{1-6}$ alkoxyl, 3 to 8 membered unsaturated heterocyclyl, wherein said heterocyclyl can optionally be further mono- or independently multi-substituted by $C_{1-3}$ alkyl.

12. The compound of claim 1, wherein Ring A is

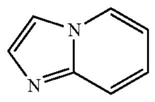

or

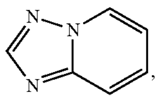

, $R^3$ is selected from methyl or methoxyl, $R^4$ is selected from absent, methyl, cyano, methoxyl, pyrazolyl, oxazolyl, wherein said pyrazolyl or oxazolyl can optionally be further mono- or independently multi-substituted by $C_{1-3}$ alkyl.

13. A compound having a structure of Formula Ie

Formula Ie

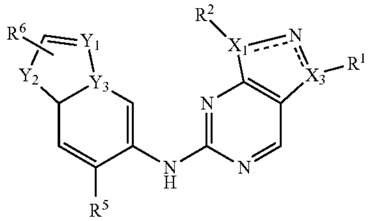

and a pharmaceutically acceptable salt thereof, wherein, one of $X_1$ and $X_3$ is N and the other one is C, dash line "$\cdots\cdots$" means the bond between $X_1$ and N, and between N and $X_3$ can be single or double bonds, provided that at least one of the bonds between $X_1$ and N, and between N and $X_3$ is single bond;

$R^1$ is $C_{1-3}$ alkyl, $R^2$ is cyclopentyl, cyclohexanyl, tetrahydropyranyl or 8-oxabicyclo[3.2.1]octan-3-yl, which can be optionally mono- or independently multi substituted by halogen or $C_{1-3}$ alkoxyl, $Y_1$, $Y_2$, and $Y_3$ are each independently C or N, provided that at least one of $Y_1$, $Y_2$, and $Y_3$ is N;

$R^5$ is halogen or $C_{1-3}$ alkyl, $R^6$ is $C_{1-3}$ alkyl.

14. The compound of claim 13, wherein $R^2$ is un-substituted cyclopentyl.

15. The compound of claim 13, wherein $Y_3$ is N and at least one of $Y_1$ and $Y_2$ is N.

16. The compound of claim 13, wherein $R^5$ is methyl.

17. A compound selected from the group consisting of:
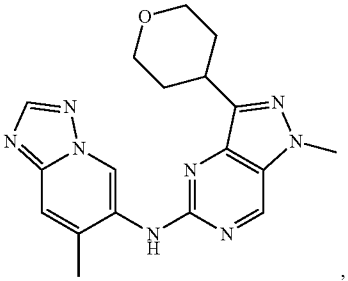
,
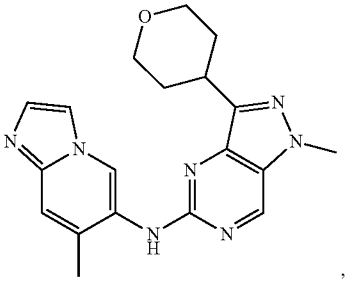
,
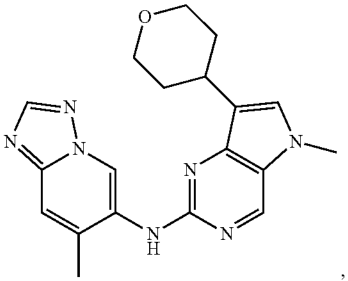
,
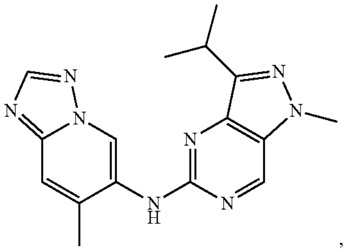
,
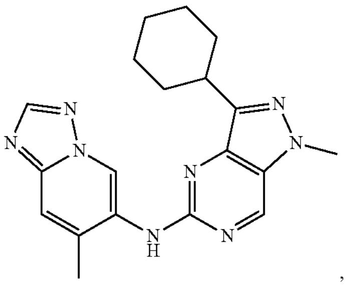
,
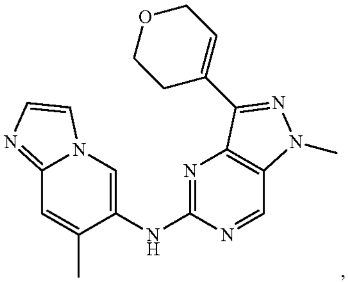
,
-continued
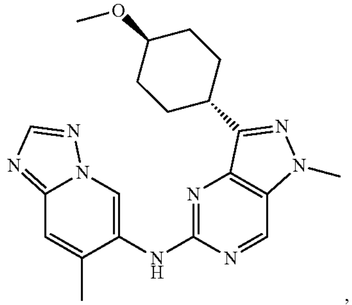
,
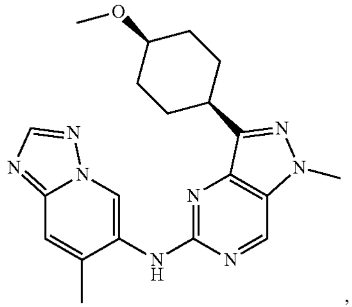
,
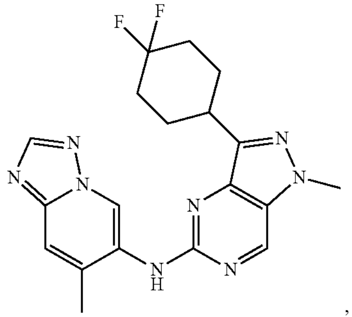
,
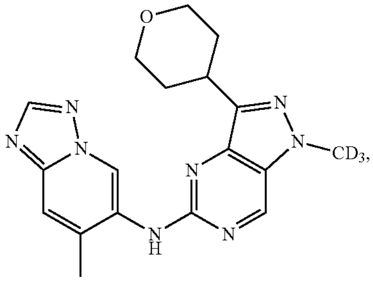
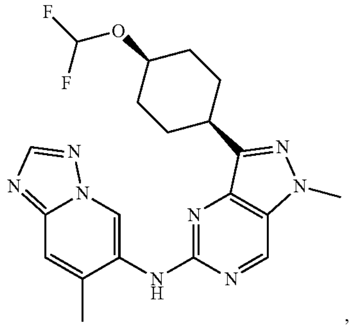
, -continued
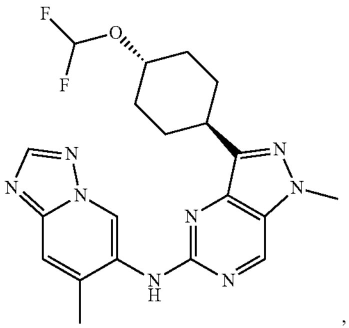
,
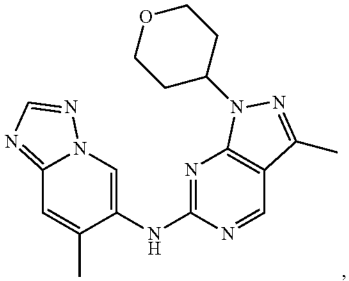
,
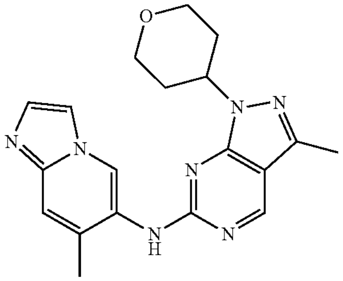
,
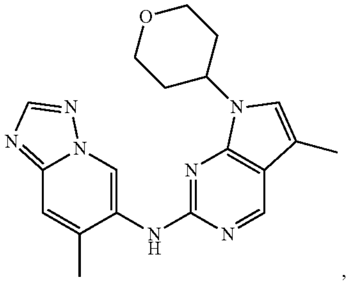
,
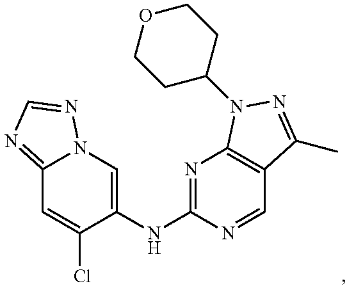
,
-continued
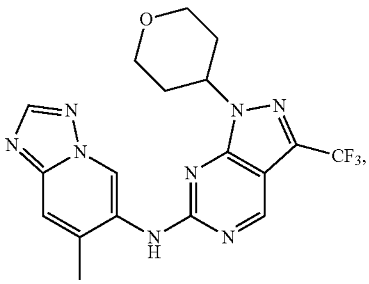
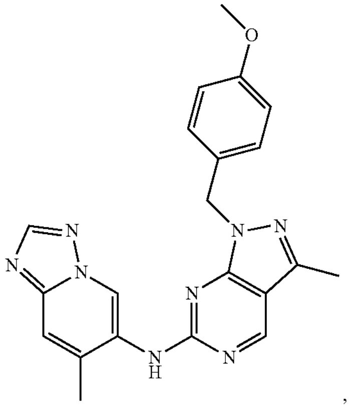
,
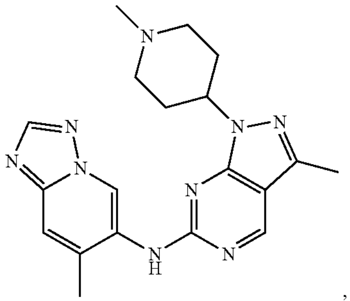
,
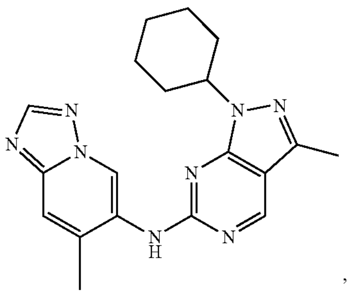
,
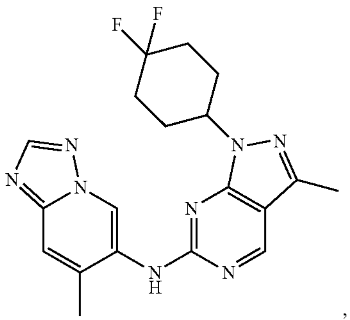
,

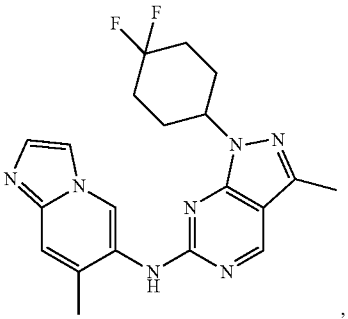
,
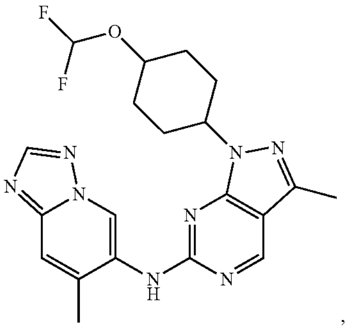
,
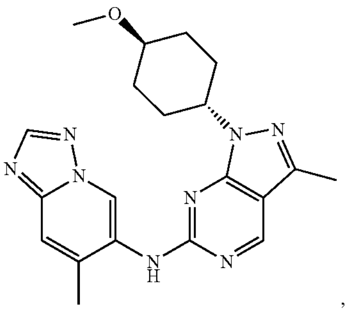
,
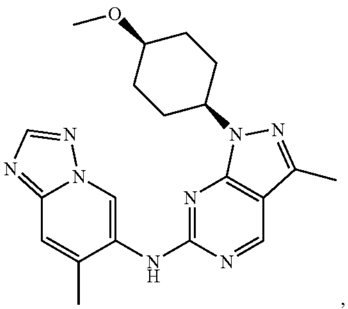
,
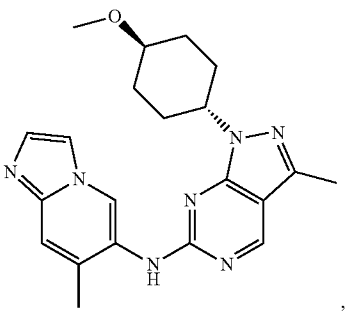
,
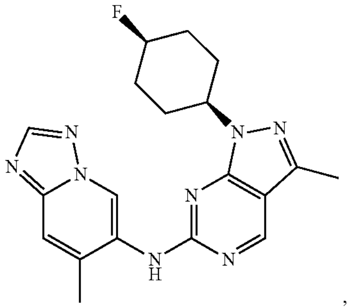
,
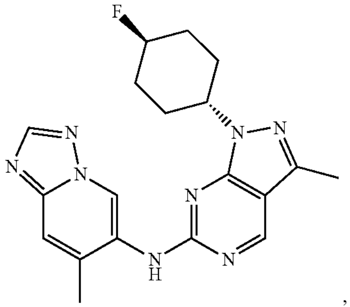
,
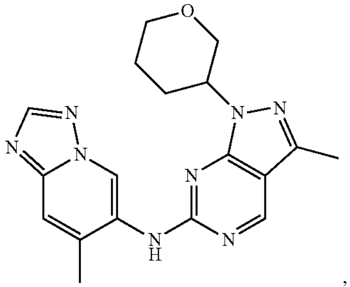
,
(isomer 1)
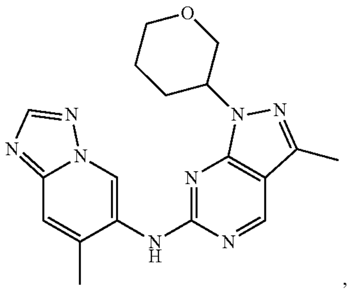
,
(isomer 2)
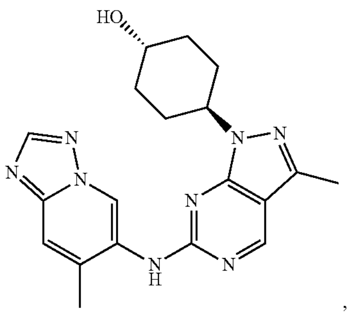
, -continued
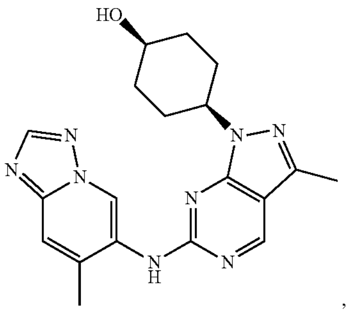
,
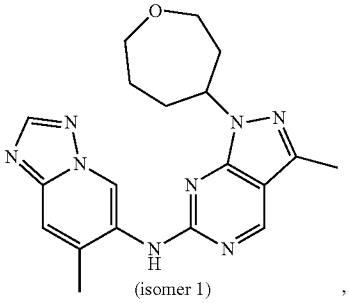
(isomer 1)
,
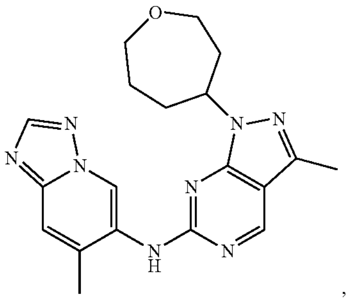
,
(isomer 2)
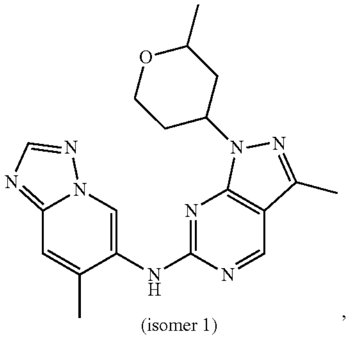
(isomer 1)
,
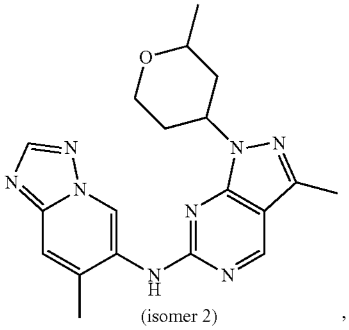
(isomer 2)
,
-continued
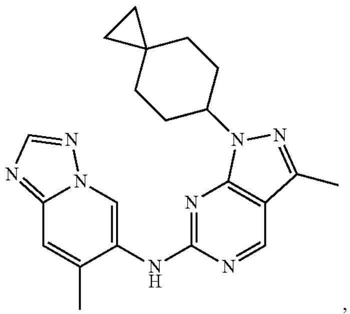
,
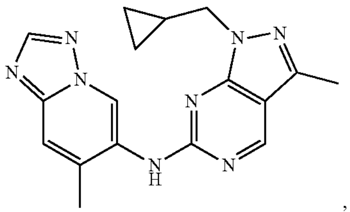
,
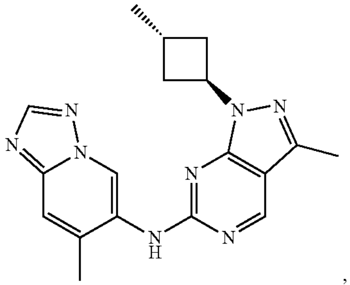
,
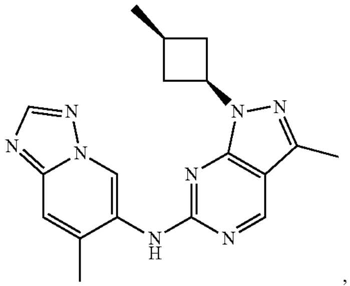
,
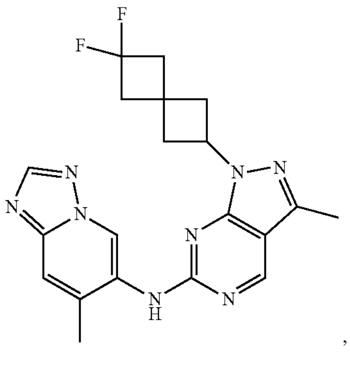
, -continued
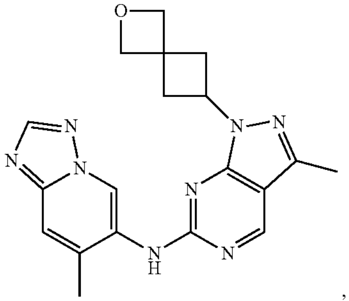
,
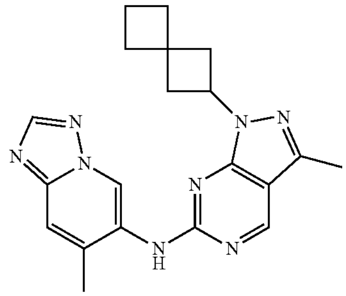
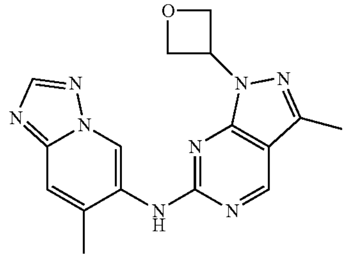
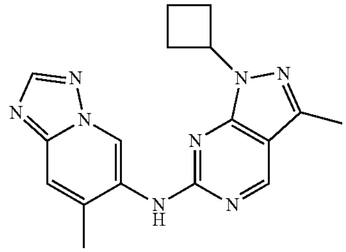
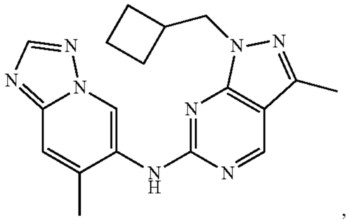
,
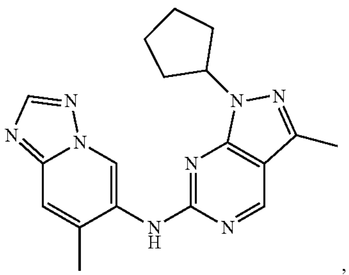
,
-continued
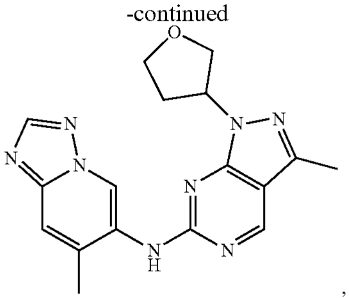
,
(isomer 1)
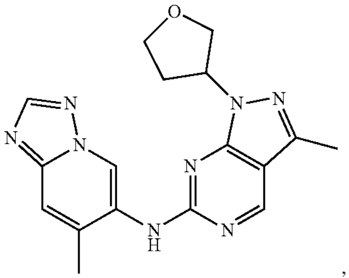
,
(isomer 2)
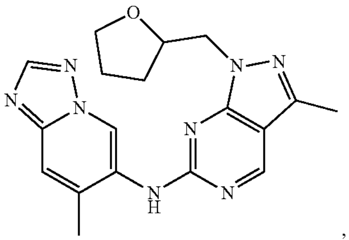
,
(isomer 1)
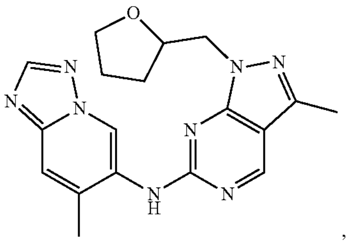
,
(isomer 2)
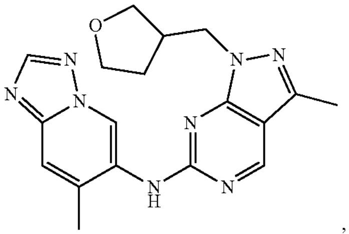
,
(isomer 1)
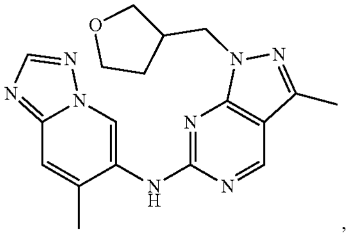
,
(isomer 2)

-continued
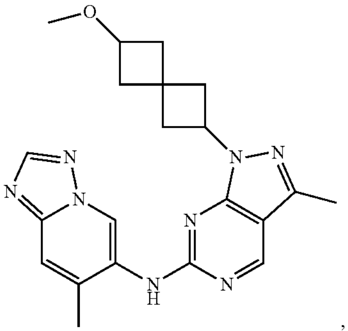
,
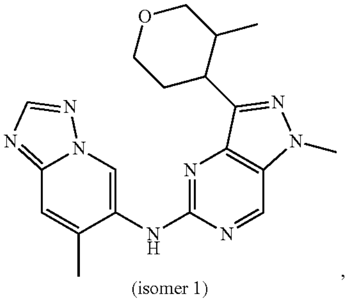
(isomer 1)
,
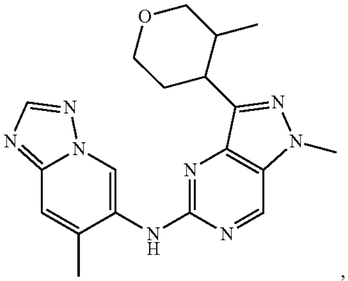
(isomer 2)
,
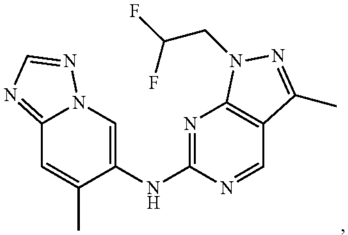
,
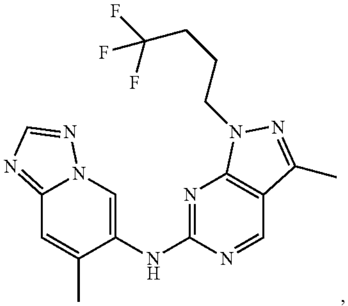
,
-continued
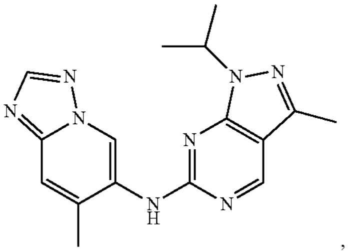
,
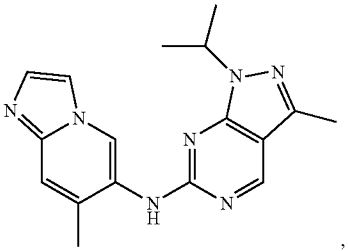
,
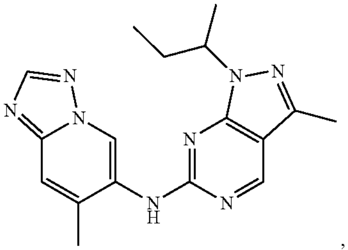
(isomer 1)
,
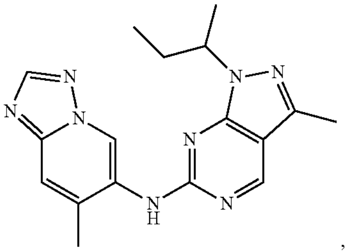
(isomer 2)
,
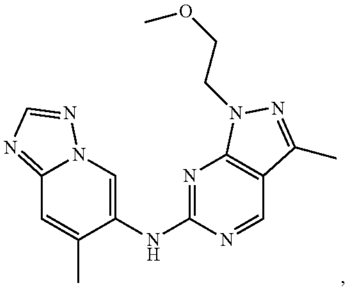
,
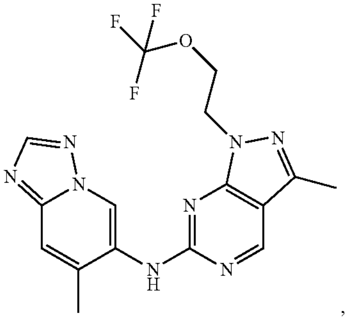
, -continued
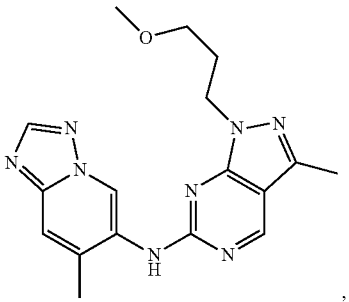
,
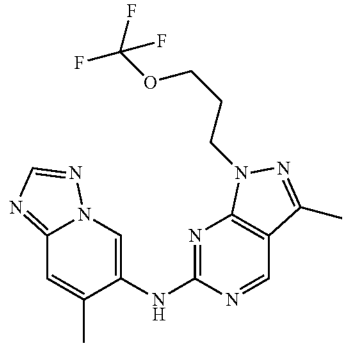
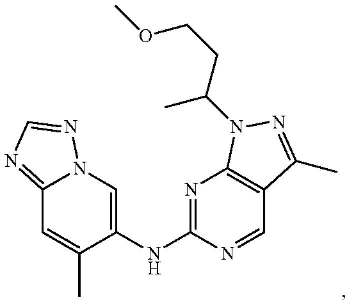
(isomer 1)
,
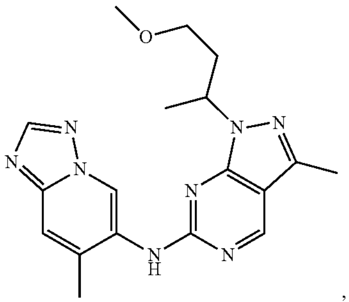
(isomer 2)
,
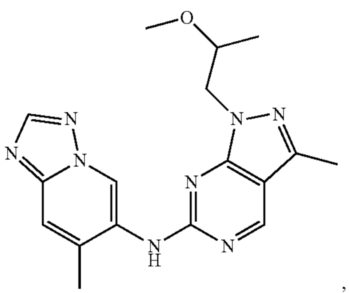
(racemate)
,
-continued
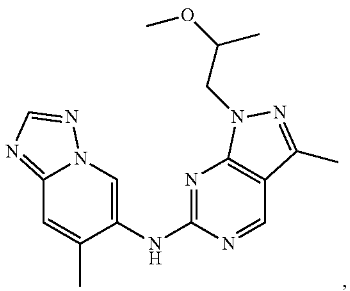
(isomer 1)
,
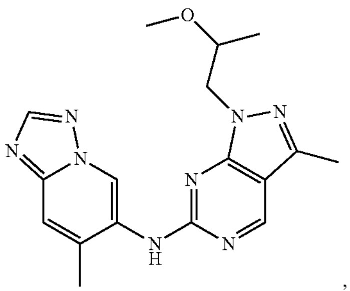
(isomer 2)
,
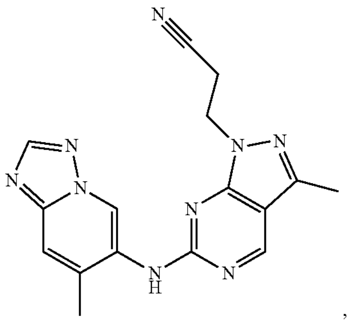
,
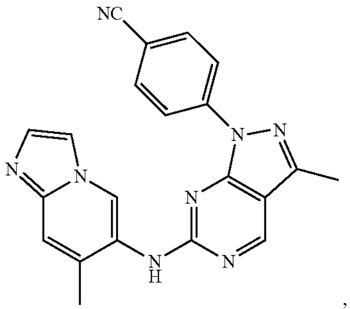
,
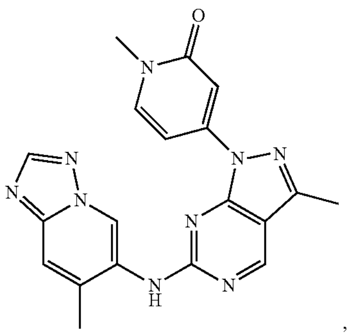
,

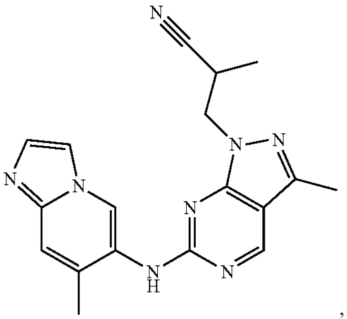
,
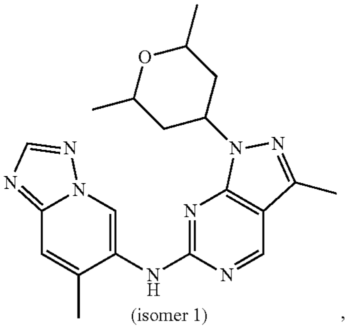
(isomer 1)
,
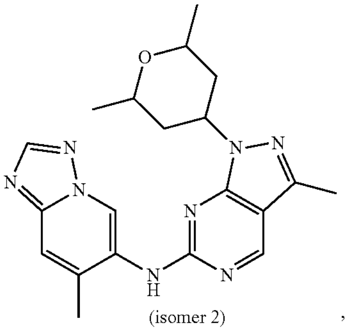
(isomer 2)
,
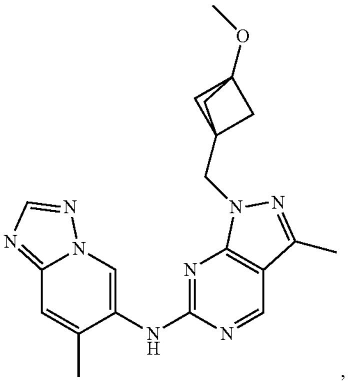
,
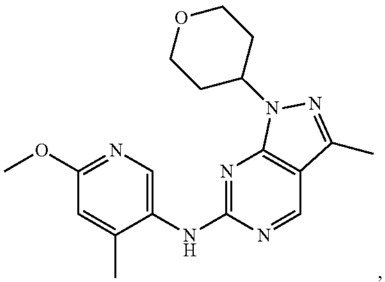
,
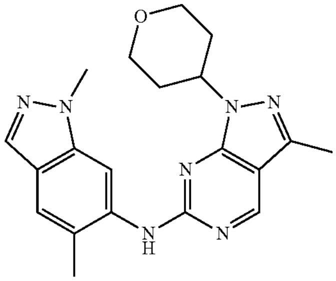
,
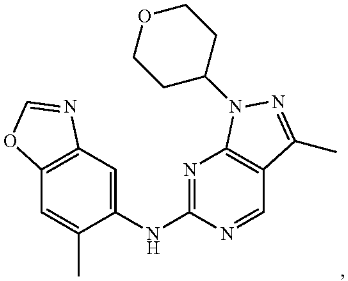
,
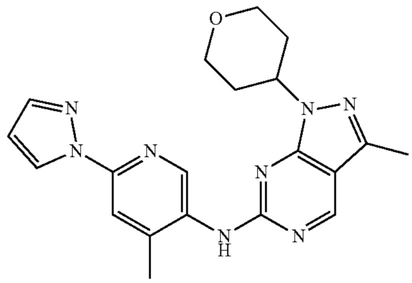
,
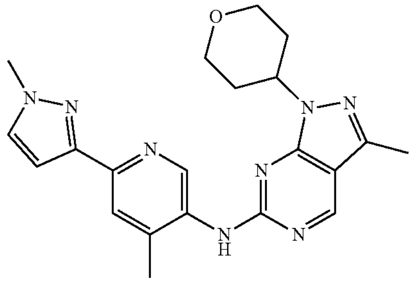
,
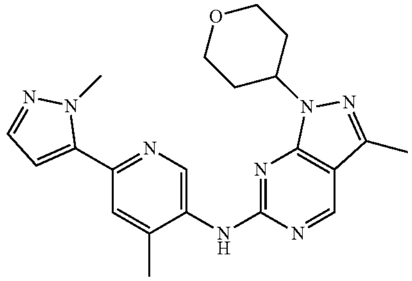
, -continued
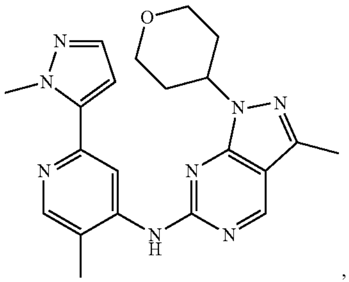
,
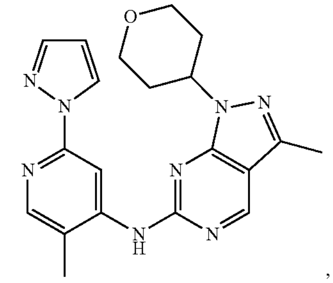
,
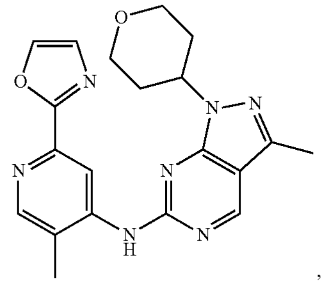
,
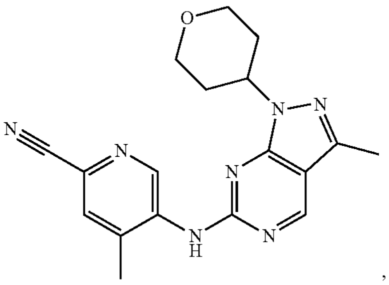
,
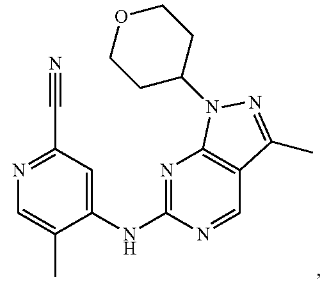
,
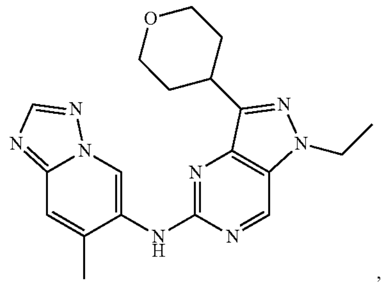
,
-continued
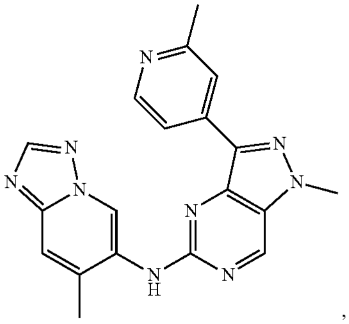
,
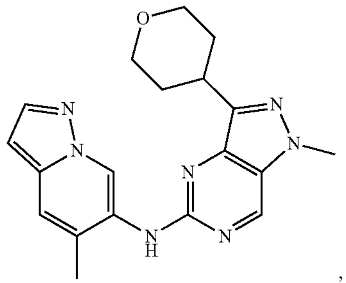
,
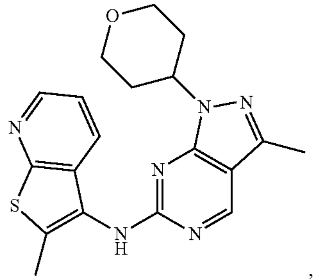
,
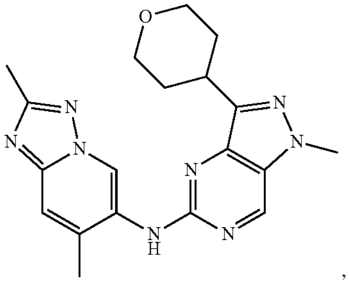
,
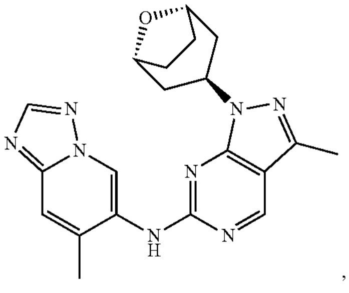
, -continued
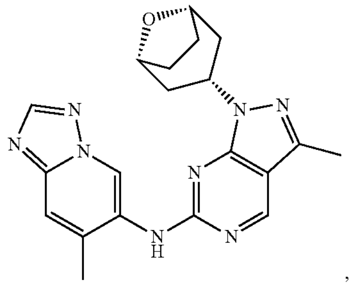
,
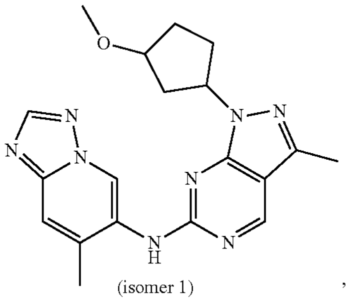
(isomer 1)
,
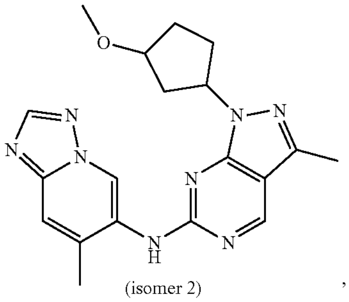
(isomer 2)
,
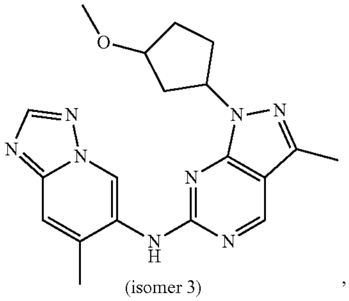
(isomer 3)
,
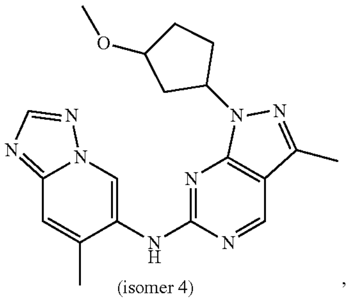
(isomer 4)
,
-continued
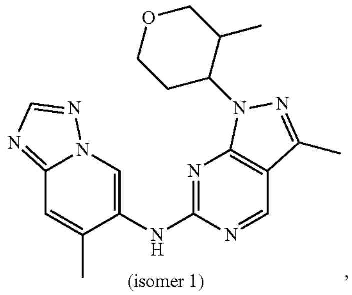
(isomer 1)
,
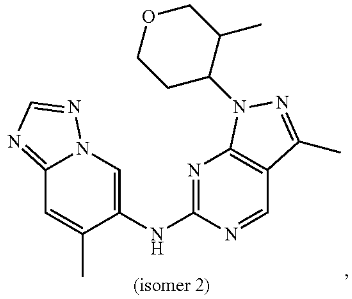
(isomer 2)
,
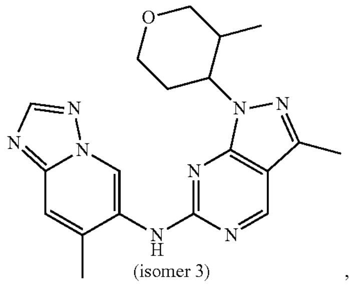
(isomer 3)
,
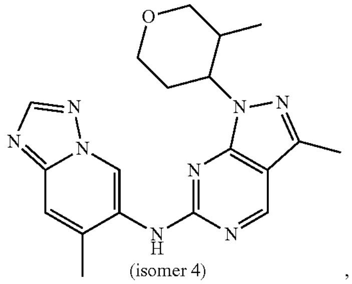
(isomer 4)
,
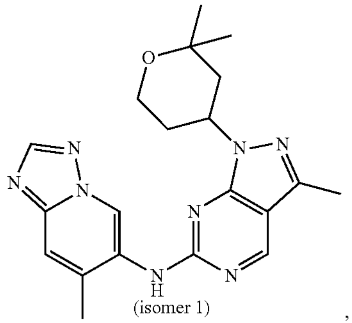
(isomer 1)
, -continued
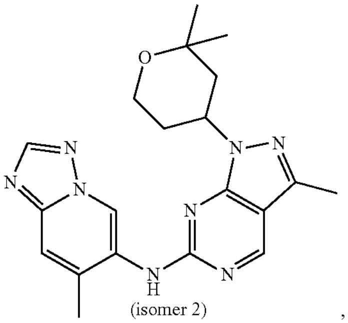
(isomer 2)
,
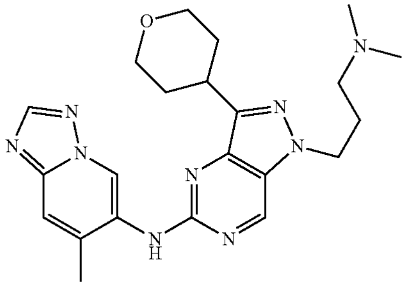
,
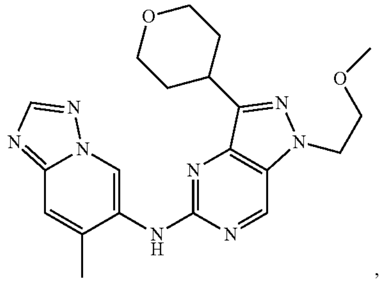
,
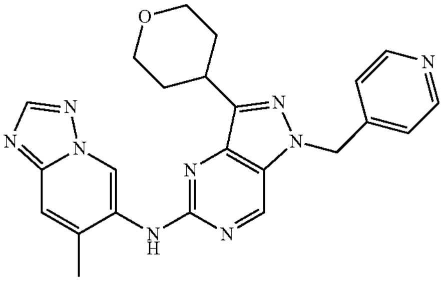
,
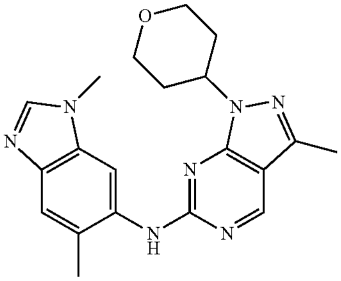
-continued
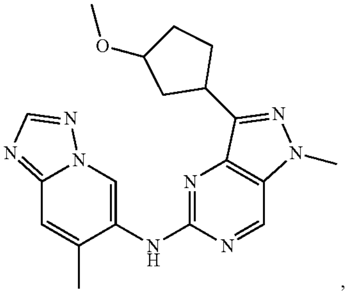
,
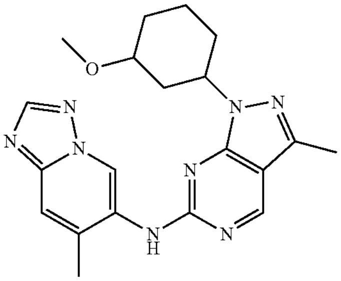
,
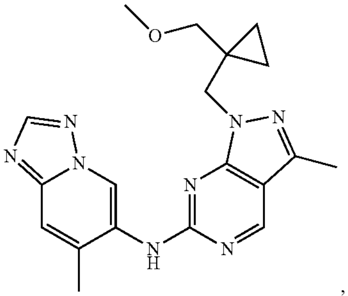
,
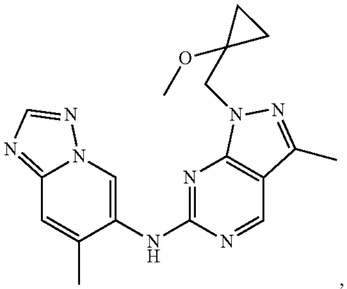
,
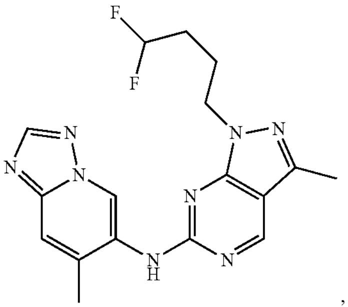
, -continued
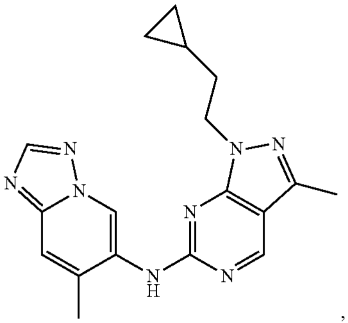
,
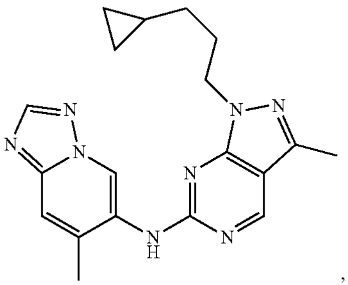
,
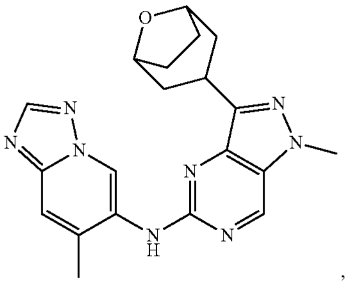
,
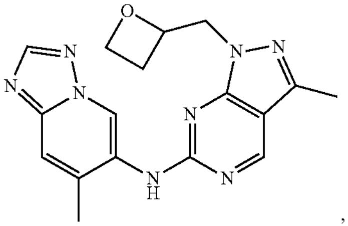
,
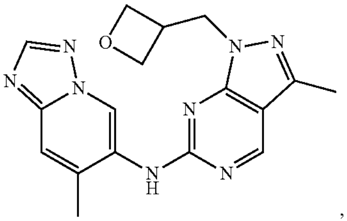
,
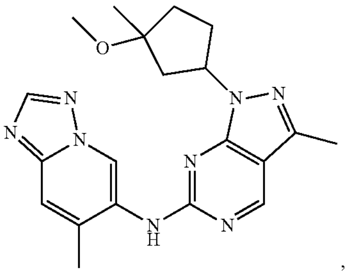
,
-continued
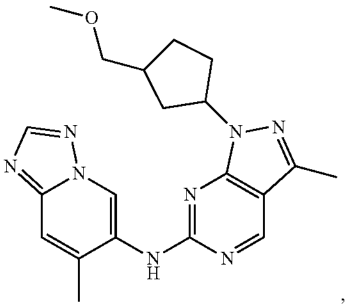
,
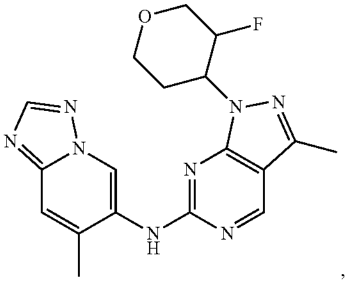
,
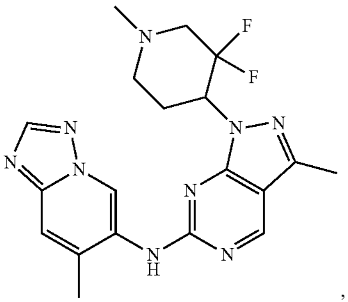
,
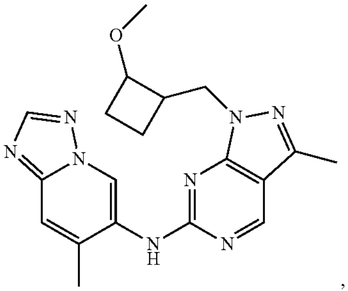
,
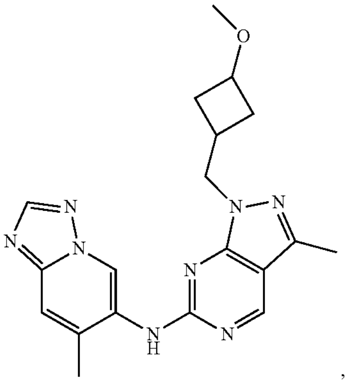
, -continued
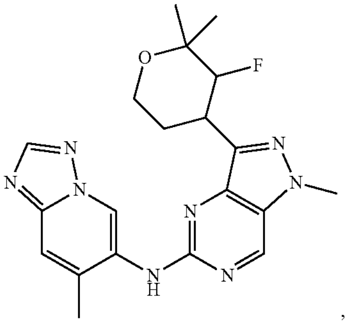
,
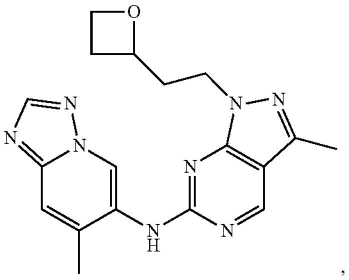
,
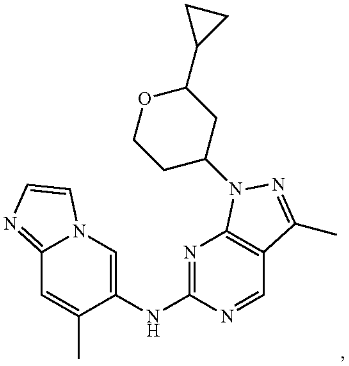
,
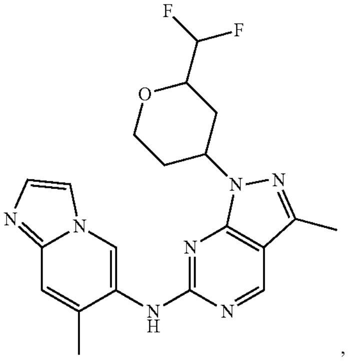
,
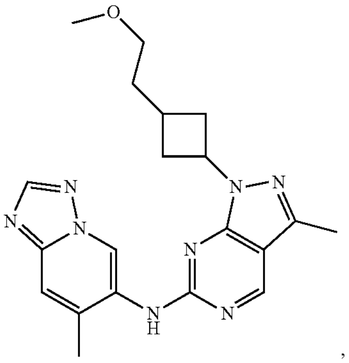
,
-continued
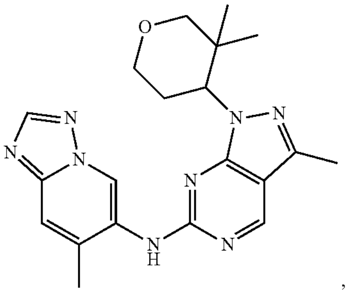
,
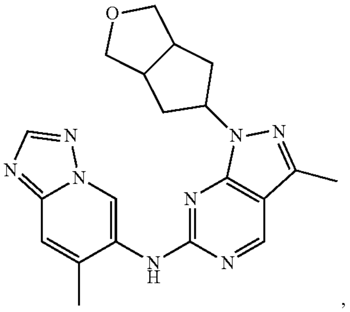
,
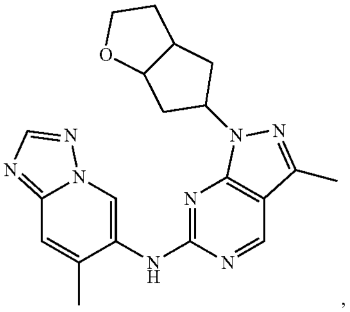
,
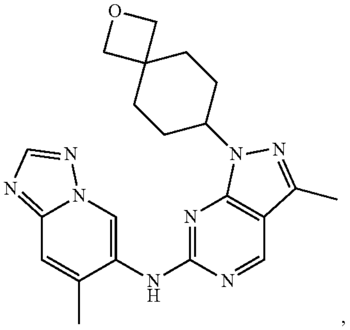
,
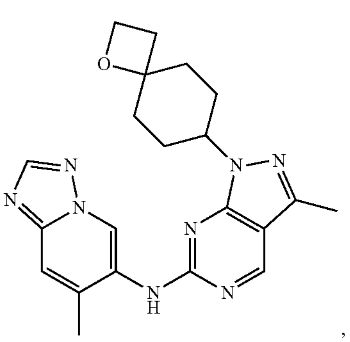
, -continued

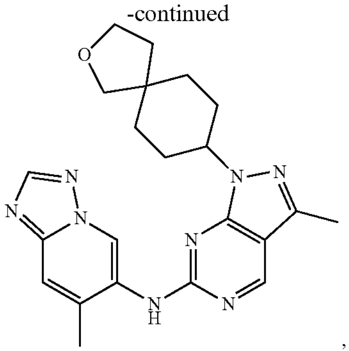

,

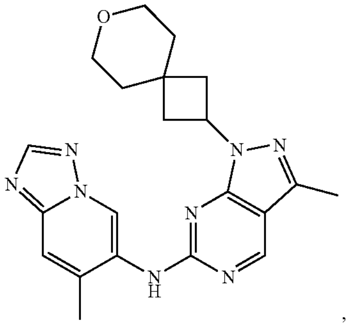

, or a pharmaceutically acceptable salt thereof.

18. The compound of Formula (I), or a pharmaceutically acceptable salt thereof, according to claim 1, in crystalline form.

19. A pharmaceutical composition comprising one or more compounds of Formula (I), or pharmaceutically acceptable salts thereof according to claim 1 as a first active ingredient, and a pharmaceutically acceptable diluent, excipient or carrier.

20. A method of treating a DNA-PK related disorder in a subject, comprising administering to the subject an effective amount of one or more compounds, or pharmaceutically acceptable salts thereof of claim 1, wherein the DNA-PK related disorder is non-small cell lung cancer (NSCLC), prostate cancer, breast cancer, ovarian cancer, cervical cancer, melanoma, myeloma, hepatocellular carcinoma, gastric cancer, thyroid cancer, esophageal cancer or nasopharyngeal cancer.

21. The method according to claim 20, wherein the subject is a warm blooded animal.

22. The method according to claim 20, wherein the DNA-PK related disorder is NSCLC, prostate cancer, or breast cancer.

23. A compound of Formula (I), or pharmaceutically acceptable salt thereof, as claimed in claim 1, in combination with Bleomycin.

24. The method according to claim 21, wherein the warm blooded animal is human.

25. The component of claim 1, wherein Ring A is selected from the group consisting of:

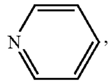, 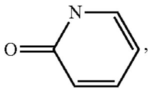, 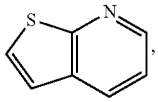,

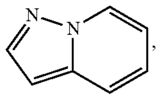, 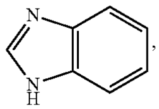, 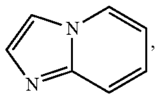,

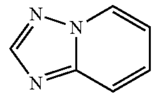, 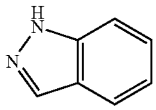, 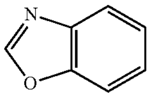 and

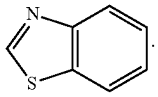.

* * * * *